(12) United States Patent
Hu et al.

(10) Patent No.: US 8,168,647 B2
(45) Date of Patent: May 1, 2012

(54) VINBLASTINE DERIVATIVES, THEIR PREPARATION, USE AND PHARMACEUTICAL COMPOSITIONS COMPRISING THE SAID DERIVATIVES

(75) Inventors: Lihong Hu, Shanghai (CN); Xu Shen, Shanghai (CN); Hualiang Jiang, Shanghai (CN); Liguang Lou, Shanghai (CN); Hong Ding, Shanghai (CN); Yong Shao, Shanghai (CN); Hankun Zhang, Shanghai (CN)

(73) Assignee: Shanghai Institute of Materia Medica Chinese Academy of Sciences, Pudong, Shanghai (CN)

( * ) Notice: Subject to any disclaimer, the term of this patent is extended or adjusted under 35 U.S.C. 154(b) by 289 days.

(21) Appl. No.: 12/449,180

(22) PCT Filed: Dec. 17, 2007

(86) PCT No.: PCT/CN2007/003624
§ 371 (c)(1),
(2), (4) Date: Oct. 8, 2009

(87) PCT Pub. No.: WO2008/092335
PCT Pub. Date: Aug. 7, 2008

(65) Prior Publication Data
US 2010/0113498 A1 May 6, 2010

(51) Int. Cl.
*C07D 519/04* (2006.01)
*A61K 31/475* (2006.01)
*A61P 35/00* (2006.01)

(52) U.S. Cl. .................................. 514/281; 540/478
(58) Field of Classification Search .................. 540/478; 514/281
See application file for complete search history.

(56) References Cited

FOREIGN PATENT DOCUMENTS

| CN | 1854143 | 11/2006 |
|---|---|---|
| FR | 2 434 171 A1 | 3/1980 |
| WO | WO 99/62912 A1 | 12/1999 |

OTHER PUBLICATIONS

Jordan et al., "Mechanism of Inhibition of Cell Proliferation by Vinca Alkaloids", Cancer Research, American Association for Cancer Research, U.S. vol. 51, No. 8, Apr. 15, 1991, pp. 2212-2222.
Supplementary European Search Report for corresponding EP 07 86 6193, mailed Nov. 12, 2010, 7 pages.
International Search Report for PCT/CN2007/003624 mailed Mar. 20, 2008.
Li, Weihong et al., BM6, "A new Semi-Synthetic Vinca Alkaloid, Exhibits its potent in Vivo Anti-Tumor Activities Via its High Binding Affinity for Tubulin and Improved Pharmacokinetic Profiles", Cancer Biology & Therapy, May 2007, vol. 6, No. 5, pp. 787-794.
Shao, Yong et al., "Synthesis and Structure-Activity Relationships Study of Novel Anti-Tumor Carbamate Anhydrovinblastine Analogues", Bioorganic & Medicinal Chemistry, May 2007, vol. 15, No. 15, pp. 5062-5075.
Kutney, James P. et al., "Studies on the Synthesis of Bisindole Alkaloids", XI. Novel isomers of vinblastine. Heterocycles, 1977, vol. 6, No. 7, pp. 905-910.
Bolcskei, Hedvig et al., "New Antitumor Hydroxymethyl Derivatives of Vinblastine", Journal of the Indian Chemical Society, 1977, vol. 74, No. 11-12, pp. 904-907.
Camplejohn: "A Critical Review of the Use of Vincristine (VCR) as a Tumour Cell Synchronizing Agent in Cancer Therapy," Department of Dermatology, Medical College of George, *Cell Tissue Kinet.* (1980) 13, pp. 327-335.
Owellen et al.: "Inhibition of Tubulin-Microtubule Polymerization by Drugs of the *Vinca* Alkaloid Class," The Oncology Center, The Johns Hopkins University School of Medicine, Baltimore, Maryland, Cancer Research 36, pp. 1499-1502, Apr. 1976.
Bruchovsky et al.: "Effects of Vinblastine on the Proliferative Capacity of L Cells and Their Progress Through the Division Cycle," Department of Medical Biophysics, University of Toronto, Ontario, Canada, Mar. 1965, pp. 1232-1237.
Cros et al.: "Experimental Antitumor Activity of Navelbine®," Seminars in Oncology, vol. 16, No. 2, Suppl. 4, Apr. 1989, pp. 15-20.
Himes et al.: "Action of the *Vinca* Alkaloids Vincristine, Vinblastine, and Desacetyl Vinblastine Amide on Microtubules in Vitro," Department of Biochemistry, University of Kansas, Lawrence, Kansas and R.L. Smith Research Center, University of Kansas, Kansas City, Missouri, Cancer Research vol. 36, pp. 3798-3802, (1976).
Boloskei et al.: "New Antitumor Hydroxymethyl Derivatives of Vinblastine," Budapest, Hungary, vol. 74, Nov.-Dec. 1997, pp. 904-907.

*Primary Examiner* — Bruck Kifle
(74) *Attorney, Agent, or Firm* — Nixon & Vanderhye P.C.

(57) ABSTRACT

The invention provides vinblastine derivatives represented by the following formula 1 or their physiologically acceptable salts, their preparation, use and pharmaceutical compositions comprising the said derivatives. The said vinblastine derivatives show inhibiting activities against tumor cell lines and can be used as medicaments for treating malignant tumors.

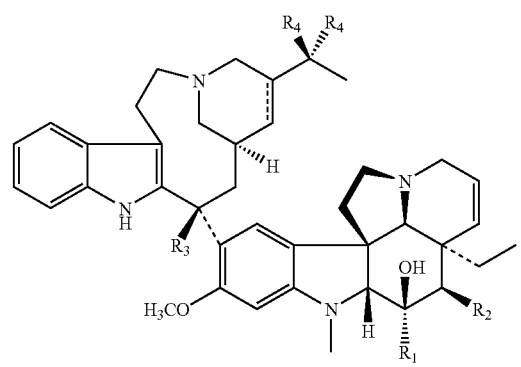

4 Claims, No Drawings

VINBLASTINE DERIVATIVES, THEIR PREPARATION, USE AND PHARMACEUTICAL COMPOSITIONS COMPRISING THE SAID DERIVATIVES

This application is the U.S. national phase of International Application No. PCT/CN2007/003624 filed 17 Dec. 2007, which designated the U.S., and claims priority to Chinese application No. 200710036923.2, filed 29 Jan. 2007 the entire contents of each of which are hereby incorporated by reference.

FIELD OF THE INVENTION

The present invention generally relates to the field of pharmaceutical chemistry. More particularly, the present invention relates to novel vinblastine derivatives, the preparation and use thereof and pharmaceutical compositions comprising the same. The vinblastine derivatives show inhibiting activities against tumor cell lines, and can be used as medicaments for treating malignant tumors.

BACKGROUND OF THE INVENTION

Tumor is one of the malignant diseases that threaten human health. Every year, more than 5,000,000 peoples die for tumors throughout the world. In China, more than 1,600,000 peoples are newly found to be sufferring from tumors and the peoples died for them have exceeded 1,300,000 each year. Hence, it has been a worldwide focus to develop anti-cancer medicaments.

Vinca alkaloids anti-tumor agents are a type of bisindole alkaloids having anti-cancer activities. They are isolated from *Catharanthus roseus* (L.) G. Don and *Catharanthus roseus* (L.) G. Don cv. Flavus which are perivinkle plants of Apocynaceae family. Natural Vinca alkaloids can be biosynthesized through coupling catharanthine and vindoline, which are mono-indole alkaloids rich in the plants.

Currently, there are four Vinca alkaloids or derivatives thereof in clinical use, i.e., vinblastine (VLB), vincristine (VCR), vindesine (VDS) and vinorelbine (NVB).

Vinca alkaloids anti-tumor agents are cell cycle specific agents that mainly function in the G2 phase (post-synthetic phase of DNA) of tumor cells. It is reported that the mechanism of action of Vinca alkaloids anti-tumor agents are that they bind with tubulin inhibiting the formation of microtubules from the polymerization of tublin dimers, and also induce the disruption of the cytoskeleton blocking the formation of mitotic spindles and arresting the tumor cell divison and proliferation at mitotic metaphase, and thus exhibit the antineoplastic activity (R. J. Owellen and C. A. Hartke, Cancer Res., 1976, 36, 1499-1504; R. N. Kersey, Cancer Res., 1976, 36, 3798-3806; R. S. Camplrjohn, Cell Tissue Kinet., 1980, 13, 327-332). The tubulin binding affinity of Vinca alkaloids anti-tumor agents has a poorly linear correlation with their inhibiting activities against cell growth. It is generally considered that the differences of the activities and side effects among Vinca alkaloids anti-tumor agents are mainly resulted from the differences of their uptake and retention in tumor tissues.

A small change in the structure of a vinblastine analog may cause great variation in its anti-tumor spectra and toxicity and side effect spectra. For example, the only difference between vinblastine and vincristine is that a N-methyl group is substituted by a N-aldehyde group. However, vincristine exhits good inhibiting activity against Rhabdoid Tumors in vivo, and vinblastine shows no efficacy. In addition, they are completely different in their toxicity spectra. The major toxicities are peripheral neurotoxicity for vincristine and anaemia and reduction of leucocyte for vinblastine (N. Bruchovsky et al., Cancer Res. 1965, 25, 1232-1238). Vinorelbine has a poorer inhibiting activity on P388 and L1210 cell lines than vinblastine and vincristine, but a better inhibiting activity on lung cancer than other vinblastine analogs. Therefore, it has been a first-line agent for treating clinically nonsmall-cell lung cancers (S. Cros, et al., Seminars in Oncology, 1989, 16, 15-20).

Therefore, there is a need to develop novel vinblastine derivatives with better anti-tumor activities and reduced toxicity and side effects through designing and sysnthesizing a series of new derivatives based on the research results on the structure-activity relationship, followed by extensive biologic assay in vitro and in vivo, since the anti-tumor activities of vinblastine analogs in vivo lack direct relation with that in vitro, and a small change in the structures of vinblastine analogs may result in great difference in their anti-tumor sprectra and toxicity sprectra. The present inventors have found novel vinblastine derivatives with strong anti-tumor activity through synthesizing a series of vinblastine analogs by coupling a modified vindoline with a catharanthine, followed by evalutated in vivo and in vitro.

SUMMARY OF THE INVENTION

The present invention is proposed and made to solve the above mentioned problems.

One object of the present invention is to provide a class of novel vinblastine derivatives with anti-tumor activity.

Another object of the present invention is to provide a process to prepare the above vinblastine derivatives.

Another object of the present invention is to provide phamaceutical compositions comprising the above vinblastine derivatives.

Another object of the present invention is to provide uses of the above vinblastine derivatives and the compositions comprising the same.

According to a technical solution of the invention, there is provided a class of vinblastine derivatives having the following structure represented by formula 1 or physiologically acceptable salts thereof,

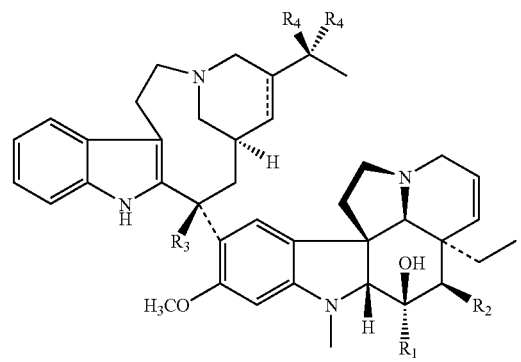

1

Wherein,
"⸺" represents a double bond or a single bond,
R₁ is

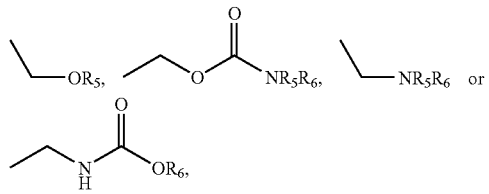

R₂ is —OR₇,
R₃ is

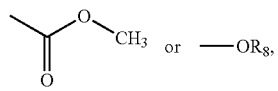

wherein, R₅, R₆, R₇ and R₈ are independently hydrogen, $C_1$-$C_5$ alkylacyl, $C_3$-$C_8$ cycloalkylacyl, $C_2$-$C_4$ unsatuated hydrocarbylacyl, $C_6$-$C_{12}$ arylacyl, $C_1$-$C_5$ alkyl, $C_3$-$C_8$ cycloalkyl, $C_2$-$C_4$ unsatuated hydrocarbyl or $C_6$-$C_{12}$ aryl,
R₄ is hydrogen or fluorine.

The physiologically acceptable salts refer to physiologically acceptable salts formed by the derivatives of the invention with various acids, wherein the acids include organic or inorganic acids, for example, hydrochloric acid, sulphuric acid, phosphonic acid, acetic acid, tartaric acid, benzoic acid, maleic acid, succinic acid, citric acid, etc.

Preferably, a vinblastine derivative according to the invention has a structure represented by one of the following formulas BM1-BM80,

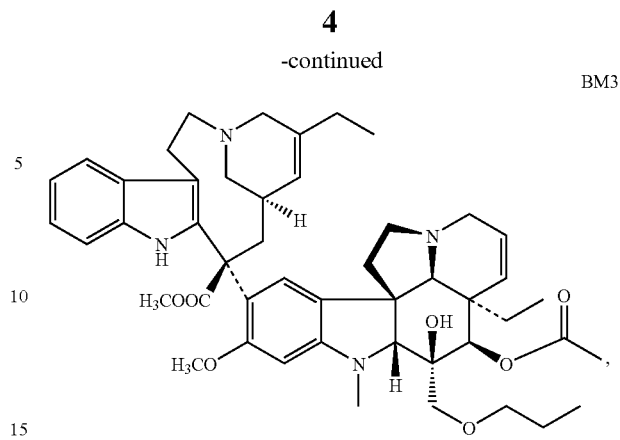

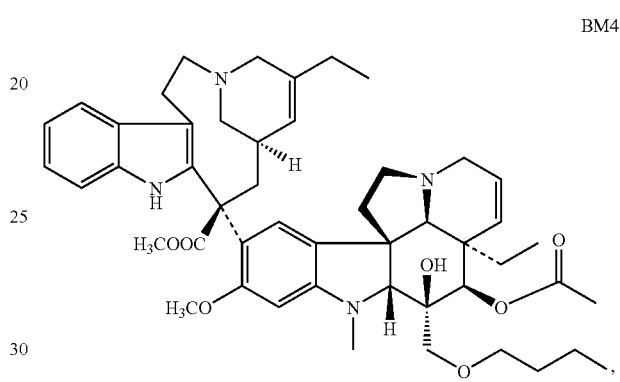

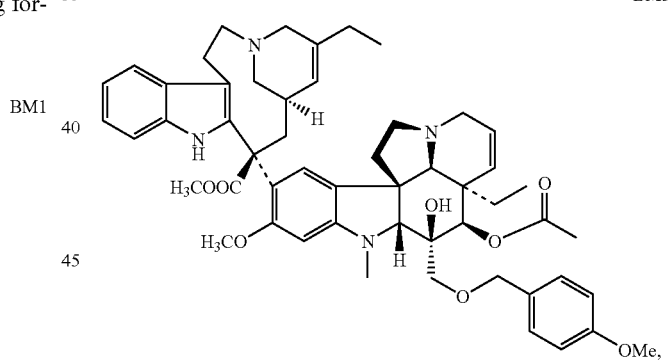

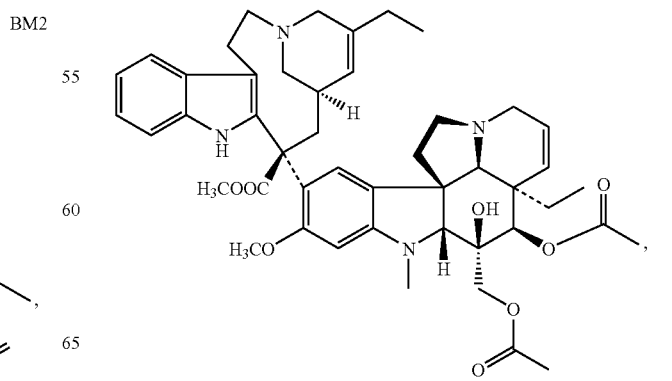

BM7
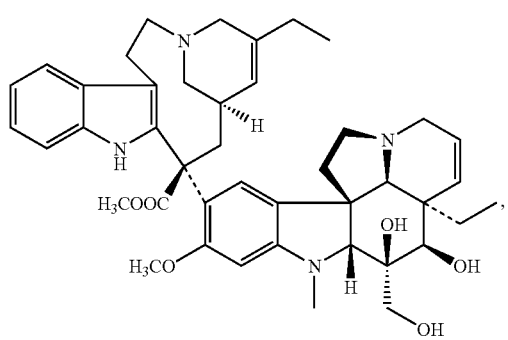
BM8
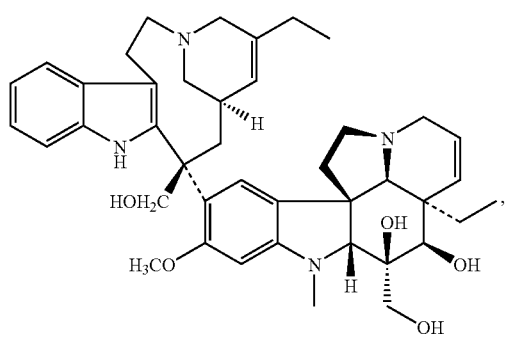
BM9
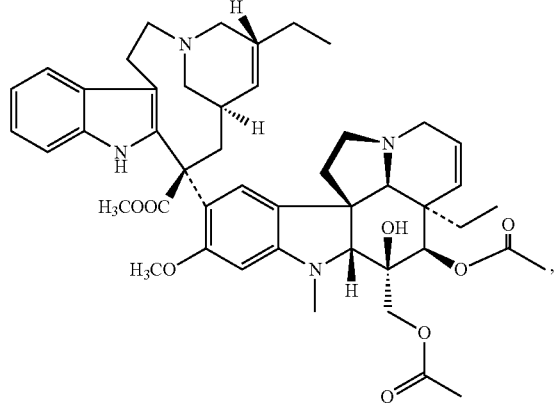
BM10
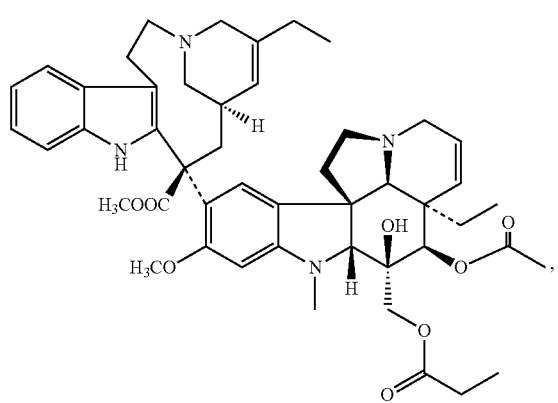
BM11
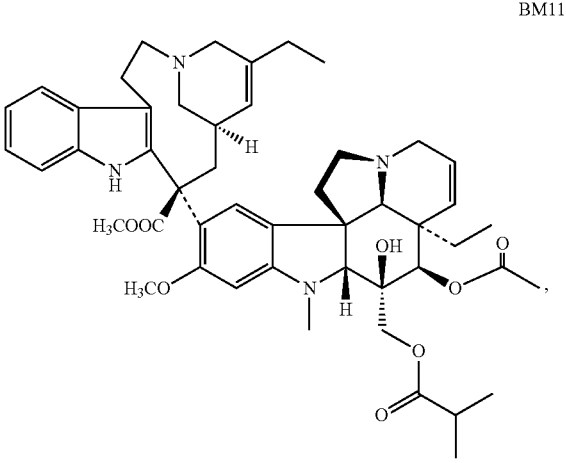
BM12
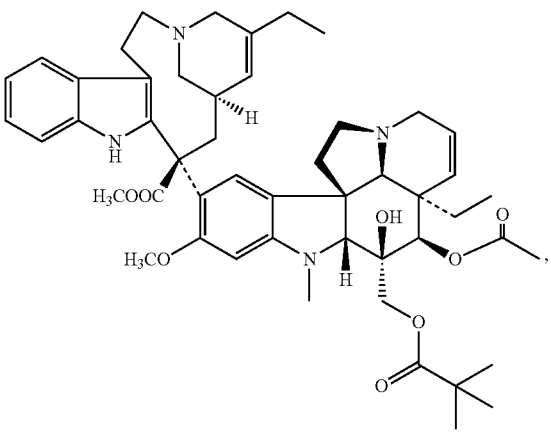
BM13
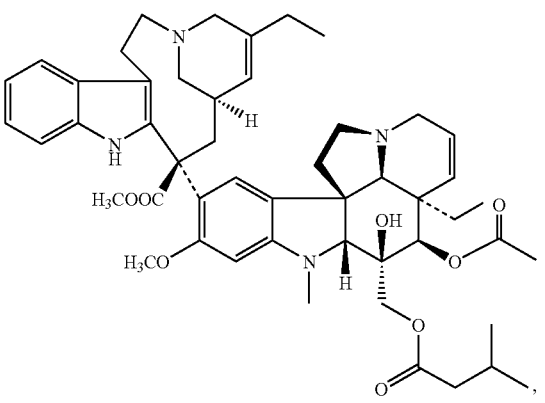

-continued
BM14
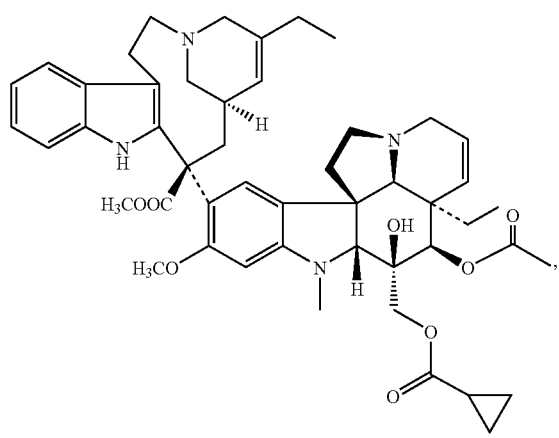
BM17
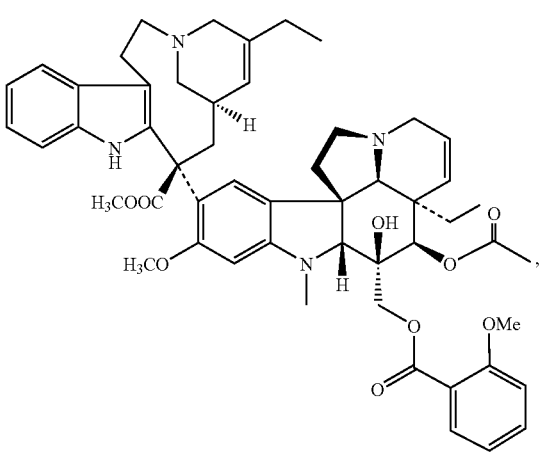
BM15
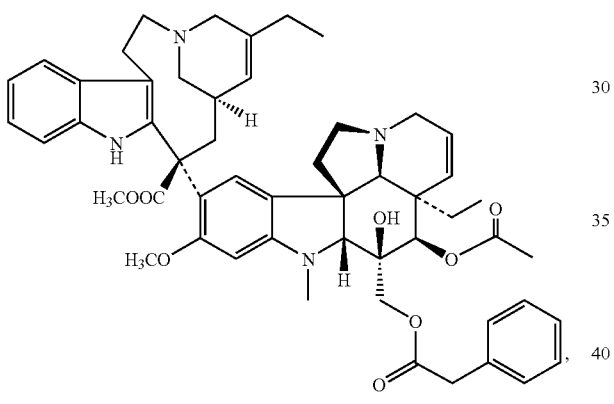
BM18
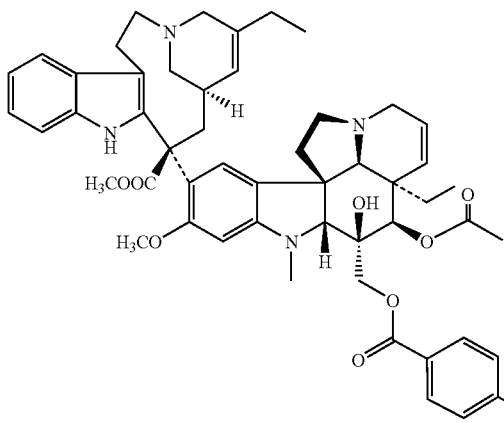
BM16
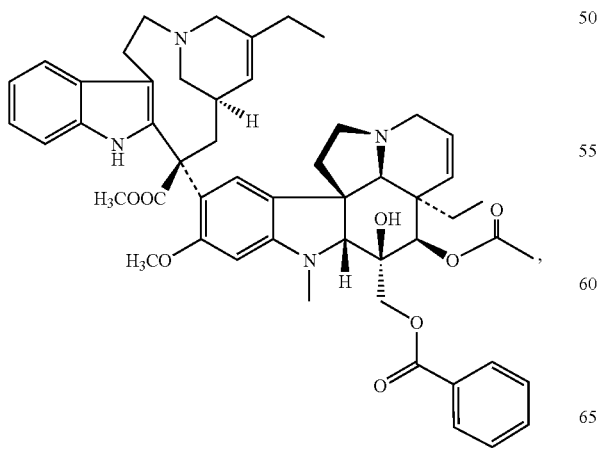
BM19
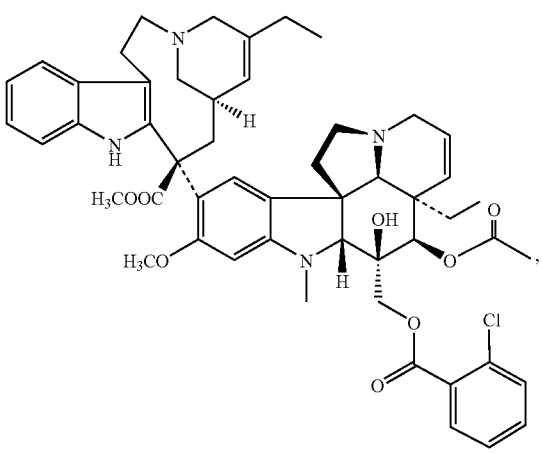

BM20
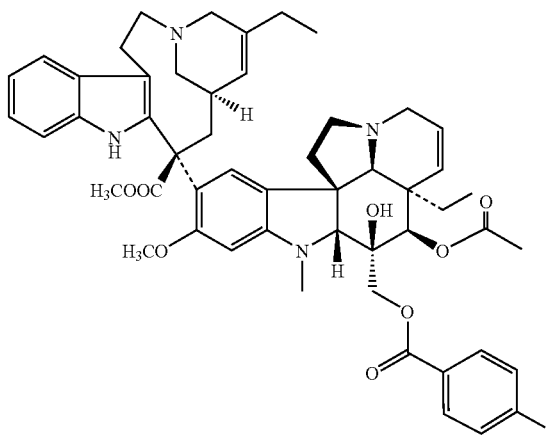
BM21
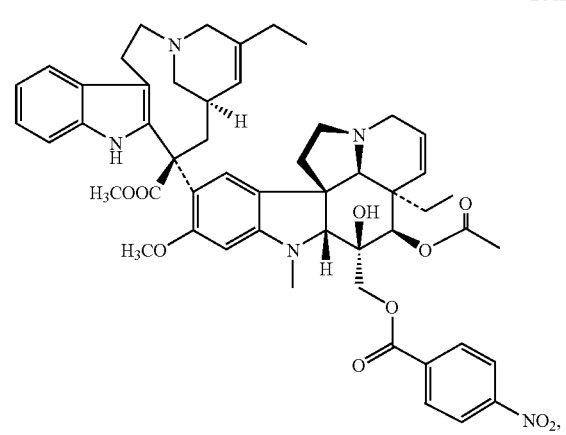
BM22
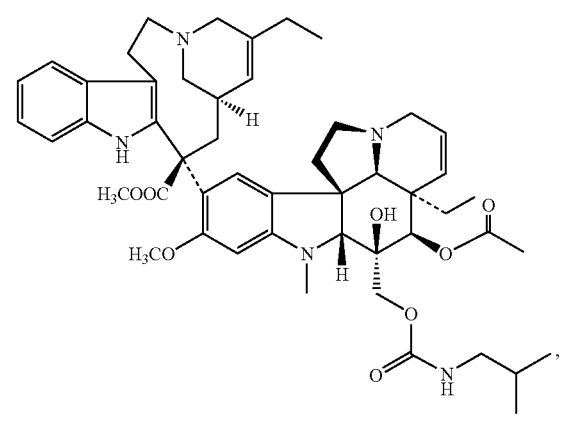
BM23
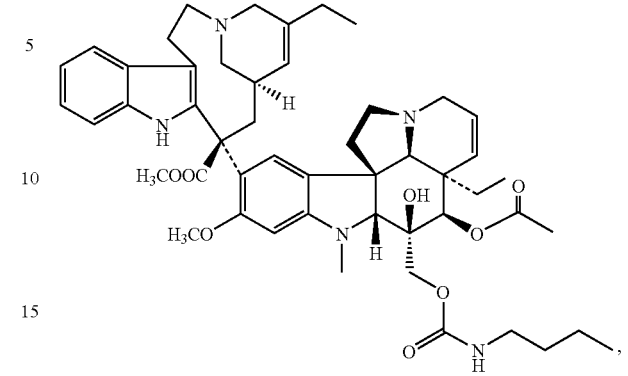
BM24
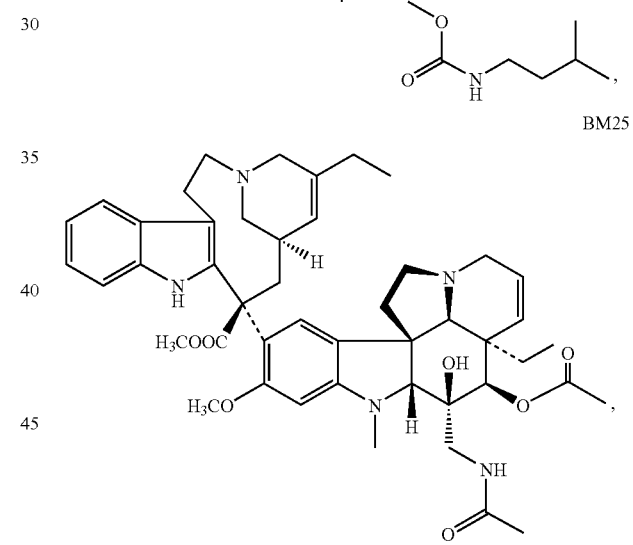
BM25
BM26
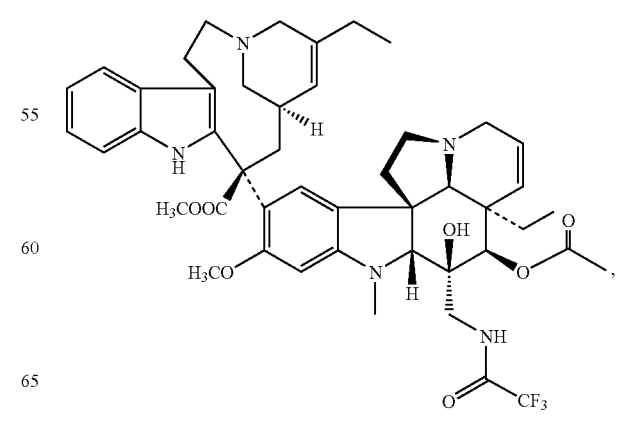

BM27
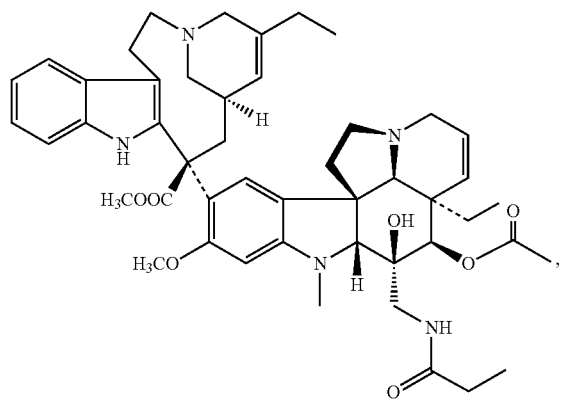
BM28
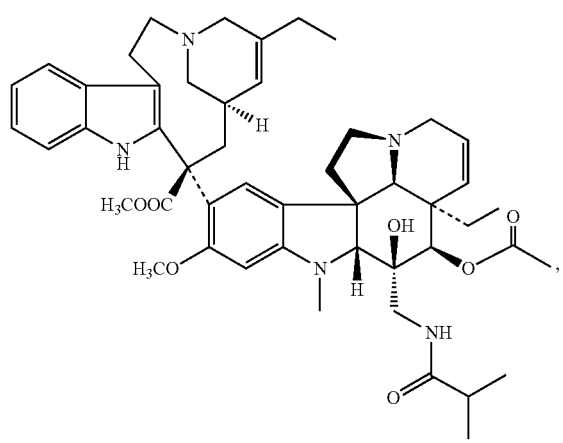
BM29
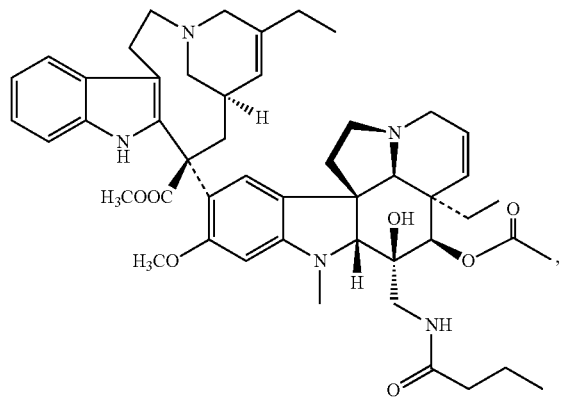
BM30
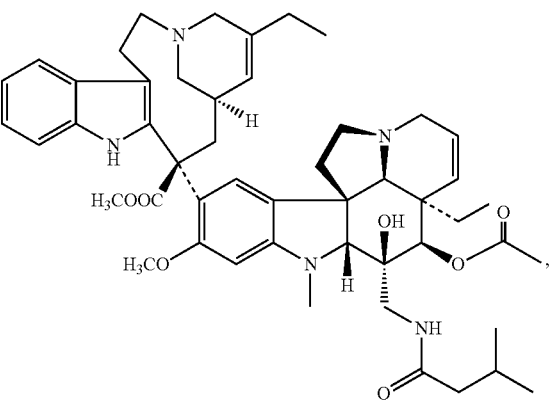
BM31
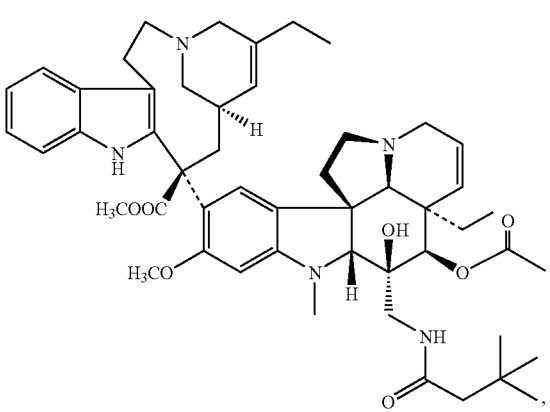
BM32
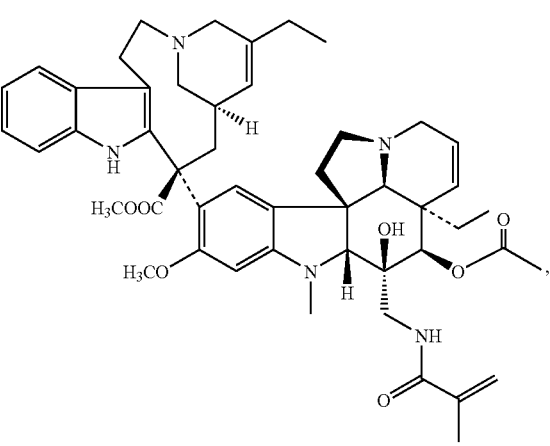

BM33
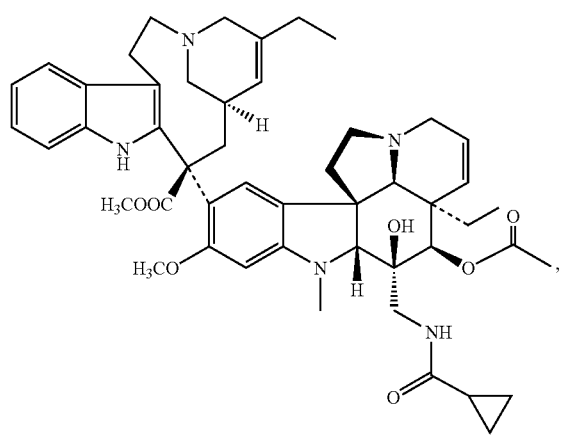
BM36
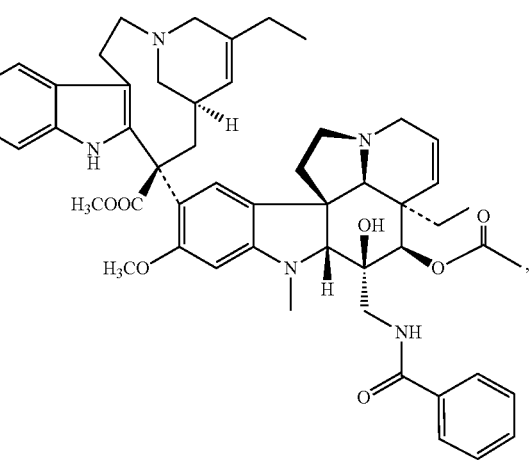
BM34
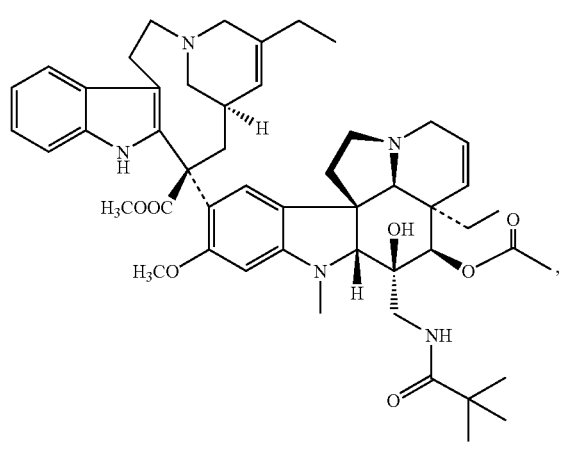
BM37
BM35
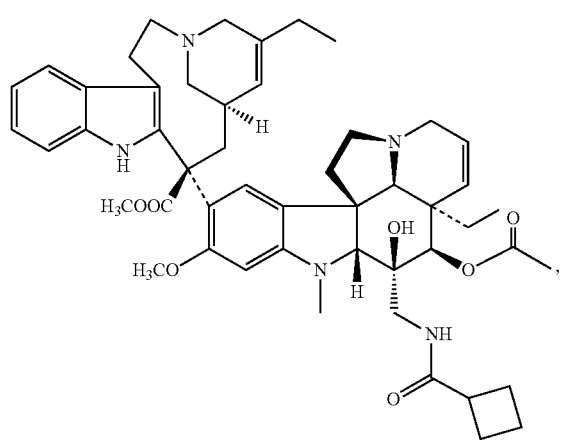
BM38
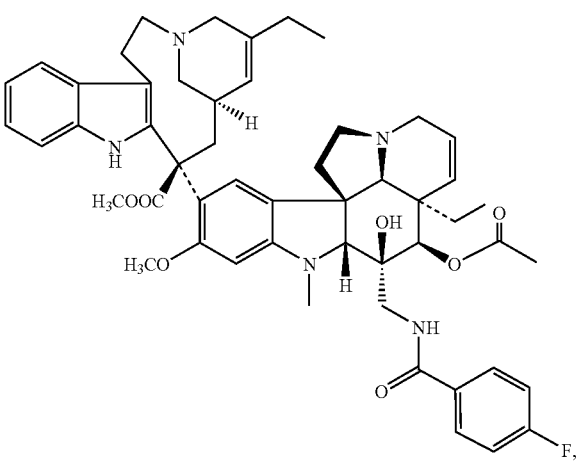

-continued
BM39
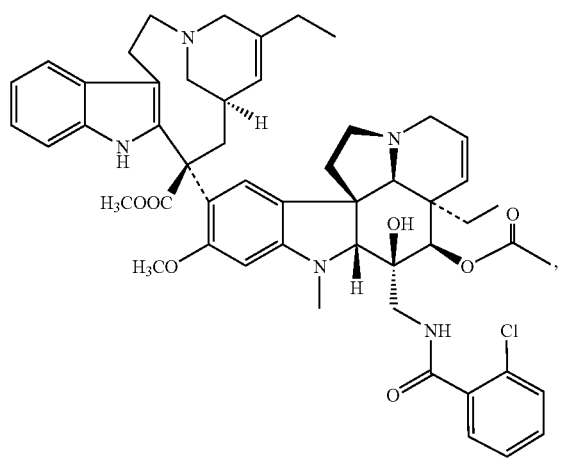
BM42
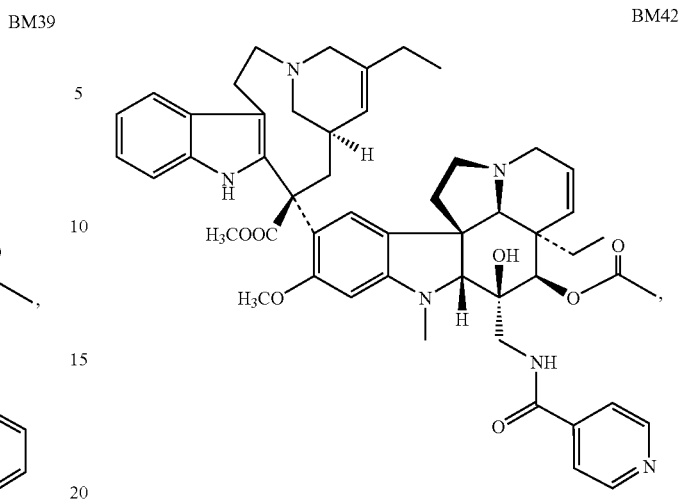
BM40
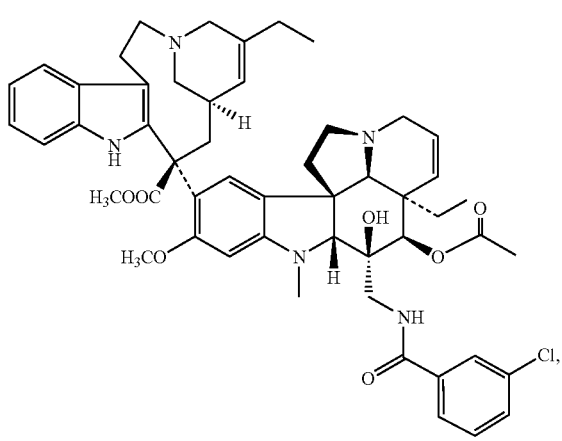
BM43
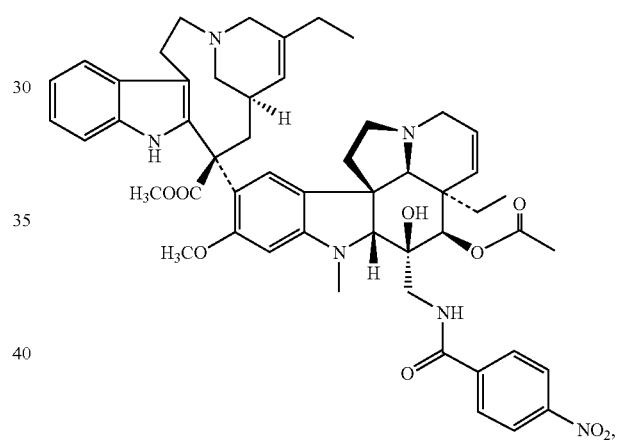
BM41
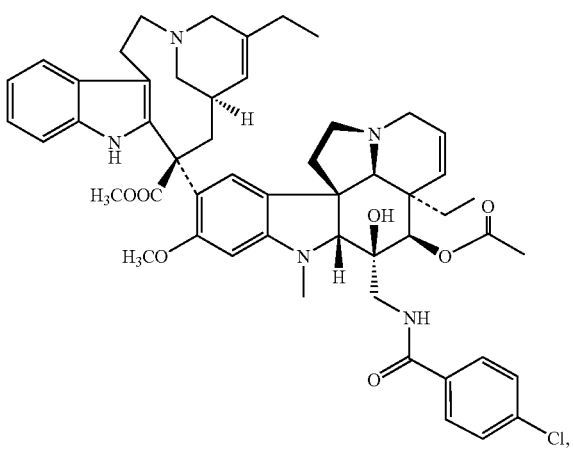
BM44
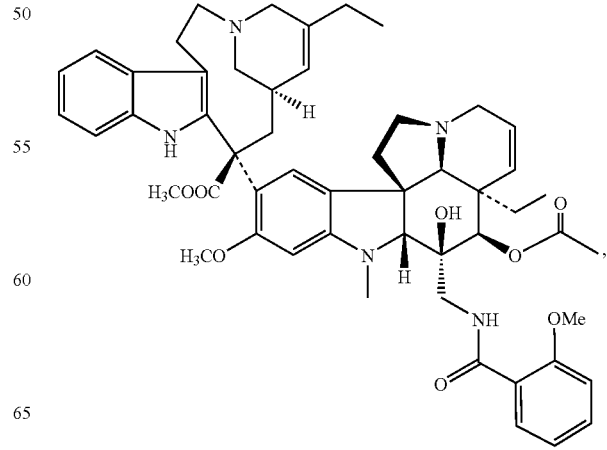

BM45
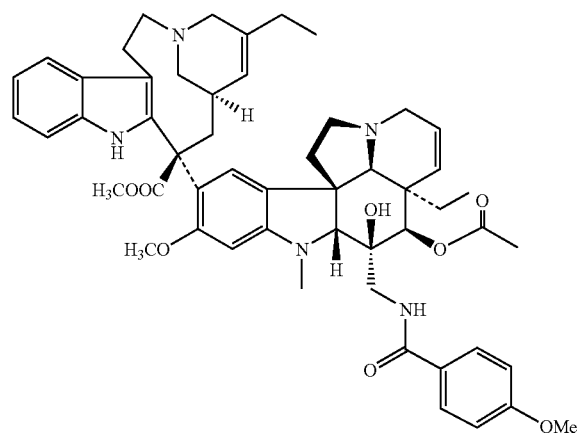
BM46
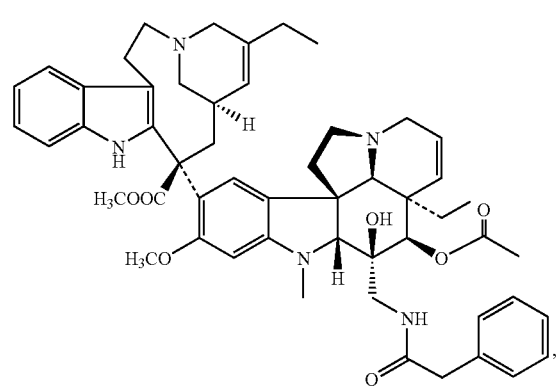
BM47
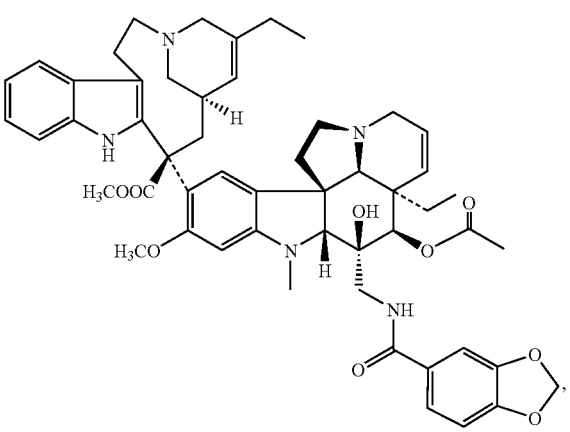
BM48
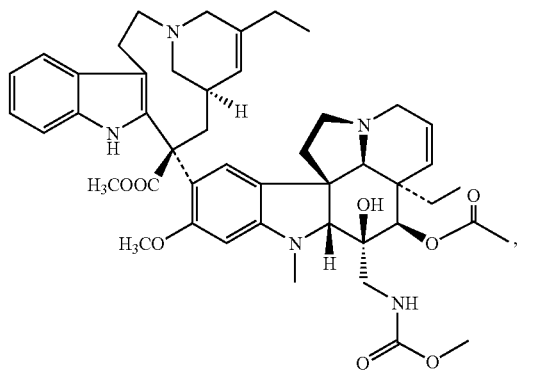
BM49
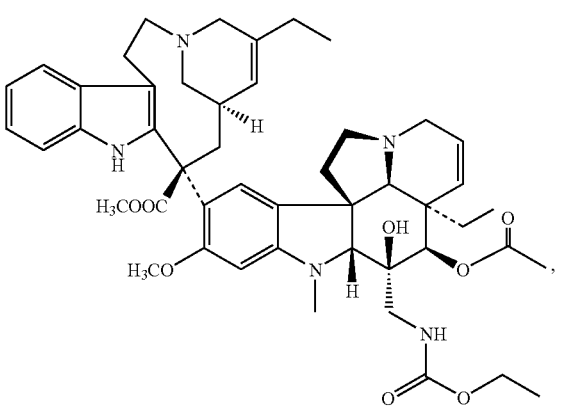
BM50
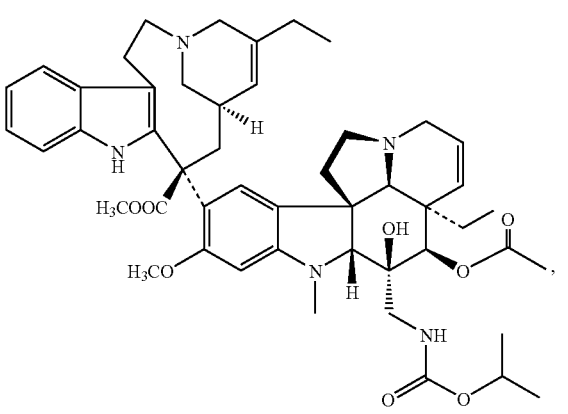
BM51
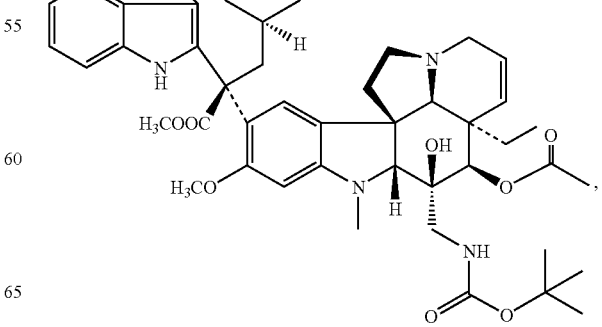

BM52
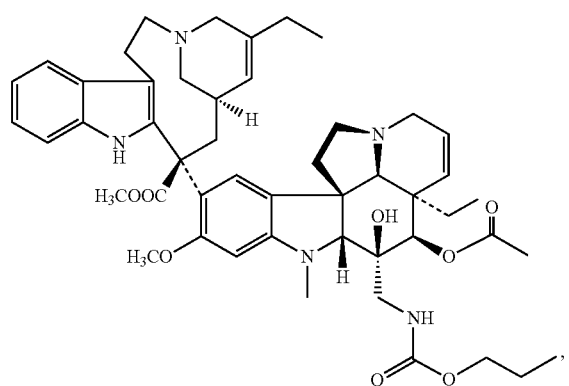
BM53
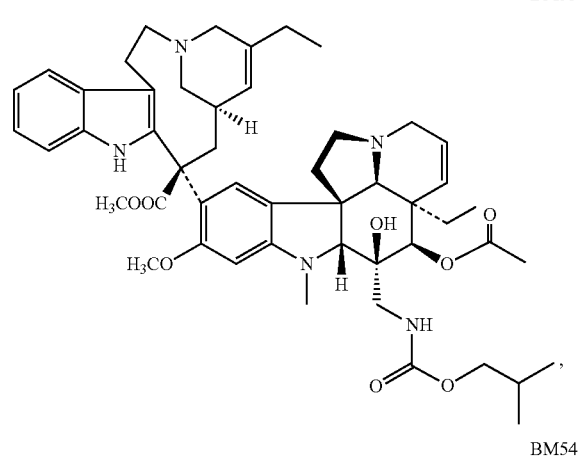
BM54
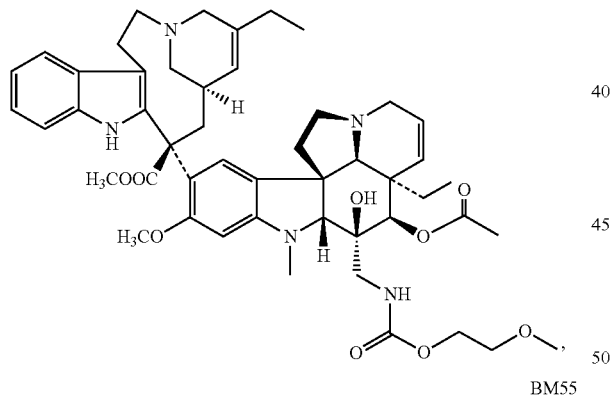
BM55
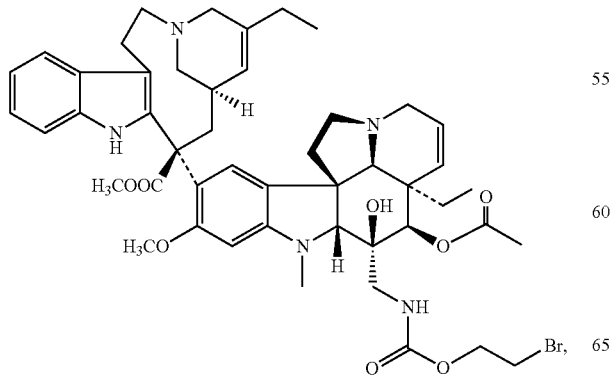
BM56
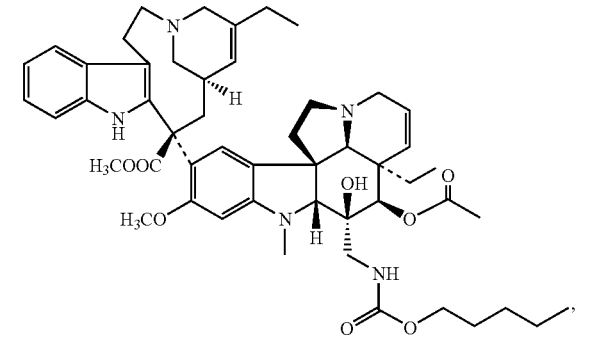
BM57
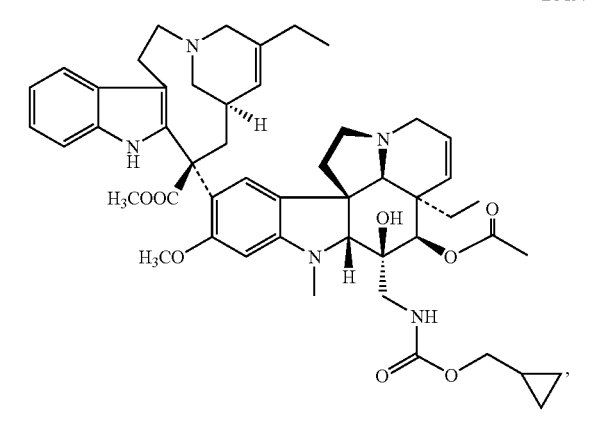
BM58
BM59

BM60
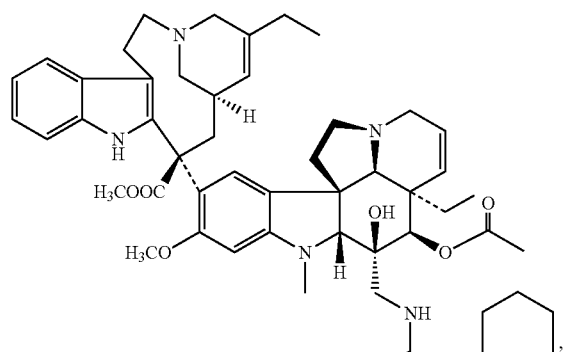
BM64
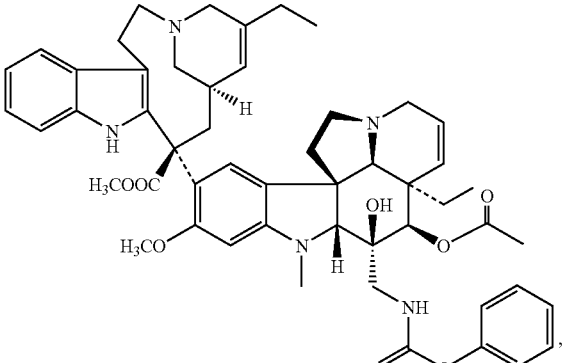
BM61
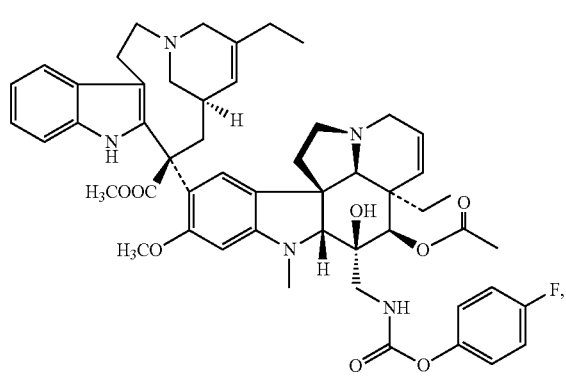
BM65
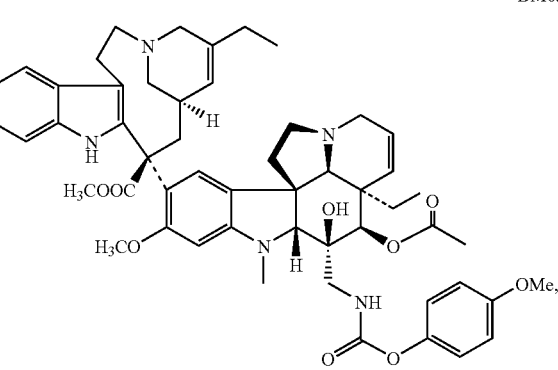
BM62
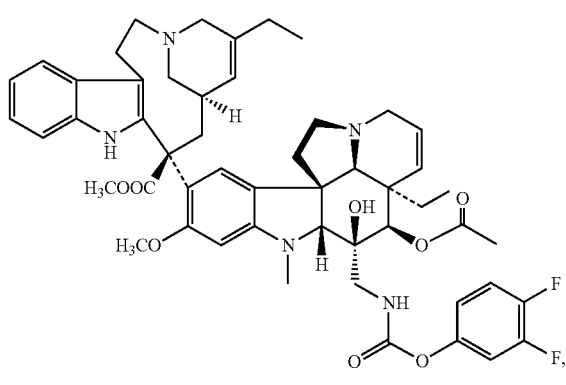
BM66
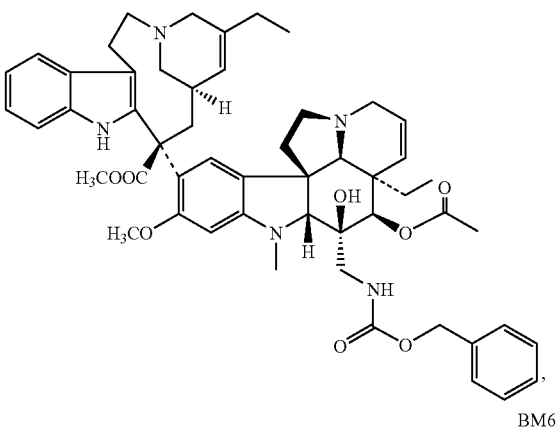
BM63
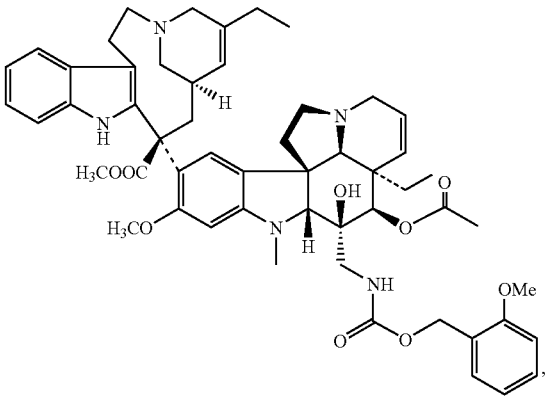
BM67

-continued
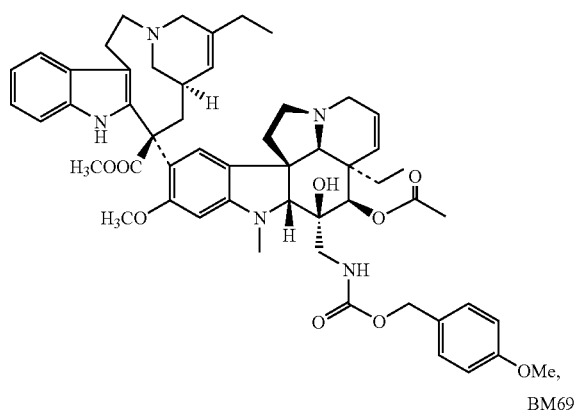
BM68
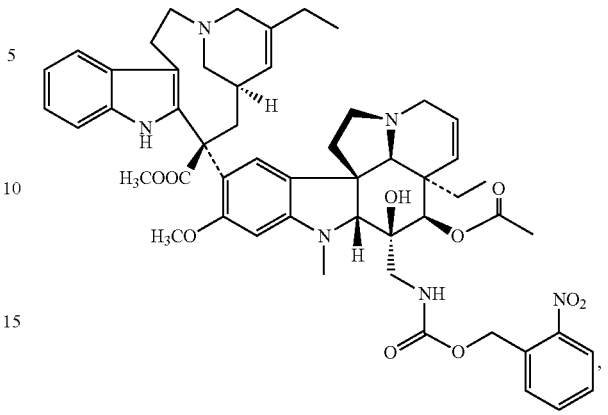
BM72
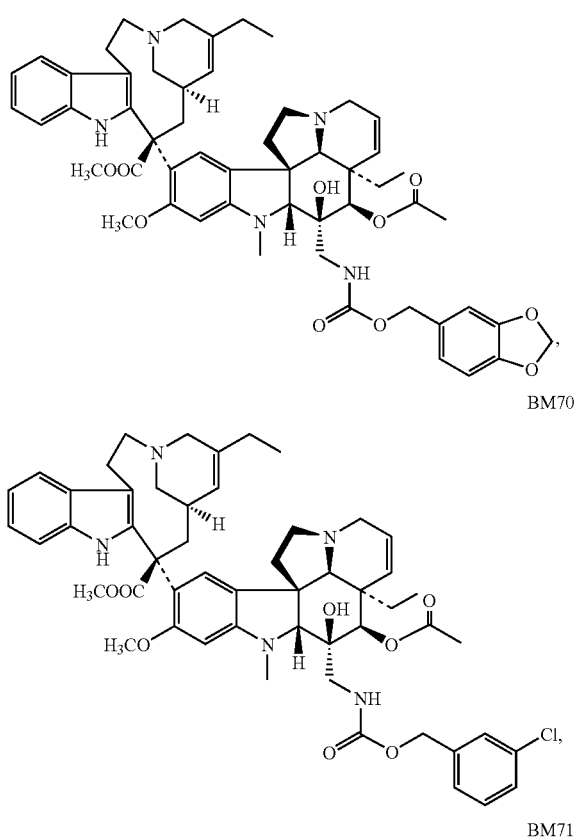
BM69
BM70
BM71
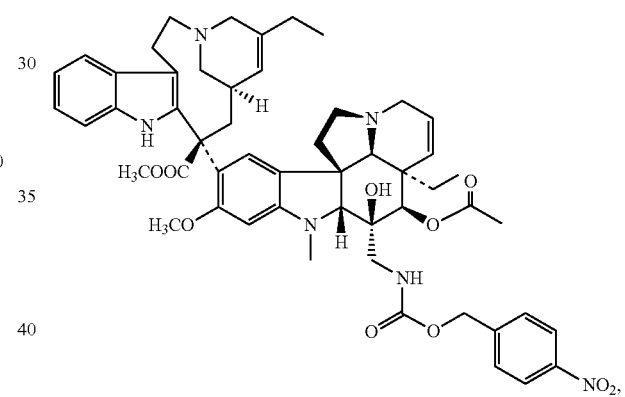
BM73
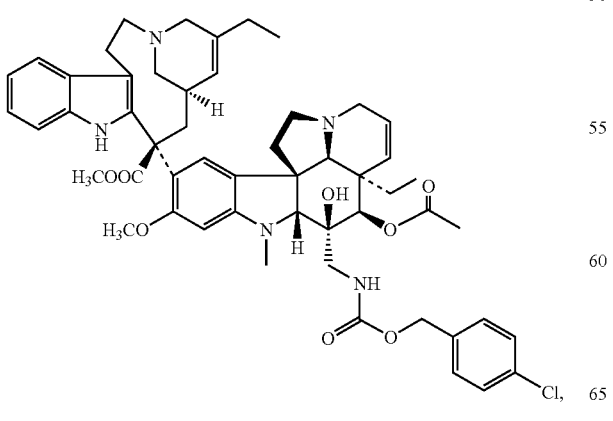
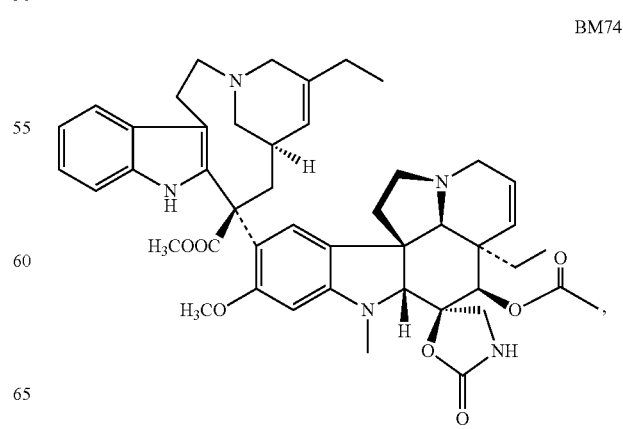
BM74

BM75
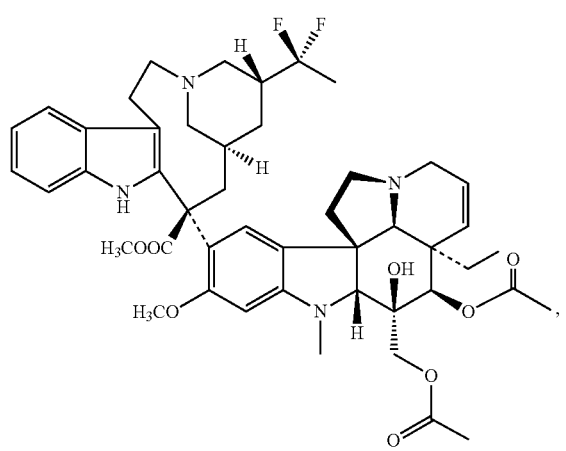
BM76
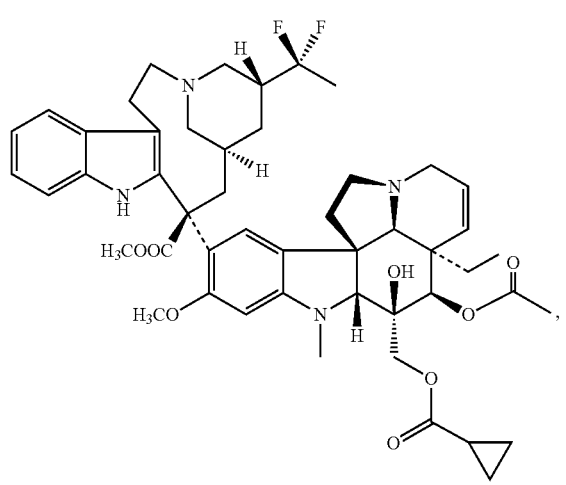
BM77
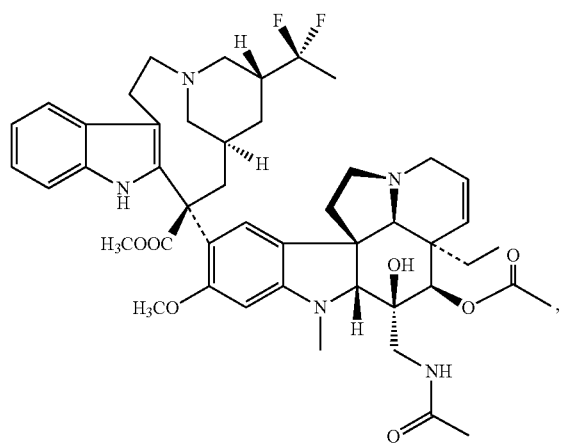
BM78
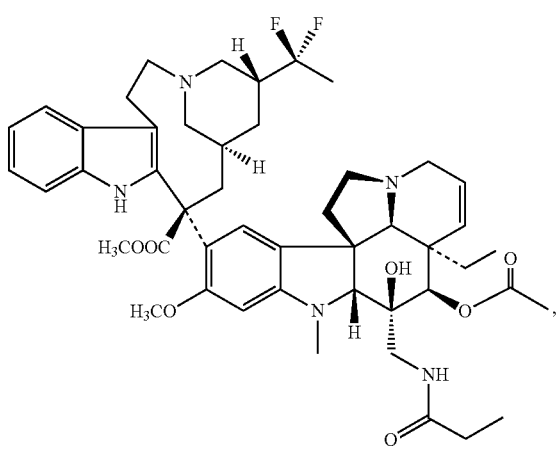
BM79
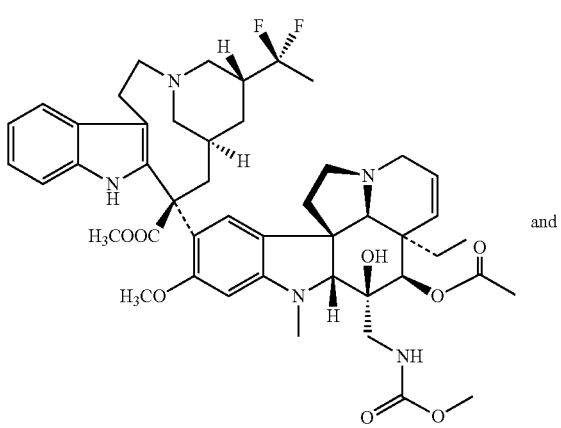
and
BM80
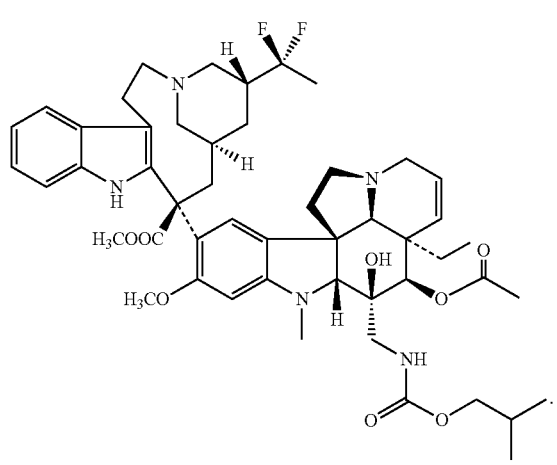

The present invention further provides a method for preparing the above vinblastine derivatives, which comprises:

1) Reduction of Vindoline,

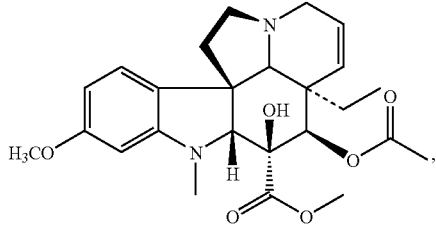

which is used as a raw material, to give an intermediate compound A,

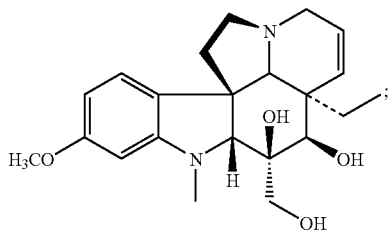

2) Epoxidization, azide substitution and reduction of the intermediate compound A to obtain an intermediate compound B,

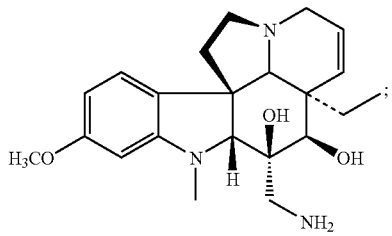

3) Alkylation or acylation of the intermediate compound A to obtain intermediate compounds C

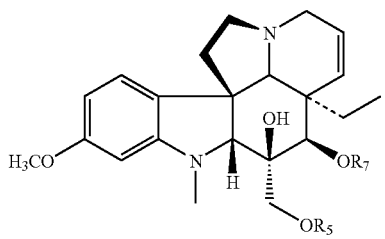

or D

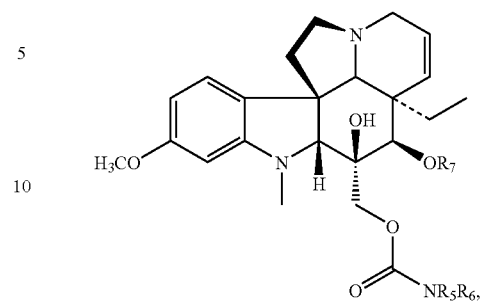

and alkylation or acylation of the intermediate compound B respectively to produce intermediate compounds E

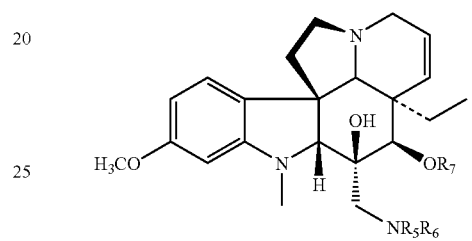

and F

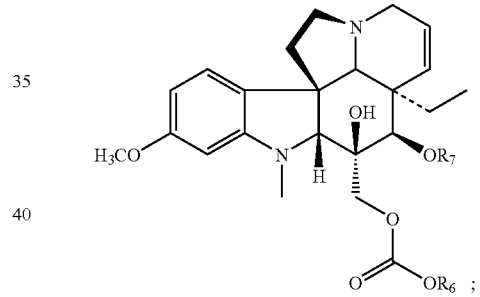

4) Coupling of the intermediate compounds C to F with catharanthine respectively, or further reduction, alkylation, acylation, or fluoration of the coupling products to prepare the vinblastine derivatives of the invention, Wherein, $R_5$, $R_6$ and $R_7$ have the same definitions as the above.

Preferably, in the process according to the invention, the solvent used in the alkylations is selected from the group consisting of dichlormethane, chloroform and tetrahydrofuran, the phase transfer catalyst used in the alkylations is selected from the group consisting of tetrabutylammonium iodide and tetrabutylammonium bromide, and the temperature for the alkylations may be in the range from 0° C. to room temperature or in the range from 50° C. to 100° C. depended on the reaction conditions necessary for a specific compound.

Preferably, in the process according to the invention, the catalyst is selected from the group consisting of triethylamine, diisopropyl ethyl amine, pyridine and 4-(N,N-dimethyl)aminopyridine (DMAP) in the acylation, and the acylating agent is selected from the group consisting of an anhydride, an acyl chloride, a ligand formed from an anhydride and thiazolidine-2-thione (or benzotriazole) and a ligand formed from an acyl chloride and thiazolidine-2-thione in the acylation.

Preferably, in the process according to the invention, the catalyst is selected from the group consisting of sodium hydride, triethylamine, diisopropyl ethyl amine, pyridine or 4-(N,N-dimethyl)aminopyridine (DMAP), and the raw material is selected from the group consisting of an isocyanate and a ligand formed from an amine and a carbonyl diimidazole (CDI) during the synthesis of intermediate compound D.

Preferably, in the method according to the invention, the catalyst is selected from the group consisting of triethylamine, diisopropylethylamine (DIPEA), pyridine or 4-(N,N-dimethyl)aminopyridine (DMAP), and the raw material is selected from the group consisting of a chloroformate and a chloroformate synthesized from an alcohol and solid phosgene during the synthesis of intermediate compound F.

In particular, in the method according to the invention, the intermediate compound A is prepared by the reduction of vindoline which is used as the raw material, and then epoxidized, azidized and reduced to form intermediate compound B. Intermediate compounds C to F can be synthesized respectively by furnishing the structure of the intermediate compound A or B with a series of reactions such as alkylation or acylation. The vinblastine derivatives of the invention are thereafter produced by coupling the intermediate compounds C to F with catharanthine respectively, or by further reduction, alkylation, acylation, or fluoration of the coupled products. Generally, Thin-layer chromatography (TLC) is used for monitering the progress of a reaction. After the reaction is completed, the reaction mixture is extracted with organic solvents such as ethyl acetate, dichlormethane (DCM) and chloroform. Then the combined organic phase is washed sequently with saturated sodium bicarbonate solution, water and saturated sodium chloride solution, dried over anhydrous magnesium sulfate or anhydrous sodium sulfate, and concentrated at a low temperature under a reduced pressure to remove the solvent. The intermediate compounds and final products are identified with nuclear magnetic resonance spectrum or mass spectrum.

The synthetic routes for the intermediate compounds A to B are shown below:

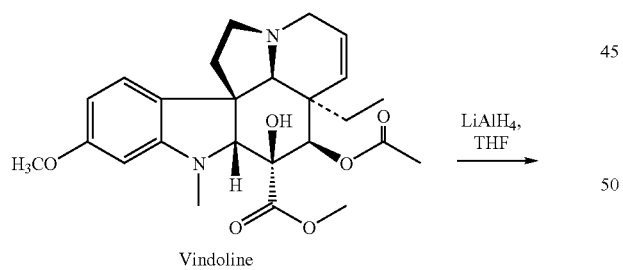

Vindoline

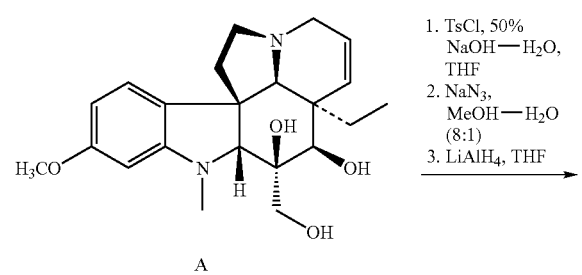

A

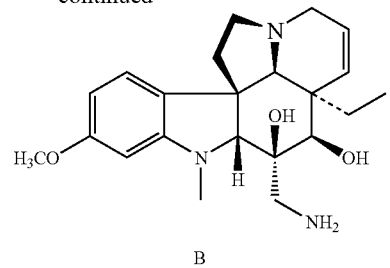

B

Vindoline was reduced by lithium-aluminum hydride (LiAlH$_4$) in tetrahydrofunan to provide intermediate compound A. Then, the intermediate compound A was treated with p-toluene sulfonylchloride under a basic condition to give an epoxide, which was thereafter subjected to a ring-opening reaction with sodium azide, followed by reduction with LiAlH$_4$ in tetrahydrofunan to obtain the intermediate compound B.

The synthetic routes for intermediate compounds C to F are as follows, wherein the compound A or B is used as a raw material.

1. The Synthetic Routes for Compound C

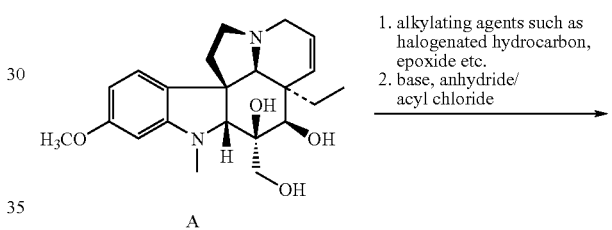

A

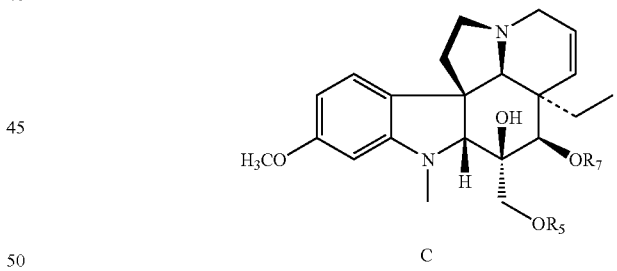

C

The compound A was dissolved in dichloromethane, chloroform or tetrahydrofunan, followed by addition of a 50% sodium hydroxide solution. The reaction mixture was treated with alkylating agents such as halogenated hydrocarbon and epoxide in the presence of a phase transfer catalyst such as tetrabutylammonium iodide or tetrabutylammonium bromide at a reaction temperature from 0° C. to room temperature or from 50° C. to 100° C. to give a dialkyl substituted product C, or a monoalkyl substituted product which was then treated with anhydride, acyl chloride in the presence of a base such as triethylamine, diisopropyl ethyl amine, pyridine or 4-(N,N-dimethyl amino)pyridine to provide product C. Alternatively, the compound A was directly treated with an anhydride or an acyl chloride in the presence of a base to obtain di-acylated product C.

2. The Synthetic Routes for Compound D

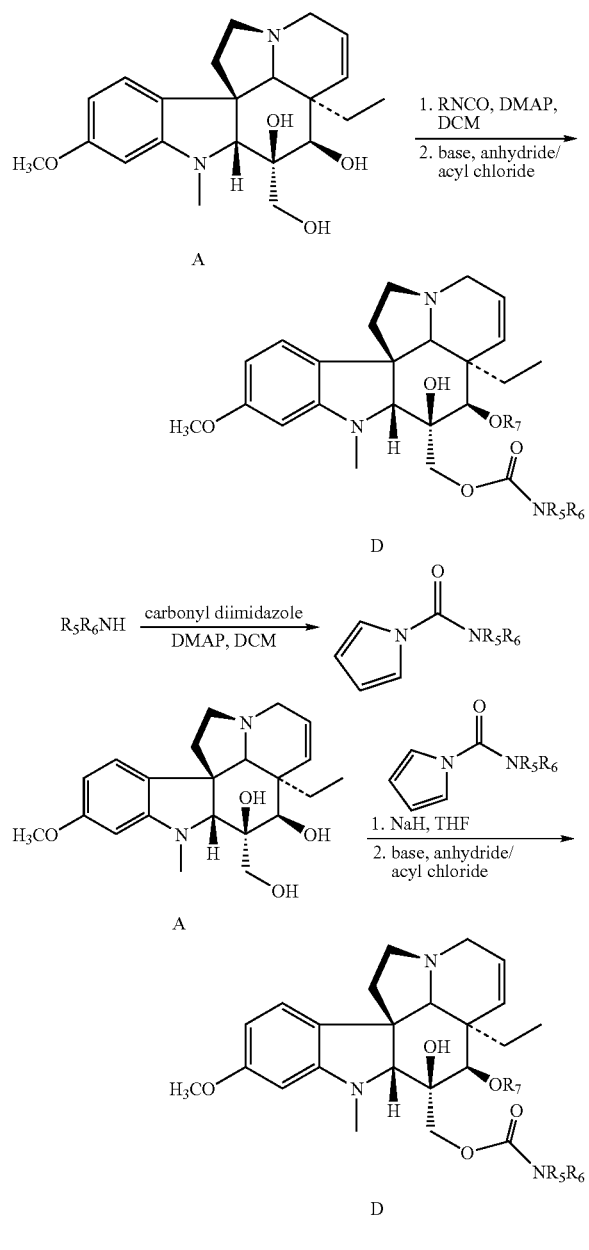

Procedure 1: An amine was dissolved in dichloromethane or tetrahydrofunan under argon atmosphere, followed by addition of an appropriate amount of a base (triethylamine, diisopropyl ethyl amine, pyridine or 4-(N,N-dimethyl)aminopyridine). To the reaction mixture, a solution of solid phosgene in dichloromethane or tetrahydrofunan was slowly added dropwisely under ice bath, then the reaction was allowed to react for half an hour under ice bath and then for a few hours at room temperature to obtain an isocyanate. After the addition of an appropriate amount of the base (triethylamine, diisopropylethylamine, pyridine or 4-(N,N-dimethyl)aminopyridine) under ice bath, a solution of the compound A in dichloromethane or tetrahydrofunan was slowly added dropwisely. The reaction was allowed to react for half an hour under ice bath and then for three hours at room temperature. After the reaction was completed, saturated sodium bicarbonate solution was added therein and the reaction mixture was extracted with dichloromethane. Then the combined organic phase was dried over anhydrous sodium sulfate, concentrated under reduced pressure, and then treated with anhydride or acyl chloride in the presence of a base (triethylamine, diisopropylethylamine, pyridine or 4-(N,N-dimethyl)aminopyridine) to give carbamate derivative D.

Procedure 2: An amine was dissolved in dichloromethane or tetrahydrofunan under argon atmosphere, followed by addition of an appropriate amount of a base (triethylamine, diisopropyl ethyl amine, pyridine or 4-(N,N-dimethyl)aminopyridine). Then carbonyl diimidazole was added therein. After reacted for 24 hours at room temperature, the reaction mixture was evaporated to dryness to obtain an intermediate, which was then added into a solution of sodium hydride and compound A in tetrahydrofunan. The reaction mixture was allowed to react for 8 hours at room temperature. After the reaction was completed, saturated sodium bicarbonate solution was added therein and the reaction mixture was extrated with ethyl acetate. The combined organic phase was dried over anhydrous sodium sulfate, concentrated under reduced pressure, and then treated with anhydride or acyl chloride in the presence of a base (triethylamine, diisopropylethylamine, pyridine or 4-(N,N-dimethyl)aminopyridine) to provide carbamate derivative D.

3. The Synthetic Routes for Intermediate E

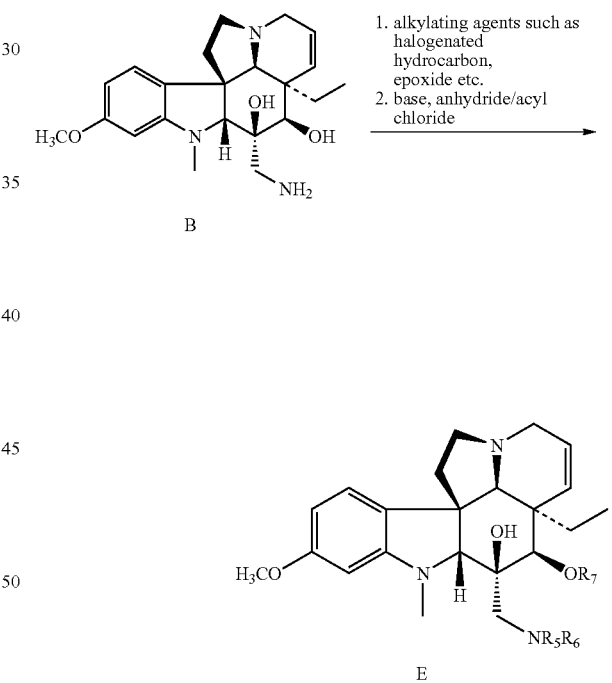

Compound B was dissolved in dichloromethane or chloroform, and treated with anhydride or acyl chloride in the presence of a base (triethylamine, diisopropyl ethyl amine, pyridine or 4-(N,N-dimethyl)amino pyridine) to obtain di-acylated product E, or directly alkylated with an alkylating agent such as a halogenated hydrocarbon or an epoxide to obtain mono- or di-alkylated product E. Alternatively, compound B was dissolved in tetrahydrofunan, followed by addition of sodium hydride and ligand III (N-acylthiazolidine-2-thione) under argon atmosphere to react to give a monoacylated product, which was then treated with an anhydride or an acyl chloride to obtain di-isoacylated product E.

4. The synthetic routes for ligand III (N-acylthiazolidine-2-thione)

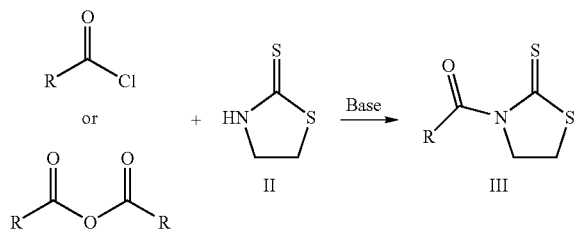

A Heterocyclic compound of thiazolidine-2-thione II was dissolved in dichloromethane or chloroform, and treated with an anhydride or an acyl chloride in the presence of a base (triethylamine, diisopropyl ethyl amine, pyridine or 4-(N,N-dimethyl)aminopyridine) to obtain ligand III (N-acylthiazolidine-2-thione).

5. The Synthetic Routes for Compound F

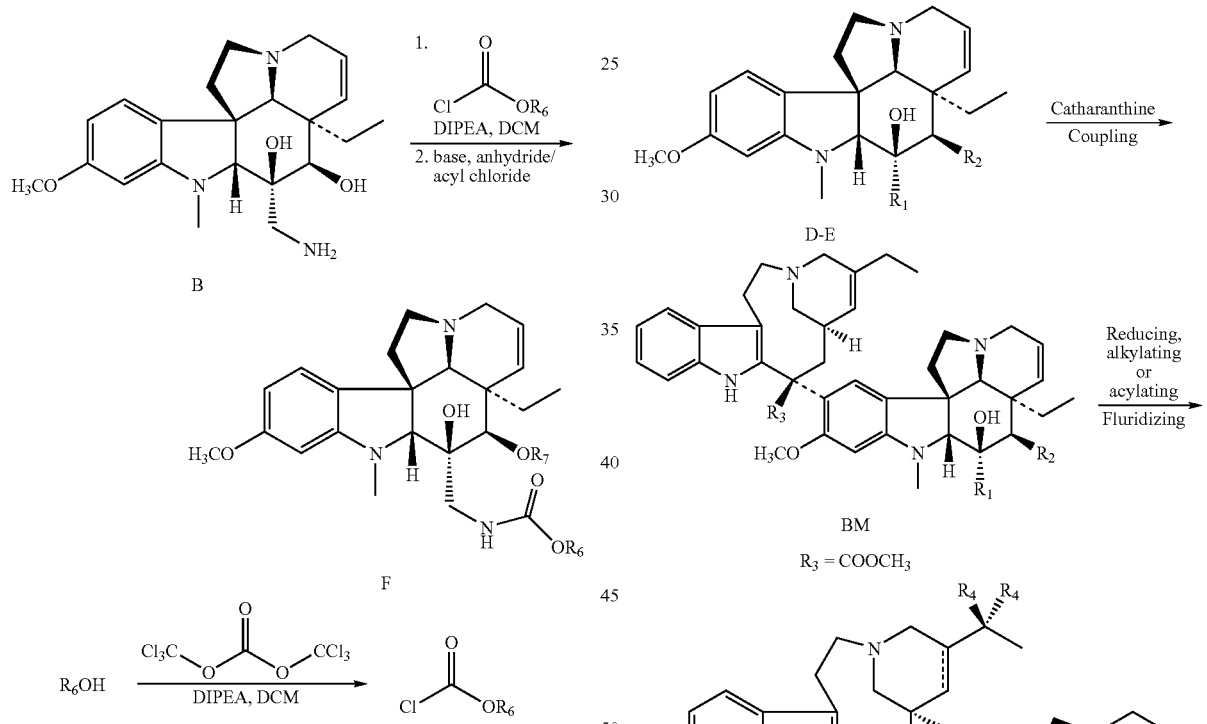

An alcohol was dissolved in dichloromethane or tetrahydrofunan under argon atmosphere, followed by addition of an appropriate amount of a base (triethylamine, diisopropyl ethyl amine, pyridine or 4-(N,N-dimethyl)aminopyridine). To the reaction mixture, a solution of solid phosgene in dichloromethane or tetrahydrofunan was added dropwisely under ice bath, then the reaction was allowed to react for half an hour under ice bath and then for a few hours at room temperature to obtain a chlorofomate. After the addition of an appropriate amount of the base (triethylamine, diisopropylethylamine, pyridine or 4-(N,N-dimethyl)aminopyridine) under ice bath, a solution of the compound B in dichloromethane or tetrahydrofunan was slowly added dropwisely. The reaction was allowed to react for half an hour under ice bath and then for three hours at room temperature. After the reaction was completed, saturated sodium bicarbonate solution was added therein and the reaction mixture was extracted with dichloromethane. Then the combined organic phase was dried over anhydrous sodium sulfate, concentrated under reduced pressure, and then treated with an anhydride or an acyl chloride in the presence of a base (triethylamine, diisopropylethylamine, pyridine or 4-(N,N-dimethyl)aminopyridine) to give carbamate derivative F.

Then, compounds C to F were coupled with catharanthine respectively to provide the compounds of the invention, that is, compounds BM and BM'. The coupling reaction was performed in a buffer solution with a pH value at about 2, which is prepared with glycine, sodium chloride, 0.1N hydrochloric acid and water, using ferric(III) chloride as a catalyst. For the detailed procedure, see J. Vukovic et al., Tetrahedron, 1988, 44, 325-331. The yield of compound BM from the coupling reaction is typically about 50%-80%. Fluoridization was carried out at −40° C. for 1 hour in anhydrous fluohydric acid using antimonium(V) fluoride as a catalyst to obtain compound BM' with a yield of about 40% (J. Fahy etc., J. Am. Chem. Soc. 1997, 119, 8567).

The invention also provides a composition comprising a therapeutically effective amount of the above vinblastine derivative or physiologically acceptable salt thereof.

The invention further provides uses of the above vinblastine derivative or physiologically acceptable salt thereof in preparing medicaments for treating tumors.

The invention still further provides a pharmaceutical composition for treating tumors, which comprises the above vinblastine derivative or physiologically acceptable salt thereof as an active component.

A series of novel vinblastine derivatives were designed and synthesized in the present invention. The compounds have good inhibiting activities against tumor cell lines such as human lung cancer cell line (A-549) and human cervical carcinoma cell line (Hela), and thus can be used to prepare medicaments for treating malignant tumors. The compounds of the invention are synthesized simply and easily, and the raw materials thereof are rich.

DETAILED DESCRIPTION

Best Mode for Carrying Out the Invention

The present invention will be described in detail with reference to following examples, but the present invention is not limited to these examples.

In the following examples, $^1$H-NMR spectra were measured on a Varian Mercury AMX300 instrument. MS was obtained on a Model VG ZAB-HS or VG-7070 as well as Esquire 3000 plus-01005 (in cation or anion mode) instrument. All the solvents were re-distilled before use, and the used anhydrous solvents were subjected to being dried using standard methods. Unless otherwise specified, all the reactions were carried out under argon atmosphere and monitered with TLC, and each product was washed with saturated sodium chloride solution and dried over anhydrous magnesium sulfate at post-processing. Unless otherwise stated, all products were purified by column chromatography using silica gels, and the used silica gel is $GF_{254}$ with a particle size of 200-300 mesh, which is commercially available form Qingdao Haiyang Chemical Co. Ltd or Yantai Yuanbo Silica Gel Co.

PREPARATION EXAMPLES

Preparation Example 1

Preparation of Compound A

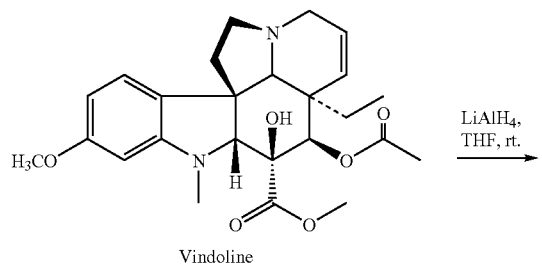

Vindoline

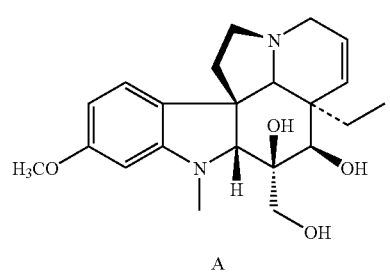

A 456 mg (1 mmol) of vindoline was dissolved in 20 mL of anhydrous tetrahydrofunan under argon atmosphere, followed by slow addition of 230 mg (6 mmol) of lithium-aluminum hydride under ice bath at 0° C. After 4 h of stirring at room temperature, the reaction was quenched with 0.23 mL of water, and 0.23 mL of 15% sodium hydroxide solution and 0.69 mL of water were then sequently added therein. After stirred for 5 minutes, the reaction mixture was suction-filtered through a fitted funnel and the filtrate was dried over anhydrous sodium sulfate and concentrated under reduced pressure. The resultant was recrystallized in acetone to obtain the compound A as a white solid in 85%-90% yield.

$^1$H NMR (CDCl$_3$, 300 MHz): δ: 8.73 (brs, 1H), 6.82 (d, J=8.1 Hz, 1H), 6.24 (d, J=8.1 Hz, 1H), 6.06 (s, 1H), 5.80 (dd, J=10.2, 4.8 Hz, 1H), 5.60 (d, J=10.2 Hz, 1H), 3.93 (d, J=14.1 Hz, 1H), 3.71 (s, 3H), 3.54 (s, 1H), 2.95 (s, 3H), 2.51 (s, 1H), 2.43 (m, 1H), 2.16 (m, 1H), 1.77 (m, 1H), 1.30 (m, 1H), 0.86 (m, 1H), 0.56 (t, J=8.4 Hz, 3H);

$^{13}$C NMR (CDCl$_3$, 75 MHz): δ: 160.8 (C), 154.5 (C), 130.8 (CH), 126.4 (C), 124.1 (CH), 122.7 (CH), 104.4 (CH), 96.2 (CH), 80.7 (CH), 77.4 (C), 75.1 (CH), 68.3 (CH), 65.2 (CH$_2$), 55.2 (OCH$_3$), 51.6 (CH$_2$), 51.6 (C), 51.2 (CH$_2$), 44.7 (CH$_2$), 43.6 (C), 40.2 (CH$_3$), 32.3 (CH$_2$), 7.7 (CH$_3$);

ESIMS (m/e) 387.3 [M+1]$^+$.

Preparation Example 2

Preparation of Compound B

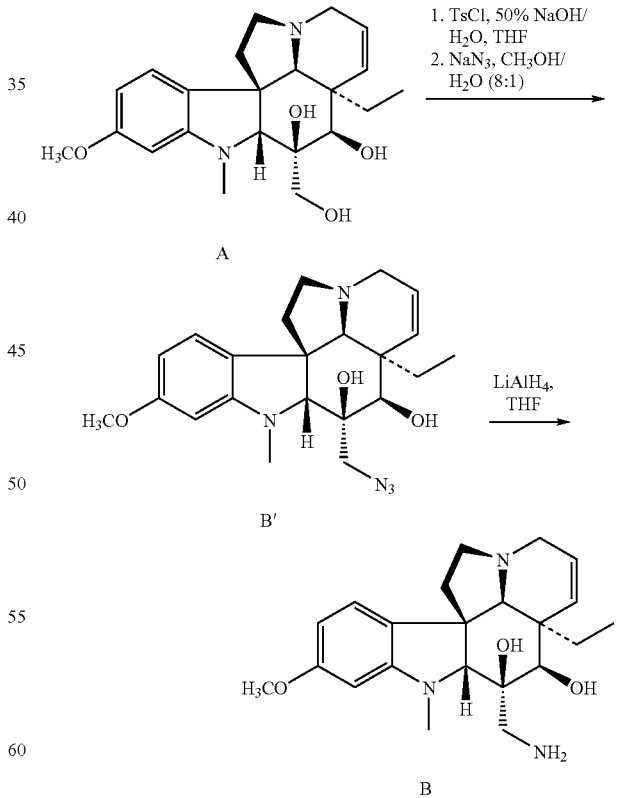

In a 100 mL two-necked round bottom flask, 3.86 g (10.00 mmol) of compound A was dissolved in 25 mL of THF, followed by the addition of 50% NaOH solution (1 g NaOH:1 g H$_2$O). After 0.5 h of stirring at 50° C., 2.10 g (1.1 eq, 11.00 mmol) of toluene-4-sulfonyl chloride was added, and the reaction mixture was warmed to 80° C. and stirred for 1 h. After the reaction was completed, the reaction mixture was extracted with ethyl acetate, and the organic phase was dried over anhydrous magnesium sulfate and concentrated under reduced pressure to obtain an epoxide as an oily intermediate, which was used in the next step without purification.

In a 250 mL round bottom flask, the oily intermediate was dissolved in 80 mL of methanol and 10 mL of water, followed by sequent addition of 3.25 g (5 eq) of sodium azide and 1.4 g (3 eq) of ammonium chloride. After refluxed for 24 h at 90° C., the reaction mixture was extracted with ethyl acetate, and the organic phase was dried over anhydrous magnesium sulfate, concentrated under reduced pressure, and purified by silica gel chromatography (eluted with petroleum ether:acetone=8:1 v/v) to obtain 2.87 g of the compound B' as a white powder, which was then reduced with lithium-aluminium hydride under argon atmosphere to give the compound B as a white powder in 70% yield.

$^1$H NMR (CDCl$_3$, 300 MHz): δ: 8.75 (brs, 1H), 6.87 (d, J=8.1 Hz, 1H), 6.30 (d, J=8.1 Hz, 1H), 6.10 (s, 1H), 5.88 (dd, J=9.3, 4.8 Hz, 1H), 5.61 (d, J=9.3 Hz, 1H), 3.87 (d, J=13.2 Hz, 1H), 3.78 (s, 3H), 3.61 (s, 1H), 2.93 (s, 3H), 2.54 (s, 1H), 2.43 (m, 1H), 2.16 (m, 1H), 1.77 (m, 1H), 1.30 (m, 1H), 0.86 (m, 1H), 0.58 (t, J=7.5 Hz, 3H);

$^{13}$C NMR (CDCl$_3$, 75 MHz): δ: 160.8 (C), 154.5 (C), 132.1 (CH), 126.4 (C), 122.9 (CH), 122.9 (CH), 104.3 (CH), 96.2 (CH), 84.6 (CH), 78.4 (CH), 75.9 (C), 68.3 (CH), 55.5 (OCH$_3$), 52.6 (C), 51.6 (CH$_2$), 51.4 (CH$_2$), 49.8 (CH$_2$), 45.3 (CH$_2$), 43.8 (C), 41.5 (CH$_3$), 32.6 (CH$_2$), 7.9 (CH$_3$).

Preparation Example 3

Preparation of Compound C1

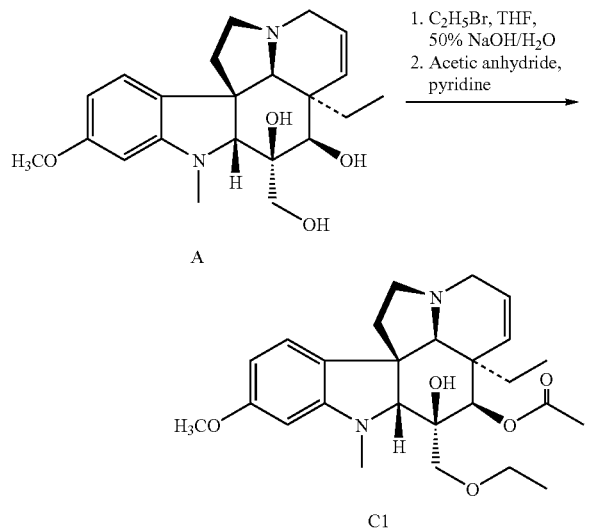

Then 50 mL of water was added thereto, and the reaction mixture was extracted with methylene chloride (10 mL×3). The combined organic phase was dried over anhydrous magnesium sulfate and concentrated under reduced pressure to obtain a concentrate. The concentrate was dissolved in 1 mL of pyridine under argon atmosphere, followed by addition of 1 mL of acetic anhydride. After 8 h of stirring at room temperature, 30 mL of ethyl acetate and 10 mL of saturated sodium bicarbonate solution were added thereto and the stirring continued for 2 minutes. After the water layer was removed and pyridine was washed off with water (20 mL×3), the ethyl acetate layer was dried, concentrated and purified by silica gel chromatography (eluted with petroleum:acetone=6:1 v/v) to give 263 mg of compound C1 as a white powder in 58% yield.

$^1$H NMR (CDCl$_3$, 300 MHz): δ: 8.80 (brs, 1H), 6.84 (d, J=8.1 Hz, 1H), 6.24 (dd, J=8.1, 2.1 Hz, 1H), 6.08 (d, J=2.1 Hz, 1H), 5.84 (dd, J=10.2, 4.8 Hz, 1H), 5.37 (d, J=10.2 Hz, 1H), 4.97 (s, 1H), 3.76 (s, 3H), 3.71 (s, 1H), 2.93 (s, 3H), 2.76 (d, J=15.9 Hz, 1H), 2.58 (s, 1H), 2.40 (m, 1H), 2.11 (s, 3H), 1.22 (m, 1H), 1.20 (t, J=7.2 Hz, 3H), 0.96 (m, 1H), 0.50 (t, J=7.2 Hz, 3H);

$^{13}$C NMR (CDCl$_3$, 75 MHz): δ: 171.0 (C), 161.1 (C), 154.8 (C), 130.4 (CH), 126.2 (C), 124.2 (CH), 122.7 (CH), 104.3 (CH), 96.0 (CH), 80.9 (CH), 77.6 (C), 77.6 (CH), 72.7 (CH$_2$), 68.0 (CH), 66.8 (CH$_2$), 55.4 (OCH$_3$), 52.0 (C), 52.0 (CH$_2$), 50.9 (CH$_2$), 44.8 (CH$_2$), 42.6 (C), 39.1 (CH$_3$), 31.7 (CH$_2$), 21.1 (CH$_3$), 15.1 (CH$_3$), 7.6 (CH$_3$).

Preparation Example 4

Preparation of Compound C2

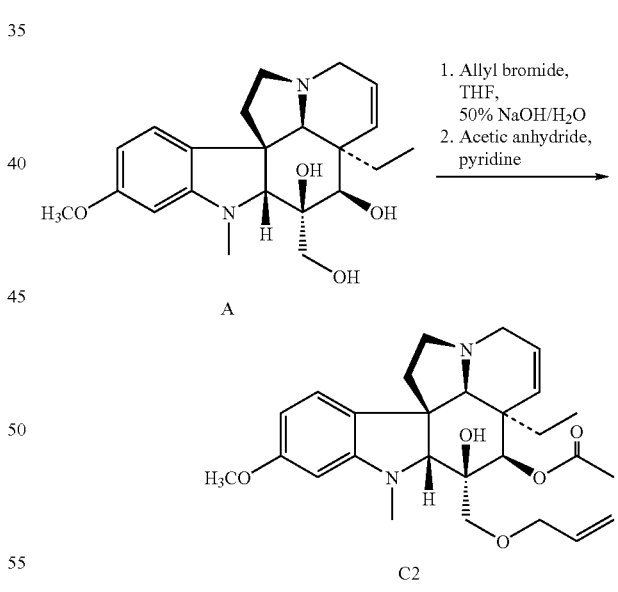

386 mg (1 mmol) of compound A was dissolved in 10 mL of tetrahydrofunan under argon atmosphere, followed by addition of 50% sodium hydroxide solution (1 g of sodium hydroxide was dissolved in 1 g of water). After 0.5 h of stirring at 60° C., 0.15 mL of ethyl bromide and 50 mg of tetrabutylammonium iodide were added, and the reaction continued for 6 h. The reaction mixture was cooled to the room temperature and transferred into a separating funnel.

386 mg (1 mmol) of compound A was dissolved in 10 mL of tetrahydrofunan under argon atmosphere, followed by addition of 50% sodium hydroxide solution (1 g of sodium hydroxide was dissolved in 1 g of water). After 0.5 h of stirring at 60° C., 0.17 mL of allyl bromide and 50 mg of tetrabutylammonium iodide were added, and the reaction continued for 4 h. The reaction mixture was cooled to the room temperature and transferred into a separating funnel. Then 50 mL of water was added thereto, and the reaction mixture was extracted with methylene chloride (10 mL×3).

The combined organic phase was dried over anhydrous magnesium sulfate and concentrated under reduced pressure to obtain a concentrate. The concentrate was dissolved in 1 mL of pyridine under argon atmosphere, followed by addition of 1 mL of acetic anhydride. After 8 h of stirring at room temperature, 30 mL of ethyl acetate and 10 mL of saturated sodium bicarbonate solution were added thereto and the stirring continued for 2 minutes. After the water layer was removed and pyridine was washed off with water (20 mL×3), the ethyl acetate layer was dried, concentrated and purified by silica gel chromatography (eluted with petroleum ether:acetone=6:1 v/v) to give 286 mg of compound C2 as a white powder in 61% yield.

$^1$H NMR (CDCl$_3$, 300 MHz): δ: 8.80 (brs, 1H), 6.79 (d, J=8.1 Hz, 1H), 6.19 (dd, J=8.1, 2.1 Hz, 1H), 6.03 (d, J=2.1 Hz, 1H), 5.85 (m, 1H), 5.79 (dd, J=10.2, 4.5 Hz, 1H), 5.31 (d, J=10.2 Hz, 1H), 5.17 (d, J=17.1 Hz, 1H), 5.07 (d, J=10.2 Hz, 1H), 4.92 (s, 1H), 3.96 (m, 2H), 3.70 (s, 3H), 3.64 (s, 1H), 2.89 (s, 3H), 2.72 (d, J=15.0 Hz, 1H), 2.52 (s, 1H), 2.40 (m, 1H), 2.04 (s, 3H), 1.15 (m, 1H), 0.91 (m, 1H), 0.45 (t, J=7.2 Hz, 3H).

Preparation Example 5

Preparation of Compound C3

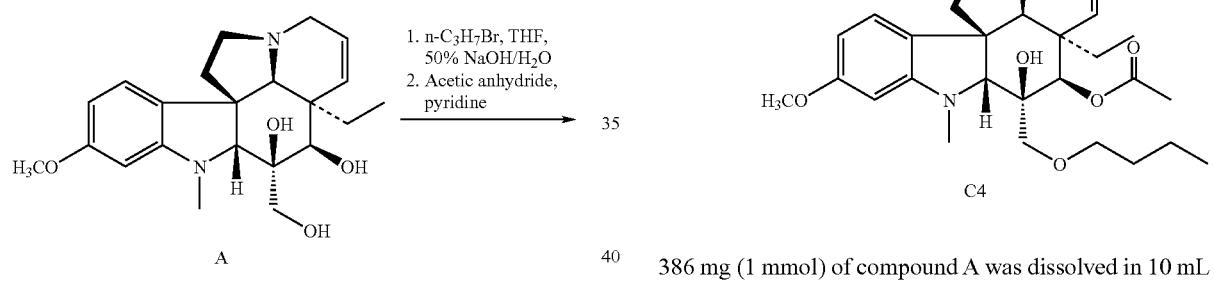

Compound C3 was prepared following the procedure for preparing compound C1 (Preparation example 3).

$^1$H NMR (CDCl$_3$, 300 MHz): δ: 8.80 (brs, 1H), 6.86 (d, J=8.1 Hz, 1H), 6.26 (dd, J=8.1, 2.1 Hz, 1H), 6.10 (d, J=2.1 Hz, 1H), 5.87 (dd, J=10.5, 4.8 Hz, 1H), 5.38 (d, J=10.5 Hz, 1H), 5.00 (s, 1H), 3.79 (s, 3H), 3.72 (s, 1H), 3.52-3.26 (m, 6H), 2.95 (s, 3H), 2.77 (d, J=15.9 Hz, 1H), 2.58 (s, 1H), 2.50-2.40 (m, 1H), 2.31-2.19 (m, 2H), 2.12 (s, 3H), 1.73-1.55 (m, 2H), 1.32-1.20 (m, 1H), 1.05-0.95 (m, 1H), 0.89 (t, J=7.2 Hz, 3H), 0.51 (t, J=7.2 Hz, 3H).

Preparation Example 6

Preparation of Compound C4

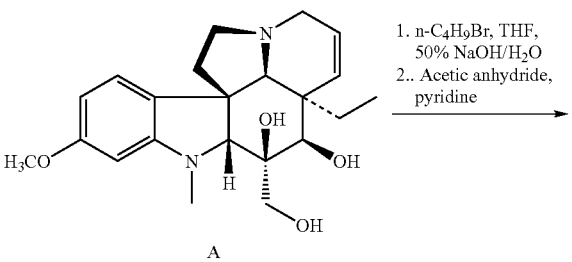

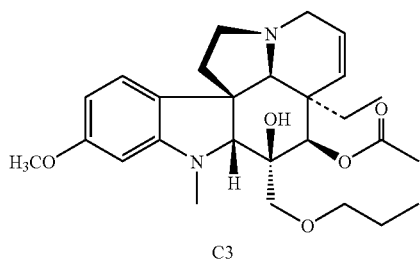

386 mg (1 mmol) of compound A was dissolved in 10 mL of tetrahydrofunan under argon atmosphere, followed by addition of 50% sodium hydroxide solution (1 g of sodium hydroxide is dissolved in 1 g of water). After 0.5 h of stirring at 60° C., 0.21 mL of n-butyl bromide and 50 mg of tetrabutylammonium iodide were added, and the reaction continued for 6 h. The reaction mixture was cooled to the room temperature and transferred into a separating funnel. Then 50 mL of water was added thereto, and the reaction mixture was extracted with methylene chloride (10 mL×3). The combined organic phase was dried over anhydrous magnesium sulfate and concentrated under reduced pressure to obtain a concentrate. The concentrate was dissolved in 1 mL of pyridine under argon atmosphere, followed by addition of 1 mL of acetic anhydride. After 8 h of stirring at room temperature; 30 mL of chloroform and 10 mL of saturated sodium bicarbonate solution were added and the stirring continued for 2 minutes. After the water layer was removed and pyridine was washed off with water (20 mL×3), the organic layer was dried, concentrated and purified by silica gel chromatography (eluted with petroleum ether:acetone=6:1 v/v) to give 262 mg of the compound C4 as a white powder in 56% yield.

$^1$H NMR (CDCl$_3$, 300 MHz): δ: 8.80 (brs, 1H), 6.83 (d, J=8.1 Hz, 1H), 6.22 (dd, J=8.1, 2.4 Hz, 1H), 6.06 (d, J=2.4 Hz, 1H), 5.81 (dd, J=10.2, 4.8 Hz, 1H), 5.37 (d, J=10.2 Hz, 1H), 4.96 (s, 1H), 3.74 (s, 3H), 3.68 (s, 1H), 2.90 (s, 3H), 2.74 (d, J=16.2 Hz, 1H), 2.54 (s, 1H), 2.40 (m, 1H), 2.09 (s, 3H), 1.54 (m, 1H), 0.92 (m, 1H), 0.85 (t, J=7.2 Hz, 3H), 0.48 (t, J=7.2 Hz, 3H).

Preparation Example 7

Preparation of Compound C5

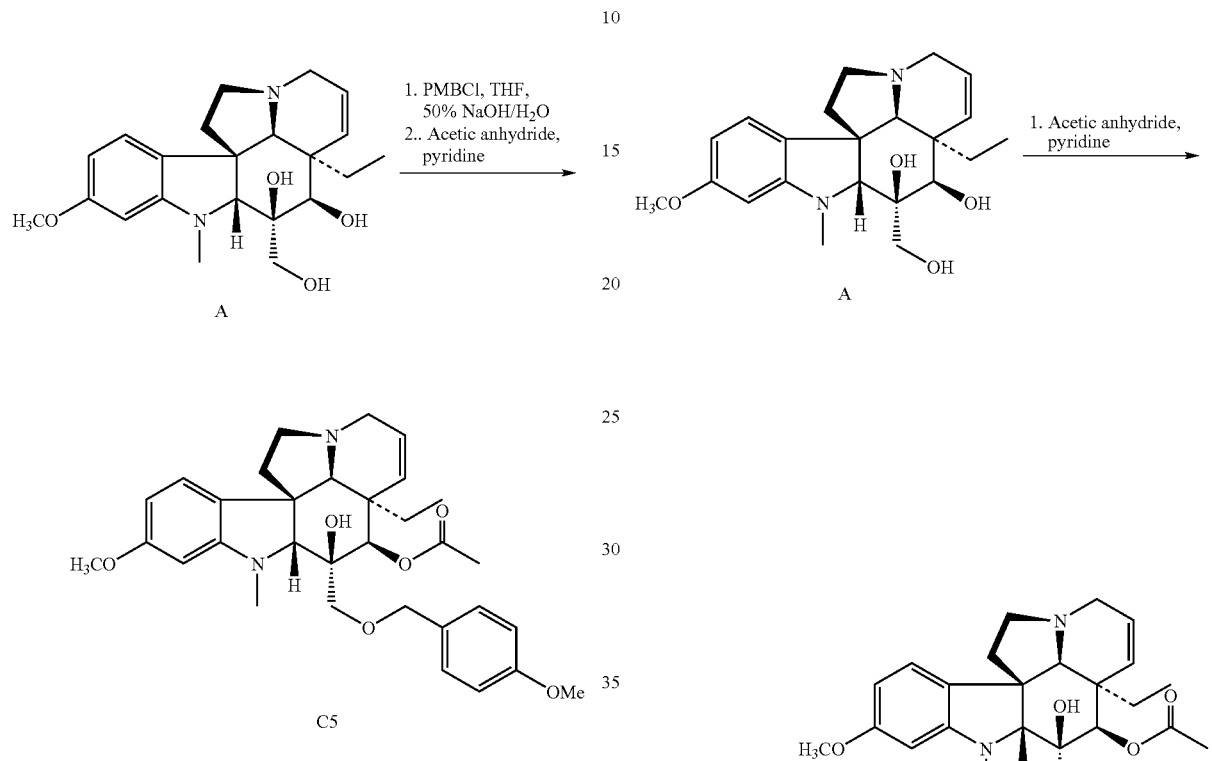

386 mg (1 mmol) of compound A was dissolved in 10 mL of tetrahydrofunan under argon atmosphere, followed by addition of 50% sodium hydroxide solution (1 g of sodium hydroxide is dissolved in 1 g of water). After 0.5 h of stirring at 60° C., 0.25 mL of methoxyl benzyl chloride and 50 mg of tetrabutylammonium iodide were added, and the reaction continued for 6 h. The reaction mixture was cooled to the room temperature and transferred into a separating funnel. Then 50 mL of water was added thereto, and the reaction mixture was extracted with methylene chloride (10 mL×3). The combined organic phase was dried over anhydrous magnesium sulfate and concentrated under reduced pressure to obtain a concentrate. The concentrate was dissolved in 1 mL of pyridine under argon atmosphere, followed by addition of 1 mL of acetic anhydride. After 8 h of stirring at room temperature, 30 mL of ethyl acetate and 10 mL of saturated sodium bicarbonate solution were added, and the stirring continued for 10 minutes. After the water layer was removed and pyridine was washed off with water (20 mL×3), the ethyl acetate layer was dried, concentrated and purified by silica gel chromatography (eluted with petroleum ether:acetone=6:1 v/v) to give 356 mg of the compound C5 as a white powder in 65% yield.

$^1$H NMR (CDCl$_3$, 300 MHz): δ: 7.08 (d, J=8.1 Hz, 2H), 6.85 (d, J=8.1 Hz, 1H), 6.70 (d, J=8.1 Hz, 2H), 6.25 (d, J=8.1 Hz, 1H), 6.09 (s, 1H), 5.51 (dd, J=10.2, 4.2 Hz, 1H), 5.36 (d, J=10.2 Hz, 1H), 4.98 (s, 1H), 4.58 (q, J=11.7 Hz, 2H), 3.74 (s, 6H), 3.54 (s, 1H), 3.51-3.32 (m, 4H), 2.93 (s, 3H), 2.77 (d, J=16.2 Hz, 1H), 2.58 (s, 1H), 2.44 (m, 1H), 2.26 (m, 2H), 2.04 (s, 3H), 1.25 (m, 1H), 0.93 (m, 1H), 0.50 (t, J=7.2 Hz, 3H).

Preparation Example 8

Preparation of Compound C6

386 mg (1 mmol) of compound A was dissolved in 1 mL of pyridine under argon atmosphere, followed by addition of 1 mL of acetic anhydride. After 8 h of stirring at room temperature, 30 mL of ethyl acetate and 10 mL of saturated sodium bicarbonate solution were added, and the stirring continued for 2 minutes. After the water layer was removed and the pyridine was washed off with water (20 mL×3), the ethyl acetate layer was dried, concentrated and purified by silica gel, chromatography (eluted with petroleum:acetone=6:1 v/v) to give 361 mg of the compound C6 as a white powder in 77% yield.

$^1$H NMR (CDCl$_3$, 300 MHz): δ: 9.02 (brs, 1H), 6.86 (d, J=8.1 Hz, 1H), 6.28 (d, J=8.1 Hz, 1H), 6.11 (s, 1H), 5.87 (dd, J=9.9, 3.3 Hz, 1H), 5.35 (d, J=9.9 Hz, 1H), 5.00 (s, 1H), 4.08 (d, J=10.8 Hz, 2H), 3.76 (s, 3H), 3.62 (s, 1H), 3.40 (m, 2H), 2.84 (s, 3H), 2.81 (m, 1H), 2.61 (s, 1H), 2.47 (m, 1H), 2.25 (m, 1H), 2.16 (m, 1H), 2.11 (s, 6H), 1.27 (m, 1H), 0.96 (m, 1H), 0.49 (t, J=7.2 Hz, 3H).

Preparation Example 9

Preparation of ligand III (N-acyl thiazolidine-2-thione)

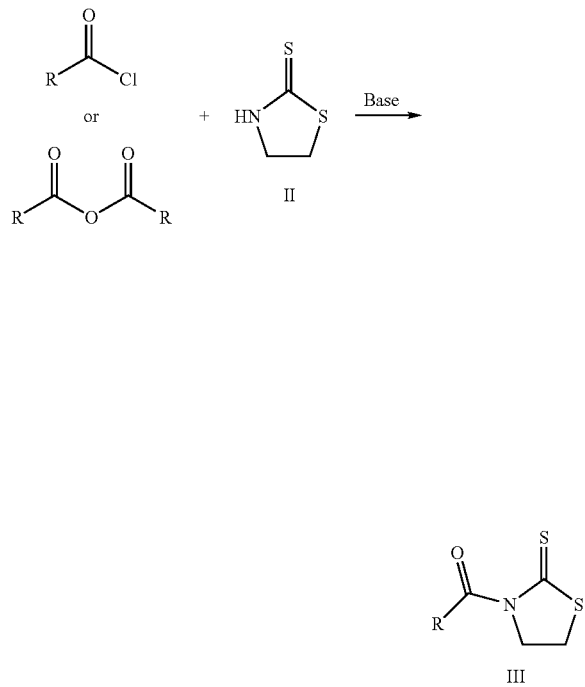

Thiazolidine-2-thione (0.1 mol) was dissolved in anhydrous methylene chloride (50 mL), followed by addition of Triethylamine (0.13 mmol). Then a methylene chloride solution (20 mL) containing acyl chloride or anhydride (0.11 mol) was slowly added dropwise under ice bath, wherein the acyl chloride was prepared from the corresponding acid by refluxing in thionyl chloride or reacting with oxalyl chloride at room temperature in a solution of anhydrous methylene chloride treated by refluxing with calcium hydride. The reaction was carried out for a few hours at room temperature while monitored by TLC, and then quenched when the raw material was exhausted completely. After the reaction was completed, the reaction mixture was washed with water. The organic layer was dried over anhydrous magnesium sulfate and concentrated under reduced pressure. The resultant product was recrystallized from ether-hexane to give the ligand III (N-acyl thiazolidine-2-thione).

1: 3-benzoyl-thiazolidine-2-thione $^1$H NMR (CDCl$_3$, 300 MHz): δ: 7.71 (d, J=6.9, 2H), 7.51-7.38 (m, 3H), 4.51 (t, J=7.25 Hz, 2H), 3.44 (t, J=7.25 Hz, 2H).

2: 3-pivalyl-thiazolidine-2-thione $^1$H NMR (CDCl$_3$, 300 MHz): δ: 1.41 (s, 9H), 3.48 (t, J=7.2 Hz, 2H), 4.19 (t, J=7.2 Hz, 2H); $^{13}$C NMR (CDCl$_3$, 75 MHz): δ: 200.6 (C), 187.8 (C), 57.3 (CH$_2$), 44.5 (CH$_2$), 31.6 (C), 27.7 (CH$_3$).

3: 3-(4-fluorine-benzoyl)-thiazolidine-2-thione $^1$H NMR (CDCl$_3$, 300 MHz): δ: 7.74 (d, J=6.9, 2H), 7.08 (d, J=6.9, 2H), 4.51 (t, J=7.2 Hz, 2H), 3.44 (t, J=7.25 Hz, 2H).

4: 3-isobutylacyl-thiazolidine-2-thione $^1$H NMR (CDCl$_3$, 300 MHz): δ: 4.54 (t, J=7.2 Hz, 2H), 4.46 (m, 1H), 3.27 (t, J=7.2 Hz, 2H), 1.20 (d, J=6.6 Hz, 6H).

Preparation Example 10

Preparation of Compound C7

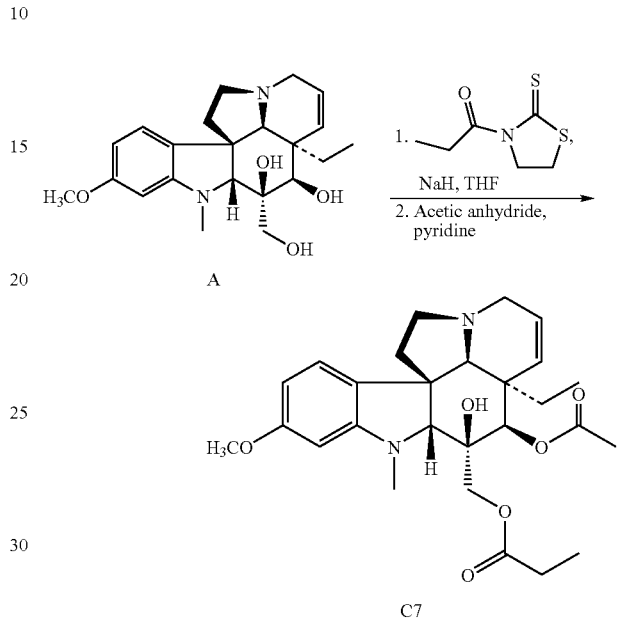

The compound A (1.0 mmol) and 3-propionyl-thiazolidine-2-thione (1.1 mmol) were dissolved in 10 mL of tetrahydrofunan, followed by addition of sodium hydride (60%, 1 mmol) under argon atmosphere. After stirred for 1-4 h at room temperature, the reaction mixture was washed with 1 mL of saturated ammonium chloride solution and extracted with chloroform. The organic phase was dried over magnesium sulfate and concentrated under reduced pressure. The concentrate was dissolved in 1 mL of pyridine under argon atmosphere, followed by addition of 1 mL of acetic anhydride. After 8 h of stirring at room temperature, 30 mL of ethyl acetate and 10 mL of saturated sodium bicarbonate solution were added, and the stirring continued for 2 minutes. After the water layer was removed and pyridine was washed off with water (20 mL×3), the ethyl acetate layer was dried, concentrated and purified by silica gel chromatography to obtain compound C7.

$^1$H NMR (CDCl$_3$, 300 MHz): δ: 8.96 (brs, 1H), 6.89 (d, J=8.1 Hz, 1H), 6.31 (d, J=8.1 Hz, 1H), 6.14 (s, 1H), 5.87 (dd, J=10.2, 3.6 Hz, 1H), 5.37 (d, J=10.2 Hz, 1H), 5.04 (s, 1H), 4.23 (d, J=11.4 Hz, 1H), 4.03 (d, J=11.4 Hz, 1H), 3.80 (s, 3H), 3.64 (s, 1H), 3.46 (m, 2H), 2.87 (s, 3H), 2.81 (d, J=15.9 Hz, 1H), 2.64 (s, 1H), 2.51 (m, 1H), 2.44 (q, J=7.2 Hz, 2H), 2.29 (m, 2H), 2.15 (s, 3H), 1.32 (m, 1H), 1.16 (t, J=7.2 Hz, 3H), 1.03 (m, 1H), 0.53 (t, J=7.2 Hz, 3H);

$^{13}$C NMR (CDCl$_3$, 75 MHz): δ: 173.9 (C), 170.5 (C), 160.8 (C), 154.2 (C), 129.9 (CH), 125.7 (C), 124.0 (CH), 122.5 (CH), 104.6 (CH), 96.1 (CH), 81.4 (CH), 76.6 (CH), 76.0 (C), 67.6 (CH), 66.3 (CH$_2$), 55.1 (OCH$_3$), 51.9 (C), 51.6 (CH$_2$), 50.6 (CH$_2$), 44.4 (CH$_2$), 42.4 (C), 39.7 (CH$_3$), 31.3 (CH$_2$), 27.3 (CH$_2$), 20.7 (CH$_3$), 9.0 (CH$_3$), 7.4 (CH$_3$).

Preparation Example 11

Preparation of Compound C8

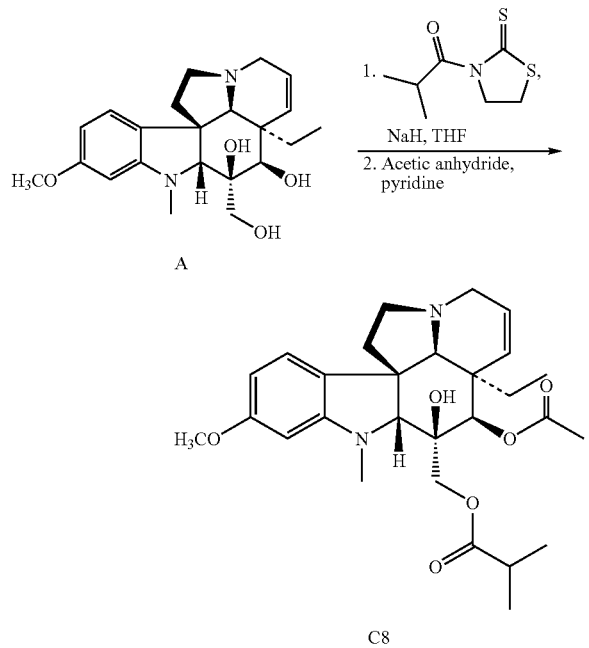

Compound C8 was prepared following the procedure for preparing compound C7.

$^1$H NMR (CDCl$_3$, 300 MHz): δ: 8.83 (brs, 1H), 6.89 (d, J=8.1 Hz, 1H), 6.31 (dd, J=8.1, 2.4 Hz, 1H), 6.13 (d, J=2.4 Hz, 1H), 5.87 (dd, J=10.2, 3.6 Hz, 1H), 5.36 (d, J=10.2 Hz, 1H), 5.03 (s, 1H), 4.25 (d, J=11.7 Hz, 1H), 4.01 (d, J=11.7 Hz, 1H), 3.79 (s, 3H), 3.62 (s, 1H), 3.45 (m, 2H), 2.88 (s, 3H), 2.80 (d, J=15.9 Hz, 1H), 2.69 (m, 1H), 2.62 (s, 1H), 2.51 (m, 1H), 2.29 (m, 2H), 2.13 (s, 3H), 1.32 (m, 1H), 1.19 (dd, J=6.6, 1.2 Hz, 6H), 1.03 (m, 1H), 0.52 (t, J=7.2 Hz, 3H).

Preparation Example 12

Preparation of Compound C9

Compound C9 was prepared following the procedure for preparing compound C7.

$^1$H NMR (CDCl$_3$, 300 MHz): δ: 9.02 (brs, 1H), 6.89 (d, J=8.1 Hz, 1H), 6.30 (d, J=8.1 Hz, 1H), 6.12 (s, 1H), 5.84 (dd, J=9.3, 3.3 Hz, 1H), 5.33 (d, J=9.3 Hz, 1H), 5.01 (s, 1H), 4.32 (d, J=11.4 Hz, 1H), 3.94 (d, J=11.4 Hz, 1H), 3.79 (s, 3H), 3.60 (s, 1H), 3.48 (m, 2H), 2.89 (s, 3H), 2.81 (m, 1H), 2.63 (s, 1H), 2.50 (m, 1H), 2.25 (m, 1H), 2.16 (m, 1H), 2.06 (s, 3H), 1.27 (m, 1H), 1.24 (s, 9H), 0.96 (m, 1H), 0.50 (t, J=7.2 Hz, 3H).

Preparation Example 13

Preparation of Compound C10

Compound C10 was prepared following the procedure for preparing compound C7.

$^1$H NMR (CDCl$_3$, 300 MHz): δ: 8.83 (brs, 1H), 6.89 (d, J=8.1 Hz, 1H), 6.31 (dd, J=8.1, 2.4 Hz, 1H), 6.13 (d, J=2.1 Hz, 1H), 5.88 (dd, J=10.5, 3.6 Hz, 1H), 5.37 (d, J=10.5 Hz, 1H), 5.03 (s, 1H), 4.26 (d, J=11.4 Hz, 1H), 4.00 (d, J=11.4 Hz, 1H), 3.80 (s, 3H), 3.64 (s, 1H), 3.48 (m, 2H), 2.89 (s, 3H), 2.81 (d, J=15.9 Hz, 1H), 2.64 (s, 1H), 2.51 (m, 1H), 2.29 (m, 4H), 2.15

(s, 3H), 1.32 (m, 1H), 1.03 (m, 1H), 0.97 (d, J=6.6 Hz, 6H), 0.89 (m, 1H), 0.52 (t, J=7.2 Hz, 3H).

Preparation Example 14

Preparation of Compound C11

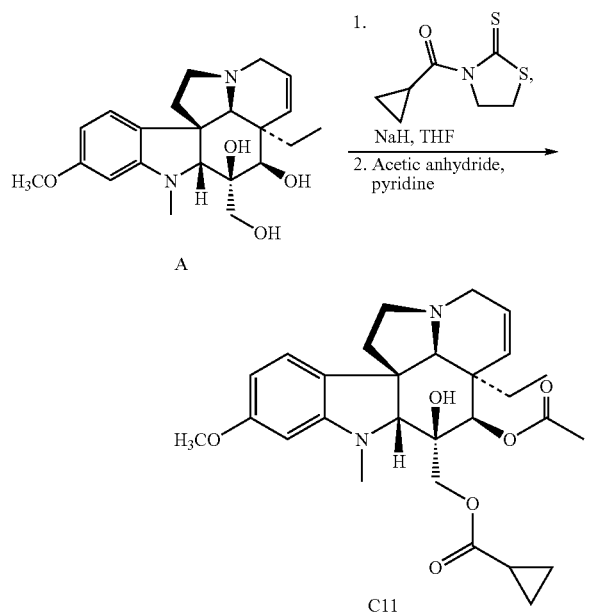

Compound C11 was prepared following the procedure for preparing compound C7.

$^{1}$H NMR (CDCl$_{3}$, 300 MHz): δ: 8.95 (brs, 1H), 6.90 (d, J=8.1 Hz, 1H), 6.32 (dd, J=8.1, 2.4 Hz, 1H), 6.14 (d, J=2.4 Hz, 1H), 5.89 (dd, J=10.2, 3.6 Hz, 1H), 5.38 (d, J=10.2 Hz, 1H), 5.04 (s, 1H), 4.24 (d, J=11.7 Hz, 1H), 4.03 (d, J=11.7 Hz, 1H), 3.80 (s, 3H), 3.68 (s, 1H), 3.45 (m, 2H), 2.90 (s, 3H), 2.81 (d, J=14.1 Hz, 1H), 2.65 (s, 1H), 2.50 (m, 1H), 2.51 (m, 1H), 2.30 (m, 2H), 2.14 (s, 3H), 1.74 (m, 1H), 1.32 (m, 2H), 1.01 (m, 2H), 0.86 (m, 2H), 0.53 (t, J=7.2 Hz, 3H).

Preparation Example 15

Preparation of Compound C12

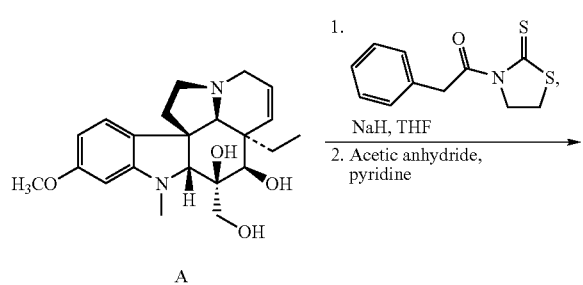

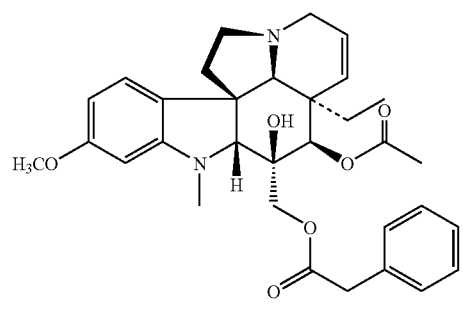

The compound A (1.0 mmol) and 3-phenylacetyl-thiazolidine-2-thione (1.1 mmol) were dissolved in 10 mL of anhydrous tetrahydrofunan, followed by addition of sodium hydride (60%, 1 mmol) under argon atmosphere. After stirred for 1-4 h at room temperature, the reaction mixture was washed with 1 mL of saturated ammonium chloride solution and then extracted with chloroform, and the combined organic phase was dried over magnesium sulfate and concentrated under reduced pressure. The concentrate was then dissolved in 1 mL of pyridine under argon atmosphere, followed by addition of 1 mL of acetic anhydride. After 8 h of stirring at room temperature, 30 mL of ethyl acetate and 10 mL of saturated sodium bicarbonate solution were added and the stirring continued for 2 minutes. After the water layer was removed and pyridine was washed off with water (20 mL×3), the ethyl acetate layer was dried, concentrated and purified by silica gel chromatography to obtain compound C12.

$^{1}$H NMR (CDCl$_{3}$, 300 MHz): δ: 9.02 (brs, 1H), 7.22 (m, 5H), 6.86 (d, J=8.4 Hz, 1H), 6.29 (d, J=8.4 Hz, 1H), 6.05 (s, 1H), 5.87 (dd, J=10.2, 3.9 Hz, 1H), 5.37 (d, J=10.2 Hz, 1H), 4.99 (s, 1H), 4.30 (d, J=11.1 Hz, 1H), 3.95 (d, J=11.1 Hz, 1H), 3.78 (s, 3H), 3.72 (s, 2H), 3.48 (m, 2H), 2.81 (m, 1H), 2.63 (s, 1H), 2.56 (s, 3H), 2.47 (m, 1H), 2.25 (m, 1H), 2.16 (m, 2H), 2.12 (s, 3H), 1.27 (m, 1H), 0.96 (m, 1H), 0.48 (t, J=7.2 Hz, 3H).

Preparation Example 16

Preparation of Compound C13

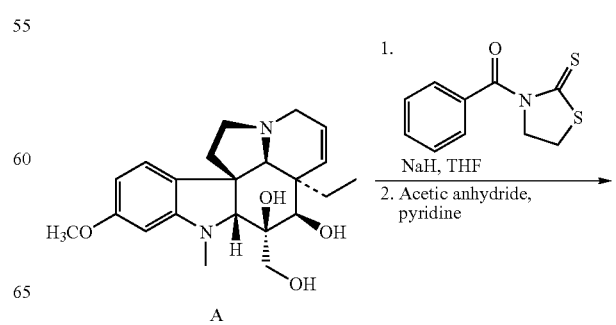

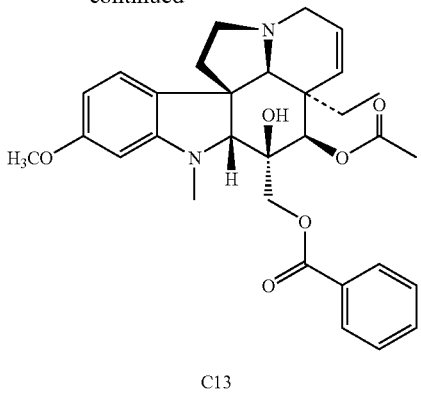

C13

Compound C13 was prepared following the procedure for preparing compound C7.

$^1$H NMR (CDCl$_3$, 300 MHz): δ: 8.94 (brs, 1H), 8.08 (d, J=7.5 Hz, 2H), 7.56 (t, J=7.5 Hz, 1H), 7.44 (t, J=7.5 Hz, 2H), 6.91 (d, J=8.4 Hz, 1H), 6.32 (d, J=8.4 Hz, 1H), 6.11 (s, 1H), 5.89 (dd, J=10.2, 3.9 Hz, 1H), 5.39 (d, J=10.2 Hz, 1H), 5.13 (s, 1H), 4.57 (d, J=11.4 Hz, 1H), 4.20 (d, J=11.4 Hz, 1H), 3.79 (s, 3H), 3.74 (s, 1H), 3.51-3.38 (m, 2H), 2.92 (s, 3H), 2.82 (d, J=15.6 Hz, 1H), 2.67 (s, 1H), 2.51 (m, 1H), 2.31 (m, 2H), 2.14 (s, 3H), 1.32 (m, 1H), 0.79 (m, 1H), 0.54 (t, J=7.2 Hz, 3H).

Preparation Example 17

Preparation of Compound C14

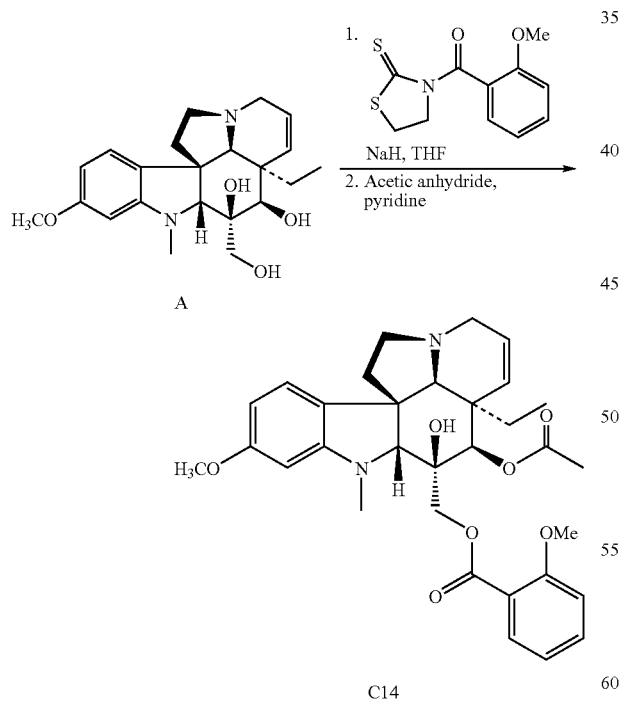

C14

Compound C14 was prepared following the procedure for preparing compound C7.

$^1$H NMR (CDCl$_3$, 300 MHz): δ: 8.86 (brs, 1H), 7.86 (d, J=7.5 Hz, 1H), 7.47 (t, J=7.5 Hz, 1H), 6.97 (t, J=7.5 Hz, 1H), 6.97 (d, J=7.5 Hz, 1H), 6.90 (d, J=8.4 Hz, 1H), 6.31 (d, J=8.4 Hz, 1H), 6.12 (s, 1H), 5.88 (dd, J=10.5, 3.6 Hz, 1H), 5.38 (d, J=10.5 Hz, 1H), 5.12 (s, 1H), 4.49 (d, J=11.4 Hz, 1H), 4.19 (d, J=11.4 Hz, 1H), 3.87 (s, 3H), 3.79 (s, 3H), 3.74 (s, 1H), 3.50-3.36 (m, 2H), 2.95 (s, 3H), 2.80 (d, J=15.6 Hz, 1H), 2.66 (s, 1H), 2.54 (m, 1H), 2.31 (m, 2H), 2.14 (s, 3H), 1.36 (m, 1H), 1.03 (m, 1H), 0.53 (t, J=7.2 Hz, 3H).

Preparation Example 18

Preparation of Compound C15

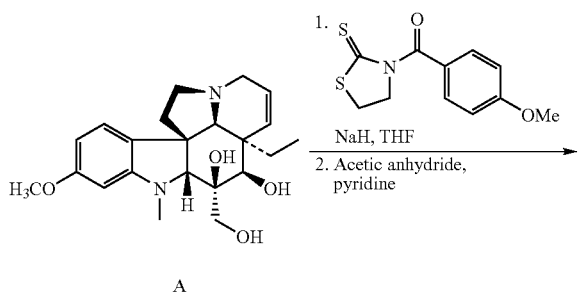

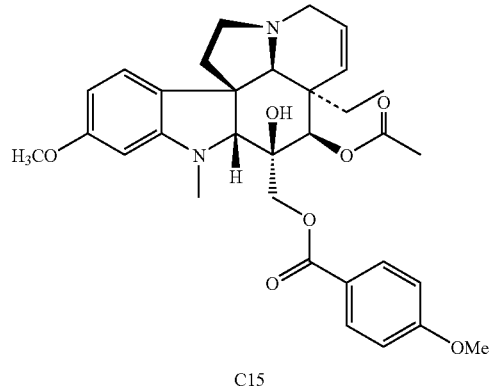

C15

Compound C15 was prepared following the procedure for preparing compound C7.

$^1$H NMR (CDCl$_3$, 300 MHz): δ: 8.86 (brs, 1H), 7.97 (d, J=8.7 Hz, 1H), 6.84 (d, J=8.7 Hz, 3H), 6.24 (d, J=8.7 Hz, 1H), 6.04 (s, 1H), 5.81 (dd, J=10.5, 4.5 Hz, 1H), 5.32 (d, J=10.5 Hz, 1H), 5.07 (s, 1H), 4.46 (d, J=11.7 Hz, 1H), 4.11 (d, J=11.7 Hz, 1H), 3.74 (s, 3H), 3.69 (s, 3H), 3.66 (s, 1H), 3.42-3.30 (m, 2H), 2.84 (s, 3H), 2.73 (d, J=16.2 Hz, 1H), 2.60 (s, 1H), 2.43 (m, 1H), 2.24 (m, 2H), 2.05 (s, 3H), 1.28 (m, 1H), 1.00 (m, 1H), 0.48 (t, J=7.2 Hz, 3H).

Preparation Example 19

Preparation of Compound C16

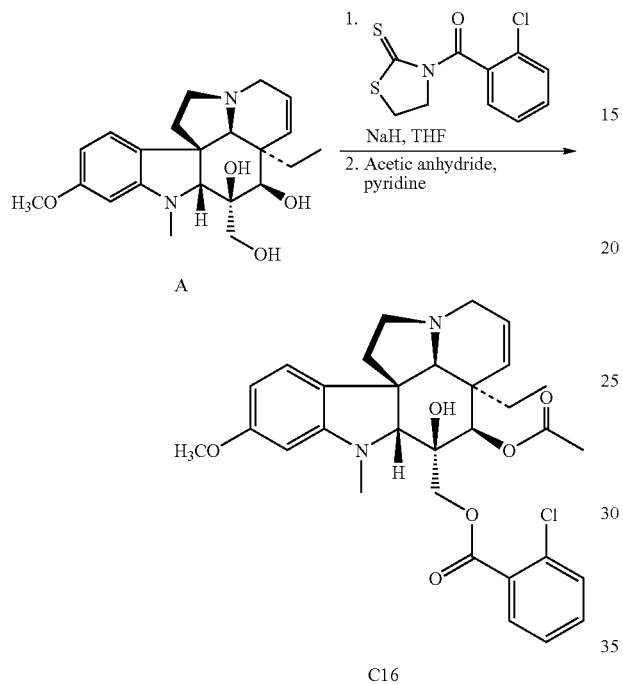

C16

Compound C16 was prepared following the procedure for preparing compound C7.

$^1$H NMR (CDCl$_3$, 300 MHz): δ: 8.79 (brs, 1H), 7.79 (d, J=7.2 Hz, 1H), 7.29 (m, 2H), 7.20 (m, 1H), 6.79 (t, J=8.1 Hz, 1H), 6.20 (d, J=8.1 Hz, 1H), 6.02 (s, 1H), 5.78 (dd, J=10.5, 3.6 Hz, 1H), 5.29 (d, J=10.5 Hz, 1H), 5.01 (s, 1H), 4.44 (d, J=11.4 Hz, 1H), 4.16 (d, J=11.4 Hz, 1H), 3.63 (s, 3H), 3.61 (s, 1H), 3.37-3.24 (m, 2H), 2.89 (s, 3H), 2.69 (d, J=15.9 Hz, 1H), 2.54 (s, 1H), 2.39 (m, 1H), 2.16 (m, 2H), 2.01 (s, 3H), 1.25 (m, 1H), 0.95 (m, 1H), 0.43 (t, J=7.2 Hz, 3H).

Preparation Example 20

Preparation of Compound C17

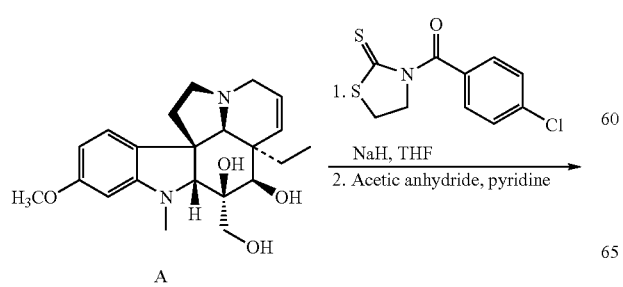

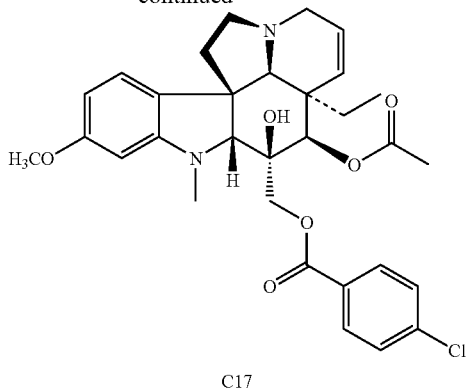

C17

Compound C17 was prepared following the procedure for preparing compound C7.

$^1$H NMR (CDCl$_3$, 300 MHz): δ: 8.85 (brs, 1H), 7.92 (d, J=7.2 Hz, 2H), 7.29 (d, J=7.2 Hz, 2H), 6.82 (d, J=8.4 Hz, 1H), 6.22 (d, J=8.4 Hz, 1H), 6.02 (s, 1H), 5.78 (dd, J=3.6 Hz, 1H), 5.30 (d, J=10.5 Hz, 1H), 5.04 (s, 1H), 4.47 (d, J=11.4 Hz, 1H), 4.13 (d, J=11.4 Hz, 1H), 3.65 (s, 3H), 3.61 (s, 1H), 3.38-3.27 (m, 2H), 2.82 (s, 3H), 2.71 (d, J=15.9 Hz, 1H), 2.59 (s, 1H), 2.43 (m, 1H), 2.19 (m, 2H), 2.02 (s, 3H), 1.26 (m, 1H), 0.97 (m, 1H), 0.46 (t, J=7.2 Hz, 3H).

Preparation Example 21

Preparation of Compound C18

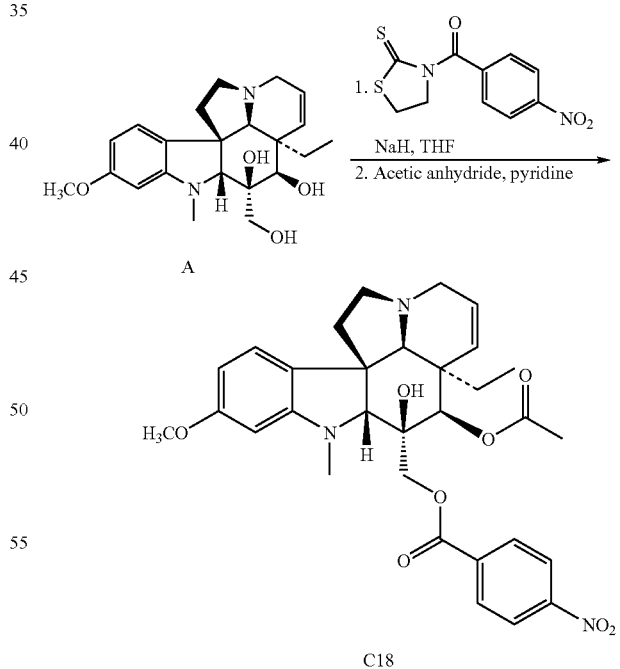

C18

Compound C18 was prepared following the procedure for preparing compound C7.

$^1$H NMR (CDCl$_3$, 300 MHz): δ: 8.88 (brs, 1H), 8.14 (s, 4H), 6.83 (d, J=8.1 Hz, 1H), 6.22 (d, J=8.4 Hz, 1H), 6.02 (s, 1H), 5.80 (dd, J=9.9, 3.6 Hz, 1H), 5.31 (d, J=9.9 Hz, 1H), 5.03 (s, 1H), 4.51 (d, J=11.1 Hz, 1H), 4.18 (d, J=11.1 Hz, 1H), 3.65

(s, 3H), 3.61 (s, 1H), 3.41-3.28 (m, 2H), 2.84 (s, 3H), 2.74 (d, J=16.2 Hz, 1H), 2.61 (s, 1H); 2.43 (m, 1H), 2.20 (m, 2H), 2.02 (s, 3H), 1.23 (m, 1H), 0.95 (m, 1H), 0.45 (t, J=7.2 Hz, 3H).

Preparation Example 22

Preparation of Compound D1

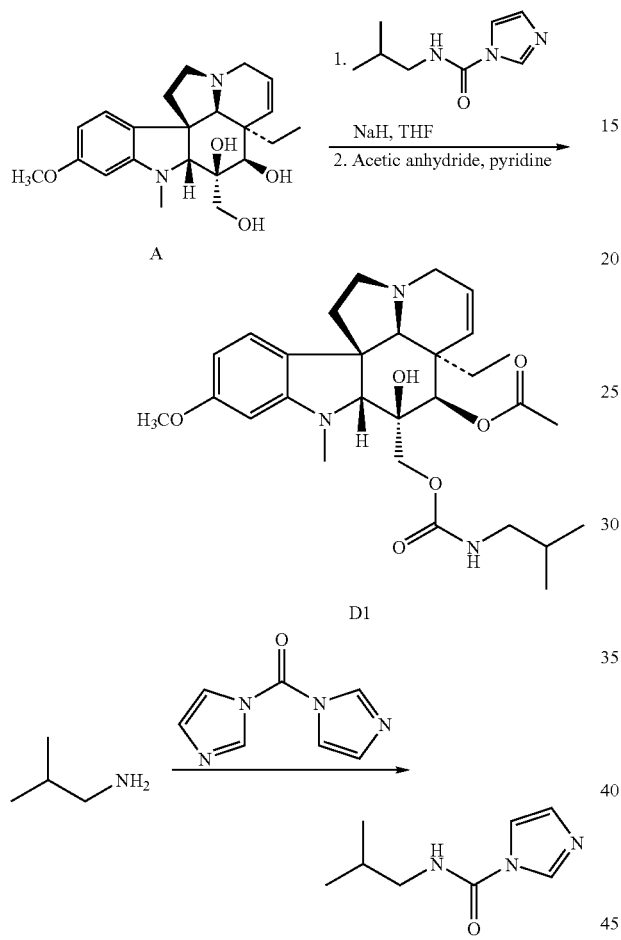

2.4 mmol (0.24 mL) of isobutyl amine was slowly added dropwise into a solution of carbonyl diimidazole (CDI, 1.1 eq, 428 mg) in methylene chloride (10 mL) under ice bath. After 0.5 h of stirring, the ice bath was removed, and the reaction continued for a further 24 h at room temperature. After quenched with 20 mL of water, the reaction mixture was extracted with methylene chloride (10 mL×3). The combined organic phase was dried over anhydrous magnesium sulfate, filtrated and concentrated under reduced pressure to obtain a crude intermediate. 1 mmol of compound A and the crude intermediate were dissolved in 20 mL of tetrahydrofunan under argon atmosphere, followed by addition of 88 mg of 60% sodium hydride (2.2 mmol). After 6 h of stirring at room temperature, 10 mL of saturated ammonium chloride solution and 10 mL of water were added thereto, and the reaction mixture was extracted with ethyl acetate (10 mL×3). The combined organic phase was dried over anhydrous magnesium sulfate and concentrated under reduced pressure. The concentrate was dissolved in 1 mL of pyridine, followed by addition of 1 mL of acetic anhydride. After 8 h of stirring at room temperature, 30 mL of ethyl acetate and 10 mL of saturated sodium bicarbonate solution were added and the stirring continued for 2 minutes. After the water layer was removed and pyridine was washed off with water (20 mL×3), the ethyl acetate layer was dried, concentrated and purified by silica gel chromatography (eluted with petroleum ether:acetone=4:1 v/v) to give 212 mg of compound D1 as a white powder in 40% yield.

$^1$H NMR (CDCl$_3$, 300 MHz): δ: 9.10 (s), 6.88 (d, J=8.4 Hz, 1H), 6.30 (d, J=8.4 Hz, 1H), 6.12 (s, 1H), 5.88 (dd, J=10.2, 4.5 Hz, 1H), 5.36 (d, J=10.2 Hz, 1H), 5.04 (s, 1H), 4.98 (m, 1H), 4.08 (d, J=11.1 Hz, 2H), 3.79 (s, 3H), 3.63 (s, 1H), 3.55-3.37 (m, 2H), 3.01 (t, J=6.6 Hz, 1H), 2.88 (s, 3H), 2.82 (d, J=15.9 Hz, 1H), 2.63 (s, 1H), 2.50 (q, J=9.3 Hz, 1H), 2.31 (m, 2H), 2.13 (s, 3H), 1.76-1.70 (m, 2H), 1.31 (m, 1H), 1.02 (m, 1H), 0.90 (d, J=6.9 Hz, 6H), 0.52 (t, J=7.2 Hz, 3H).

$^{13}$C NMR (CDCl$_3$, 75 MHz): δ: 170.4 (C), 160.7 (C), 156.1 (C), 154.1 (C), 129.9 (CH), 125.5 (C), 123.9 (CH), 122.4 (CH), 104.4 (CH), 95.9 (CH), 81.1 (CH), 76.5 (CH), 76.0 (C), 67.5 (CH), 66.9 (CH$_2$), 55.0 (OCH$_3$), 51.7 (C), 51.5 (CH$_2$), 50.5 (CH$_2$), 48.1 (CH$_2$), 44.3 (CH$_2$), 42.4 (C), 39.4 (CH$_3$), 31.1 (CH$_2$), 28.4 (CH), 20.6 (CH$_3$), 19.6 (2CH$_3$), 7.3 (CH$_3$).

Preparation Example 23

Preparation of Compound D2

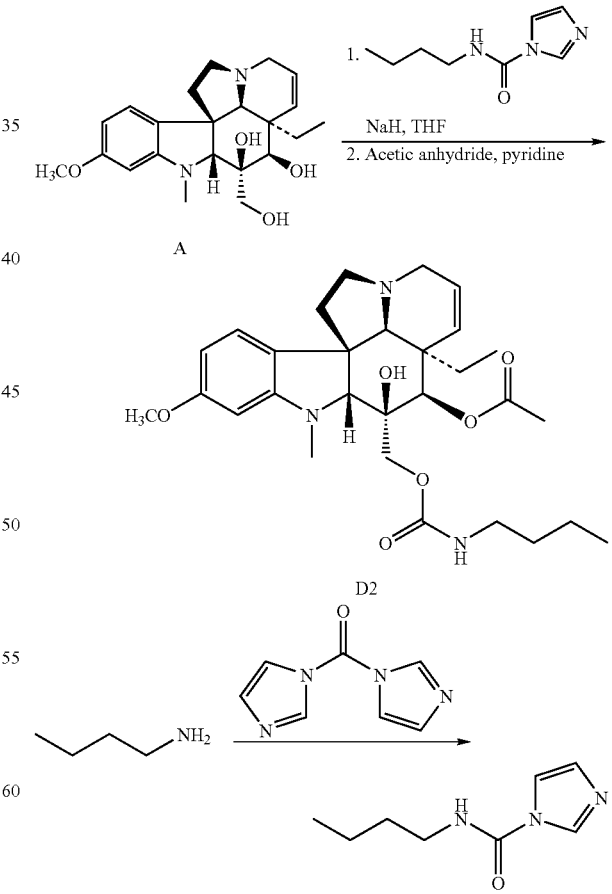

Compound D2 was prepared following the procedure for preparing compound D1.

¹H NMR (CDCl₃, 300 MHz): δ: 9.10 (s), 6.86 (d, J=8.4 Hz, 1H), 6.30 (d, J=8.4 Hz, 1H), 6.12 (s, 1H), 5.89 (dd, J=10.2, 2.4 Hz, 1H), 5.36 (d, J=10.2 Hz, 1H), 5.04 (s, 1H), 4.89 (m, 1H), 4.10 (s, 2H), 3.79 (s, 3H), 3.63 (s, 1H), 3.52-3.37 (m, 2H), 3.18 (q, J=6.9 Hz, 1H), 2.88 (s, 3H), 2.82 (d, J=15.9 Hz, 1H), 2.63 (s, 1H), 2.50 (q, J=9.3 Hz, 1H), 2.31-2.26 (m, 2H), 2.14 (s, 3H), 1.52-1.41 (m, 2H), 1.38-1.22 (m, 3H), 1.05-0.98 (m, 1H), 1.02 (m, 1H), 0.91 (t, J=7.2 Hz, 3 H), 0.52 (t, J=7.5 Hz, 3H).

Preparation Example 24

Preparation of Compound D3

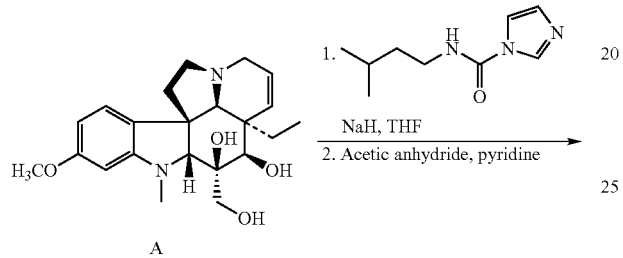

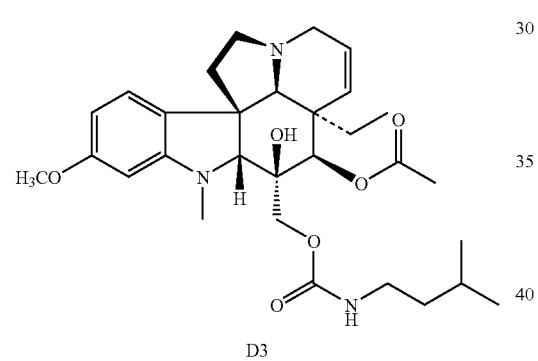

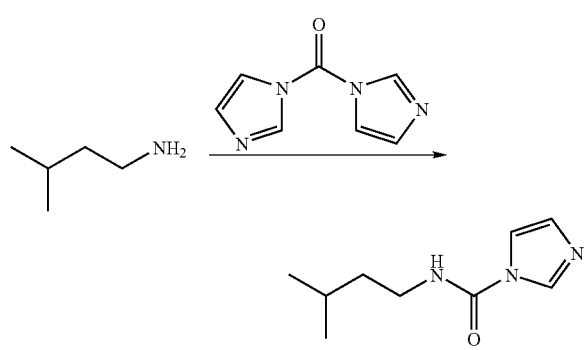

Compound D3 was prepared following the procedure for preparing compound D1.

¹H NMR (CDCl₃, 300 MHz): δ: 9.10 (s), 6.88 (d, J=8.4 Hz, 1H), 6.30 (d, J=8.4 Hz, 1H), 6.13 (s, 1H), 5.89 (dd, J=10.2, 2.4 Hz, 1H), 5.36 (d, J=10.2 Hz, 1H), 5.04 (s, 1H), 4.88 (m, 1H), 4.10 (s, 2H), 3.79 (s, 3H), 3.63 (s, 1H), 3.55-3.37 (m, 2H), 3.19 (q, J=8.1 Hz, 1H), 2.88 (s, 3H), 2.81 (d, J=15.9 Hz, 1H), 2.63 (s, 1H), 2.50 (q, J=9.3 Hz, 1H), 2.34-2.28 (m, 2H), 2.14 (s, 3H), 1.68-1.56 (m, 1H), 1.34-1.26 (m, 2H), 1.04-0.98 (m, 1H), 1.02 (m, 1H), 0.90 (d, J=2.4 Hz, 6H), 0.52 (t, J=7.2 Hz, 3H).

Preparation Example 25

Preparation of Compound E1

385 mg (1 mmol) of compound B was dissolved in 1 mL of pyridine under argon atmosphere, followed by addition of 1 mL of acetic anhydride. After 8 h of stirring at room temperature, 30 mL of ethyl acetate and 10 mL of saturated sodium bicarbonate solution were added and the stirring continued for 2 minutes. After the water layer was removed and the pyridine was washed off with water (20 mL×3), the ethyl acetate layer was dried, concentrated and purified by silica gel chromatography (eluted with petroleum ether:acetone=2:1 v/v) to give 417 mg of compound E1 as a white powder in 89% yield.

¹H NMR (CDCl₃, 300 MHz): δ: 6.81 (d, J=8.1 Hz, 1H), 6.24 (d, J=8.1 Hz, 1H), 6.17 (d, J=7.2 Hz, 1H), 6.08 (s, 1H), 5.82 (dd, J=10.2, 4.5 Hz, 1H), 5.35 (d, J=10.2 Hz, 1H), 4.92 (s, 1H), 3.78 (s, 3H), 3.65 (m, 2H), 3.41 (m, 2H), 3.33 (s, 1H), 3.28 (m, 1H), 2.98 (d, J=13.2 Hz, 1H), 2.79 (s, 3H), 2.73 (d, J=4.8 Hz, 1H), 2.59 (s, 1H), 2.47 (m, 1H), 2.16 (m, 2H), 2.09 (s, 1H), 2.03 (s, 3H), 1.92 (s, 3H), 1.22 (m, 1H), 0.94 (m, 1H), 0.45 (t, J=7.2 Hz, 3H).

¹³C NMR (CDCl₃, 75 MHz): δ: 170.4 (C), 170.3 (C), 161.0 (C), 154.3 (C), 130.3 (CH), 125.5 (C), 124.1 (CH), 122.6 (CH), 105.1 (CH), 96.6 (CH), 82.1 (CH), 77.0 (CH), 75.8 (C), 67.3 (CH), 55.3 (OCH₃), 52.2 (C), 51.5 (CH₂), 50.8 (CH₂), 44.6 (CH$_2$), 43.7 (CH$_2$), 42.8 (C), 40.6 (CH$_3$), 31.2 (CH$_2$), 23.3 (CH$_3$), 20.9 (CH$_3$), 7.5 (CH$_3$).

Preparation Example 26

Preparation of Compound E2

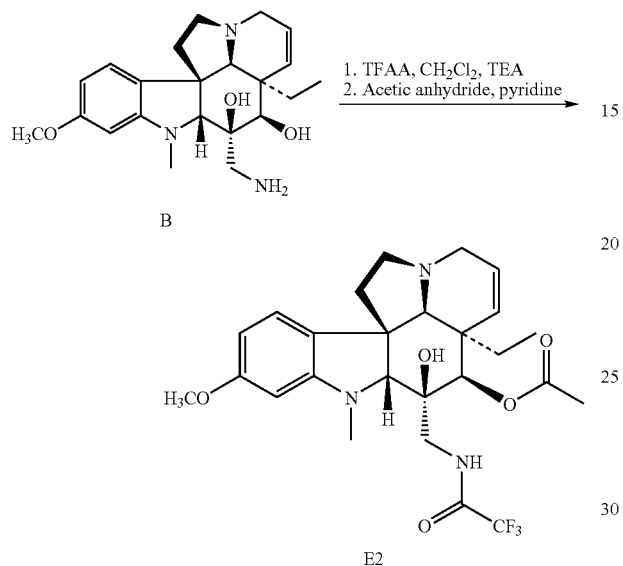

Compound E2 was prepared following the procedure for preparing compound E3.

$^1$H NMR (CDCl$_3$, 300 MHz): δ: 9.44 (brs, 1H), 7.18 (d, J=7.2 Hz, 1H), 6.88 (d, J=8.1 Hz, 1H), 6.35 (d, J=8.1 Hz, 1H), 6.17 (s, 1H), 6.08 (s, 1H), 5.91 (dd, J=10.2, 4.5 Hz, 1H), 5.38 (d, J=10.2 Hz, 1H), 4.99 (s, 1H), 3.79 (s, 3H), 3.79-3.74 (m, 1H), 3.49 (dd, J=15.9, 4.8 Hz, 1H), 3.43-3.37 (m, 1H), 3.33 (s, 1H), 3.18 (d, J=13.5 Hz, 1H), 2.87 (s, 3H), 2.85 (d, J=15.9 Hz, 1H), 2.70 (s, 1H), 2.61-2.52 (m, 1H), 2.34-2.16 (m, 2H), 2.11 (s, 3H), 1.33-1.23 (m, 1H), 1.06-0.97 (m, 1H), 0.54 (t, J=7.2 Hz, 3H).

Preparation Example 27

Preparation of Compound E3

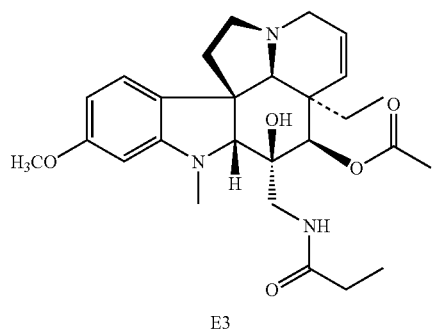

Compound B (1.0 mmol) and ligand III (3-propionyl-thiazolidine-2-thione) (1.1 mmol) were dissolved in 10 mL of anhydrous tetrahydrofunan, followed by addition of sodium hydride (60%, 1 mmol) under argon atmosphere. After 1-4 h of stirring at room temperature, 1 mL of saturated ammonium chloride solution was added, and the reaction mixture was extracted with chloroform. The organic phase was dried over magnesium sulfate and concentrated under reduced pressure. The concentrate was dissolved in 1 mL of pyridine under argon atmosphere, followed by addition of 1 mL of acetic anhydride. After 8 h of stirring at room temperature, 30 mL of ethyl acetate and 10 mL of saturated sodium bicarbonate solution were added and the stirring continued for 2 minutes. After the water layer was removed and pyridine was washed off with water (20 mL×3), the ethyl acetate layer was dried, concentrated and purified by silica gel chromatography to obtain compound E3.

$^1$H NMR (CDCl$_3$, 300 MHz): δ: 9.20 (s, 1H), 6.88 (d, J=8.1 Hz, 1H), 6.32 (dd, J=8.1, 2.1 Hz, 1H), 6.16 (d, J=5.7 Hz, 1H), 6.15 (d, J=2.1 Hz, 1H), 5.89 (dd, J=10.2, 4.2 Hz, 1H), 5.36 (d, J=10.2 Hz, 1H), 4.99 (s, 1H), 3.79 (s, 3H), 3.74 (m, 1H), 3.50 (dd, J=15.9, 4.5 Hz, 1H), 3.39 (m, 1H), 3.39 (s, 1H), 3.03 (d, J=13.2 Hz, 1H), 2.86 (s, 3H), 2.83 (d, J=15.9 Hz, 1H), 2.66 (s, 1H), 2.53 (dd, J=18.0, 9.6 Hz, 1H), 2.33-2.19 (m, 2H), 2.22 (q, J=7.5 Hz, 2H), 2.11 (s, 3H), 1.36-1.29 (m, 1H), 1.15 (t, J=7.5 Hz, 3H), 1.04-0.98 (m, 1H), 0.52 (t, J=7.2 Hz, 3H).

Preparation Example 28

Preparation of Compound E4

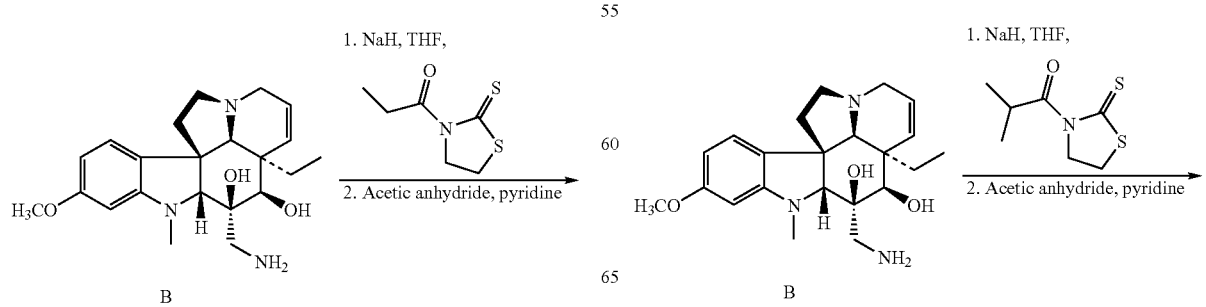

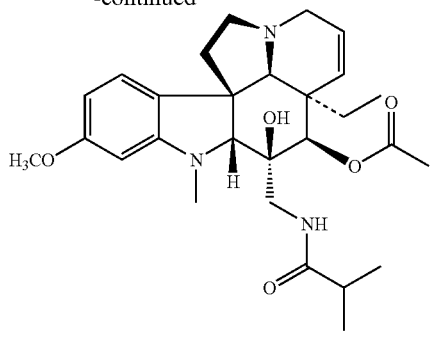

E4

Compound E4 was prepared following the procedure for preparing compound E3.

$^1$H NMR (CDCl$_3$, 300 MHz): δ: 9.20 (brs, 1H), 6.88 (d, J=8.4 Hz, 1H), 6.32 (dd, J=8.4, 2.1 Hz, 1H), 6.19 (d, J=8.1 Hz, 1H), 6.15 (d, J=2.1 Hz, 1H), 5.89 (dd, J=10.2, 3.6 Hz, 1H), 5.36 (d, J=10.2 Hz, 1H), 4.98 (s, 1H), 3.79 (s, 3H), 3.74 (m, 1H), 3.48 (dd, J=15.9, 5.4 Hz, 1H), 3.38 (m, 1H), 3.38 (s, 1H), 2.99 (d, J=13.2 Hz, 1H), 2.84 (s, 3H), 2.83 (d, J=15.9 Hz, 1H), 2.66 (s, 1H), 2.54-2.48 (m, 1H), 2.42-2.33 (m, 1H), 2.29-2.18 (m, 2H), 2.11 (s, 3H), 1.37-1.27 (m, 1H), 1.15 (d, J=2.1 Hz, 3H) 1.13 (d, J=2.1 Hz, 3H), 1.07-0.98 (m, 1H), 0.52 (t, J=7.2 Hz, 3H).

Preparation Example 29

Preparation of Compound E5

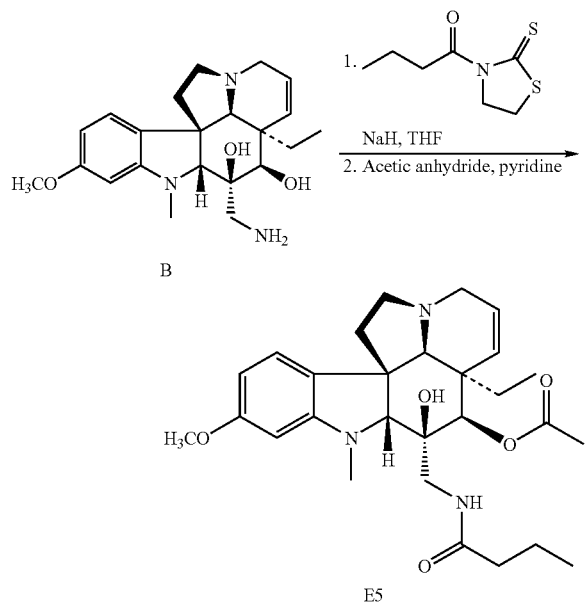

E5

Compound E5 was prepared following the procedure for preparing compound E3.

$^1$H NMR (CDCl$_3$, 300 MHz): δ: 9.23 (brs, 1H), 6.88 (d, J=8.4 Hz, 1H), 6.32 (d, J=8.4 Hz, 1H), 6.16 (d, J=8.1 Hz, 1H), 6.15 (s, 1H), 5.89 (dd, J=10.2, 4.8 Hz, 1H), 5.37 (d, J=10.2 Hz, 1H), 5.01 (s, 1H), 3.79 (s, 3H), 3.74 (m, 1H), 3.48 (dd, J=15.9, 5.4 Hz, 1H), 3.38 (m, 1H), 3.41 (s, 1H), 3.04 (d, J=14.4 Hz, 1H), 2.86 (s, 3H), 2.83 (d, J=15.9 Hz, 1H), 2.67 (s, 1H), 2.61-2.52 (m, 1H), 2.34-2.16 (m, 2H), 2.19 (t, J=7.2 Hz, 2H), 2.11 (s, 3H), 1.70-1.63 (m, 2H), 1.37-1.27 (m, 1H), 0.91 (t, J=7.2 Hz, 3H), 1.03-0.85 (m, 1H), 0.51 (t, J=7.2 Hz, 3H).

Preparation Example 30

Preparation of Compound E6

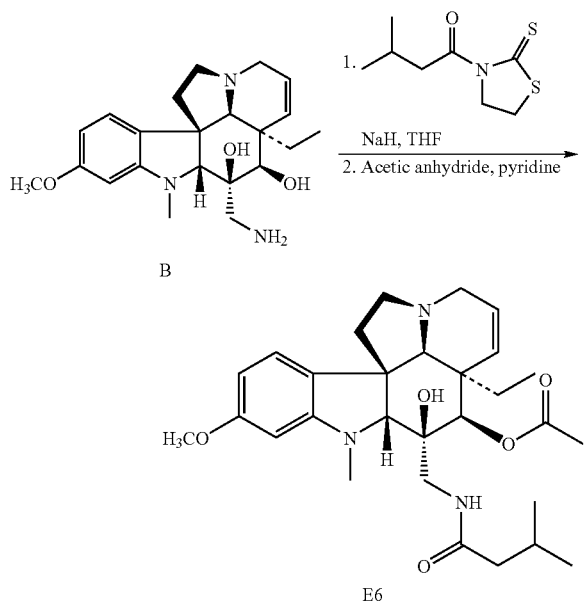

E6

Compound E6 was prepared following the procedure for preparing compound E3.

$^1$H NMR (CDCl$_3$, 300 MHz): δ: 9.25 (brs, 1H), 6.87 (d, J=8.1 Hz, 1H), 6.31 (dd, J=8.1, 2.1 Hz, 1H), 6.15 (d, J=2.1 Hz, 1H), 6.10 (d, J=8.1 Hz, 1H), 5.89 (dd, J=10.5, 3.6 Hz, 1H), 5.36 (d, J=10.5 Hz, 1H), 5.00 (s, 1H), 3.79 (s, 3H), 3.79-3.72 (m, 1H), 3.48 (dd, J=15.9, 5.1 Hz, 1H), 3.42-3.34 (m, 1H), 3.39 (s, 1H), 3.03 (d, J=13.2 Hz, 1H), 2.86 (s, 3H), 2.83 (d, J=15.9 Hz, 1H), 2.63 (s, 1H), 2.57-2.48 (m, 1H), 2.35-2.16 (m, 3H), 2.11 (s, 3H), 2.10 (d, J=9.9 Hz, 2H), 1.37-1.27 (m, 1H), 0.94 (d, J=6.3 Hz, 6H), 1.03-0.85 (m, 1H), 0.51 (t, J=7.2 Hz, 3H).

Preparation Example 31

Preparation of Compound E7

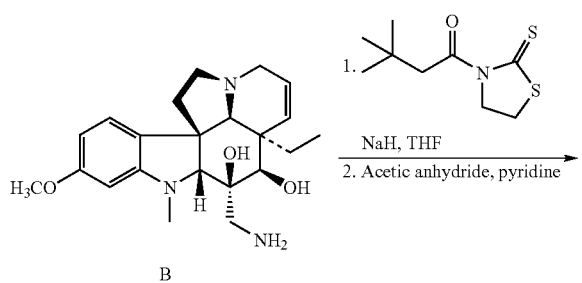

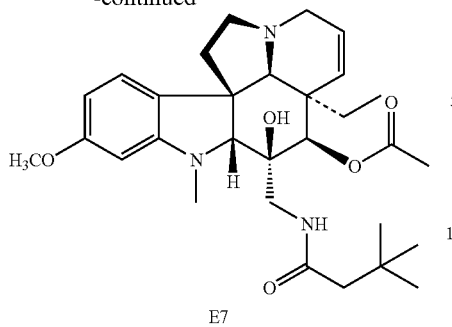

E7

Compound E7 was prepared following the procedure for preparing compound E3.

$^1$H NMR (CDCl$_3$, 300 MHz): δ: 9.25 (brs, 1H), 6.88 (d, J=8.1 Hz, 1H), 6.32 (dd, J=8.1, 2.1 Hz, 1H), 6.15 (d, J=2.1 Hz, 1H), 6.10 (d, J=8.1 Hz, 1H), 5.89 (dd, J=9.9, 3.3 Hz, 1H), 5.36 (d, J=9.9 Hz, 1H), 5.02 (s, 1H), 3.79 (s, 3H), 3.79-3.72 (m, 1H), 3.48 (dd, J=15.9, 5.1 Hz, 1H), 3.42-3.34 (m, 1H), 3.42 (s, 1H), 3.03 (d, J=13.2 Hz, 1H), 2.87 (s, 3H), 2.83 (d, J=15.9 Hz, 1H), 2.64 (s, 1H), 2.57-2.48 (m, 1H), 2.35-2.16 (m, 2H), 2.12 (s, 3H), 2.10 (s, 2H), 1.37-1.27 (m, 1H), 0.94 (d, J=6.3 Hz, 6H), 1.03 (s, 9H), 0.87-0.80 (m, 1H), 0.50 (t, J=7.2 Hz, 3H).

Preparation Example 32

Preparation of Compound E8

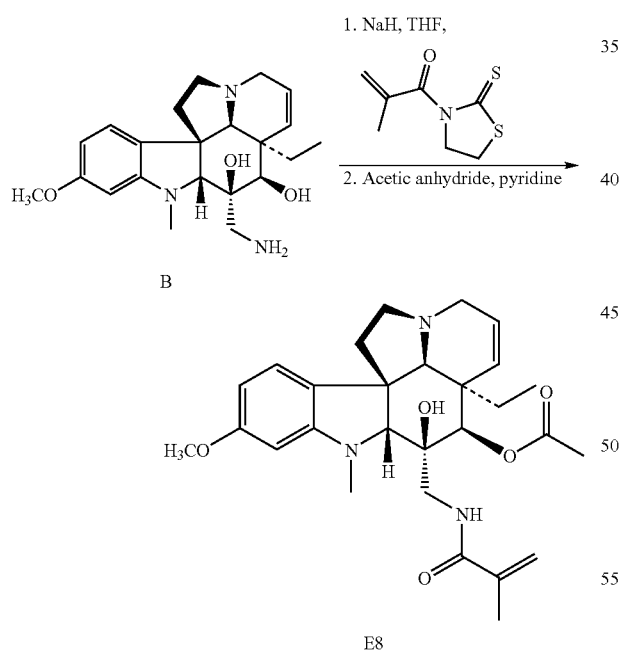

E8

Compound E8 was prepared following the procedure for preparing compound E3.

$^1$H NMR (CDCl$_3$, 300 MHz): δ: 9.15 (s, 1H), 6.88 (d, J=8.4 Hz, 1H), 6.59 (d, J=7.2 Hz, 1H), 6.32 (dd, J=8.4, 2.1 Hz, 1H), 6.15 (d, J=2.1 Hz, 1H), 5.89 (dd, J=10.2, 3.6 Hz, 1H), 5.70 (s, 1H), 5.37 (d, J=10.5 Hz, 1H), 5.31 (s, 1H), 5.00 (s, 1H), 3.86-3.79 (m, 1H), 3.79 (s, 3H), 3.48 (dd, J=15.9, 4.8 Hz, 1H), 3.42-3.36 (m, 1H), 3.39 (s, 1H), 3.09 (d, J=13.8 Hz, 1H), 2.88 (s, 3H), 2.81 (d, J=16.2 Hz, 1H), 2.68 (s, 1H), 2.58-2.49 (m, 1H), 2.32-2.15 (m, 2H), 2.10 (s, 3H), 1.96 (s, 3H), 1.37-1.30 (m, 1H), 1.09-0.99 (m, 1H), 0.54 (t, J=7.2 Hz, 3H).

Preparation Example 33

Preparation of Compound E9

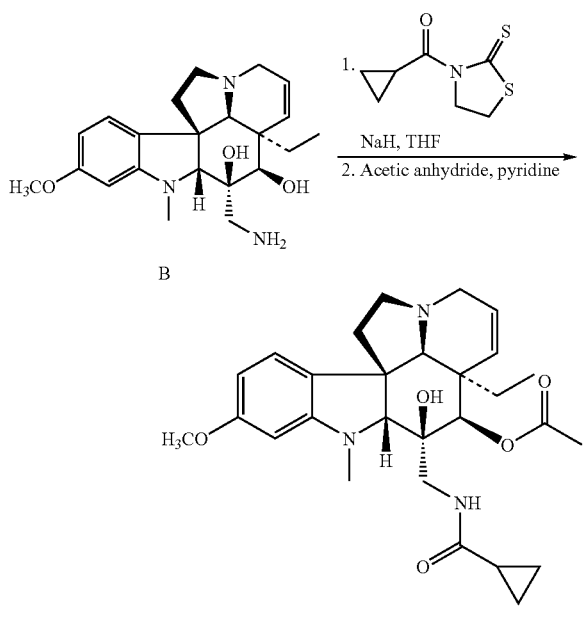

E9

Compound E9 was prepared following the procedure for preparing compound E3.

$^1$H NMR (CDCl$_3$, 300 MHz): δ: 9.02 (s, 1H), 6.87 (d, J=8.1 Hz, 1H), 6.31 (dd, J=8.1, 2.4 Hz, 2H), 6.14 (d, J=2.4 Hz, 1H), 5.89 (d, J=10.2, 3.6 Hz, 1H), 5.37 (d, J=10.2 Hz, 1H), 5.01 (s, 1H), 3.75 (s, 3H), 3.75-3.70 (m, 1H), 3.51 (dd, J=15.9, 4.5 Hz, 1H), 3.43 (s, 1H), 3.43-3.35 (m, 1H), 3.09 (d, J=13.5 Hz, 1H), 2.86 (s, 3H), 2.82 (d, J=15.9 Hz, 1H), 2.65 (s, 1H), 2.58-2.49 (m, 1H), 2.34-2.20 (m, 2H), 2.10 (s, 3H), 1.44-1.29 (m, 2H), 1.18-1.07 (m, 1H), 1.00-0.91 (m, 2H), 0.76-0.67 (m, 2H), 0.52 (t, J=7.5 Hz, 3H).

Preparation Example 34

Preparation of Compound E10

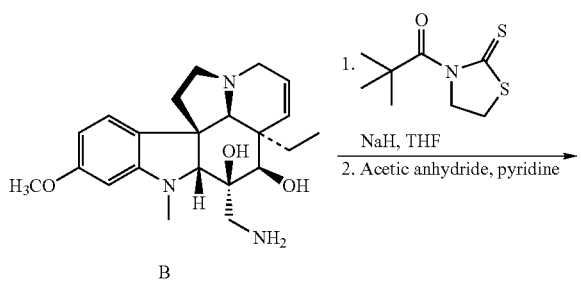

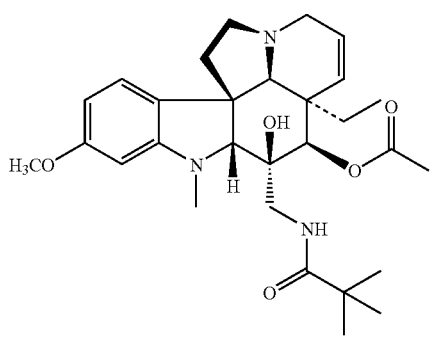

E10

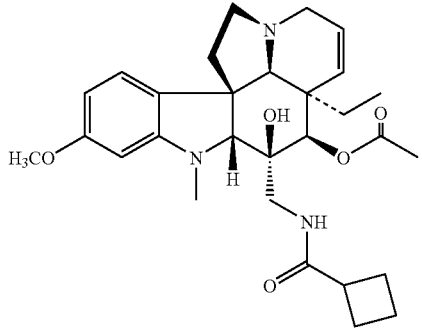

E11

Compound B (1.0 mmol) and ligand III (3-pivalyl-thiazo-lidine-2-thione) (1.1 mmol) were dissolved in 10 mL of anhydrous tetrahydrofunan under argon atmosphere, followed by addition of sodium hydride (60%, 1 mmol). After 1-4 h of stirring at room temperature, 1 mL of saturated ammonium chloride solution was added, and the reaction mixture was extracted with chloroform. The organic phase was dried over magnesium sulfate and concentrated under reduced pressure. The concentrate was dissolved in 1 mL of pyridine under argon atmosphere, followed by addition of 1 mL of acetic anhydride. After 8 h of stirring at room temperature, 30 mL of ethyl acetate and 10 mL of saturated sodium bicarbonate solution were added and the stirring continued for 2 minutes. After the water layer was removed and pyridine was washed off with water (20 mL×3), the ethyl acetate layer was dried, concentrated and purified by silica gel chromatography to obtain compound E10.

$^1$H NMR (CDCl$_3$, 300 MHz): δ: 6.85 (d, J=8.4 Hz, 1H), 6.44 (d, J=8.1 Hz, 1H), 6.29 (d, J=8.1 Hz, 1H), 6.08 (s, 1H), 5.84 (dd, J=9.9, 4.2 Hz, 1H), 5.61 (d, J=9.9 Hz, 1H), 4.97 (s, 1H), 3.74 (s, 3H), 3.65 (m, 2H), 3.41 (m, 2H), 3.33 (s, 1H), 3.28 (m, 1H), 2.98 (d, J=13.2 Hz, 1H), 2.84 (s, 3H), 2.73 (d, J=4.8 Hz, 1H), 2.59 (s, 1H), 2.47 (m, 1H), 2.16 (m, 2H), 2.09 (s, 1H), 2.05 (s, 3H), 1.92 (s, 3H), 1.30 (m, 1H), 1.17 (s, 9H), 0.90 (m, 1H), 0.57 (t, J=7.2 Hz, 3H).

Preparation Example 35

Preparation of Compound E11

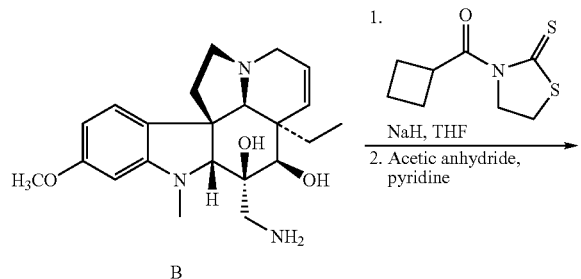

Compound E11 was prepared following the procedure for preparing compound E3.

$^1$H NMR (CDCl$_3$, 300 MHz): δ: 9.17 (s, 1H), 6.87 (d, J=8.1 Hz, 1H), 6.32 (dd, J=8.1, 2.1 Hz, 1H), 6.14 (d, J=2.1 Hz, 1H), 6.07 (d, J=7.8 Hz, 1H), 5.89 (dd, J=10.5, 3.6 Hz, 1H), 5.36 (d, J=10.5 Hz, 1H), 4.98 (s, 1H), 3.80-3.73 (m, 1H), 3.79 (s, 3H), 3.47 (dd, J=15.9, 4.8 Hz, 1H), 3.42-3.34 (m, 1H), 3.37 (s, 1H), 3.05-3.00 (m, 2H), 2.85 (s, 3H), 2.81 (d, J=15.9 Hz, 1H), 2.66 (s, 1H), 2.54-2.48 (m, 1H), 2.32-2.12 (m, 6H), 2.10 (s, 3H), 1.98-1.87 (m, 2H), 1.36-1.25 (m, 1H), 1.05-0.98 (m, 1H), 0.52 (t, J=7.2 Hz, 3H).

Preparation Example 36

Preparation of Compound E12

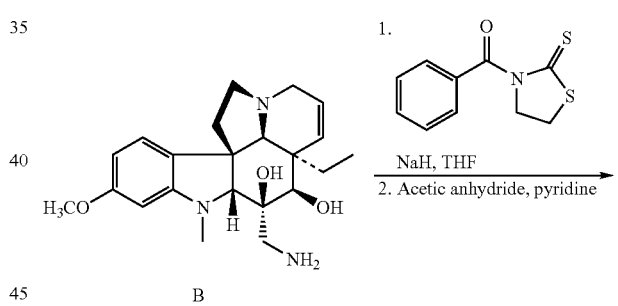

Compound E12 was prepared following the procedure for preparing compound E3.

$^1$H NMR (CDCl$_3$, 300 MHz): δ: 9.28 (brs, 1H), 7.79 (d, J=6.9 Hz, 2H), 7.44 (m, 3H), 6.91 (s, 1H), 6.89 (d, J=8.1 Hz, 1H), 6.33 (d, J=8.1 Hz, 1H), 6.17 (s, 1H), 5.91 (m, 1H), 5.40 (d, J=10.5 Hz, 1H), 5.06 (s, 1H), 3.93 (m, 1H), 3.79 (s, 3H), 3.55-3.41 (m, 3H), 3.25 (d, J=12.9 Hz, 1H), 2.91 (s, 3H), 2.83 (m, 1H), 2.55 (m, 1H), 2.70 (s, 1H), 2.25 (m, 1H), 2.10 (m, 3H), 2.09 (s, 3H), 1.05 (m, 1H), 0.87 (m, 1H), 0.54 (t, J=7.5 Hz, 3H).

Preparation Example 37

Preparation of Compound E13

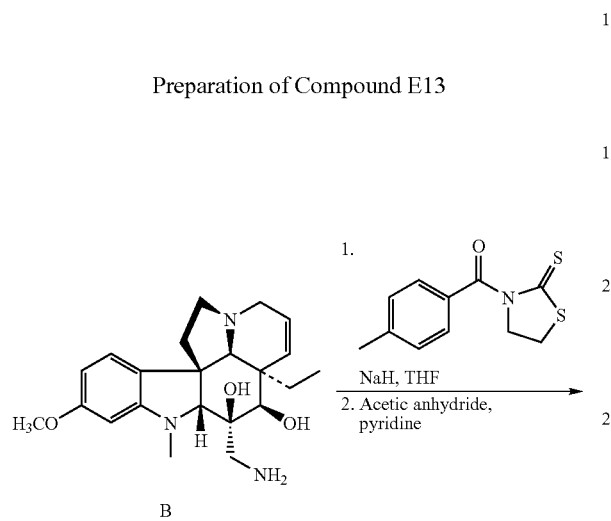

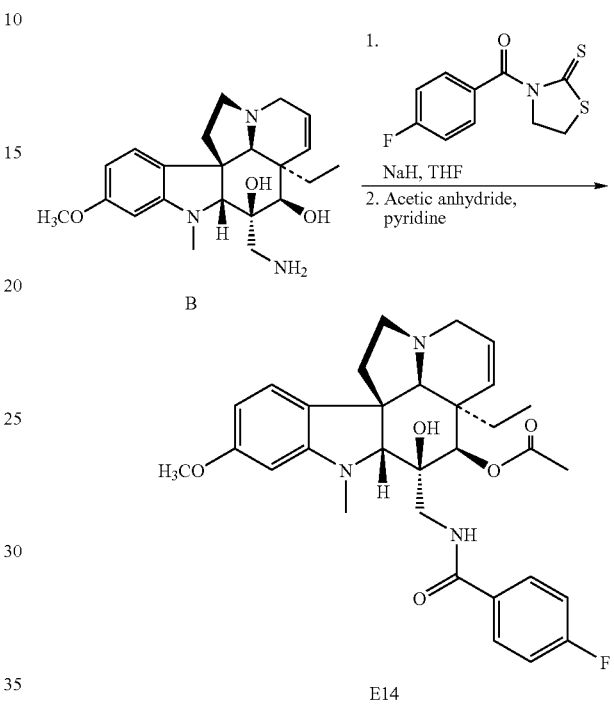

E13

Compound E13 was prepared following the procedure for preparing compound E3.

$^1$H NMR (CDCl$_3$, 300 MHz): δ: 9.23 (brs, 1H), 7.69 (d, J=8.1 Hz, 2H), 7.23 (d, J=8.1 Hz, 2H), 6.89 (d, J=8.1 Hz, 2H), 6.33 (dd, J=8.1, 2.1 Hz, 1H), 6.16 (d, J=2.1 Hz, 1H), 5.91 (dd, J=10.2, 3.9 Hz, 1H), 5.39 (d, J=10.2 Hz, 1H), 5.06 (s, 1H), 3.94 (dd J=13.5, 8.1 Hz, 1H), 3.79 (s, 3H), 3.53-3.38 (m, 2H), 3.46 (s, 1H), 3.24 (d, J=13.5 Hz, 1H), 2.90 (s, 3H), 2.83 (d, J=15.9 Hz, 1H), 2.69 (s, 1H), 2.60-2.50 (m, 1H), 2.39 (s, 3H), 2.34-2.20 (m, 2H), 2.17 (s, 1H), 2.09 (s, 3H), 1.38-1.31 (m, 1H), 1.08-1.01 (m, 1H), 0.54 (t, J=7.5 Hz, 3H).

Preparation Example 38

Preparation of Compound E14

E14

Compound E14 was prepared following the procedure for preparing compound E3.

$^1$H NMR (CDCl$_3$, 300 MHz): δ: 9.28 (s, 1H), 7.79 (t, J=8.1 Hz, 2H), 7.11 (t, J=8.1 Hz, 2H), 6.89 (d, J=8.4 Hz, 1H), 6.34 (d, J=8.4 Hz, 1H), 6.17 (s, 1H), 5.91 (dd, J=10.2, 2.4 Hz, 1H), 5.40 (d, J=10.2 Hz, 1H), 5.05 (s, 1H), 3.97-3.90 (m, 1H), 3.79 (s, 3H), 3.53-3.41 (m, 2H), 3.45 (s, 1H), 3.24 (d, J=13.2 Hz, 1H), 2.90 (s, 3H), 2.85 (d, J=15.9 Hz, 1H), 2.70 (s, 1H), 2.60-2.51 (m, 1H), 2.30-2.17 (m, 2H), 2.09 (s, 3H), 1.37-1.30 (m, 1H), 1.08-1.01 (m, 1H), 0.55 (t, J=7.5 Hz, 3H).

Preparation Example 39

Preparation of Compound E15

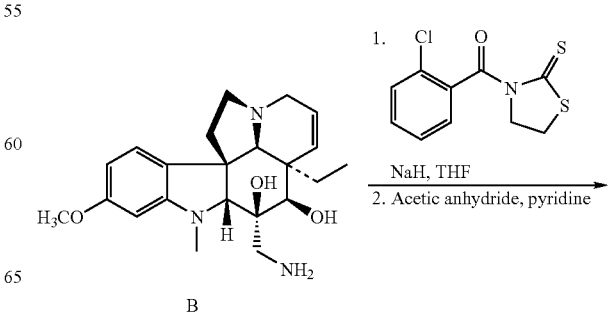

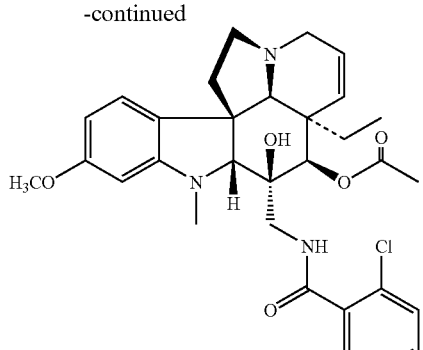

E15

Compound E15 was prepared following the procedure for preparing compound E3.

$^1$H NMR (CDCl$_3$, 300 MHz): δ: 9.16 (s, 1H), 7.51 (d, J=6.6 Hz, 1H), 7.30-7.17 (m, 3H), 6.83 (d, J=9.0 Hz, 1H), 6.80 (d, J=9.9 Hz, 1H), 6.23 (d, J=9.9 Hz, 1H), 6.07 (s, 1H), 5.79 (dd, J=10.2, 4.8 Hz, 1H), 5.30 (d, J=10.2 Hz, 1H), 4.98 (s, 1H), 3.94-3.87 (m, 1H), 3.67 (s, 3H), 3.42 (s, 1H), 3.37 (dd, J=15.9, 4.8 Hz, 1H), 3.27-3.23 (m, 1H), 3.15 (d, J=13.5 Hz, 1H), 2.88 (s, 3H), 2.74 (d, J=16.5 Hz, 1H), 2.57 (s, 1H), 2.47-2.38 (m, 1H), 2.24-2.07 (m, 2H), 2.02 (s, 3H), 1.31-1.19 (m, 1H), 1.02-0.89 (m, 1H), 0.44 (t, J=7.2 Hz, 3H).

Preparation Example 40

Preparation of Compound E16

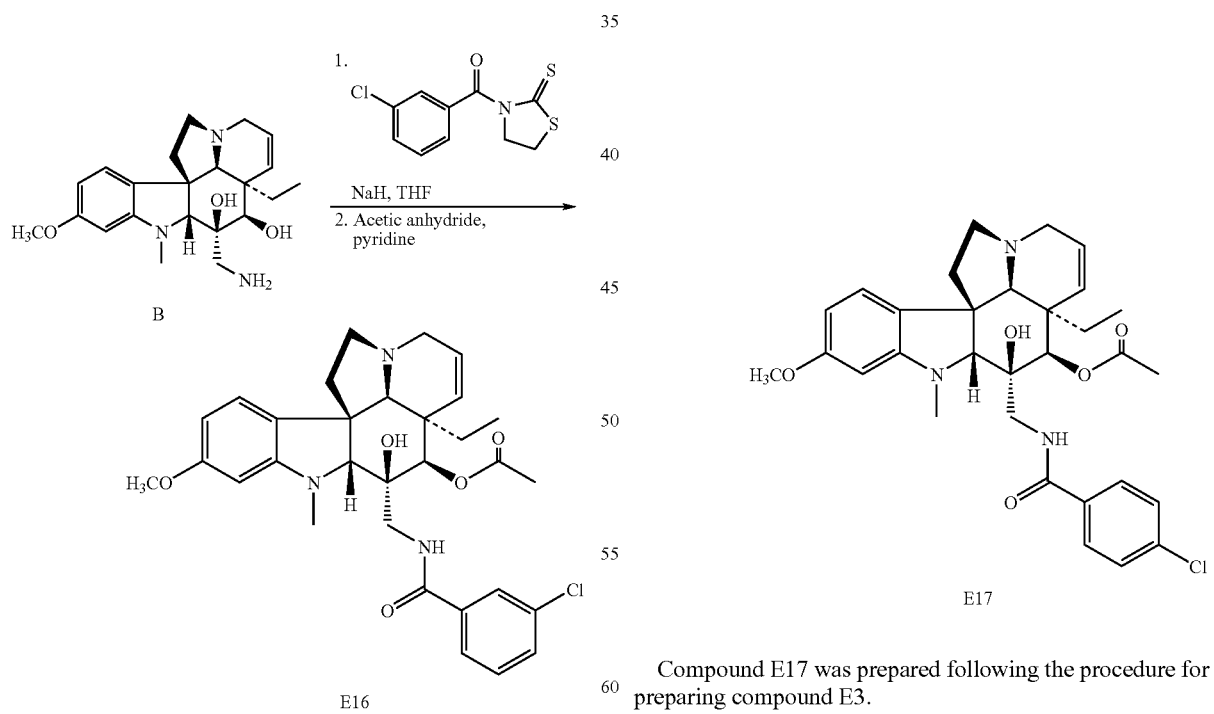

E16

Compound E16 was prepared following the procedure for preparing compound E3.

$^1$H NMR (CDCl$_3$, 300 MHz): δ: 9.29 (brs, 1H), 7.77 (s, 1H), 7.65 (d, J=7.5 Hz, 1H), 7.47 (d, J=7.5 Hz, 1H), 7.37 (t, J=7.5 Hz, 1H), 6.95 (d, J=6.6 Hz, 1H), 6.89 (d, J=8.1 Hz, 1H), 6.34 (d, J=8.1 Hz, 1H), 6.18 (s, 1H), 5.92 (dd, J=10.5, 4.5 Hz, 1H), 5.40 (d, J=10.5 Hz, 1H), 5.05 (s, 1H), 3.95 (dd, J=13.2, 7.5 Hz, 1H), 3.80 (s, 3H), 3.54-3.42 (m, 2H), 3.44 (s, 1H), 3.24 (d, J=13.5 Hz, 1H), 2.91 (s, 3H), 2.84 (d, J=16.5 Hz, 1H), 2.71 (s, 1H), 2.58-2.53 (m, 1H), 2.29-2.23 (m, 2H), 2.10 (s, 3H), 1.37-1.30 (m, 1H), 1.08-1.01 (m, 1H), 0.55 (t, J=7.5 Hz, 3H).

Preparation Example 41

Preparation of Compound E17

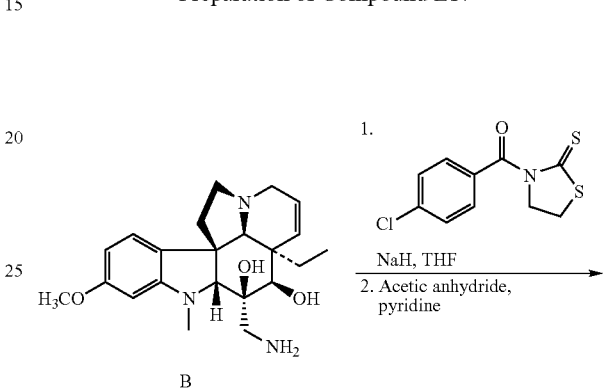

E17

Compound E17 was prepared following the procedure for preparing compound E3.

$^1$H NMR (CDCl$_3$, 300 MHz): δ: 9.21 (brs, 1H), 7.64 (d, J=8.7 Hz, 2H), 7.28 (d, J=8.7 Hz, 1H), 6.89 (d, J=7.2 Hz, 1H), 6.81 (d, J=8.1 Hz, 1H), 6.25 (d, J=8.1 Hz, 1H), 6.08 (s, 1H), 5.83 (dd, J=9.9, 4.5 Hz, 1H), 5.31 (d, J=9.9 Hz, 1H), 4.97 (s, 1H), 3.88-3.80 (m, 1H), 3.68 (s, 3H), 3.43-3.31 (m, 2H), 3.37 (s, 1H), 3.18 (d, J=13.5 Hz, 1H), 2.81 (s, 3H), 2.76 (d, J=16.5

Hz, 1H), 2.62 (s, 1H), 2.47 (q, J=9.3 Hz, 1H), 2.24-2.13 (m, 2H), 1.97 (s, 3H), 1.28-1.19 (m, 1H), 1.02-0.93 (m, 1H), 0.46 (t, J=7.2 Hz, 3H).

Preparation Example 42

Preparation of Compound E18

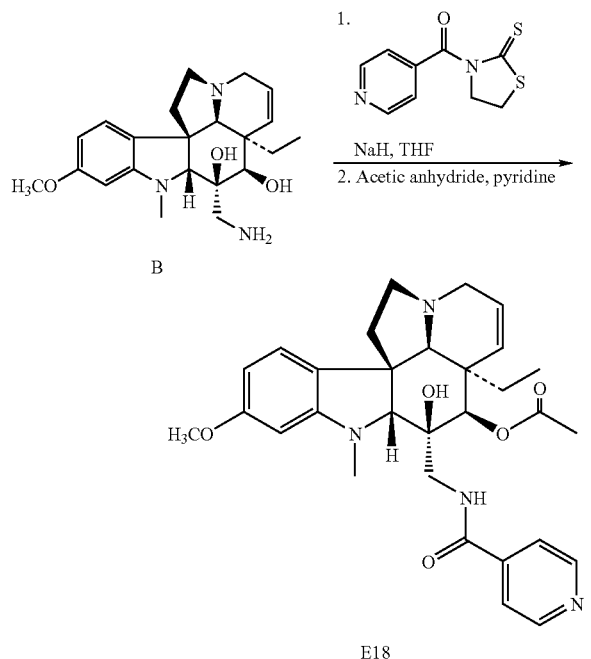

Compound E18 was prepared following the procedure for preparing compound E3.

$^1$H NMR (CDCl$_3$, 300 MHz): δ: 9.37 (brs, 1H), 8.74 (d, J=3.9 Hz, 2H), 7.62 (d, J=3.9 Hz, 2H), 7.10 (d, J=5.4 Hz, 1H), 6.90 (d, J=8.4 Hz, 1H), 6.35 (d, J=8.4 Hz, 1H), 6.18 (s, 1H), 5.91 (dd, J=10.2, 4.5 Hz, 1H), 5.40 (d, J=10.2 Hz, 1H), 5.05 (s, 1H), 3.99-3.92 (m, 1H), 3.80 (s, 3H), 3.52-3.42 (m, 2H), 3.42 (s, 1H), 3.26 (d, J=13.5 Hz, 1H), 2.90 (s, 3H), 2.86 (d, J=16.5 Hz, 1H), 2.72 (s, 1H), 2.57 (q, J=9.6 Hz, 1H), 2.26-2.17 (m, 2H), 2.09 (s, 3H), 1.31-1.25 (m, 1H), 1.08-1.03 (m, 1H), 0.56 (t, J=7.2 Hz, 3H).

Preparation Example 43

Preparation of Compound E19

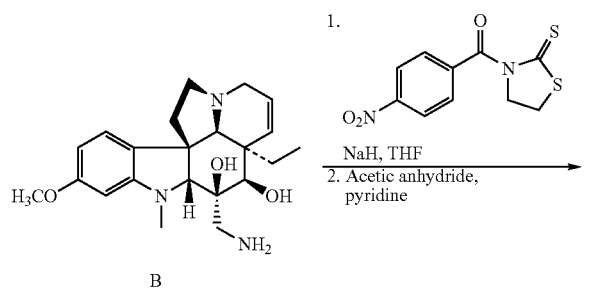

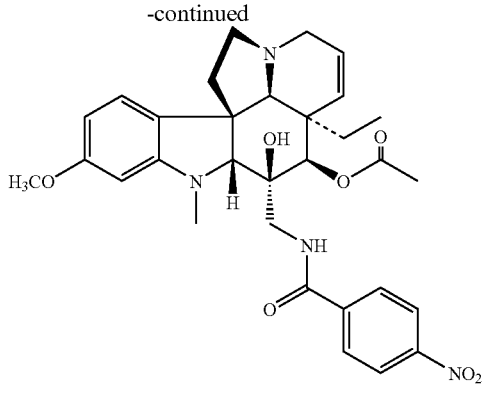

Compound E19 was prepared following the procedure for preparing compound E3.

$^1$H NMR (CDCl$_3$, 300 MHz): δ: 9.37 (s, 1H), 8.29 (d, J=8.7 Hz, 2H), 7.93 (d, J=8.7 Hz, 2H), 7.11 (d, J=5.4 Hz, 1H), 6.90 (d, J=7.8 Hz, 1H), 6.36 (d, J=7.8 Hz, 1H), 6.18 (s, 1H), 5.91 (dd, J=10.2, 4.5 Hz, 1H), 5.40 (d, J=10.2 Hz, 1H), 5.05 (s, 1H), 4.01-3.94 (m, 1H), 3.80 (s, 3H), 3.53-3.42 (m, 2H), 3.43 (s, 1H), 3.27 (d, J=13.5 Hz, 1H), 2.91 (s, 3H), 2.86 (d, J=16.5 Hz, 1H), 2.73 (s, 1H), 2.62-2.53 (m, 1H), 2.33-2.17 (m, 2H), 2.09 (s, 3H), 1.36-1.25 (m, 1H), 1.08-1.01 (m, 1H), 0.56 (t, J=7.2 Hz, 3H).

Preparation Example 44

Preparation of Compound E20

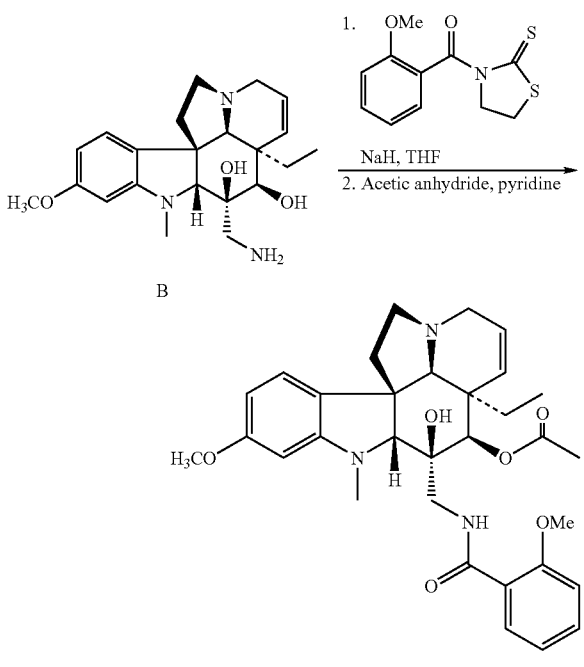

Compound E20 was prepared following the procedure for preparing compound E3.

$^1$H NMR (CDCl$_3$, 300 MHz): δ: 9.09 (s, 1H), 8.45 (d, J=7.8 Hz, 1H), 8.15 (d, J=7.5 Hz, 1H), 7.43 (t, J=7.8 Hz, 1H), 7.06

(t, J=7.8 Hz, 1H), 6.97 (d, J=7.8 Hz, 1H), 6.88 (d, J=8.4 Hz, 1H), 6.30 (d, J=8.4 Hz, 1H), 6.14 (s, 1H), 5.88 (dd, J=10.2, 4.8 Hz, 1H), 5.37 (d, J=10.2 Hz, 1H), 5.07 (s, 1H), 4.01-3.93 (m, 1H), 3.94 (s, 3H), 3.79 (s, 3H), 3.54-3.30 (m, 2H), 3.49 (s, 1H), 3.26 (d, J=13.5 Hz, 1H), 2.88 (s, 3H), 2.83 (d, J=16.5 Hz, 1H), 2.65 (s, 1H), 2.58-2.49 (m, 1H), 2.35-2.16 (m, 2H), 2.01 (s, 3H), 1.42-1.35 (m, 1H), 1.08-1.01 (m, 1H), 0.52 (t, J=7.2 Hz, 3H).

Preparation Example 45

Preparation of Compound E21

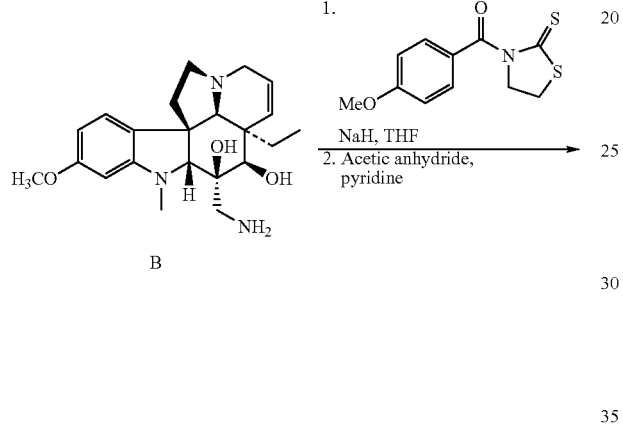

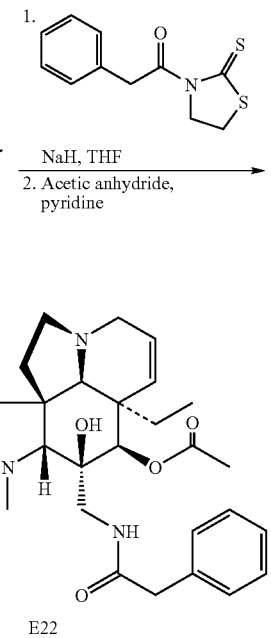

Compound E21 was prepared following the procedure for preparing compound E3.

$^1$H NMR (CDCl$_3$, 300 MHz): δ: 9.04 (brs, 1H), 7.19 (d, J=8.4 Hz, 2H), 6.87 (d, J=8.4 Hz, 2H), 6.85 (d, J=8.1 Hz, 1H), 6.32 (dd, J=8.1, 2.1 Hz, 1H), 6.16 (d, J=8.1 Hz, 1H), 6.02 (s, 1H), 5.87 (dd, J=10.2, 3.6 Hz, 1H), 5.32 (d, J=10.2 Hz, 1H), 4.89 (s, 1H), 3.86-3.82 (m, 1H), 3.81 (s, 3H), 3.79 (s, 3H), 3.48 (s, 1H), 3.48-3.41 (m, 1H), 3.35-3.27 (m, 1H), 3.16 (s, 1H), 2.92 (d, J=13.5 Hz, 1H), 2.80 (d, J=15.9 Hz, 1H), 2.64 (s, 3H), 2.53-2.44 (m, 1H), 2.26-2.00 (m, 2H), 2.09 (s, 3H), 1.39-1.27 (m, 1H), 1.03-0.91 (m, 1H), 0.51 (t, J=7.2 Hz, 3H).

Preparation Example 46

Preparation of Compound E22

Compound E22 was prepared following the procedure for preparing compound E3.

$^1$H NMR (CDCl$_3$, 300 MHz): δ: 7.26-7.20 (m, 5H), 6.79 (d, J=8.4 Hz, 1H), 6.25 (d, J=8.4 Hz, 1H), 6.10 (d, J=9.0 Hz, 1H), 5.95 (s, 1H), 5.81 (dd, J=10.2, 4.2 Hz, 1H), 5.26 (d, J=10.2 Hz, 1H), 4.83 (s, 1H), 3.79-3.73 (m, 1H), 3.73 (s, 3H), 3.48 (s, 2H), 3.38 (dd, J=15.9, 5.1 Hz, 1H), 3.30-3.20 (m, 1H), 3.08 (s, 1H), 2.86 (d, J=13.8 Hz, 1H), 2.74 (d, J=15.9 Hz, 1H), 2.55 (s, 3H), 2.47-2.38 (m, 1H), 2.20-1.93 (m, 2H), 2.02 (s, 1H), 1.30-1.19 (m, 1H), 0.94-0.89 (m, 1H), 0.45 (t, J=7.2 Hz, 3H).

Preparation Example 47

Preparation of Compound E23

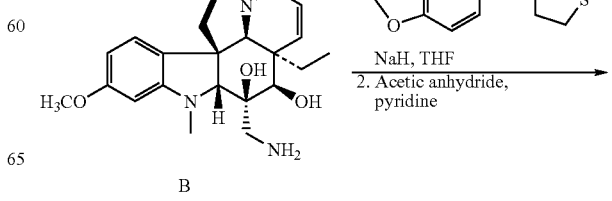

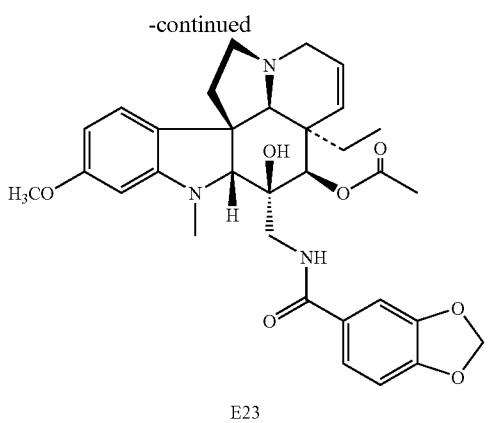

E23

Compound E23 was prepared following the procedure for preparing compound E3.

$^1$H NMR (CDCl$_3$, 300 MHz): δ: 9.26 (brs, 1H), 7.32 (d, J=8.1 Hz, 1H), 7.28 (s, 1H), 6.88 (d, J=8.4 Hz, 1H), 6.83 (d, J=8.1 Hz, 1H), 6.82 (s, 1H), 6.33 (d, J=8.4 Hz, 1H), 6.16 (d, J=2.1 Hz, 1H), 6.02 (s, 2H), 5.91 (dd, J=10.2, 3.6 Hz, 1H), 5.39 (d, J=10.2 Hz, 1H), 5.04 (s, 1H), 3.89 (dd J=13.5, 8.1 Hz, 1H), 3.79 (s, 3H), 3.54-3.42 (m, 2H), 3.45 (s, 1H), 3.22 (d, J=13.5 Hz, 1H), 2.89 (s, 3H), 2.83 (d, J=15.9 Hz, 1H), 2.69 (s, 1H), 2.60-2.51 (m, 1H), 2.33-2.10 (m, 2H), 2.09 (s, 3H), 1.37-1.25 (m, 1H), 1.07-1.00 (m, 1H), 0.54 (t, J=7.5 Hz, 3H).

Preparation Example 48

Preparation of Compound F1

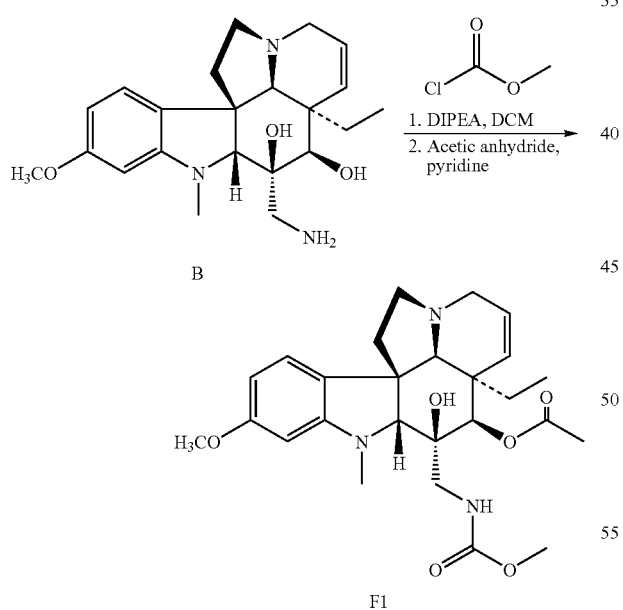

To a solution of compound B (1.0 mmol) in methylene chloride (10 mL) was added diisopropylethylamine (1.2 mmol, 0.21 mL), followed by slowly dropwise addition of methyl chloroformate (1.2 mmol, 93 µL) under ice bath. After 0.5 h of stirring, the ice bath was removed, and the reaction continued for a further 24 h at room temperature. After quenched with 10 mL of saturated sodium bicarbonate solution, the reaction mixture was extracted triply with methylene chloride (10 mL×3). The combined organic phase was dried over anhydrous sodium sulfate and concentrated under reduced pressure. The concentrate was dissolved in 1 mL of pyridine, followed by addition of 1 mL of acetic anhydride. After 8 h of stirring at room temperature, 30 mL of ethyl acetate and 10 mL of saturated sodium bicarbonate solution were added and the stirring continued for 2 minutes. After the water layer was removed and pyridine was washed off with water (20 mL×3), the ethyl acetate layer is dried, concentrated and purified by silica gel chromatography (eluted with petroleum ether:acetone=6:1 v/v) to give 300 mg of compound F1 as a white powder in 62% yield.

$^1$H NMR (CDCl$_3$, 300 MHz): δ: 9.04 (s), 6.84 (d, J=8.1 Hz, 1H), 6.28 (dd, J=8.1, 2.1 Hz, 1H), 6.12 (d, J=2.1 Hz, 1H), 5.85 (dd, J=10.2, 4.5 Hz, 1H), 5.34 (d, J=10.2 Hz, 1H), 5.29 (s, 1H), 4.98 (s, 1H), 3.82 (s, 3H), 3.75 (s, 3H), 3.47 (m, 1H), 3.40 (s, 1H), 3.32 (m, 3H), 3.09 (d, J=12.6 Hz, 1H), 2.87 (s, 3H), 2.82 (d, J=15.6 Hz, 1H), 2.59 (s, 1H), 2.49 (m, 1H), 2.30-2.12 (m, 2H), 2.08 (s, 3H), 1.27 (m, 1H), 0.98 (m, 1H), 0.49 (t, J=7.5 Hz, 3H).

$^{13}$C NMR (CDCl$_3$, 75 MHz): δ: 170.7 (C), 161.1 (C), 157.3 (C), 154.5 (C), 130.5 (CH), 125.8 (C), 124.2 (CH), 122.7 (CH), 105.2 (CH), 96.8 (CH), 82.0 (CH), 77.2 (CH), 76.0 (C), 67.5 (CH), 55.4 (OCH$_3$), 52.3 (C), 52.2 (OCH$_3$), 51.7 (CH$_2$), 50.9 (CH$_2$), 45.2 (CH$_2$), 44.8 (CH$_2$), 42.9 (C), 40.7 (CH$_3$), 31.5 (CH$_2$), 21.0 (CH$_3$), 7.6 (CH$_3$).

Preparation Example 49

Preparation of Compound F2

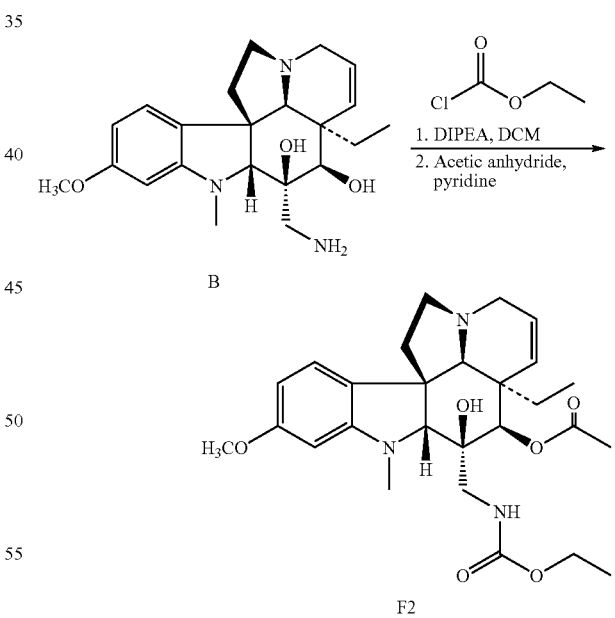

Compound F2 was prepared following the procedure for Preparation of compound F1.

$^1$H NMR (CDCl$_3$, 300 MHz): δ: 9.05 (s), 6.86 (d, J=8.1 Hz, 1H), 6.30 (dd, J=8.1, 2.4 Hz, 1H), 6.14 (d, J=2.4 Hz, 1H), 5.87 (dd, J=10.2, 4.5 Hz, 1H), 5.34 (d, J=10.2 Hz, 1H), 5.26 (s, 1H), 5.00 (s, 1H), 4.09 (q, J=6.9 Hz, 1H), 3.78 (s, 3H), 3.51 (m, 1H), 3.43 (s, 1H), 3.35 (m, 2H), 3.11 (d, J=12.3 Hz, 1H), 2.90 (s, 3H), 2.81 (d, J=15.9 Hz, 1H), 2.62 (s, 1H), 2.50 (m,

1H), 2.26-2.17 (m, 2H), 2.10 (s, 3H), 1.27 (m, 1H), 1.22 (t, J=6.9 Hz, 3H), 1.00 (m, 1H), 0.51 (t, J=7.5 Hz, 3H).

Preparation Example 50

Preparation of Compound F3

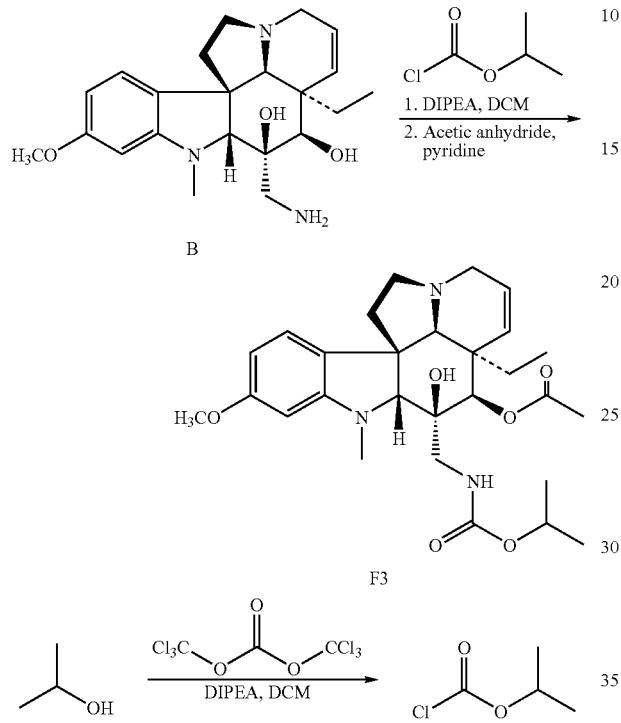

To a solution of isopropanol (2.4 mmol, 0.18 mL) in 10 mL of methylene chloride was added diisopropylethylamine (2.4 mmol, 0.42 mL) under argon atmosphere, followed by dropwise addition of a solution of solid phosgene (0.9 mmol, 270 mg) in methylene chloride (5 mL) under ice bath. After 0.5 h of stirring under ice bath and 1 h at room temperature, another diisopropylethylamine (1.0 mmol, 0.21 mL) was added under ice bath, and the resulted mixture was slowly added dropwise into a solution of compound B (1 mmol) in methylene chloride (3 mL). After 0.5 h of stirring under ice bath and 3 h at room temperature, 10 mL of saturated sodium bicarbonate solution was added, and the reaction mixture was extracted with methylene chloride (10 mL×3). The organic phase was dried over anhydrous sodium sulfate and concentrated under reduced pressure. The concentrate was dissolved in 1 mL of pyridine, followed by addition of 1 mL of acetic anhydride. After 8 h of stirring at room temperature, 30 mL of ethyl acetate and 10 mL of saturated sodium bicarbonate solution were added and the stirring continued for 2 minutes. After the water layer was removed and pyridine was washed off with water (20 mL×3), the ethyl acetate layer was dried, concentrated and purified by silica gel chromatography (eluted with petroleum ether:acetone=6:1 v/v) to give 222 mg of compound F3 as a white powder in 43% yield.

$^1$H NMR (CDCl$_3$, 300 MHz): δ: 9.01 (s), 6.78 (d, J=8.1 Hz, 1H), 6.21 (dd, J=8.1, 1.8 Hz, 1H), 6.04 (d, J=1.8 Hz, 1H), 5.78 (dd, J=10.2, 3.9 Hz, 1H), 5.27 (d, J=10.2 Hz, 1H), 5.17 (d, J=6.6 Hz, 1H), 4.92 (s, 1H), 4.79 (m, 1H), 3.67 (s, 3H), 3.40 (m, 2H), 3.35 (s, 1H), 3.24 (m, 1H), 3.02 (d, J=12.6 Hz, 1H), 2.80 (s, 3H), 2.73 (d, J=16.2 Hz, 1H), 2.54 (s, 1H), 2.42 (m, 1H), 2.22-2.11 (m, 2H), 2.00 (s, 3H), 1.20 (m, 1H), 1.11 (d, J=6.0 Hz, 6H), 0.95 (m, 1H), 0.42 (t, J=7.2 Hz, 3H).

Preparation Example 51

Preparation of Compound F4

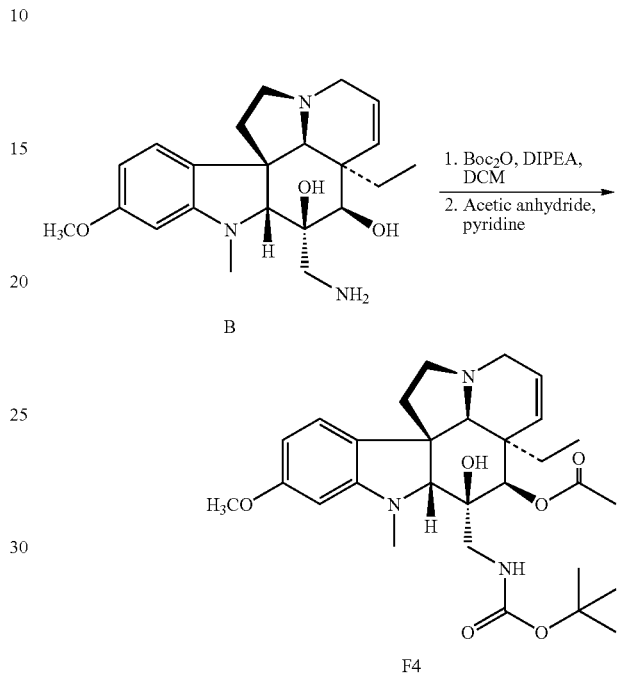

Compound F4 was prepared following the procedure for preparing compound F1.

$^1$H NMR (CDCl$_3$, 300 MHz): δ: 9.01 (s), 6.79 (d, J=8.1 Hz, 1H), 6.21 (dd, J=8.1, 1.8 Hz, 1H), 6.04 (d, J=1.8 Hz, 1H), 5.80 (dd, J=10.2, 4.5 Hz, 1H), 5.28 (d, J=10.2 Hz, 1H), 5.22 (s, 1H), 4.92 (s, 1H), 3.67 (s, 3H), 3.40 (m, 2H), 3.35 (s, 1H), 3.25 (m, 1H), 3.03 (d, J=12.3 Hz, 1H), 2.80 (s, 3H), 2.73 (d, J=15.9 Hz, 1H), 2.54 (s, 1H), 2.43 (m, 1H), 2.22-2.06 (m, 2H), 2.00 (s, 3H), 1.36 (s, 9H), 1.20 (m, 1H), 0.90 (m, 1H), 0.50 (t, J=7.2 Hz, 3H).

Preparation Example 52

Preparation of Compound F5

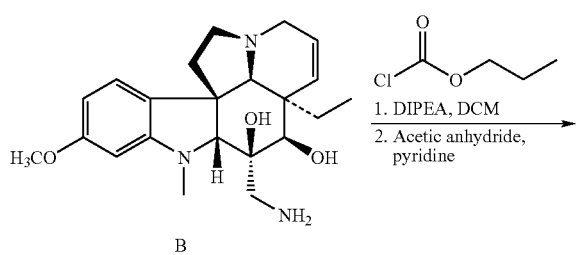

-continued

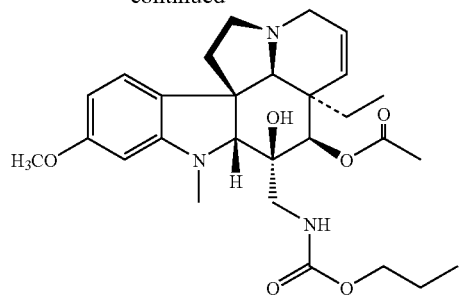

F5

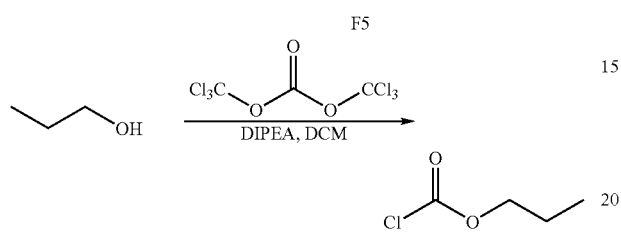

Compound F5 was prepared following the procedure for preparing compound F3.

¹H NMR (CDCl₃, 300 MHz): δ: 8.95 (s), 6.76 (d, J=8.4 Hz, 1H), 6.19 (dd, J=8.4, 1.8 Hz, 1H), 6.02 (d, J=1.8 Hz, 1H), 5.77 (dd, J=10.2, 4.2 Hz, 1H), 5.25 (d, J=10.2 Hz, 1H), 5.20 (s, 1H), 4.89 (s, 1H), 3.88 (t, J=6.3 Hz, 2H), 3.63 (s, 3H), 3.40-3.36 (m, 1H), 3.33 (s, 1H), 3.23 (m, 1H), 3.10 (m, 1H), 3.01 (d, J=12.6 Hz, 1H), 2.78 (s, 3H), 2.71 (d, J=16.2 Hz, 1H), 2.52 (s, 1H), 2.40 (q, J=9.0 Hz, 1H), 2.16-2.11 (m, 2H), 1.90 (s, 3H), 1.53-1.46 (m, 2H), 1.22-1.14 (m, 1H), 0.92-0.83 (m, 1H), 0.80 (t, J=7.2 Hz, 3H), 0.40 (t, J=7.5 Hz, 3H).

Preparation Example 53

Preparation of Compound F6

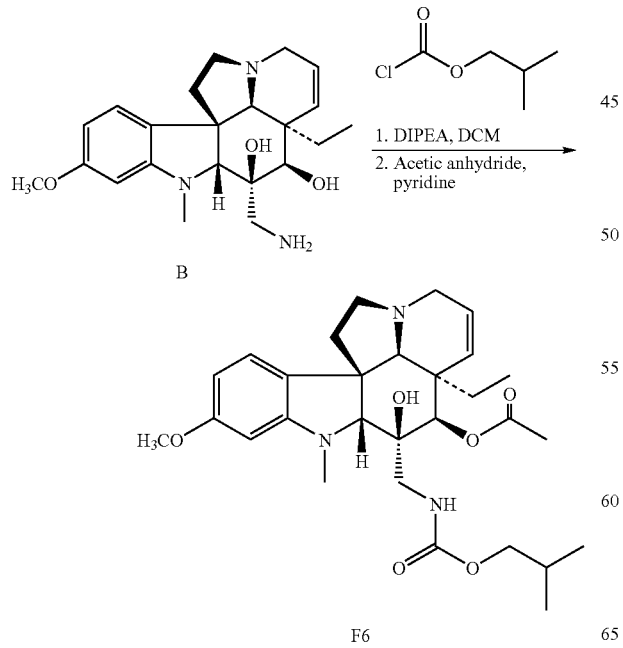

Compound F6 was prepared following the procedure for preparing compound F1.

¹H NMR (CDCl₃, 300 MHz): δ: 9.01 (s), 6.79 (d, J=8.1 Hz, 1H), 6.21 (dd, J=8.1, 1.8 Hz, 1H), 6.04 (d, J=1.8 Hz, 1H), 5.80 (dd, J=10.2, 4.5 Hz, 1H), 5.28 (d, J=10.2 Hz, 1H), 5.22 (s, 1H), 4.92 (s, 1H), 3.73 (d, J=6.3 Hz, 2H), 167 (s, 3H), 3.40 (m, 2H), 3.35 (s, 1H), 3.25 (m, 1H), 3.03 (d, J=12.3 Hz, 1H), 2.80 (s, 3H), 2.73 (d, J=15.9 Hz, 1H), 2.54 (s, 1H), 2.43 (m, 1H), 2.22-2.06 (m, 2H), 2.00 (s, 3H), 1.78 (m, 1H), 1.20 (m, 1H), 0.90 (m, 1H), 0.80 (d, J=6.6 Hz, 6H), 0.42 (t, J=6.9 Hz, 3H).

Preparation Example 54

Preparation of Compound F7

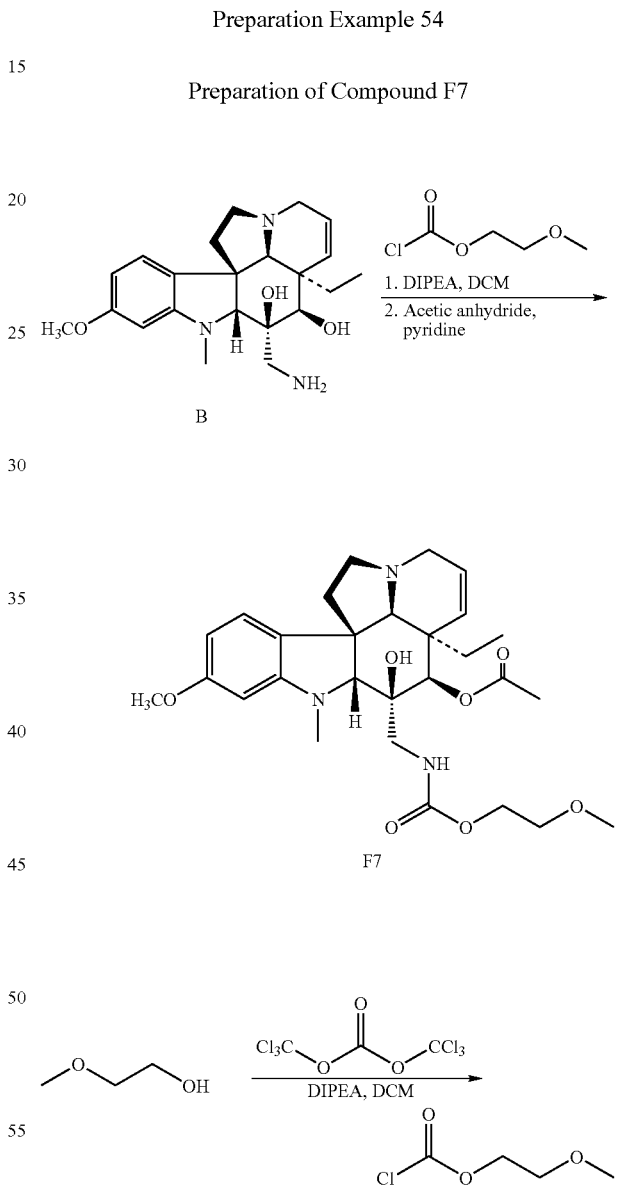

Compound F7 was prepared following the procedure for preparing compound F3.

¹H NMR (CDCl₃, 300 MHz): δ: 8.98 (s), 6.81 (d, J=8.4 Hz, 1H), 6.24 (d, J=8.4 Hz, 1H), 6.07 (s, 1H), 5.80 (dd, J=10.2, 4.2 Hz, 1H), 5.39 (d, J=7.2 Hz, 1H), 5.30 (d, J=10.2 Hz, 1H), 4.94 (s, 1H), 4.14 (t, J=6.3 Hz, 2H), 3.71 (s, 3H), 3.50 (t, J=6.3 Hz, 2H), 3.50-3.18 (m, 3H), 3.38 (s, 1H), 3.30 (s, 3H), 3.05 (d, J=12.6 Hz, 1H), 2.83 (s, 3H), 2.75 (d, J=15.3 Hz, 1H), 2.56 (s,

1H), 2.45 (q, J=9.0 Hz, 1H), 2.24-2.08 (m, 2H), 2.04 (s, 3H), 1.26-1.18 (m, 1H), 0.99-0.87 (m, 1H), 0.45 (t, J=7.2 Hz, 3H).

Preparation Example 55

Preparation of Compound F8

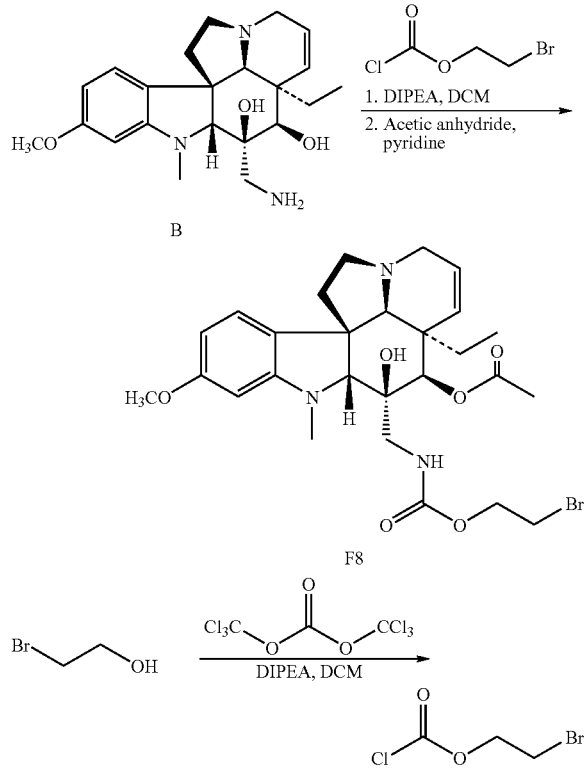

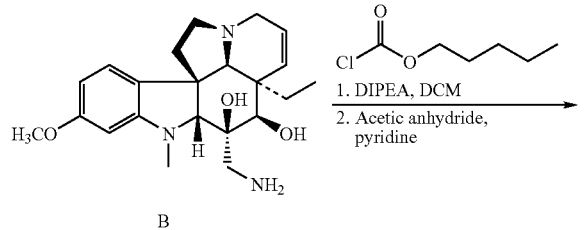

Compound F8 was prepared following the procedure for preparing compound F3.

$^1$H NMR (CDCl$_3$, 300 MHz): δ: 9.12 (s), 6.87 (d, J=8.4 Hz, 1H), 6.32 (dd, J=8.4, 2.4 Hz, 1H), 6.15 (d, J=2.4 Hz, 1H), 5.89 (dd, J=10.5, 3.6 Hz, 1H), 5.43 (m, 1H), 5.38 (d, J=10.5 Hz, 1H), 5.01 (s, 1H), 4.35 (t, J=6.3 Hz, 2H), 3.79 (s, 3H), 3.49 (t, J=6.3 Hz, 2H), 3.52-3.30 (m, 3H), 3.43 (s, 1H), 3.14 (d, J=13.2 Hz, 1H), 2.91 (s, 3H), 2.83 (d, J=14.7 Hz, 1H), 2.64 (s, 1H), 2.53 (q, J=9.0 Hz, 1H), 2.25-2.10 (m, 2H), 2.12 (s, 3H), 1.26-1.18 (m, 1H), 1.10-0.87 (m, 1H), 0.52 (t, J=7.2 Hz, 3H).

Preparation Example 56

Preparation of Compound F9

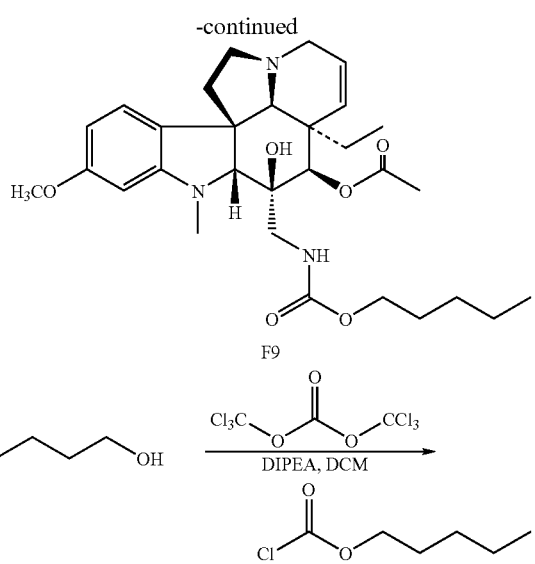

Compound F9 was prepared following the procedure for preparing compound F3.

$^1$H NMR (CDCl$_3$, 300 MHz): δ: 9.05 (s), 6.82 (d, J=8.1 Hz, 1H), 6.25 (dd, J=8.1, 2.1 Hz, 1H), 6.04 (d, J=2.1 Hz, 1H), 5.82 (dd, J=10.2, 3.3 Hz, 1H), 5.31 (d, J=10.2 Hz, 1H), 5.25 (d, J=10.2 Hz, 1H), 4.96 (s, 1H), 3.97 (t, J=6.3 Hz, 2H), 3.71 (s, 3H), 3.45 (m, 2H), 3.39 (s, 1H), 3.29 (m, 1H), 3.07 (d, J=12.3 Hz, 1H), 2.84 (s, 3H), 2.77 (d, J=15.9 Hz, 1H), 2.58 (s, 1H), 2.46 (m, 1H), 2.26-2.10 (m, 2H), 2.05 (s, 3H), 1.53 (m, 2H), 1.26 (m, 5H), 0.93 (m, 1H), 0.74 (m, 5H), 0.46 (t, J=7.2 Hz, 3H).

Preparation Example 57

Preparation of Compound F10

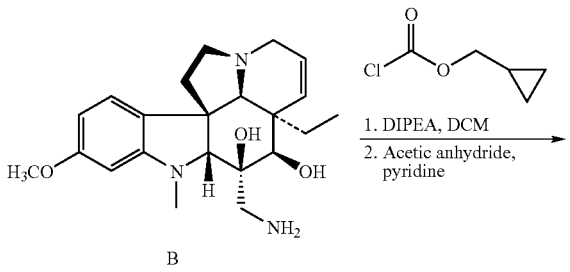

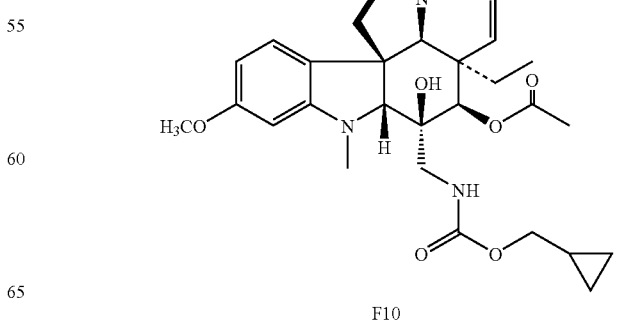

1H), 2.32-2.14 (m, 4H), 2.10 (s, 3H), 2.01 (m, 2H), 1.73 (m, 1H), 1.57 (m, 1H), 1.28 (m, 1H), 0.98 (m, 1H), 0.51 (t, J=7.2 Hz, 3H).

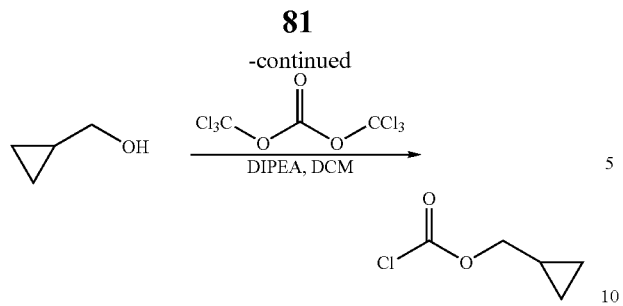

Compound F10 was prepared following the procedure for preparing compound F3.

¹H NMR (CDCl₃, 300 MHz): δ: 9.07 (s), 6.86 (d, J=8.4 Hz, 1H), 6.30 (dd, J=8.4, 2.4 Hz, 1H), 6.14 (d, J=2.4 Hz, 1H), 5.87 (dd, J=10.2, 4.5 Hz, 1H), 5.36 (d, J=10.2 Hz, 2H), 5.00 (s, 1H), 3.86 (d, J=7.2 Hz, 2H), 3.78 (s, 3H), 3.50 (m, 2H), 3.45 (s, 1H), 3.34 (m, 1H), 3.12 (d, J=12.6 Hz, 1H), 2.90 (s, 3H), 2.81 (d, J=15.9 Hz, 1H), 2.62 (s, 1H), 2.51 (m, 1H), 2.28-2.18 (m, 2H), 2.11 (s, 3H), 1.30 (m, 1H), 1.10 (m, 1H), 0.96 (m, 1H), 0.51 (t, J=7.2 Hz, 3H), 0.51 (d, J=4.8 Hz, 2H), 0.25 (d, J=4.8 Hz, 2H).

Preparation Example 58

Preparation of Compound F11

Preparation Example 59

Preparation of Compound F12

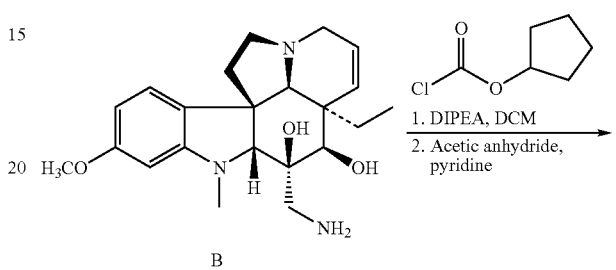

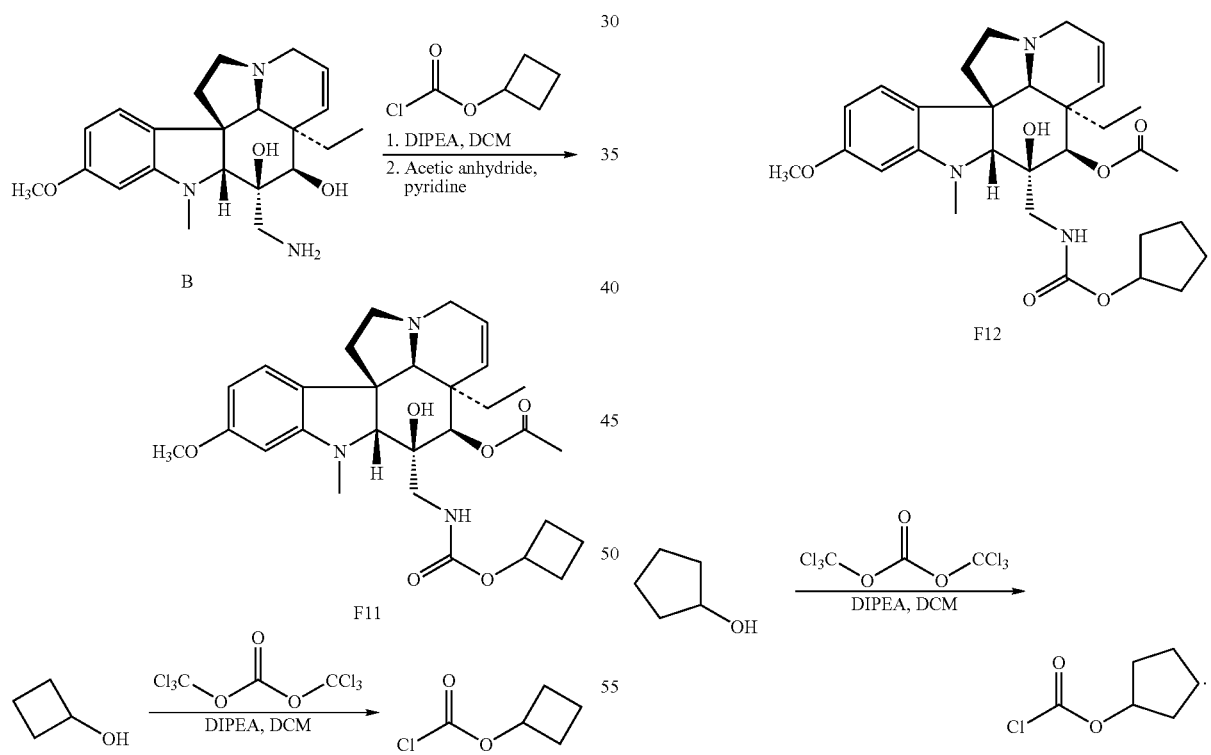

Compound F11 was prepared following the procedure for preparing compound F3.

¹H NMR (CDCl₃, 300 MHz): δ: 9.06 (s), 6.86 (d, J=8.4 Hz, 1H), 6.30 (dd, J=8.4, 2.4 Hz, 1H), 6.14 (d, J=2.4 Hz, 1H), 5.87 (dd, J=10.2, 4.8 Hz, 1H), 5.36 (d, J=10.2 Hz, 1H), 5.27 (d, J=7.5 Hz, 1H), 4.99 (s, 1H), 4.90 (m, 1H), 3.78 (s, 3H), 3.48 (m, 2H), 3.43 (s, 1H), 3.35 (m, 1H), 3.09 (d, J=12.3 Hz, 1H), 2.89 (s, 3H), 2.80 (d, J=15.9 Hz, 1H), 2.62 (s, 1H), 2.49 (m,

Compound F12 was prepared following the procedure for preparing compound F3.

¹H NMR (CDCl₃, 300 MHz): δ: 8.97 (s), 6.78 (d, J=8.4 Hz, 1H), 6.48 (dd, J=8.4, 2.4 Hz, 1H), 6.04 (d, J=2.4 Hz, 1H), 5.79 (dd, J=10.2, 4.8 Hz, 1H), 5.27 (d, J=10.2 Hz, 1H), 5.14 (d, J=7.5 Hz, 1H), 4.97 (m, 1H), 4.91 (s, 1H), 3.67 (s, 3H), 3.38 (m, 2H), 3.34 (s, 1H), 3.25 (m, 1H), 3.20 (d, J=12.3 Hz, 1H), 2.80 (s, 3H), 2.73 (d, J=15.6 Hz, 1H), 2.54 (s, 1H), 2.40 (m,

1H), 2.21-2.13 (m, 2H), 2.00 (s, 3H), 1.72 (m, 2H), 1.58 (m, 4H), 1.44 (m, 2H), 1.24 (m, 1H), 0.92 (m, 1H), 0.42 (t, J=7.2 Hz, 3H).

1H), 2.25-2.15 (m, 2H), 2.02 (s, 3H), 1.75 (m, 2H), 1.62 (m, 2H), 1.42 (m, 1H), 1.26 (m, 6H), 0.88 (m, 1H), 0.44 (t, J=7.2 Hz, 3H).

Preparation Example 60

Preparation of Compound F13

Preparation Example 61

Preparation of Compound F14

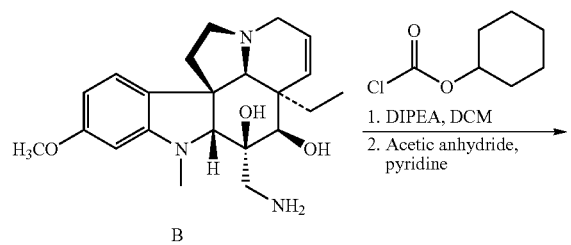
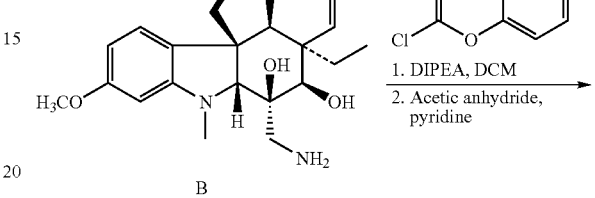
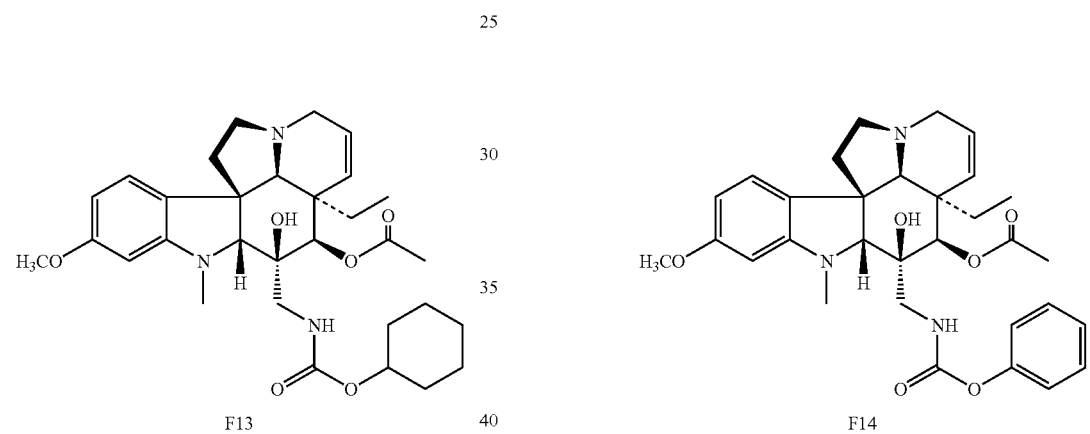
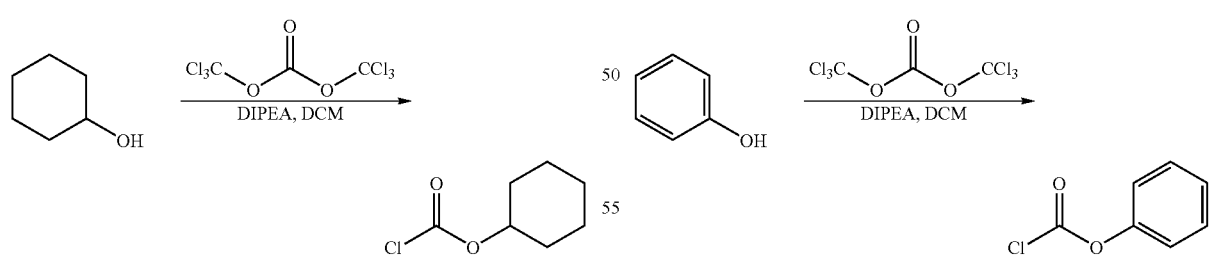

Compound F13 was prepared following the procedure for preparing compound F3.

$^1$H NMR (CDCl$_3$, 300 MHz): δ: 8.97 (s), 6.79 (d, J=8.4 Hz, 1H), 6.22 (dd, J=8.4, 2.4 Hz, 1H), 6.06 (d, J=2.4 Hz, 1H), 5.79 (dd, J=10.2, 4.8 Hz, 1H), 5.29 (d, J=10.2 Hz, 1H), 5.19 (d, J=5.7 Hz, 1H), 4.93 (s, 1H), 4.53 (m, 1H), 3.69 (s, 3H), 3.40 (m, 2H), 3.37 (s, 1H), 3.27 (m, 1H), 3.04 (d, J=12.3 Hz, 1H), 2.82 (s, 3H), 2.74 (d, J=15.6 Hz, 1H), 2.55 (s, 1H), 2.42 (m,

Compound F14 was prepared following the procedure for preparing compound F3.

$^1$H NMR (CDCl$_3$, 300 MHz): δ: 9.18 (s, 1H), 7.30 (t, J=7.2 Hz, 2H), 7.01 (m, 3H), 6.86 (dd, J=8.4, 1.8 Hz, 1H), 6.30 (dd, J=8.4, 1.8 Hz, 1H), 6.14 (s, 1H), 5.87 (dd, J=10.2, 4.5 Hz, 1H), 5.76 (d, J=7.5 Hz, 1H), 5.37 (d, J=9.9 Hz, 1H), 5.01 (s, 1H), 3.74 (s, 3H), 3.60 (m, 1H), 3.47 (s, 1H), 3.42 (m, 1H), 3.34 (m, 1H), 3.22 (d, J=12.6 Hz, 1H), 2.88 (s, 3H), 2.80 (d,

J=15.9 Hz, 1H), 2.65 (s, 1H), 2.49 (m, 1H), 2.26-2.16 (m, 2H), 2.10 (s, 3H), 1.28 (m, 1H), 1.00 (m, 1H), 0.52 (t, J=7.5 Hz, 3H).

2.49 (m, 1H), 2.30-2.16 (m, 2H), 2.08 (s, 3H), 1.28 (m, 1H), 1.00 (m, 1H), 0.51 (t, J=7.5 Hz, 3H).

Preparation Example 62

Preparation of Compound F15

Preparation Example 63

Preparation of Compound F16

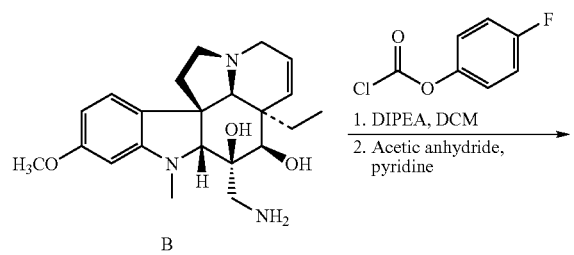

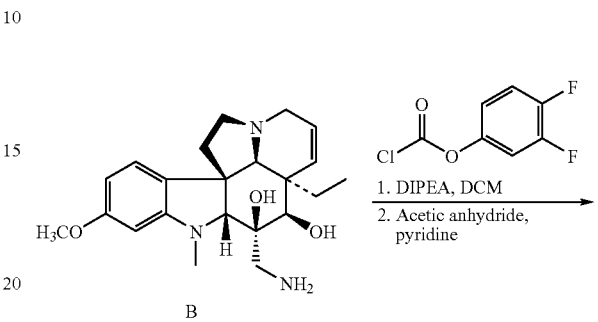

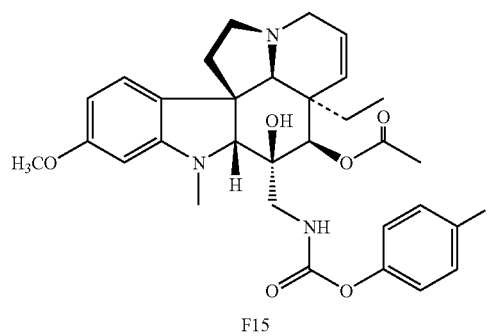

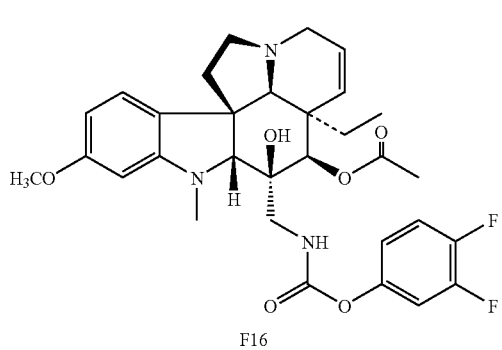

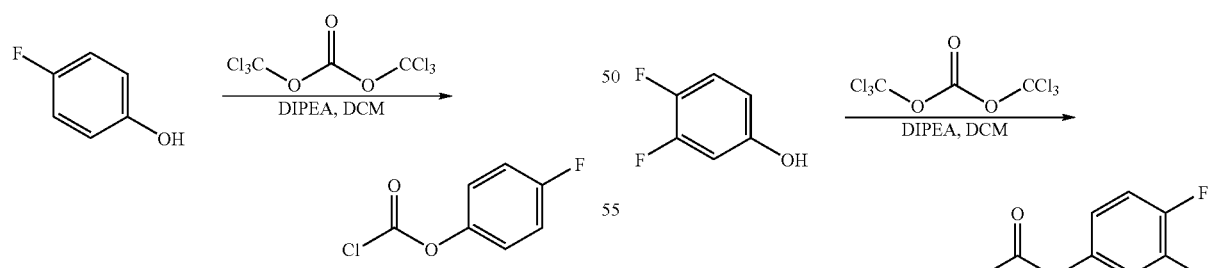

Compound F15 was prepared following the procedure for preparing compound F3.

$^1$H NMR (CDCl$_3$, 300 MHz): δ: 9.19 (s), 7.03 (m, 4H), 6.86 (dd, J=8.4, 1.8 Hz, 1H), 6.30 (dd, J=8.4, 1.8 Hz, 1H), 6.15 (s, 1H), 5.87 (dd, J=10.2, 4.5 Hz, 1H), 5.77 (d, J=7.5 Hz, 1H), 5.37 (d, J=10.2 Hz, 1H), 5.01 (s, 1H), 3.74 (s, 3H), 3.60 (m, 1H), 3.47 (s, 1H), 3.42 (m, 1H), 3.34 (m, 1H), 3.22 (d, J=12.6 Hz, 1H), 2.92 (s, 3H), 2.80 (d, J=15.9 Hz, 1H), 2.65 (s, 1H),

Compound F16 was prepared following the procedure for preparing compound F3.

$^1$H NMR (CDCl$_3$, 300 MHz): δ: 9.19 (s), 7.04 (m, 2H), 6.96 (m, 2H), 6.29 (dd, J=8.4, 1.8 Hz, 1H), 6.14 (s, 1H), 5.83 (dd, J=10.2, 4.5 Hz, 1H), 5.79 (d, J=7.5 Hz, 1H), 5.35 (d, J=10.2 Hz, 1H), 4.99 (s, 1H), 3.72 (s, 3H), 3.61 (m, 1H), 3.45 (s, 1H), 3.42 (m, 1H), 3.34 (m, 1H), 3.22 (d, J=12.6 Hz, 1H), 2.92 (s,

3H), 2.80 (d, J=15.9 Hz, 1H), 2.65 (s, 1H), 2.49 (m, 1H), 2.30-2.16 (m, 2H), 2.08 (s, 3H), 1.28 (m, 1H), 1.00 (m, 1H), 0.51 (t, J=7.5 Hz, 3H).

Preparation Example 64

Preparation of Compound F17

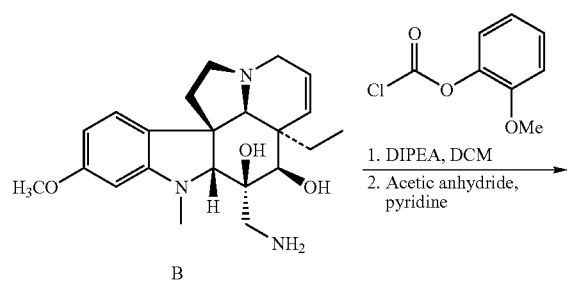
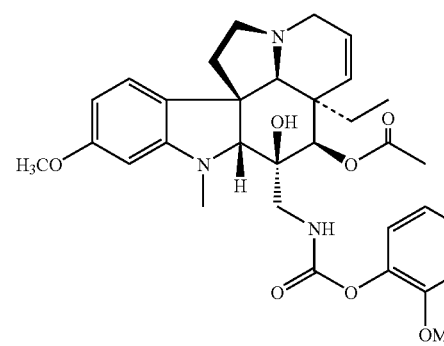
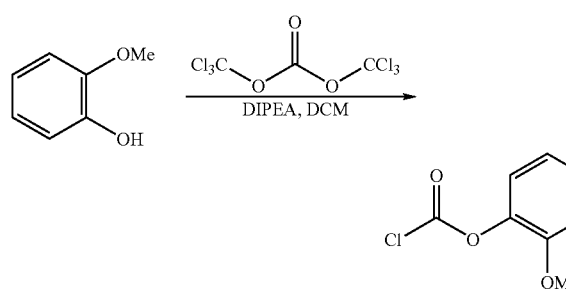

Compound F17 was prepared following the procedure for preparing compound F3.

$^1$H NMR (CDCl$_3$, 300 MHz): δ: 9.16 (s), 7.15 (t, J=7.2 Hz, 1H), 7.07 (d, J=7.2 Hz, 1H), 7.01 (m, 3H), 6.94-6.87 (m, 3H), 6.31 (dd, J=8.4, 1.8 Hz, 1H), 6.15 (s, 1H), 5.89 (dd, J=10.2, 4.5 Hz, 1H), 5.78 (d, J=8.1 Hz, 1H), 5.38 (d, J=10.5 Hz, 1H), 5.03 (s, 1H), 3.78 (s, 6H), 3.60 (m, 1H), 3.53 (s, 1H), 3.47 (m, 1H), 3.35 (m, 1H), 3.22 (d, J=12.6 Hz, 1H), 2.88 (s, 3H), 2.82 (d, J=15.9 Hz, 1H), 2.66 (s, 1H), 2.52 (m, 1H), 2.26-2.16 (m, 2H), 2.12 (s, 3H), 1.28 (m, 1H), 1.00 (m, 1H), 0.53 (t, J=7.5 Hz, 3H).

Preparation Example 65

Preparation of Compound F18

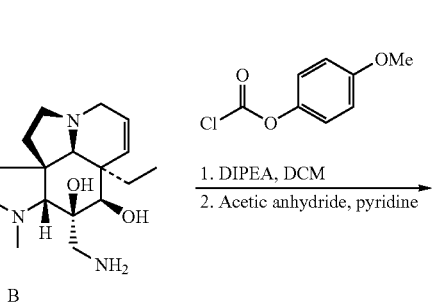
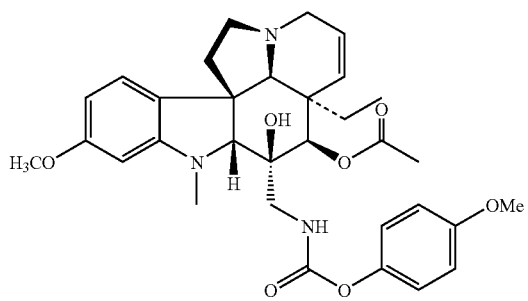
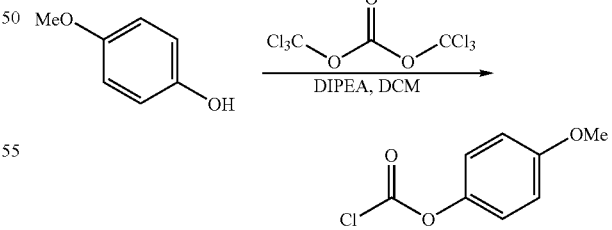

Compound F18 was prepared following the procedure for preparing compound F3.

$^1$H NMR (CDCl$_3$, 300 MHz): δ: 9.19 (s), 7.04 (d, J=7.2 Hz, 2H), 6.87 (m, 3H), 6.33 (dd, J=8.4, 1.8 Hz, 1H), 6.16 (s, 1H), 5.89 (dd, J=10.2, 4.5 Hz, 1H), 5.70 (d, J=7.8 Hz, 1H), 5.38 (d, J=10.2 Hz, 1H), 5.03 (s, 1H), 3.78 (s, 6H), 3.61 (m, 1H), 3.48 (m, 1H), 3.47 (s, 1H), 3.37 (m, 1H), 3.22 (d, J=12.6 Hz, 1H), 2.95 (s, 3H), 2.84 (d, J=15.9 Hz, 1H), 2.67 (s, 1H), 2.52 (m, 1H), 2.26-2.16 (m, 2H), 2.12 (s, 3H), 1.28 (m, 1H), 1.00 (m, 1H), 0.53 (t, J=7.5 Hz, 3H).

Preparation Example 66

Preparation of Compound F19

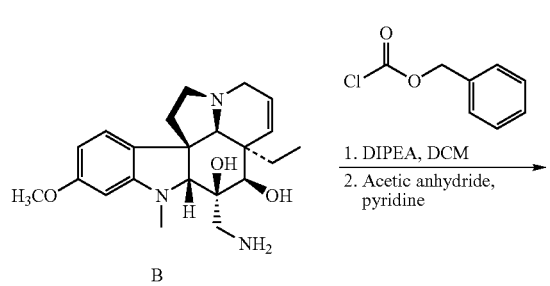

1H), 2.49 (m, 1H), 2.26-2.16 (m, 2H), 2.08 (s, 3H), 1.28 (m, 1H), 1.00 (m, 1H), 0.51 (t, J=7.5 Hz, 3H).

Preparation Example 67

Preparation of Compound F20

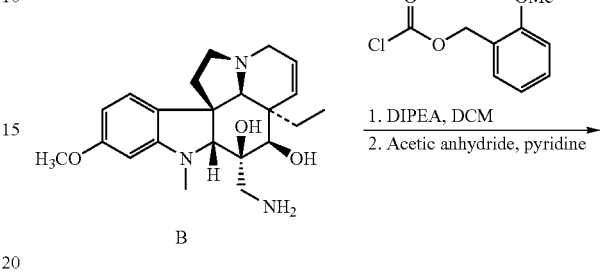

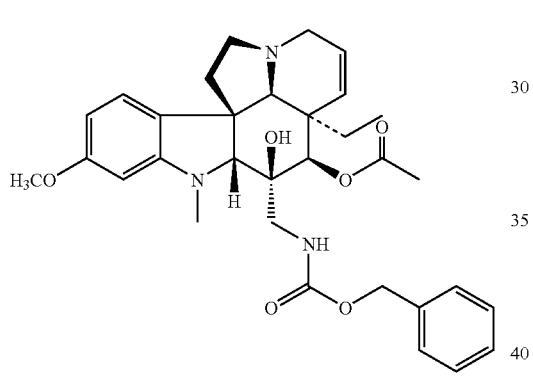

F19

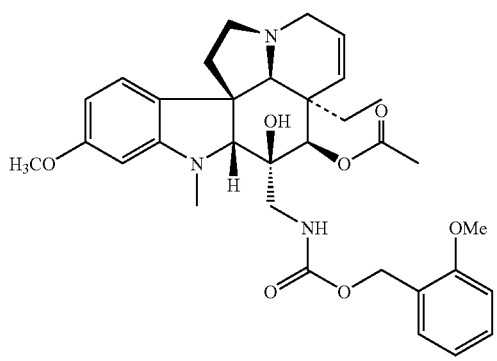

F20

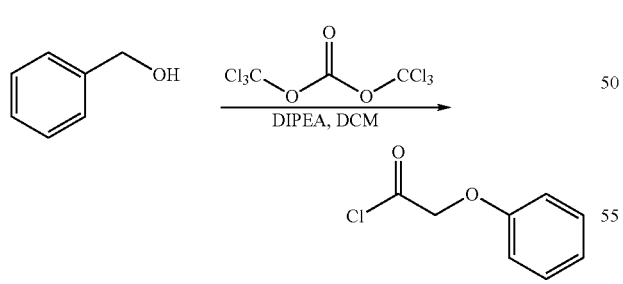

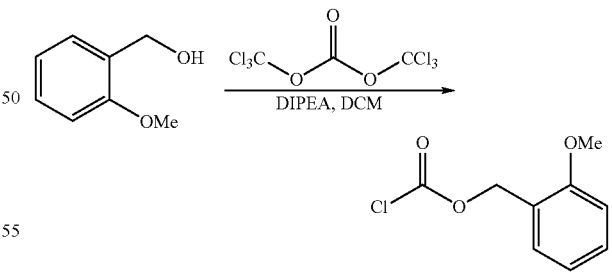

Compound F19 was prepared following the procedure for preparing compound F3.

$^1$H NMR (CDCl$_3$, 300 MHz): δ: 9.10 (s), 7.30 (m, 5H), 6.86 (d, J=8.4 Hz, 1H), 6.30 (dd, J=8.4, 2.4 Hz, 1H), 6.13 (d, J=2.4 Hz, 1H), 5.87 (dd, J=10.2, 4.5 Hz, 1H), 5.43 (d, J=7.5 Hz, 1H), 5.36 (d, J=10.2 Hz, 1H), 5.09 (s, 2H), 5.01 (s, 1H), 3.77 (s, 3H), 3.50 (m, 2H), 3.42 (s, 1H), 3.34 (m, 1H), 3.14 (d, J=12.6 Hz, 1H), 2.88 (s, 3H), 2.81 (d, J=15.9 Hz, 1H), 2.62 (s,

Compound F20 was prepared following the procedure for preparing compound F3.

$^1$H NMR (CDCl$_3$, 300 MHz): δ: 9.10 (s), 7.23 (d, J=7.2 Hz, 1H), 7.16 (t, J=7.2 Hz, 1H), 6.82 (t, J=7.2 Hz, 1H), 6.77 (d, J=8.4 Hz, 1H), 6.76 (d, J=7.2 Hz, 1H), 6.21 (dd, J=8.4, 2.4 Hz, 1H), 6.04 (s, 1H), 5.77 (dd, J=10.2, 3.9 Hz, 1H), 5.35 (d, J=6.3 Hz, 1H), 5.27 (d, J=10.2 Hz, 1H), 5.07 (s, 2H), 4.93 (s, 1H), 3.70 (s, 3H), 3.66 (s, 3H), 3.47-3.32 (m, 2H), 3.35 (s, 1H), 3.27-3.19 (m, 1H), 3.07 (d, J=12.9 Hz, 1H), 2.79 (s, 3H), 2.71

(d, J=15.9 Hz, 1H), 2.52 (s, 1H), 2.42-2.36 (m, 1H), 2.20-2.08 (m, 2H), 1.908 (s, 3H), 1.33-1.22 (m, 1H), 0.95-0.86 (m, 1H), 0.42 (t, J=7.5 Hz, 3H).

Hz, 1H), 2.53 (s, 1H), 2.40 (q, J=8.7 Hz, 1H), 2.16-2.06 (m, 2H), 1.98 (s, 3H), 1.25-1.17 (m, 1H), 0.94-0.87 (m, 1H), 0.43 (t, J=7.2 Hz, 3H).

Preparation Example 68

Preparation of Compound F21

Preparation Example 69

Preparation of Compound F22

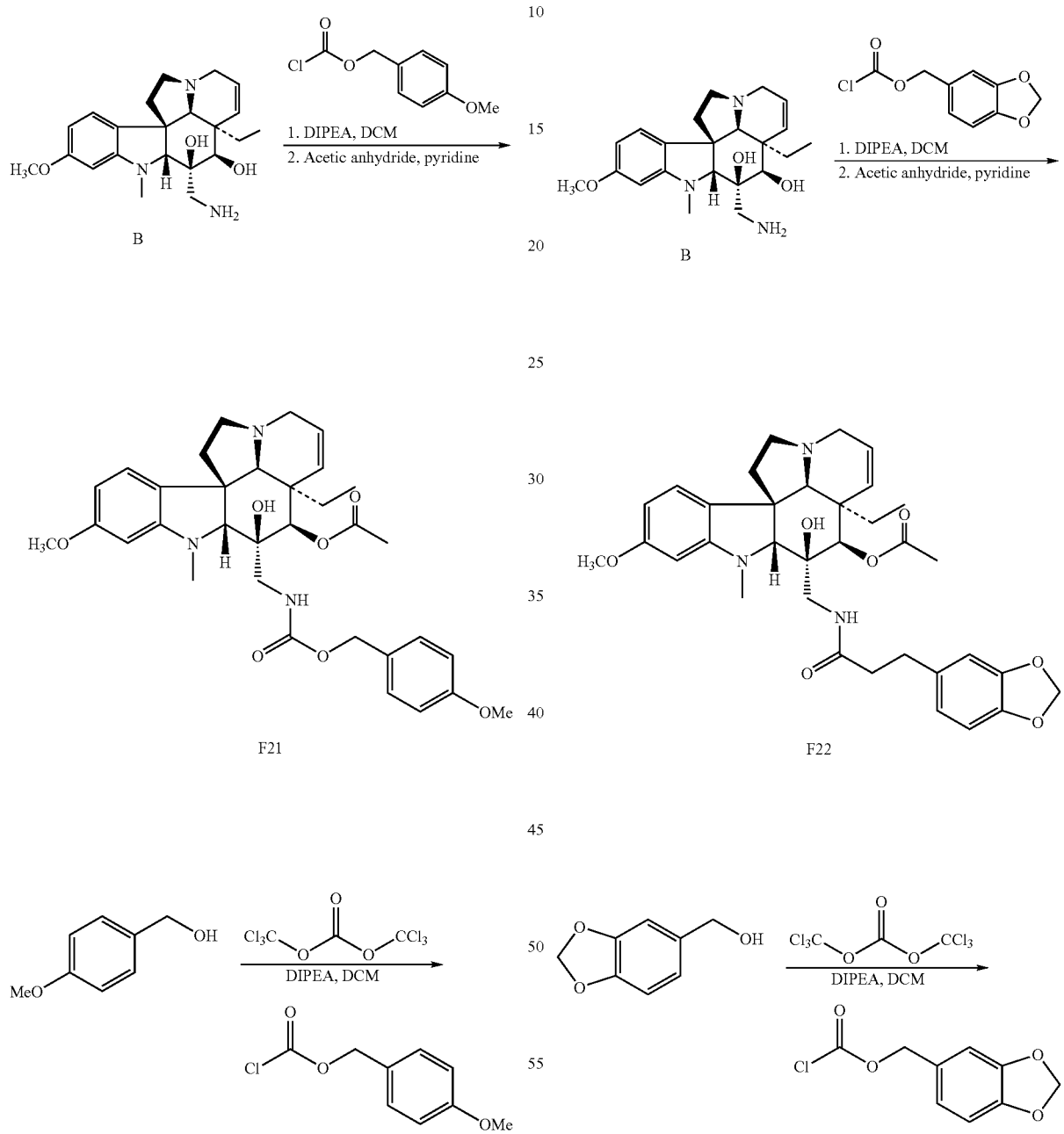

Compound F21 was prepared following the procedure for preparing compound F3.

$^1$H NMR (CDCl$_3$, 300 MHz): δ: 8.95 (s), 7.19 (d, J=8.4 Hz, 2H), 6.78 (d, J=8.4 Hz, 2H), 6.76 (d, J=8.1 Hz, 1H), 6.21 (dd, J=8.1, 1.8 Hz, 1H), 6.04 (s, 1H), 5.77 (dd, J=10.2, 4.5 Hz, 1H), 5.32 (d, J=6.3 Hz, 1H), 5.27 (d, J=10.2 Hz, 1H), 4.93 (s, 3H), 3.67 (s, 6H), 3.43-3.38 (m, 2H), 3.33 (s, 1H), 3.26-3.20 (m, 1H), 3.06 (d, J=12.3 Hz, 1H), 2.78 (s, 3H), 2.71 (d, J=16.2

Compound F22 was prepared following the procedure for preparing compound F3.

$^1$H NMR (CDCl$_3$, 300 MHz): δ: 9.00 (s), 6.83-6.67 (m, 4H), 6.25 (dd, J=8.1, 1.8 Hz, 1H), 6.08 (s, 1H), 5.84 (s, 2H), 5.80 (dd, J=10.2, 4.5 Hz, 1H), 5.39 (d, J=6.0 Hz, 1H), 5.31 (d, J=10.2 Hz, 1H), 4.96 (s, 1H), 4.92 (s, 2H), 3.70 (s, 6H), 3.50-3.42 (m, 2H), 3.37 (s, 1H), 3.31-3.25 (m, 1H), 3.10 (d, J=12.3 Hz, 1H), 2.82 (s, 3H), 2.76 (d, J=16.2 Hz, 1H), 2.57 (s,

1H), 2.45 (q, J=9.6 Hz, 1H), 2.24-2.09 (m, 2H), 2.02 (s, 3H), 1.28-1.20 (m, 1H), 0.98-0.89 (m, 1H), 0.46 (t, J=7.2 Hz, 3H).

Preparation Example 70

Preparation of Compound F23

2.56-2.47 (m, 1H), 2.33-2.17 (m, 2H), 2.09 (s, 3H), 1.37-1.28 (m, 1H), 1.06-0.94 (m, 1H), 0.52 (t, J=7.2 Hz, 3H).

Preparation Example 71

Preparation of Compound F24

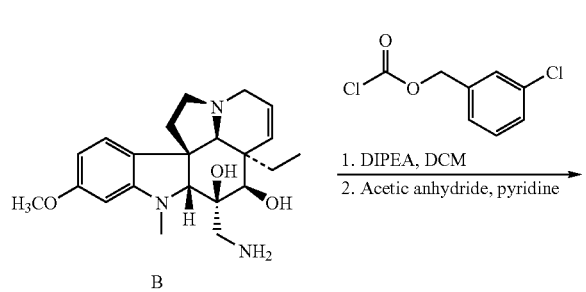
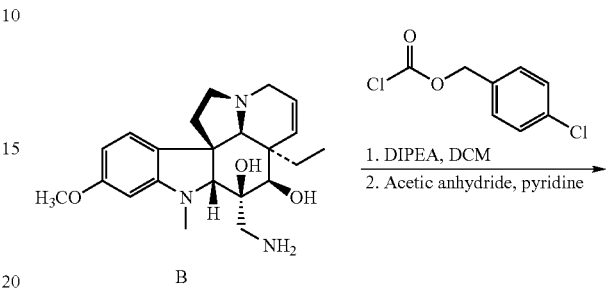

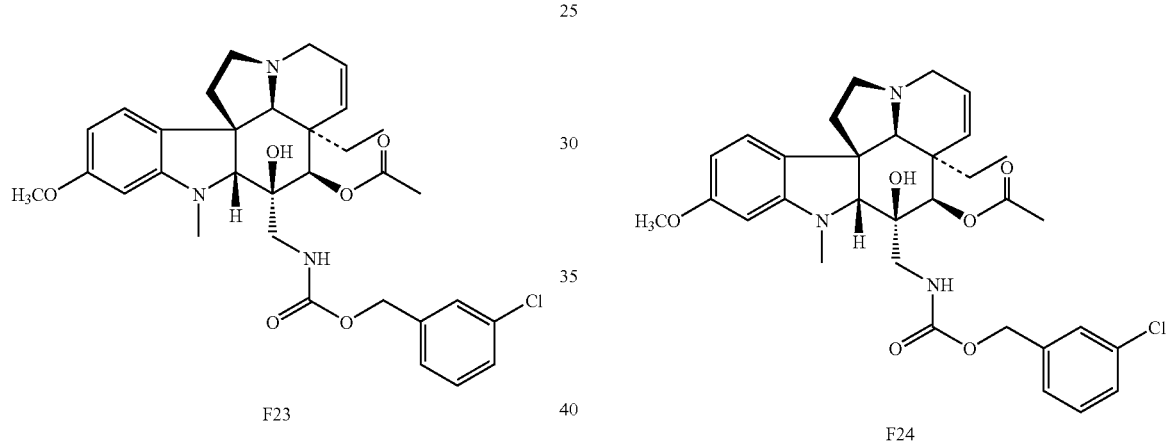

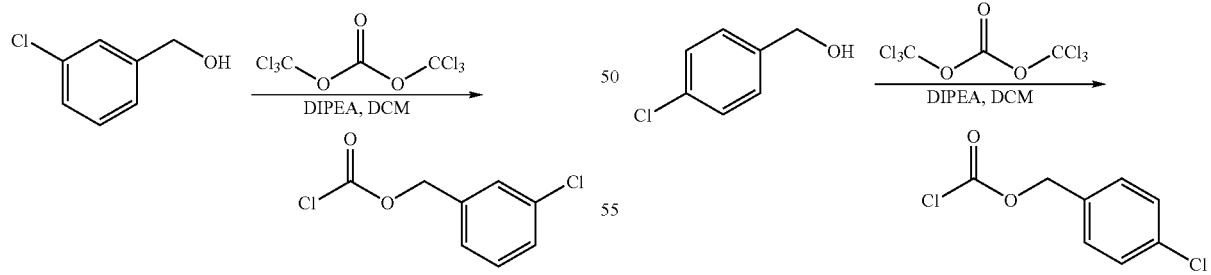

Compound F23 was prepared following the procedure for preparing compound F3.

¹H NMR (CDCl₃, 300 MHz): δ: 9.11 (s), 7.34 (s, 1H), 7.27-7.20 (m. 2H), 6.86 (d, J=8.4 Hz, 1H), 6.31 (d, J=8.4 Hz, 1H), 6.14 (s, 1H), 5.88 (dd, J=10.2, 4.5 Hz, 1H), 5.44 (d, J=6.0 Hz, 1H), 5.37 (d, J=10.2 Hz, 1H), 5.06 (s, 2H), 5.01 (s, 1H), 3.79 (s, 3H), 3.56-3.34 (m, 3H), 3.42 (s, 1H), 3.15 (d, J=12.9 Hz, 1H), 2.88 (s, 3H), 2.82 (d, J=16.2 Hz, 1H), 2.64 (s, 1H),

Compound F24 was prepared following the procedure for preparing compound F3.

¹H NMR (CDCl₃, 300 MHz): δ: 9.01 (s), 7.29 (m. 4H), 6.87 (d, J=8.4 Hz, 1H), 6.31 (d, J=8.4 Hz, 1H), 6.14 (s, 1H), 5.87 (dd, J=10.2, 4.5 Hz, 1H), 5.42 (d, J=6.6 Hz, 1H), 5.36 (d, J=10.2 Hz, 1H), 5.05 (s, 2H), 5.00 (s, 1H), 3.79 (s, 3H), 3.60-3.25 (m, 3H), 3.41 (s, 1H), 3.14 (d, J=12.6 Hz, 1H), 2.88 (s, 3H), 2.84 (d, J=16.2 Hz, 1H), 2.63 (s, 1H), 2.56-2.42 (m,

1H), 2.31-2.14 (m, 2H), 2.09 (s, 3H), 1.40-1.20 (m, 1H), 1.04-0.96 (m, 1H), 0.52 (t, J=7.2 Hz, 3H).

Preparation Example 72

Preparation of Compound F25

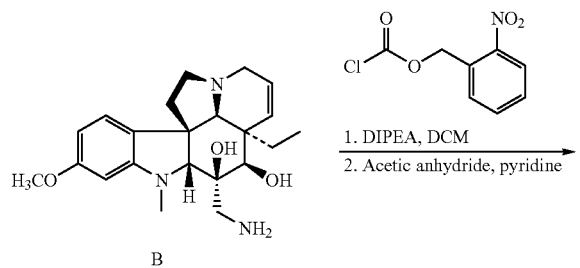

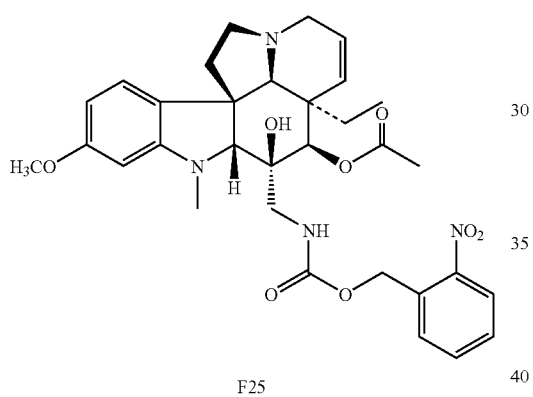

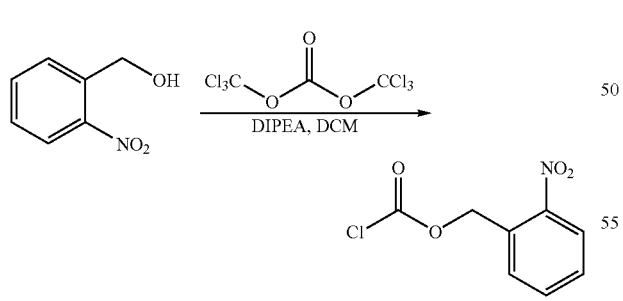

Compound F25 was prepared following the procedure for preparing compound F3.

$^1$H NMR (CDCl$_3$, 300 MHz): δ: 9.11 (s), 7.97 (d, J=8.1 Hz, 1H), 7.52 (m, 2H), 7.36 (m. 1H), 6.80 (d, J=8.4 Hz, 1H), 6.23 (d, J=8.4 Hz, 1H), 6.06 (s, 1H), 5.81 (dd, J=10.2, 4.5 Hz, 1H), 5.50 (d, J=7.5 Hz, 1H), 5.42 (s, 2H), 5.30 (d, J=10.2 Hz, 1H), 4.94 (s, 1H), 3.68 (s, 3H), 3.49-3.25 (m, 3H), 3.37 (s, 1H), 3.08 (d, J=12.9 Hz, 1H), 2.81 (s, 3H), 2.76 (d, J=16.2 Hz, 1H), 2.58 (s, 1H), 2.50-2.41 (m, 1H), 2.24-2.12 (m, 2H), 2.01 (s, 3H), 1.25-1.17 (m, 1H), 0.98-0.84 (m, 1H), 0.44 (t, J=7.2 Hz, 3H).

Preparation Example 73

Preparation of Compound F26

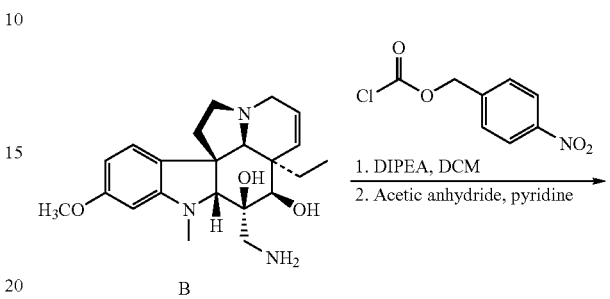

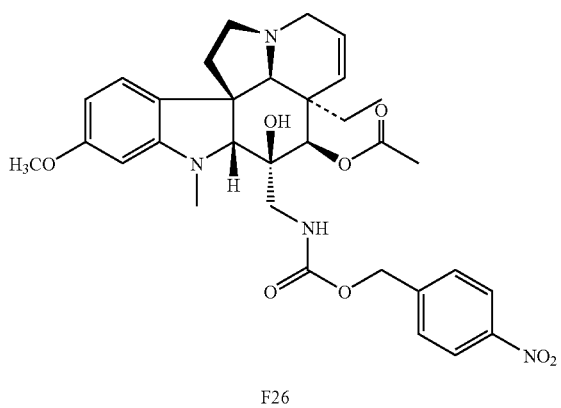

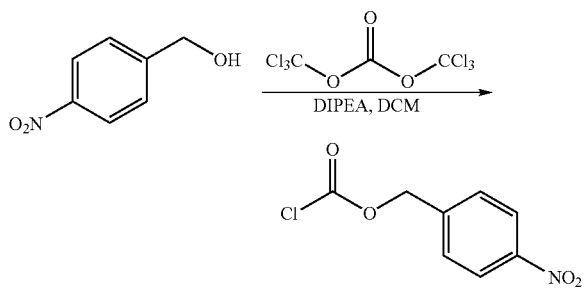

Compound F26 was prepared following the procedure for preparing compound F3.

$^1$H NMR (CDCl$_3$, 300 MHz): δ: 9.20 (s), 8.21 (d, J=8.7 Hz, 2H), 8.50 (d, J=8.7 Hz, 2H), 6.88 (d, J=8.4 Hz, 1H), 6.32 (dd, J=8.4, 2.4 Hz, 1H), 6.15 (s, 1H), 5.90 (dd, J=10.2, 3.6 Hz, 1H), 5.52 (d, J=7.5 Hz, 1H), 5.38 (d, J=10.2 Hz, 1H), 5.19 (s, 2H), 5.01 (s, 1H), 3.79 (s, 3H), 3.58-3.33 (m, 3H), 3.42 (s, 1H), 3.16 (d, J=12.9 Hz, 1H), 2.89 (s, 3H), 2.87 (d, J=16.2 Hz,

1H), 2.65 (s, 1H), 2.58-2.49 (m, 1H), 2.33-2.23 (m, 2H), 2.09 (s, 3H), 1.34-1.25 (m, 1H), 1.03-0.96 (m, 1H), 0.53 (t, J=7.2 Hz, 3H).

Preparation Example 74

Preparation of Compound F27

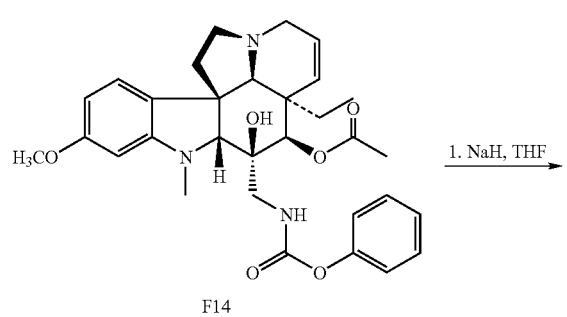

1 mmol (547 mg) of compound F14 was dissolved in 10 mL of tetrahydrofunan, followed by addition of 48 mg (1.2 eq) of sodium hydride under argon atmosphere. After 2 h of stirring at room temperature, 10 mL of saturated ammonium chloride solution was added, and the reaction mixture was extracted with ethyl acetate (10 mL×3). The combined organic phase was dried over anhydrous sodium sulfate, concentrated under reduced pressure and purified by silica gel chromatography (eluted with petroleum ether:acetone=2:1 v/v) to give 180 mg of compound F15 as a white powder in 40% yield.

$^1$H NMR (CDCl$_3$, 300 MHz): δ: 6.83 (d, J=7.8 Hz, 1H), 6.12 (d, J=7.8 Hz, 1H), 5.96 (s, 1H), 5.87 (dd, J=9.9, 4.8 Hz, 1H), 5.30 (d, J=9.9 Hz, 1H), 5.17 (s, 1H), 4.90 (s, 1H), 3.81 (s, 1H), 3.78 (s, 3H), 3.40 (dd, J=16.5, 4.8 Hz, 1H), 3.18 (s, 2H), 3.21-3.12 (m, 2H), 3.10 (s, 3H), 2.69 (d, J=16.5 Hz, 1H), 2.65 (s, 1H), 2.39-2.29 (m, 1H), 2.19-2.10 (m, 1H), 2.04 (s, 3H), 1.62-1.52 (m, 1H), 1.30-1.18 (m, 1H), 0.88 (t, J=7.2 Hz, 3H).

EXAMPLES

Example 1

Preparation of Compound BM1

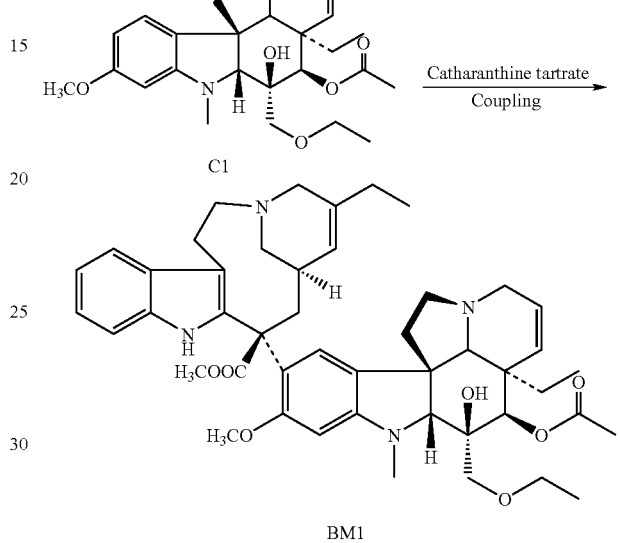

280 mg (0.58 mmol) of catharanthine tartrate and 280 mg (1.74 mmol) of anhydrous ferric (III) chloride were added into a buffer solution containing 185 mg of gelatin, 145 mg of sodium chloride, 24 mL of water and 24 mL of 0.1 N hydrochloric acid, under argon atmosphere atmosphere. After 10 minutes of stirring at room temperature, 263 mg (0.58 mmol) of compound C1 was added and the stirring continued for 8 h at room temperature. A solution of sodium borohydride (48 mg) in ammonium hydroxide (5 mL) was added dropwise under ice bath (0° C.), and allowed to react for 15-20 minutes under ice bath. The reaction mixture was extracted with methylene chloride (20 mL×4), and the methylene chloride layer was washed with saturated salt solution (20 mL×3), filtered with Celite and concentrated under reduced pressure at a low temperature. The concentrate was dissolved in 2 mL of methanol and the solution was left for 2 minutes. A white crystal was crystallized, filtered and dried to give 257 mg of compound BM1 in 56% yield.

$^1$H NMR (CDCl$_3$, 300 MHz): δ: 9.03 (s, 1H), 8.02 (s, 1H), 7.51 (d, J=7.8 Hz, 1H), 7.10 (m, 3H), 6.60 (s, 1H), 6.16 (s, 1H), 5.86 (dd, J=10.5, 4.2 Hz, 1H), 5.46 (d, J=6.0 Hz, 1H), 5.45 (d, J=10.5 Hz, 1H), 5.01 (s, 1H), 3.82 (s, 3H), 3.70 (s, 1H), 3.60 (s, 3H), 3.00 (s, 3H), 2.58 (s, 1H), 2.17 (s, 3H), 1.43 (m, 1H), 1.22 (t, J=6.9 Hz, 3H), 0.99 (t, J=7.8 Hz, 3H), 0.81 (t, J=7.2 Hz, 3H).

$^{13}$C NMR (CDCl$_3$, 75 MHz): δ: 175.1 (C), 171.3 (C), 158.0 (C), 153.9 (C), 140.1 (C), 135.1 (C), 131.3 (C), 129.9 (CH), 129.6 (C), 124.7 (CH), 124.1 (CH), 123.8 (CH), 123.8 (C), 122.4 (CH), 121.3 (C), 119.0 (CH), 118.5 (CH), 117.2 (C), 110.6 (CH), 94.5 (CH), 81.0 (CH), 77.7 (C), 76.8 (CH), 72.4 (CH$_2$), 66.9 (CH$_2$), 66.5 (CH), 56.0 (OCH$_3$), 55.6 (C), 54.6 (CH$_2$), 52.5 (OCH$_3$), 52.4 (CH$_2$), 52.3 (C), 50.5 (CH$_2$), 50.2

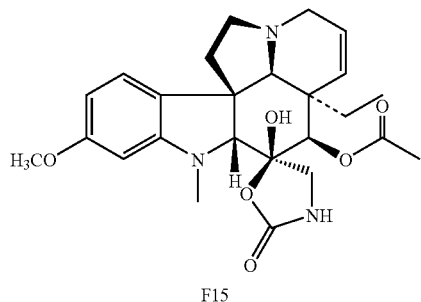

(CH$_2$), 46.1 (CH$_2$), 45.2 (CH$_2$), 42.3 (C), 39.1 (CH$_3$), 34.6 (CH$_2$), 33.1 (CH), 31.8 (CH$_2$), 28.0 (CH$_2$), 25.8 (CH$_2$), 21.2 (CH$_3$), 15.1 (CH$_3$), 12.4 (CH$_3$), 8.4 (CH$_3$).

ESIMS (m/e) 793.5 [M+1]$^+$.

Example 2

Preparation of Compound BM2

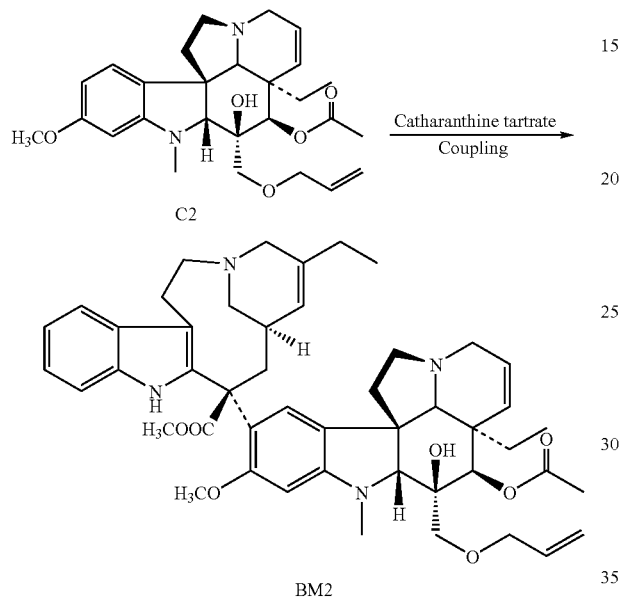

Compound BM2 was prepared as a white powder following the procedure for preparing compound BM1.

$^1$H NMR (CDCl$_3$, 300 MHz): δ: 9.01 (s, 1H), 8.01 (s, 1H), 7.52 (d, J=7.8 Hz, 1H), 7.10 (m, 3H), 6.60 (s, 1H), 6.16 (s, 1H), 5.97 (m, 1H), 5.86 (dd, J=10.2, 4.5 Hz, 1H), 5.46 (d, J=6.0 Hz, 1H), 5.45 (d, J=10.2 Hz, 1H), 5.24 (d, J=17.1 Hz, 1H), 5.14 (d, J=10.2 Hz, 1H), 5.02 (s, 1H), 4.04 (m, 2H), 3.84 (s, 3H), 3.61 (s, 3H), 3.00 (s, 3H), 2.59 (s, 1H), 2.15 (s, 3H), 1.43 (m, 1H), 1.21 (m, 1H), 1.00 (t, J=7.5 Hz, 3H), 0.82 (t, J=6.9 Hz, 3H). ESIMS (m/e) 805.4 [M+1]$^+$.

Example 3

Preparation of Compound BM3

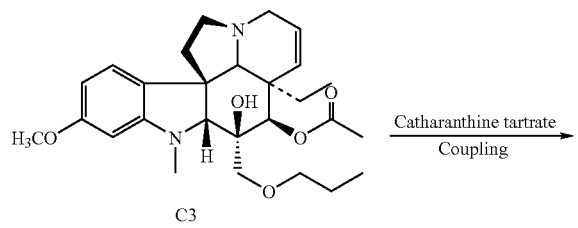

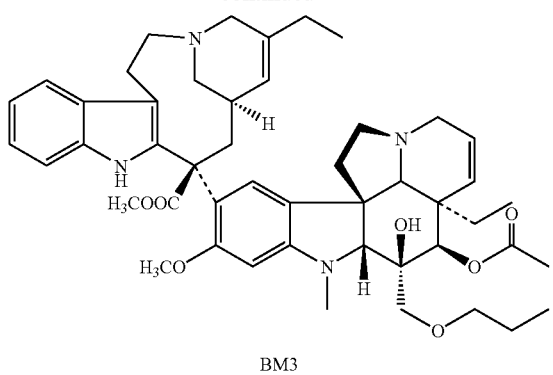

Compound BM3 was prepared as a white powder following the procedure for preparing compound BM1.

$^1$H NMR (CDCl$_3$, 300 MHz): δ: 9.00 (s, 1H), 8.02 (s, 1H), 7.52 (d, J=7.5 Hz, 1H), 7.14 (m, 3H), 6.58 (s, 1H), 6.16 (s, 1H), 5.88 (m, 1H), 5.86 (dd, J=9.6, 4.5 Hz, 1H), 5.51 (d, J=6.0 Hz, 1H), 5.45 (d, J=9.6 Hz, 1H), 5.03 (s, 1H), 3.83 (s, 3H), 3.62 (s, 3H), 3.01 (s, 3H), 2.57 (s, 1H), 2.18 (s, 3H), 1.96 (q, J=7.5 Hz, 2H), 1.43 (m, 1H), 1.21 (m, 1H), 1.01 (t, J=7.5 Hz, 3H), 0.91 (t, J=7.2 Hz, 3H), 0.82 (t, J=7.2 Hz, 3H). ESIMS (m/e) 807.3 [M+1]$^+$.

Example 4

Preparation of Compound BM4

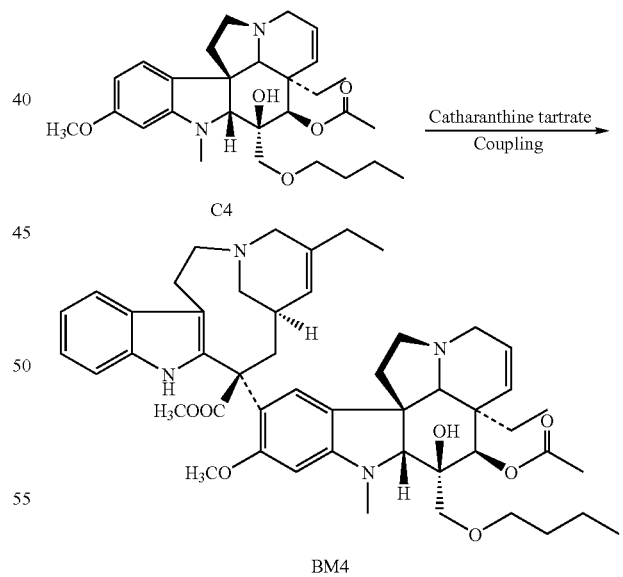

Compound BM4 was prepared as a white powder following the procedure for preparing compound BM1.

$^1$H NMR (CDCl$_3$, 300 MHz): δ: 9.04 (s, 1H), 8.01 (s, 1H), 7.51 (d, J=7.8 Hz, 1H), 7.10 (m, 3H), 6.60 (s, 1H), 6.16 (s, 1H), 5.86 (dd, J=10.5, 4.2 Hz, 1H), 5.46 (d, J=6 Hz, 1H), 5.45 (d, J=10.5 Hz, 1H), 5.02 (s, 1H), 3.82 (s, 3H), 3.74 (s, 1H), 3.60 (s, 3H), 3.00 (s, 3H), 2.58 (s, 1H), 2.17 (s, 3H), 1.00 (t, J=7.5 Hz, 3H), 0.89 (t, J=7.2 Hz, 3H), 0.82 (t, J=6.9 Hz, 3H). ESIMS (m/e) 821.5 [M+1]$^+$.

Example 5

Preparation of Compound BM5

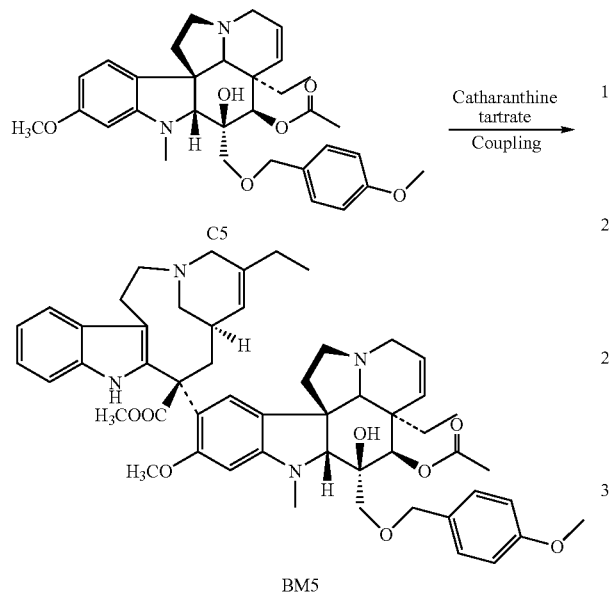

Compound BM5 was prepared as a white powder in 63% yield following the procedure for preparing compound BM1.

$^1$H NMR (DMSO-d$_6$, 300 MHz): δ 9.76 (s, 1H), 8.08 (s, 1H), 7.43 (d, J=7.2 Hz, 1H), 7.24 (d, J=7.8 Hz, 2H), 7.00 (m, 3H), 6.91 (d, J=7.8 Hz, 2H), 6.56 (s, 1H), 6.42 (s, 1H), 5.78 (dd, J=10.2, 4.5 Hz, 1H), 5.44 (m, 2H), 4.77 (s, 1H), 4.41 (q, J=11.7 Hz, 2H), 4.23 (s, 4H), 3.79 (s, 3H), 3.74 (s, 3H), 3.58 (s, 3H), 2.96 (s, 3H), 2.06 (s, 3H), 1.43 (m, 1H), 1.21 (m, 1H), 0.95 (t, J=7.5 Hz, 3H), 0.65 (t, J=6.9 Hz, 3H). ESIMS (m/e) 885.5 [M+1]$^+$.

Example 6

Preparation of Compound BM6

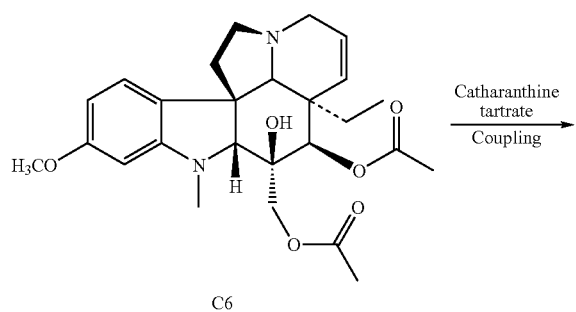

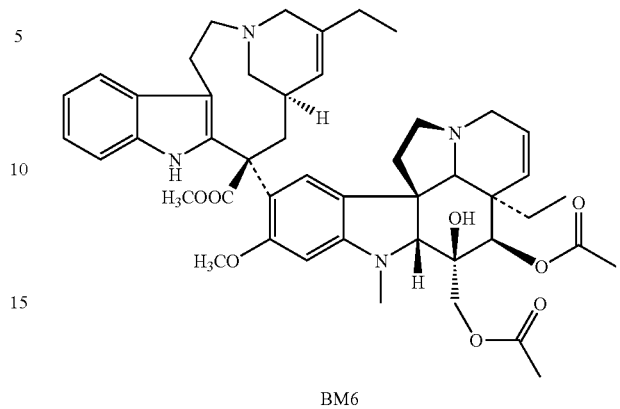

486 mg (1 mmol) of catharanthine tartrate and 486 mg (3 mmol) of anhydrous ferric (III) chloride were added into a buffer solution containing 320 mg of gelatin, 250 mg of sodium chloride, 40 mL of water and 40 mL of 0.1 N hydrochloric acid, under argon atmosphere. After 10 minutes of stirring at room temperature, 470 mg (1 mmol) of compound C6 was added and the stirring continued for 8 h at room temperature. A solution of sodium borohydride (80 mg) in ammonium hydroxide (8 mL) was added dropwise under ice bath (0° C.), and allowed to react for 15-20 minutes under ice bath. The reaction mixture was extracted with methylene chloride (40 mL×4), and the methylene chloride layer was washed with saturated salt solution (20 mL×3), filtered with Celite and concentrated under reduced pressure at low temperature. After the concentrate was dissolved in 2 mL of methanol and the solution was left for 2 minutes, a white crystal was crystallized, filtered and dried to give 475 mg of compound BM6 in 60% yield.

$^1$H NMR (CDCl$_3$, 300 MHz): δ: 9.25 (s, 1H), 8.06 (s, 1H), 7.48 (d, J=7.2 Hz, 1H), 7.10 (m, 3H), 6.59 (s, 1H), 6.17 (s, 1H), 5.86 (dd, J=10.2, 4.5 Hz, 1H), 5.41 (d, J=10.2 Hz, 1H), 5.40 (s, 1H), 5.02 (s, 1H), 4.16 (d, J=11.7 Hz, 1H), 4.12 (d, J=11.7 Hz, 1H), 3.79 (s, 3H), 3.58 (s, 3H), 2.89 (s, 3H), 2.59 (s, 1H), 2.15 (s, 3H), 2.10 (s, 3H), 1.43 (m, 1H), 1.21 (m, 1H), 0.96 (t, J=7.5 Hz, 3H), 0.79 (t, J=6.9 Hz, 3H).

$^{13}$C NMR (CDCl$_3$, 75 MHz): δ: 174.7 (C), 170.9 (C), 170.7 (C), 157.7 (C), 153.3 (C), 139.7 (C), 134.9 (C), 130.8 (C), 129.5 (CH), 129.3 (C), 124.6 (CH), 123.8 (CH), 123.5 (CH), 123.5 (C), 122.2 (CH), 121.3 (CH), 118.8 (CH), 118.3 (CH), 117.2 (C), 110.4 (CH), 94.6 (CH), 81.5 (CH), 76.6 (CH), 76.0 (C), 66.3 (CH$_2$), 66.0 (CH), 55.7 (OCH$_3$), 55.3 (C), 54.4 (CH$_2$), 52.4 (OCH$_3$), 52.3 (CH$_2$), 51.9 (C), 50.1 (CH$_2$), 49.9 (CH$_2$), 45.7 (CH$_2$), 44.9 (CH$_2$), 42.3 (C), 39.9 (CH$_3$), 34.2 (CH$_2$), 32.8 (CH), 31.4 (CH$_2$), 27.7 (CH$_2$), 25.4 (CH$_2$), 21.0 (CH$_3$), 20.9 (CH$_3$), 12.2 (CH$_3$), 8.2 (CH$_3$). ESIMS (m/e) 807.5 [M+1]$^+$.

Example 7

Preparation of Compound BM7

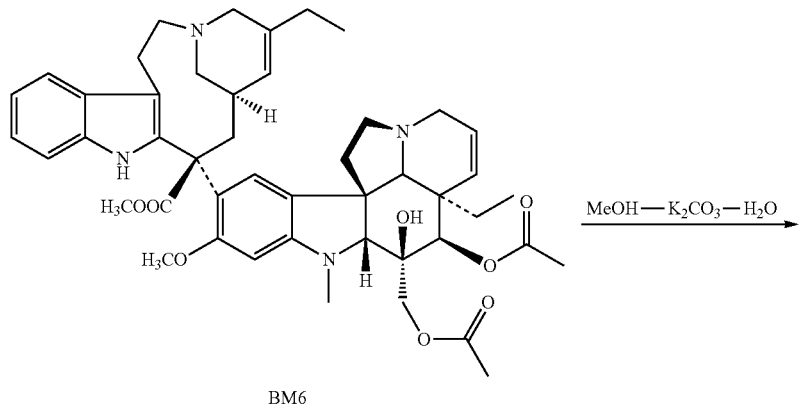

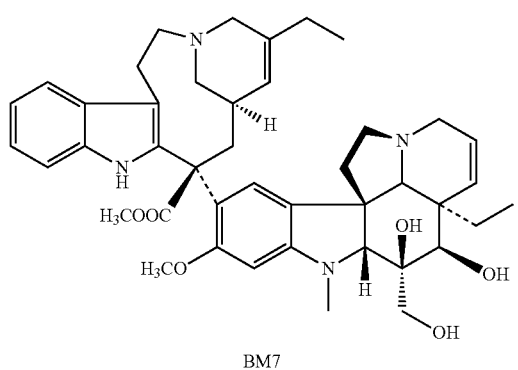

60 mg (0.07 mmol) of compound BM6 was dissolved in 20 mL of methanol, followed by addition of 1 g of 50% potassium carbonate solution. After 8 h of stirring under argon atmosphere at room temperature, the reaction mixture was concentrated, extracted with $CH_2Cl_2$ (10 mL×3). The $CH_2Cl_2$ layer was concentrated under reduced pressure to give 52 mg of compound BM7 as a white powder in 98% yield.

$^1$H NMR (CDCl$_3$, 300 MHz): δ: 8.94 (s, 1H), 8.03 (s, 1H), 7.53 (d, J=7.2 Hz, 1H), 7.13 (m, 3H), 6.59 (s, 1H), 6.17 (s, 1H), 5.86 (dd, J=10.2, 4.5 Hz, 1H), 5.70 (d, J=10.2 Hz, 1H), 5.51 (d, J=5.7 Hz, 1H), 3.82 (s, 3H), 3.59 (s, 3H), 3.01 (s, 3H), 2.53 (s, 1H), 1.01 (t, J=7.5 Hz, 3H), 0.91 (t, J=6.9 Hz, 3H).

$^{13}$C NMR (CDCl$_3$, 75 MHz): δ: 175.0 (C), 157.9 (C), 153.8 (C), 139.7 (C), 135.1 (C), 131.2 (C), 130.3 (CH), 129.4 (C), 125.1 (CH), 124.4 (C), 124.1 (CH), 123.9 (CH), 122.5 (CH), 121.2 (C), 119.0 (CH), 118.4 (CH), 117.1 (C), 110.7 (CH), 94.7 (CH), 81.0 (CH), 77.4 (C), 75.4 (CH), 66.7 (CH$_2$), 65.5 (CH), 56.0 (OCH$_3$), 55.6 (C), 54.5 (CH$_2$), 52.6 (OCH$_3$), 52.2 (CH$_2$), 52.0 (C), 50.7 (CH$_2$), 50.3 (CH$_2$), 45.9 (CH$_2$), 45.2 (CH$_2$), 43.5 (C), 40.4 (CH$_3$), 34.4 (CH$_2$), 32.8 (CH), 29.8 (CH$_2$), 28.0 (CH$_2$), 25.4 (CH$_2$), 12.4 (CH$_3$), 8.7 (CH$_3$).

ESIMS (m/e) 721.4 [M−1]$^+$.

Example 8

Preparation of Compound BM8

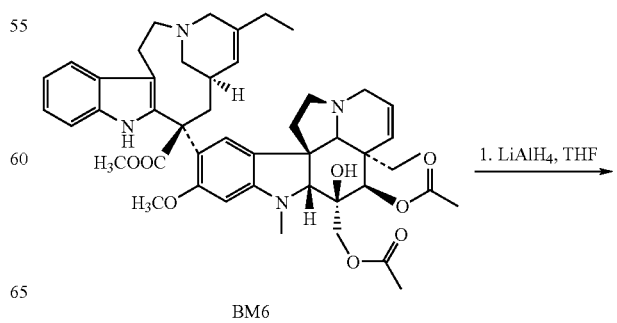

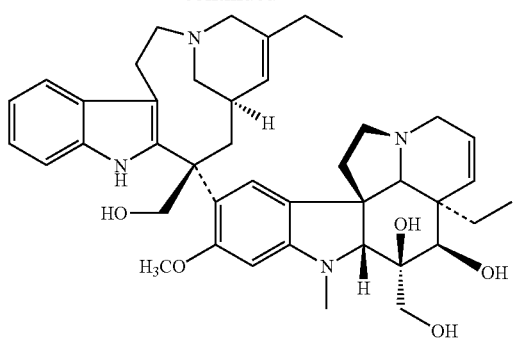

BM8

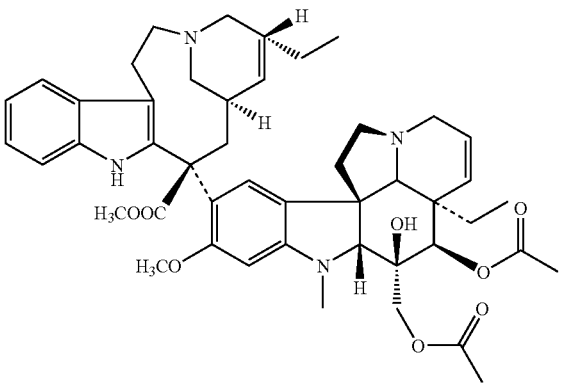

BM9

403 mg (0.5 mmol) of compound BM6 was dissolved in 20 mL of anhydrous tetrahydrofunan under argon atmosphere, followed by slow addition of 115 mg (3 mmol) of lithium-aluminum hydride under ice bath (0° C.). After 4 h of stirring at room temperature, 0.16 mL of water was added to quench the reaction. 0.16 mL of 15% sodium hydroxide solution and 0.48 mL of water were added sequently. After 5 minutes of stirring, the reaction mixture was suction-filtered through a fritted funnel, and the filtrate was dried over anhydrous sodium sulfate and concentrated under reduced pressure to give 348 mg of compound BM8 as a white solid in 98% yield.

$^1$H NMR (CDCl$_3$, 300 MHz): 8.99 (s, 1H), 7.54 (d, J=7.5 Hz, 1H), 7.20 (m, 4H), 6.15 (s, 1H), 5.84 (dd, J=10.2, 3.9 Hz, 1H), 5.51 (d, J=10.2 Hz, 1H), 5.46 (s, 1H), 3.58 (s, 3H), 3.06 (s, 3H), 2.15 (s, 6H), 0.99 (t, J=7.5 Hz, 3H), 0.66 (t, J=6.9 Hz, 3H).

$^{13}$C NMR (CDCl$_3$, 75 MHz): δ: 158.9 (C), 153.6 (C), 139.8 (C), 134.6 (C), 130.5 (C), 130.5 (CH), 129.4 (C), 124.3 (3CH), 124.3 (C), 120.9 (2CH), 120.9 (C), 118.5 (CH), 117.8 (C), 110.2 (CH), 95.0 (CH), 80.8 (CH), 77.4 (C), 75.4 (CH), 67.2 (2CH$_2$OH), 65.6 (CH), 55.2 (OCH$_3$), 55.2 (CH$_2$), 53.0 (C), 52.0 (C), 51.2 (2CH$_2$), 50.8 (CH$_2$), 48.3 (CH$_2$), 44.2 (CH$_2$), 43.6 (C), 40.5 (NCH$_3$), 34.0 (CH$_2$), 32.5 (CH), 29.7 (CH$_2$), 27.7 (CH$_2$), 25.5 (CH$_2$), 12.4 (CH$_3$), 8.2 (CH$_3$).

ESIMS (m/e) 693.4 [M−1]$^+$.

Example 9

Preparation of Compound BM9

480 mg (0.60 mmol) of compound BM6 was dissolved in 20 mL of methanol, followed by addition of Pa/C (5%, 40 mg). After 6 h of hydrogenation at room temperature under normal pressure, the completeness of the reaction was measured with a solvent system of ethyl acetate/methanol. The reaction mixture was filtered through Celite and concentrated at low temperature under reduced pressure. The concentrated was recrystallized in methanol to give 430 mg of compound BM9 as a white powder in 90% yield.

$^1$H NMR (CDCl$_3$, 300 MHz): δ: 9.25 (brs, 1H), 7.9 (s, 1H), 7.48 (d, J=7.5 Hz, 1H), 7.10 (m, 3H), 6.52 (s, 1H), 6.16 (s, 1H), 5.89 (dd, J=10.2, 4.5 Hz, 1H), 5.43 (d, J=10.2 Hz, 1H), 5.04 (s, 1H), 4.16 (d, J=11.7 Hz, 1H), 4.12 (d, J=11.7 Hz, 1H), 3.81 (s, 3H), 3.61 (s, 3H), 2.92 (s, 3H), 2.58 (s, 1H), 2.18 (s, 3H), 2.13 (s, 3H), 1.46 (m, 1H), 1.31 (m, 1H), 0.88 (t, J=7.2 Hz, 3H), 0.82 (t, J=7.2 Hz, 3H). ESIMS (m/e) 809.5 [M+1]$^+$.

Example 10

Preparation of Compound BM10

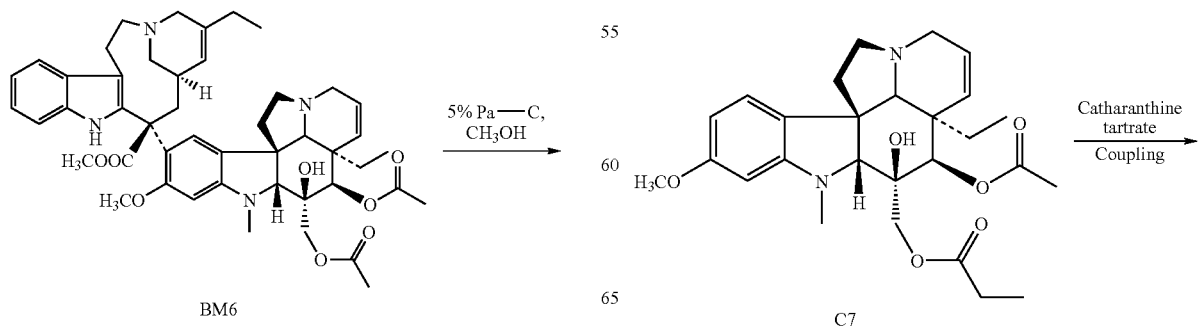

-continued

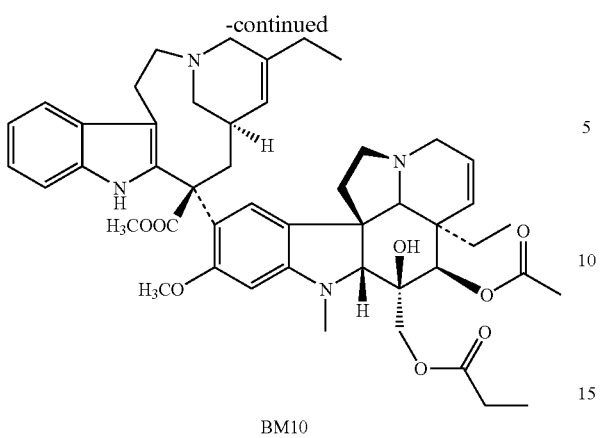

BM10

Compound BM10 was prepared as a white power following the procedure for preparing compound BM6.

$^1$H NMR (CDCl$_3$, 300 MHz): δ: 9.13 (s, 1H), 8.03 (s, 1H), 7.53 (d, J=7.5 Hz, 1H), 7.14 (m, 3H), 6.61 (s, 1H), 6.18 (s, 1H), 5.89 (dd, J=10.5, 4.5 Hz, 1H), 5.51 (d, J=6.0 Hz, 1H), 5.43 (d, J=10.5 Hz, 1H), 5.06 (s, 1H), 4.23 (d, J=11.4 Hz, 1H), 4.02 (d, J=11.4 Hz, 1H), 3.83 (s, 3H), 3.65 (s, 3H), 2.92 (s, 3H), 2.64 (s, 1H), 2.42 (q, J=7.8 Hz, 2H), 2.19 (s, 3H), 1.95 (q, J=7.5 Hz, 2H), 1.43 (m, 1H), 1.21 (m, 1H), 1.16 (t, J=7.8 Hz, 3H), 1.01 (t, J=7.5 Hz, 3H), 0.82 (t, J=7.2 Hz, 3H).

Example 11

Preparation of Compound BM11

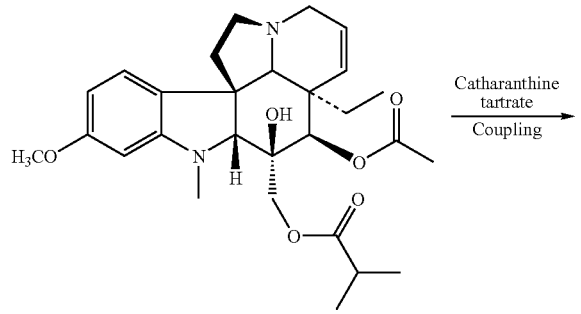

C8

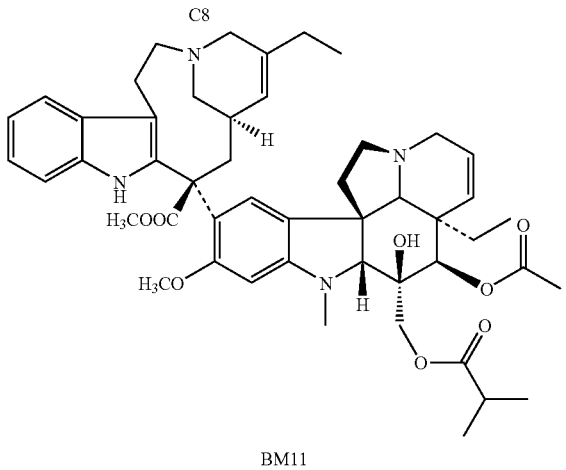

BM11

Compound BM11 was prepared as a white powder following the procedure for preparing compound BM6.

$^1$H NMR (CDCl$_3$, 300 MHz): δ: 9.00 (s, 1H), 8.02 (s, 1H), 7.52 (d, J=7.5 Hz, 1H), 7.13 (m, 3H), 6.61 (s, 1H), 6.17 (s, 1H), 5.85 (dd, J=10.2, 6.3 Hz, 1H), 5.49 (d, J=6.0 Hz, 1H), 5.41 (d, J=10.2 Hz, 1H), 5.05 (s, 1H), 4.24 (d, J=11.4 Hz, 1H), 3.99 (d, J=11.4 Hz, 1H), 3.82 (s, 3H), 3.64 (s, 3H), 2.92 (s, 3H), 2.59 (s, 1H), 2.17 (s, 3H), 1.94 (q, J=7.5 Hz, 2H), 1.47 (m, 1H), 1.21 (m, 1H), 1.19 (d, J=5.1 Hz, 6H), 1.00 (t, J=7.5 Hz, 3H), 0.81 (t, J=7.2 Hz, 3H). ESIMS (m/e) 835.3 [M+1]$^+$.

Example 12

Preparation of Compound BM12

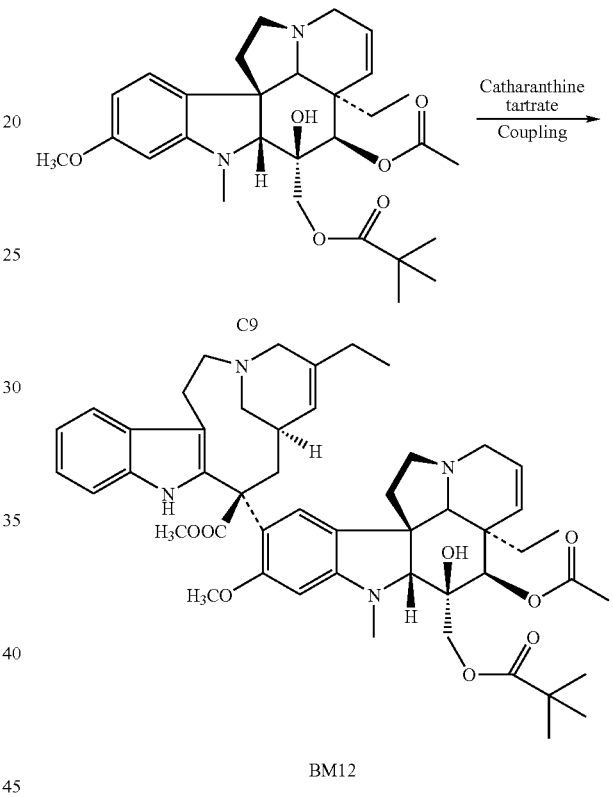

BM12

190 mg (0.39 mmol) of catharanthine tartrate and 190 mg (1.17 mmol) of anhydrous ferric(III) chloride were added into a buffer solution containing 125 mg of gelatin, 96 mg of sodium chloride, 16 mL of water and 16 mL of 0.1 N hydrochloric acid, under argon atmosphere. After 10 minutes of stirring at room temperature, 200 mg (0.39 mmol) of compound C6 was added. After 8 h of stirring at room temperature, a solution of sodium borohydride (32 mg) in ammonium hydroxide (4 mL) was added dropwise under ice bath (0° C.), and allowed to react for 15-20 minutes under ice bath. The reaction mixture was extracted with methylene chloride (40 mL×4), and the methylene chloride layer was washed with saturated salt solution (20 mL×3), filtered through Celite and concentrated under reduced pressure at low temperature. After the concentrate was dissolved in 2 mL of methanol and the solution was left for 2 minutes, a white crystal was crystallized, filtered and dried to give 158 mg of compound BM12 in 48% yield.

$^1$H NMR (DMSO-d$_6$, 300 MHz): δ: 9.86 (s, 1H), 8.21 (s, 1H), 7.44 (d, J=7.8 Hz, 1H), 7.28 (d, J=7.8 Hz, 1H), 6.99 (m, 3H), 6.47 (s, 1H), 6.30 (s, 1H), 5.73 (dd, J=10.2, 4.5 Hz, 1H), 5.45 (m, 2H), 4.82 (s, 1H), 4.32 (s, 4H), 4.11 (d, J=11.4 Hz, 1H), 3.78 (s, 3H), 3.70 (d, J=11.4 Hz, 1H), 3.57 (s, 3H), 2.93 (s, 3H), 2.70 (s, 1H), 2.08 (s, 3H), 1.15 (s, 9H), 0.96 (t, J=7.5 Hz, 3H), 0.66 (t, J=6.9 Hz, 3H). ESIMS (m/e) 849.5 [M+1]$^+$.

Example 13

Preparation of Compound BM13

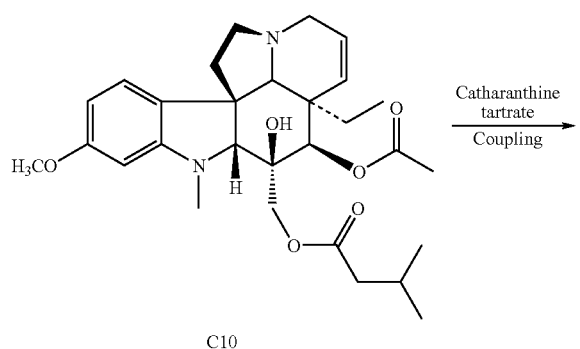

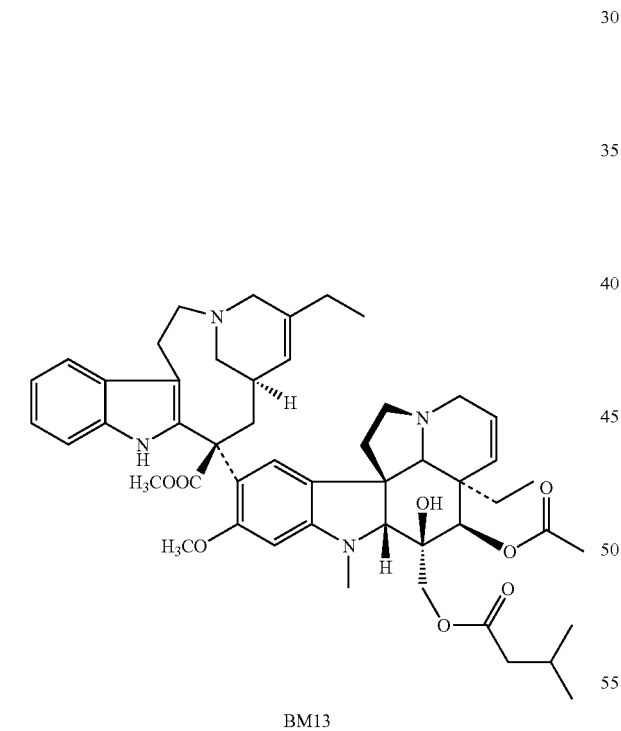

Compound BM13 was prepared as a white powder following the procedure for preparing compound BM6.

$^1$H NMR (CDCl$_3$, 300 MHz): δ: 9.05 (s, 1H), 8.02 (s, 1H), 7.53 (d, J=7.5 Hz, 1H), 7.14 (m, 3H), 6.62 (s, 1H), 6.18 (s, 1H), 5.88 (dd, J=10.2, 6.3 Hz, 1H), 5.48 (d, J=6.0 Hz, 1H), 5.43 (d, J=10.2 Hz, 1H), 5.06 (s, 1H), 4.25 (d, J=11.7 Hz, 1H), 4.00 (d, J=11.7 Hz, 1H), 3.83 (s, 3H), 3.62 (s, 3H), 2.92 (s, 3H), 2.60 (s, 1H), 2.19 (s, 3H), 1.94 (q, J=7.5 Hz, 2H), 1.47 (m, 1H), 1.21 (m, 1H), 1.01 (t, J=7.5 Hz, 3H), 0.97 (d, J=6.6 Hz, 6H), 0.82 (t, J=7.2 Hz, 3H). ESIMS (m/e) 849.5 [M+1]$^+$.

Example 14

Preparation of Compound BM14

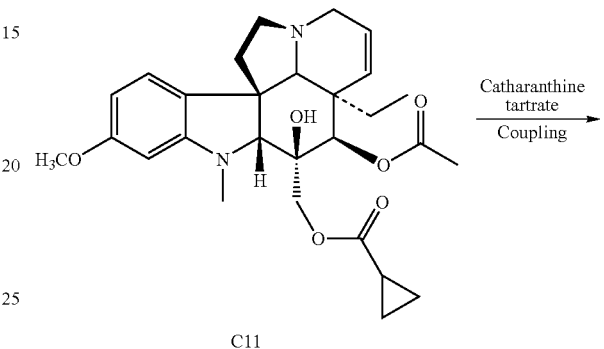

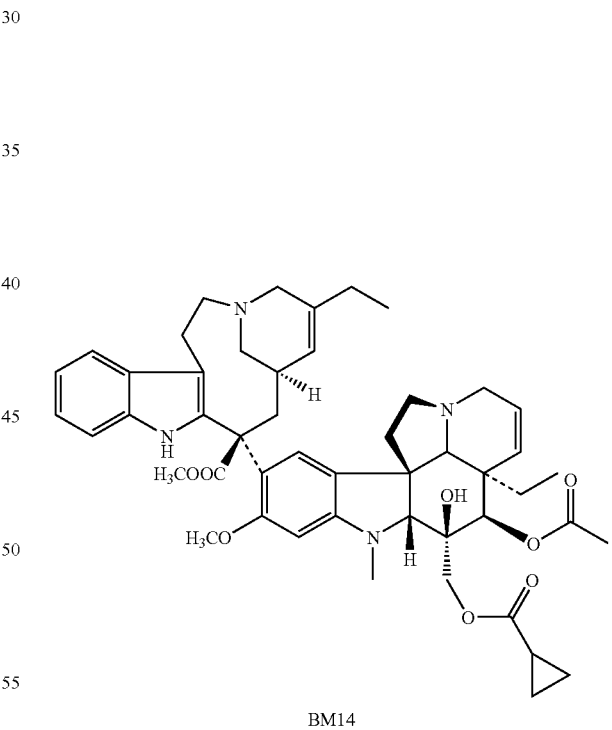

Compound BM14 was prepared as a white powder following the procedure for preparing compound BM6.

$^1$H NMR (CDCl$_3$, 300 MHz): δ: 9.14 (s, 1H), 8.03 (s, 1H), 7.53 (d, J=7.8 Hz, 1H), 7.14 (m, 3H), 6.62 (s, 1H), 6.19 (s, 1H), 5.89 (dd, J=10.2, 3.9 Hz, 1H), 5.51 (d, J=6.0 Hz, 1H), 5.44 (d, J=10.2 Hz, 1H), 5.06 (s, 1H), 4.24 (d, J=11.4 Hz, 1H), 4.02 (d, J=11.4 Hz, 1H), 3.84 (s, 3H), 3.65 (s, 1H), 3.63 (s, 3H), 2.94 (s, 3H), 2.62 (s, 1H), 2.18 (s, 3H), 1.94 (q, J=7.5 Hz,

2H), 1.47 (m, 1H), 1.21 (m, 1H), 1.01 (t, J=7.5 Hz, 5H), 0.86 (t, J=7.5 Hz, 2H), 0.82 (t, J=7.2 Hz, 3H). ESIMS (m/e) 833.5 [M+1]⁺.

Example 15

Preparation of Compound BM15

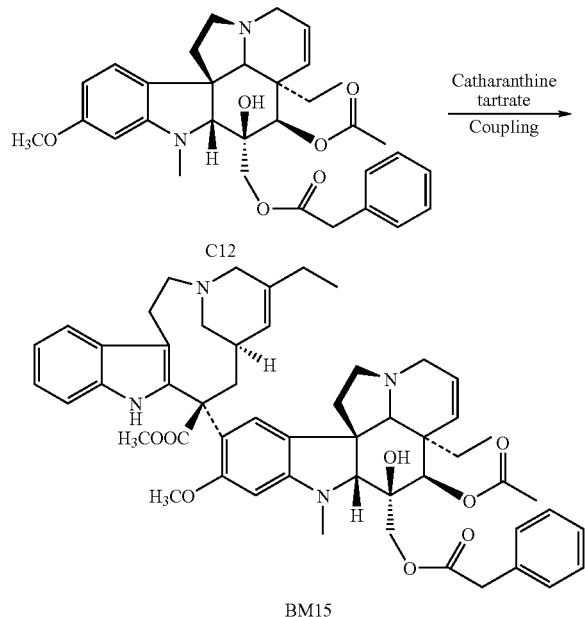

Compound BM15 was prepared as a white powder in 60% yield following the procedure for preparing compound BM6.

¹H NMR (CDCl₃, 300 MHz): δ: 9.11 (s, 1H), 8.03 (s, 1H), 7.53 (d, J=7.5 Hz, 1H), 7.29 (m, 5H), 7.14 (m, 3H), 6.62 (s, 1H), 6.11 (s, 1H), 5.88 (dd, J=10.2, 4.5 Hz, 1H), 5.46 (m, 2H), 5.04 (s, 1H), 4.32 (d, J=11.4 Hz, 1H), 3.96 (d, J=11.4 Hz, 1H), 3.82 (s, 3H), 3.72 (s, 2H), 3.61 (s, 3H), 3.44 (s, 1H), 2.60 (s, 3H), 2.59 (s, 1H), 2.17 (s, 3H), 1.94 (q, J=7.5 Hz, 2H), 1.43 (m, 1H), 1.21 (m, 1H), 1.01 (t, J=7.5 Hz, 3H), 0.83 (t, J=6.9 Hz, 3H). ESIMS (m/e) 883.5 [M+1]⁺.

Example 16

Preparation of Compound BM16

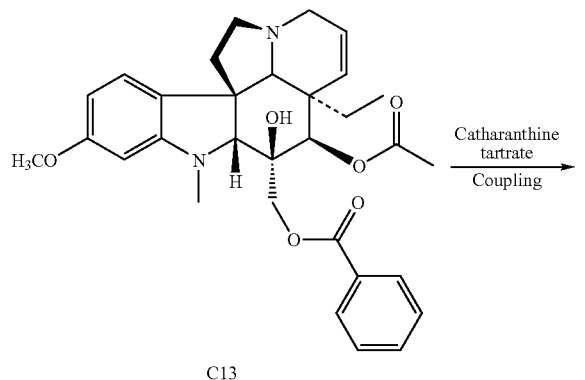

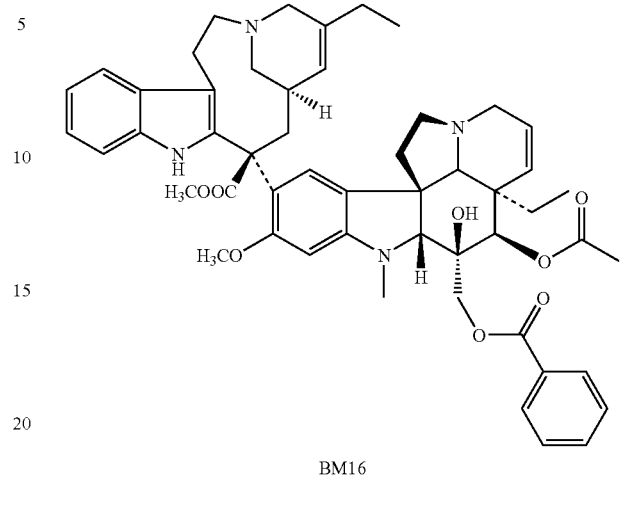

Compound BM16 was prepared as a white powder following the procedure for preparing compound BM6.

¹H NMR (CDCl₃, 300 MHz): δ: 9.12 (s, 1H), 8.09 (d, J=6.9 Hz, 2H), 8.06 (s, 1H), 7.55 (m, 2H), 7.45 (d, J=7.2 Hz, 1H), 7.44 (t, J=7.2 Hz, 1H), 7.15 (m, 3H), 6.65 (s, 1H), 6.17 (s, 1H), 5.90 (dd, J=10.2, 4.5 Hz, 1H), 5.48 (d, J=9.6 Hz, 1H), 5.45 (d, J=10.2 Hz, 1H), 5.18 (s, 1H), 4.56 (d, J=11.4 Hz, 1H), 4.20 (d, J=11.4 Hz, 1H), 3.88 (s, 3H), 3.73 (s, 1H), 3.65 (s, 3H), 2.96 (s, 3H), 2.65 (s, 1H), 2.18 (s, 3H), 1.94 (q, J=7.5 Hz, 2H), 1.43 (m, 1H), 1.21 (m, 1H), 1.00 (t, J=7.5 Hz, 3H), 0.84 (t, J=7.2 Hz, 3H). ESIMS (m/e) 869.4 [M+1]⁺.

Example 17

Preparation of Compound BM17

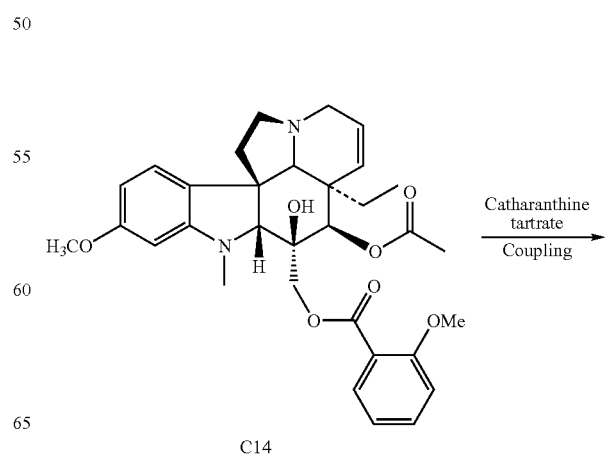

113
-continued

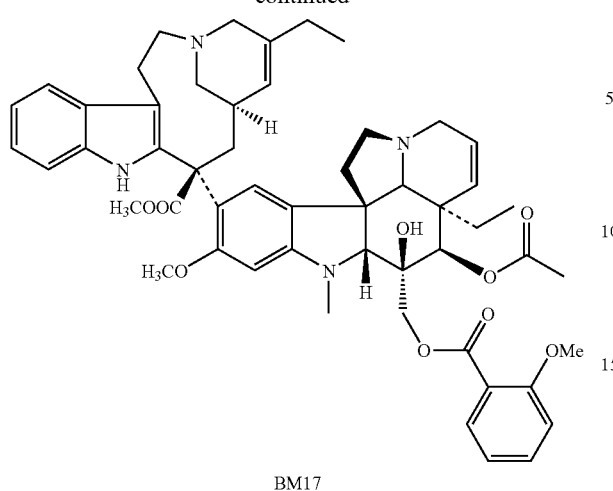

BM17

Compound BM17 was prepared as a white powder following the procedure for preparing compound BM6.

$^1$H NMR (CDCl$_3$, 300 MHz): δ: 9.07 (s, 1H), 8.05 (s, 1H), 7.87 (d, J=7.8 Hz, 1H), 7.53 (d, J=7.2 Hz, 1H), 7.46 (t, J=7.8 Hz, 1H), 7.14 (m, 3H), 7.00 (t, J=7.8 Hz, 1H), 6.95 (d, J=7.8 Hz, 1H), 6.63 (s, 1H), 6.17 (s, 1H), 5.88 (dd, J=10.2, 4.5 Hz, 1H), 5.48 (d, J=9.3 Hz, 1H), 5.44 (d, J=10.2 Hz, 1H), 5.14 (s, 1H), 4.50 (d, J=11.4 Hz, 1H), 4.18 (d, J=11.4 Hz, 1H), 3.85 (s, 3H), 3.82 (s, 3H), 3.71 (s, 1H), 3.62 (s, 3H), 2.99 (s, 3H), 2.62 (s, 1H), 2.18 (s, 3H), 1.95 (q, J=7.5 Hz, 2H), 1.43 (m, 1H), 1.21 (m, 1H), 1.00 (t, J=7.5 Hz, 3H), 0.83 (t, J=6.9 Hz, 3H). ESIMS (m/e) 899.4 [M+1]$^+$.

Example 18

Preparation of Compound BM18

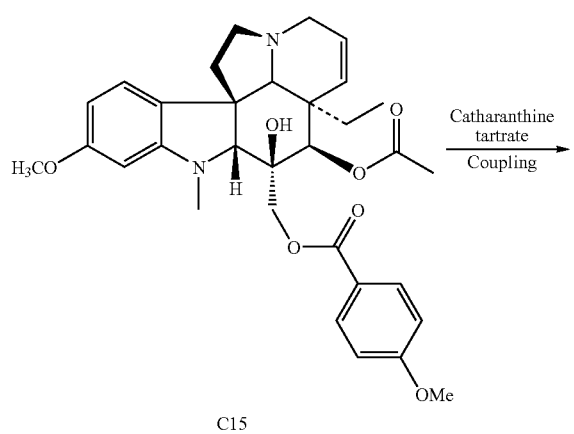

C15

114
-continued

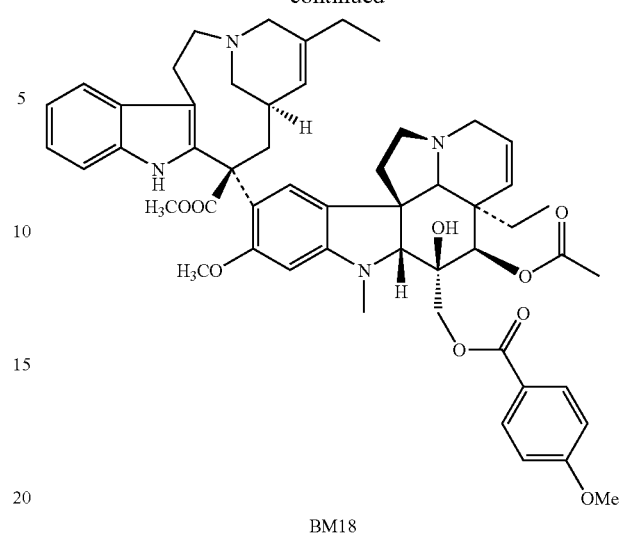

BM18

Compound BM18 was prepared as a white powder following the procedure for preparing compound BM6.

$^1$H NMR (CDCl$_3$, 300 MHz): δ: 9.10 (s, 1H), 8.06 (s, 1H), 8.04 (d, J=8.7 Hz, 2H), 7.53 (d, J=7.8 Hz, 1H), 7.14 (m, 3H), 6.92 (d, J=8.7 Hz, 2H), 6.64 (s, 1H), 6.15 (s, 1H), 5.89 (dd, J=10.5, 4.5 Hz, 1H), 5.47 (d, J=9.6 Hz, 1H), 5.44 (d, J=10.5 Hz, 1H), 5.18 (s, 1. H), 4.51 (d, J=11.4 Hz, 1H), 4.16 (d, J=11.4 Hz, 1H), 3.85 (s, 3H), 3.82 (s, 3H), 3.69 (s, 1H), 3.63 (s, 3H), 2.93 (s, 3H), 2.64 (s, 1H), 2.17 (s, 3H), 1.94 (q, J=7.5 Hz, 2H), 1.43 (m, 1H), 1.21 (m, 1H), 1.00 (t, J=7.5 Hz, 3H), 0.83 (t, J=6.9 Hz, 3H). ESIMS (m/e) 899.4 [M+1]$^+$.

Example 19

Preparation of Compound BM19

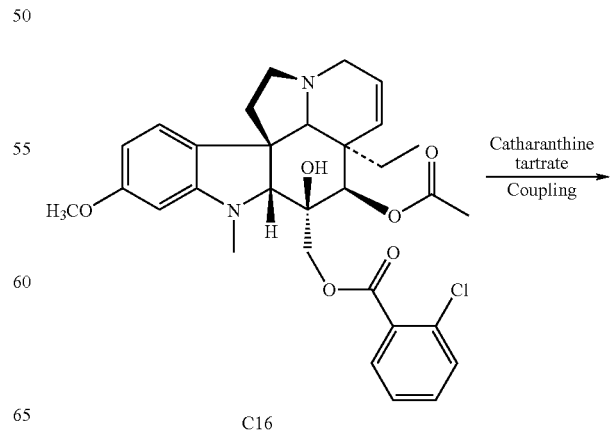

C16

115

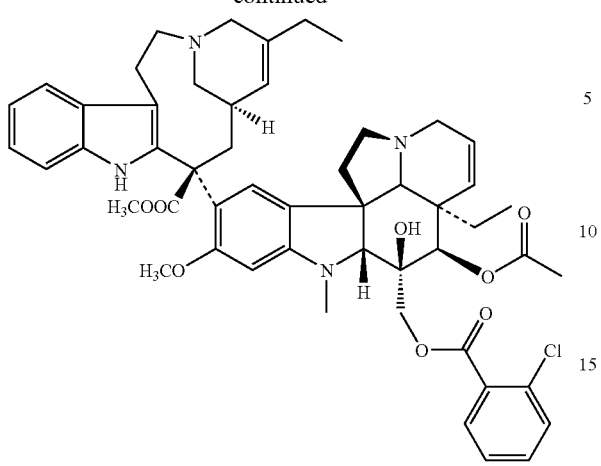

BM19

Compound BM19 was prepared as a white powder following the procedure for preparing compound BM6.

$^1$H NMR (CDCl$_3$, 300 MHz): δ: 9.10 (s, 1H), 8.05 (s, 1H), 7.89 (d, J=6.6 Hz, 1H), 7.53 (d, J=7.2 Hz, 1H), 7.42 (d, J=7.8 Hz, 2H), 7.31 (t, J=7.8 Hz, 1H), 7.14 (m, 3H), 6.63 (s, 1H), 6.18 (s, 1H), 5.89 (dd, J=10.2, 4.5 Hz, 1H), 5.48 (d, J=9.3 Hz, 1H), 5.45 (d, J=10.2 Hz, 1H), 5.14 (s, 1H), 4.52 (d, J=11.4 Hz, 1H), 4.26 (d, J=11.4 Hz, 1H), 3.82 (s, 3H), 3.68 (s, 1H), 3.62 (s, 3H), 3.00 (s, 3H), 2.62 (s, 1H), 2.19 (s, 3H), 1.94 (q, J=7.5 Hz, 2H), 1.50 (m, 1H), 1.29 (m, 1H), 1.00 (t, J=7.5 Hz, 3H), 0.83 (t, J=6.9 Hz, 3H).

ESIMS (m/e) 903.5 [M+1]$^+$.

116

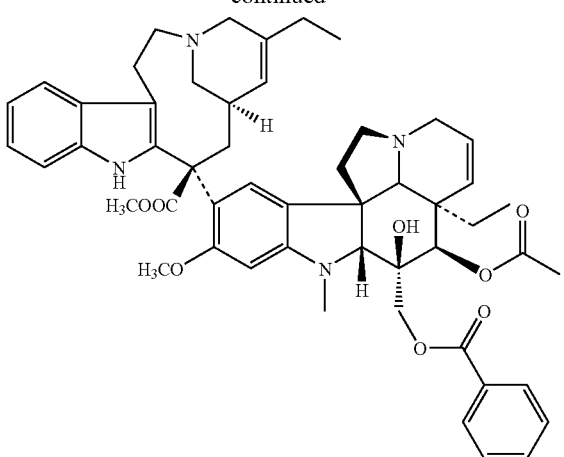

BM20

Compound BM20 was prepared as a white powder following the procedure for preparing compound BM6.

$^1$H NMR (CDCl$_3$, 300 MHz): δ: 9.15 (s, 1H), 8.06 (s, 1H), 8.02 (d, J=8.4 Hz, 2H), 7.53 (d, J=7.5 Hz, 1H), 7.41 (d, J=8.4 Hz, 2H), 7.14 (m, 3H), 6.65 (s, 1H), 6.16 (s, 1H), 5.89 (dd, J=10.2, 4.5 Hz, 1H), 5.48 (d, J=8.4 Hz, 1H), 5.44 (d, J=10.2 Hz, 1H), 5.17 (s, 1H), 4.54 (d, J=11.7 Hz, 1H), 4.20 (d, J=11.7 Hz, 1H), 3.82 (s, 3H), 3.66 (s, 1H), 3.64 (s, 3H), 2.93 (s, 3H), 2.65 (s, 1H), 2.17 (s, 3H), 1.94 (q, J=7.5 Hz, 2H), 1.53 (m, 1H), 1.29 (m, 1H), 0.98 (t, J=7.5 Hz, 3H), 0.84 (t, J=7.2 Hz, 3H).

ESIMS (m/e) 903.5 [M+1]$^+$.

Example 20

Preparation of Compound BM20

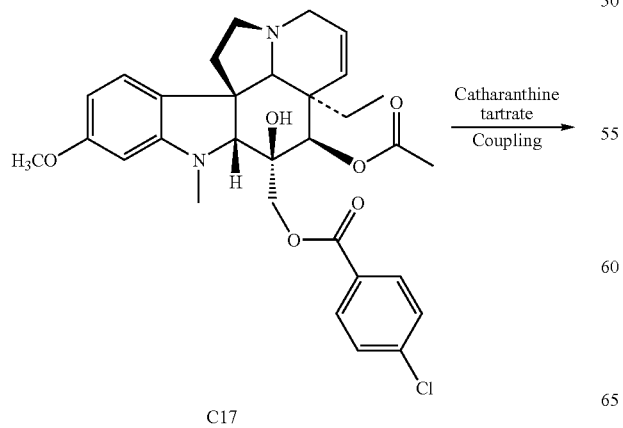

C17

Example 21

Preparation of Compound BM21

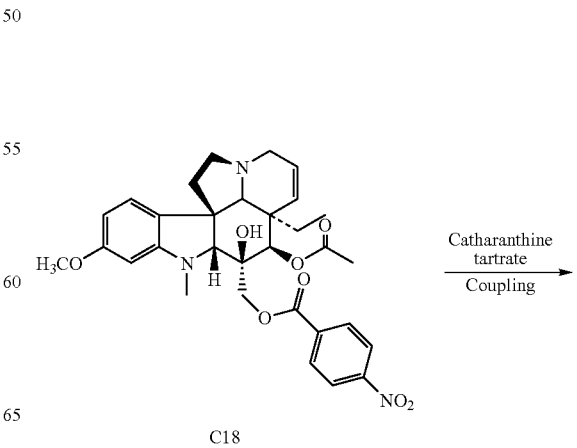

C18

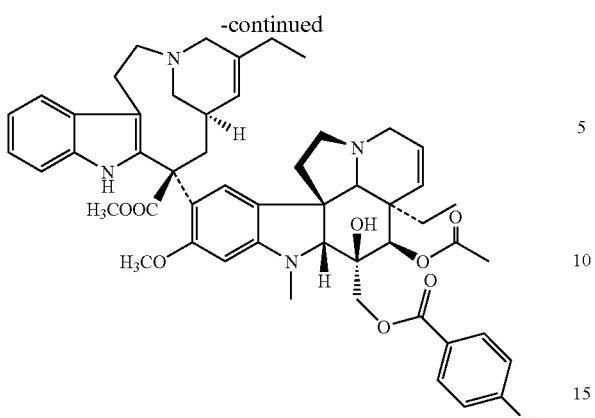

BM21

Compound BM21 was prepared as a white powder following the procedure for preparing compound BM6.

$^1$H NMR (CDCl$_3$, 300 MHz): δ: 9.18 (s, 1H), 8.28 (d, J=6.0 Hz, 4H), 8.04 (s, 1H), 7.52 (d, J=7.5 Hz, 1H), 7.14 (m, 3H), 6.61 (s, 1H), 6.17 (s, 1H), 5.89 (dd, J=10.2, 4.5 Hz, 1H), 5.53 (s, 1H), 5.44 (d, J=10.2 Hz, 1H), 5.17 (s, 1H), 4.59 (d, J=11.4 Hz, 1H), 4.26 (d, J=11.4 Hz, 1H), 3.83 (s, 3H), 3.71 (s, 1H), 3.65 (s, 3H), 2.95 (s, 3H), 2.65 (s, 1H), 2.18 (s, 3H), 1.96 (q, J=7.5 Hz, 2H), 1.53 (m, 1H), 1.29 (m, 1H), 1.01 (t, J=7.5 Hz, 3H), 0.83 (t, J=7.2 Hz, 3H).

ESIMS (m/e) 914.5 [M+1]$^+$.

Example 22

Preparation of Compound BM22

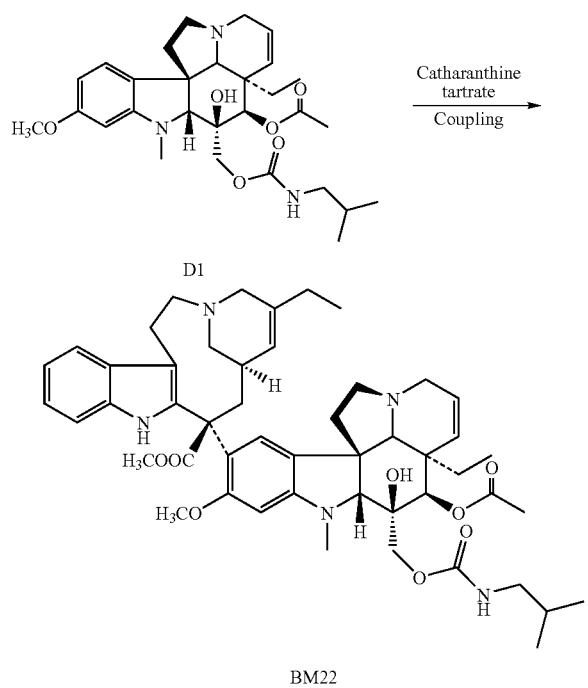

BM22

Compound BM22 was prepared as a white powder following the procedure for preparing compound BM6.

$^1$H NMR (CDCl$_3$, 300 MHz): δ: 9.29 (s, 1H), 8.02 (s, 1H), 7.53 (d, J=7.5 Hz, 1H), 7.14 (m, 3H), 6.60 (s, 1H), 6.18 (s, 1H), 5.88 (dd, J=10.2, 3.9 Hz, 1H), 5.50 (s, 1H), 5.42 (d, J=10.2 Hz, 1H), 5.07 (s, 1H), 4.96 (m, 1H), 4.10 (q, J=4.8 Hz, 2H), 3.83 (s, 3H), 3.64 (s, 3H), 3.62 (s, 1H), 2.92 (s, 3H), 2.81 (d, J=16.5 Hz, 1H), 2.61 (s, 1H), 2.18 (s, 3H), 1.94 (q, J=7.5 Hz, 2H), 1.46 (m, 1H), 1.23 (m, 1H), 1.01 (t, J=7.2 Hz, 3H), 0.90 (d, J=6.9 Hz, 6H), 0.82 (t, J=7.2 Hz, 3H).

ESIMS (m/e) 864.4 [M+1]$^+$.

Example 23

Preparation of Compound BM23

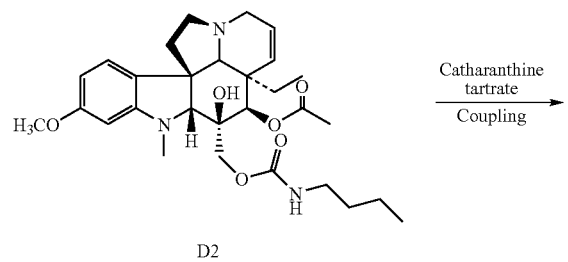

D2

BM23

Compound BM23 was prepared as a white powder following the procedure for preparing compound BM6.

$^1$H NMR (CDCl$_3$, 300 MHz): δ: 9.29 (s, 1H), 8.03 (s, 1H), 7.53 (d, J=7.5 Hz, 1H), 7.14 (m, 3H), 6.60 (s, 1H), 6.18 (s, 1H), 5.88 (dd, J=10.2, 3.9 Hz, 1H), 5.51 (s, 1H), 5.42 (d, J=10.2 Hz, 1H), 5.06 (s, 1H), 4.90 (m, 1H), 4.10 (s, 2H), 3.84 (s, 3H), 3.63 (s, 3H), 3.54 (s, 1H), 2.92 (s, 3H), 2.81 (d, J=15.6 Hz, 1H), 2.61 (s, 1H), 2.19 (s, 3H), 1.94 (q, J=7.5 Hz, 2H), 1.46 (m, 1H), 1.23 (m, 1H), 1.03 (t, J=7.5 Hz, 3H), 0.92 (d, J=7.2 Hz, 3H), 0.82 (t, J=6.9 Hz, 3H)

ESIMS (m/e) 864.3 [M+1]$^+$..

Example 24

Preparation of Compound BM24

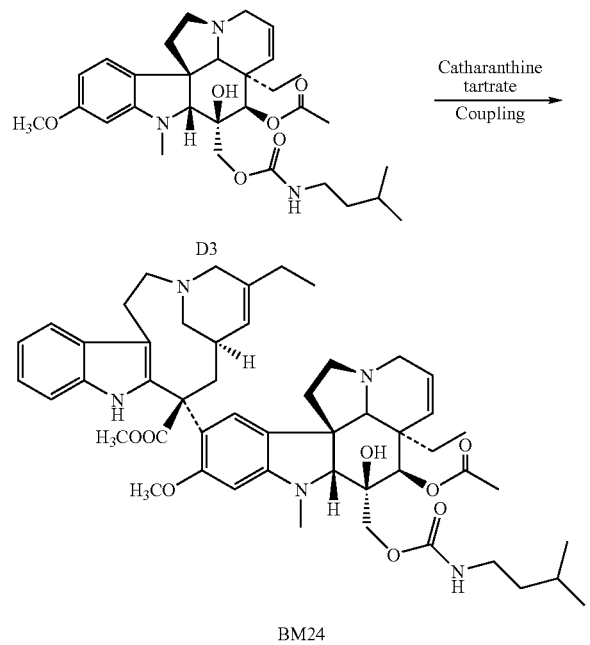

Compound BM24 was prepared as a white powder following the procedure for preparing compound BM6.

$^1$H NMR (CDCl$_3$, 300 MHz): δ: 9.26 (s, 1H), 8.02 (s, 1H), 7.53 (d, J=7.5 Hz, 1H), 7.14 (m, 3H), 6.60 (s, 1H), 6.18 (s, 1H), 5.88 (dd, J=10.2, 3.9 Hz, 1H), 5.51 (s, 1H), 5.42 (d, J=10.2 Hz, 1H), 5.06 (s, 1H), 4.85 (m, 1H), 4.10 (s, 2H), 3.84 (s, 3H), 3.63 (s, 3H), 3.59 (s, 1H), 2.92 (s, 3H), 2.81 (d, J=16.2 Hz, 1H), 2.61 (s, 1H), 2.18 (s, 3H), 1.94 (q, J=7.5 Hz, 2H), 1.46 (m, 1H), 1.38 (q, J=6.9 Hz, 2H), 1.23 (m, 1H), 1.01 (t, J=7.5 Hz, 3H), 0.91 (d, J=6.6 Hz, 6H), 0.82 (t, J=6.9 Hz, 3H).

ESIMS (m/e) 878.4 [M+1]$^+$.

Example 25

Preparation of Compound BM25

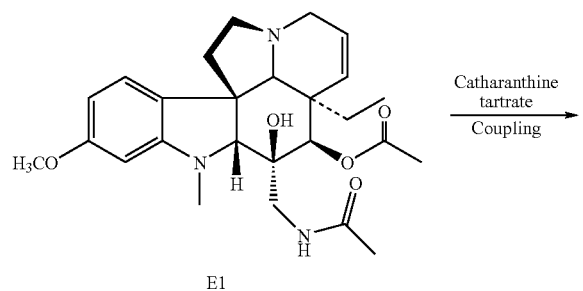

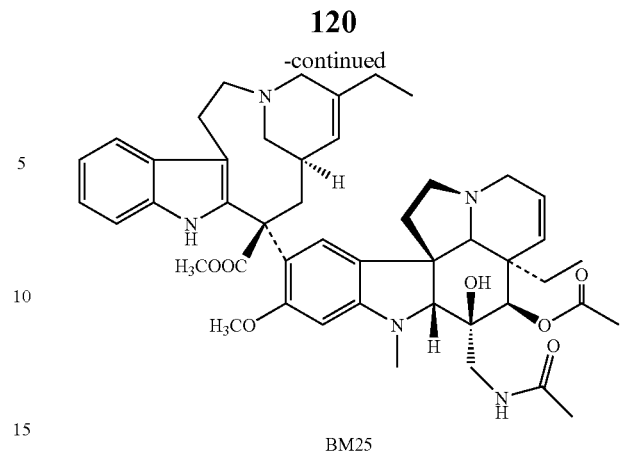

280 mg (0.58 mmol) of catharanthine tartrate and 280 mg (1.74 mmol) of anhydrous ferric chloride were added into a buffer solution containing 185 mg of gelatin, 145 mg of sodium chloride, 24 mL of water and 24 mL of 0.1 N hydrochloric acid, under argon atmosphere. After 10 minutes of stirring at room temperature, 272 mg (0.58 mmol) of compound E1 was added. After 8 h of stirring at room temperature, a solution of sodium borohydride (48 mg) in ammonium hydroxide (5 mL) was added dropwise under ice bath (0° C.), and allowed to react for 15-20 minutes under ice bath. The reaction mixture was then extracted with methylene chloride (20 mL×4), and the methylene chloride layer was washed with saturated salt solution (20 mL×3), filtered through Celite and concentrated under reduced pressure at low temperature. After the concentrate was dissolved in 2 mL of methanol and the solution was left for 2 minutes, a white crystal was crystallized, filtered and dried to give 233 mg of compound BM25 in 50% yield.

$^1$H NMR (CDCl$_3$, 300 MHz): δ: 9.33 (s, 1H), 7.95 (s, 1H), 7.45 (d, J=7.2 Hz, 1H), 7.06 (m, 3H), 6.52 (s, 1H), 6.13 (s, 1H), 6.10 (d, J=8.7 Hz, 1H), 5.81 (dd, J=10.2, 4.5 Hz, 1H), 5.42 (d, J=4.8 Hz, 1H), 5.35 (d, J=10.2 Hz, 1H), 4.96 (s, 1H), 3.76 (s, 3H), 3.55 (s, 3H), 2.82 (s, 3H), 2.55 (s, 1H), 2.07 (s, 3H), 1.93 (s, 3H), 1.43 (m, 1H), 0.93 (t, J=7.2 Hz, 3H), 0.73 (t, J=6.9 Hz, 3H).

ESIMS (m/e) 806.5 [M+1]$^+$.

Example 26

Preparation of Compound BM26

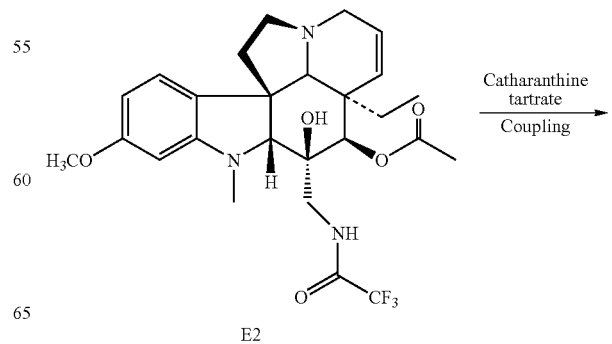

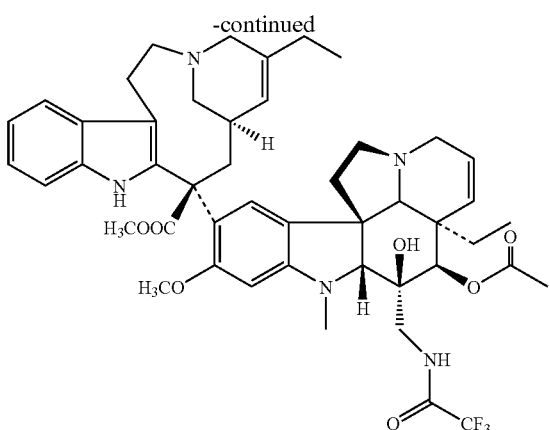

BM26

Compound BM26 was prepared following the procedure for preparing compound BM25.

$^1$H NMR (CDCl$_3$, 300 MHz): δ: 9.64 (s, 1H), 8.01 (s, 1H), 7.53 (d, J=7.8 Hz, 1H), 7.20-7.12 (m, 3H), 6.62 (s, 1H), 6.22 (s, 1H), 5.90 (dd, J=10.2, 4.2 Hz, 1H), 5.49-5.42 (m, 2H), 5.03 (s, 1H), 3.83 (s, 3H), 3.79-3.74 (m, 1H), 3.63 (s, 3H), 3.53 (d, J=16.5 Hz, 1H), 3.29 (s, 1H), 2.88 (s, 3H), 2.66 (s, 1H), 2.58 (d, J=12.9 Hz, 1H), 2.50-2.40 (m, 2H), 2.15 (s, 3H), 1.93 (q, J=7.2 Hz, 2H), 1.50-1.43 (m, 1H), 1.00 (t, J=7.5 Hz, 3H), 0.81 (t, J=7.2 Hz, 3H). ESIMS (m/e) 860.4 [M+1]$^+$.

Example 27

Preparation of Compound BM27

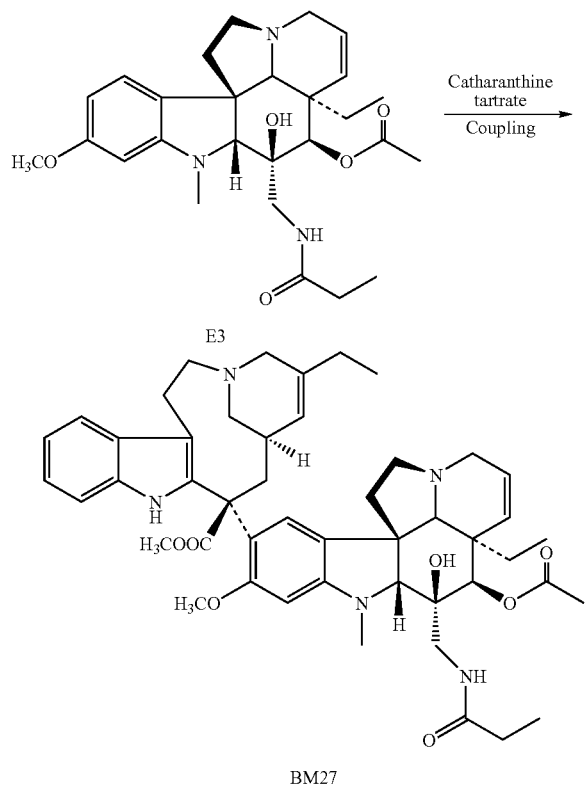

BM27

Compound BM27 was prepared following the procedure for preparing compound BM25.

$^1$H NMR (CDCl$_3$, 300 MHz): δ: 9.40 (s, 1H), 8.00 (s, 1H), 7.45 (d, J=7.5 Hz, 1H), 7.13 (m, 3H), 6.53 (s, 1H), 6.18 (d, J=7.8 Hz, 1H), 6.14 (s, 1H), 5.81 (dd, J=10.2, 3.9 Hz, 1H), 5.43 (d, J=6.3 Hz, 1H), 5.35 (d, J=10.2 Hz, 1H), 4.95 (s, 1H), 3.76 (s, 3H), 3.55 (s, 3H), 3.28 (s, 1H), 2.81 (s, 3H), 2.56 (s, 1H), 2.16 (q, J=7.8 Hz, 2H), 2.08 (s, 3H), 1.87 (q, J=7.8 Hz, 2H), 1.41 (m, 1H), 1.08 (t, J=7.8 Hz, 3H), 0.93 (t, J=7.8 Hz, 3H), 0.74 (t, J=6.9 Hz, 3H).

ESIMS (m/e) 820.5 [M+1]$^+$.

Example 28

Preparation of Compound BM28

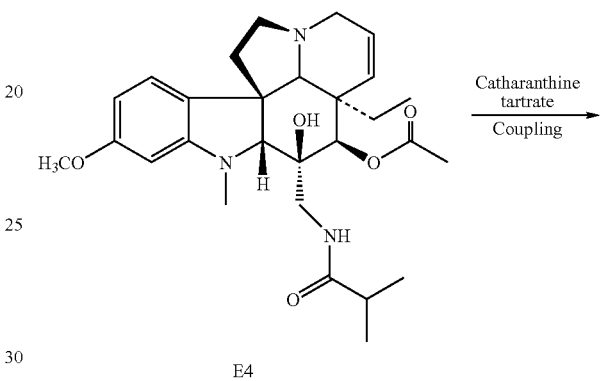

E4

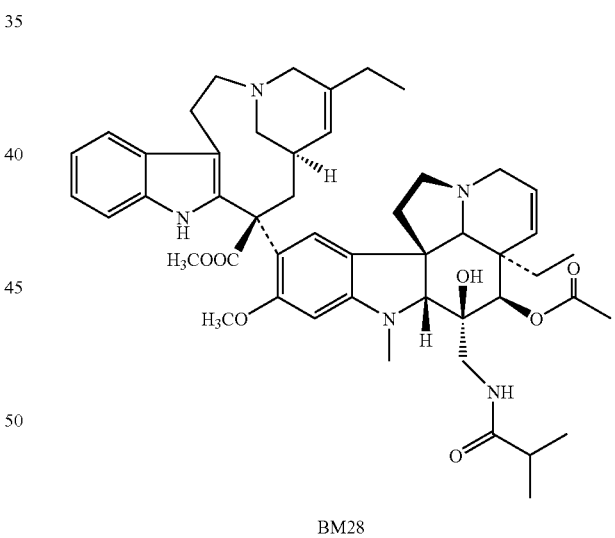

BM28

Compound BM28 was prepared following the procedure for preparing compound BM25.

$^1$H NMR (CDCl$_3$, 300 MHz): δ: 9.43 (s, 1H), 8.01 (s, 1H), 7.52 (d, J=7.5 Hz, 1H), 7.16 (m, 3H), 6.61 (s, 1H), 6.21 (s, 1H), 6.19 (s, 1H), 5.88 (dd, J=10.2, 3.6 Hz, 1H), 5.47 (d, J=6.0 Hz, 1H), 5.42 (d, J=10.2 Hz, 1H), 5.02 (s, 1H), 3.82 (s, 3H), 3.62 (s, 3H), 3.34 (s, 1H), 2.86 (s, 3H), 2.62 (s, 1H), 2.15 (s, 3H), 1.96 (q, J=7.5 Hz, 2H), 1.49 (m, 1H), 1.15 (d, J=1.8 Hz, 3H), 1.14 (d, J=1.8 Hz, 3H), 0.99 (t, J=7.5 Hz, 3H), 0.80 (t, J=7.2 Hz, 3H).

ESIMS (m/e) 834.5 [M+1]$^+$.

Example 29

Preparation of Compound BM29

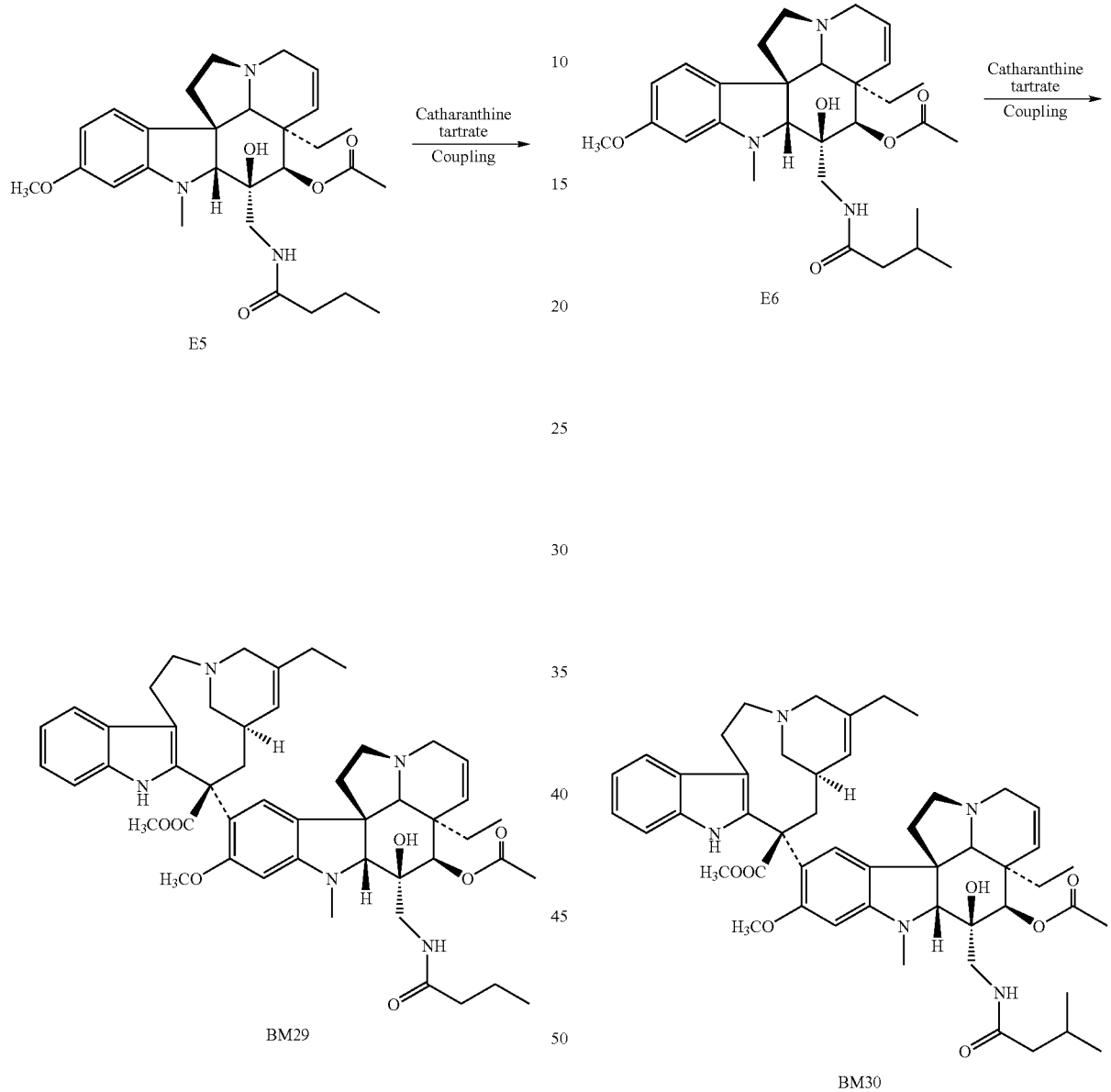

Compound BM29 was prepared following the procedure for preparing compound BM25.

$^1$H NMR (CDCl$_3$, 300 MHz): δ: 9.41 (s, 1H), 8.02 (s, 1H), 7.52 (d, J=7.8 Hz, 1H), 7.19-7.09 (m, 3H), 6.59 (s, 1H), 6.19 (s, 1H), 6.15 (d, J=7.8 Hz, 1H), 5.89 (dd, J=10.2, 6.0 Hz, 1H), 5.49 (d, J=5.7 Hz, 1H), 5.41 (d, J=10.2 Hz, 1H), 5.02 (s, 1H), 3.83 (s, 3H), 3.79-3.70 (m, 1H), 3.62 (s, 3H), 3.55 (d, J=16.5 Hz, 1H), 3.35 (s, 1H), 2.88 (s, 3H), 2.62 (s, 1H), 2.18 (t, J=7.5 Hz, 2H), 2.15 (s, 3H), 1.94 (q, J=7.2 Hz, 2H), 1.70-1.60 (m, 2H), 1.53-1.45 (m, 1H), 1.30-1.20 (m, 1H), 1.00 (t, J=7.5 Hz, 3H), 0.94 (t, J=7.5 Hz, 3H), 0.80 (t, J=7.2 Hz, 3H).

ESIMS (m/e) 834.5 [M+1]$^+$.

Example 30

Preparation of Compound BM30

Compound BM30 was prepared following the procedure for preparing compound BM25.

$^1$H NMR (CDCl$_3$, 300 MHz): δ: 9.40 (s, 1H), 8.03 (s, 1H), 7.53 (d, J=7.8 Hz, 1H), 7.19-7.09 (m, 3H), 6.58 (s, 1H), 6.19 (s, 1H), 6.15 (d, J=7.8 Hz, 1H), 5.89 (dd, J=10.2, 6.0 Hz, 1H), 5.49 (d, J=5.7 Hz, 1H), 5.41 (d, J=10.2 Hz, 1H), 5.02 (s, 1H), 3.83 (s, 3H), 3.79-3.72 (m, 1H), 3.62 (s, 3H), 3.55 (d, J=16.5 Hz, 1H), 3.35 (s, 1H), 2.88 (s, 3H), 2.62 (s, 1H), 2.15 (s, 3H), 2.10 (d, J=9.9 Hz, 2H), 1.95 (q, J=7.2 Hz, 2H), 1.69-1.59 (m, 2H), 1.53-1.45 (m, 1H), 1.31-1.21 (m, 1H), 0.99 (t, J=7.5 Hz, 3H), 0.94 (d, J=6.3 Hz, 6H), 0.80 (t, J=7.2 Hz, 3H).

ESIMS (m/e) 848.5 [M+1]$^+$.

Example 31

Preparation of Compound BM31

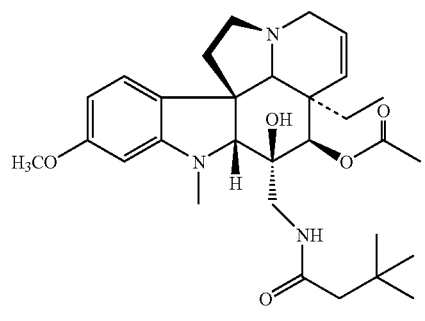

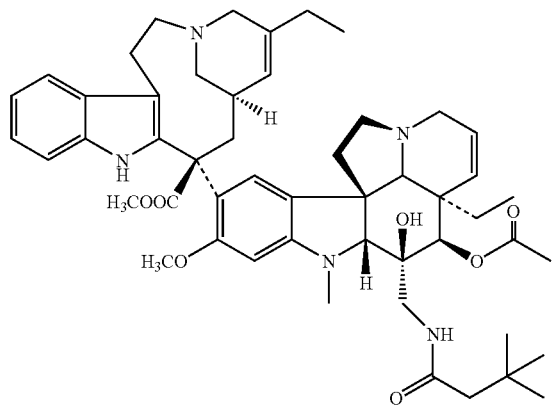

Compound BM31 was prepared following the procedure for preparing compound BM25.

$^1$H NMR (CDCl$_3$, 300 MHz): δ: 9.42 (s, 1H), 8.01 (s, 1H), 7.52 (d, J=7.8 Hz, 1H), 7.17-7.09 (m, 3H), 6.58 (s, 1H), 6.19 (s, 1H), 6.07 (d, J=7.8 Hz, 1H), 5.88 (dd, J=10.2, 3.6 Hz, 1H), 5.49 (d, J=6.0 Hz, 1H), 5.41 (d, J=10.2 Hz, 1H), 5.02 (s, 1H), 3.83 (s, 3H), 3.79-3.69 (m, 1H), 3.62 (s, 3H), 3.32 (s, 1H), 2.89 (s, 3H), 2.81 (d, J=14.1 Hz, 1H), 2.59 (s, 1H), 2.15 (s, 3H), 2.10 (s, 2H), 1.94 (q, J=7.2 Hz, 2H), 1.53-1.46 (m, 1H), 1.49 (m, 1H), 1.30-1.19 (m, 1H), 1.02 (s, 9H), 0.99 (t, J=7.5 Hz, 3H), 0.80 (t, J=7.2 Hz, 3H).

ESIMS (m/e) 862.5 [M+1]$^+$.

Example 32

Preparation of Compound BM32

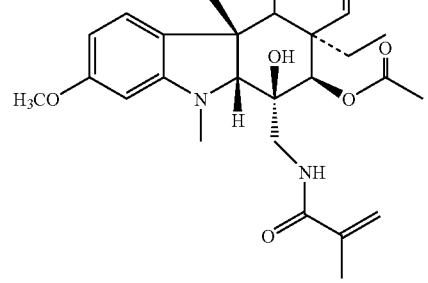

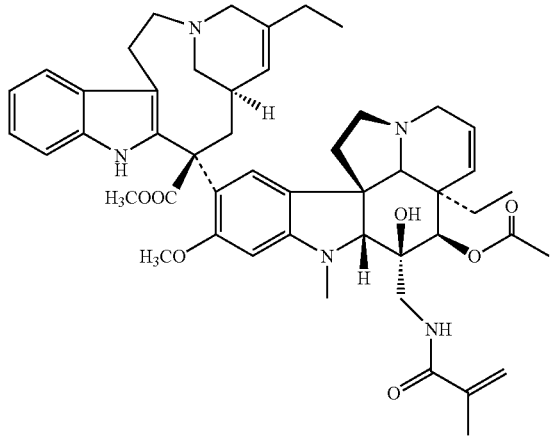

Compound BM32 was prepared following the procedure for preparing compound BM25.

$^1$H NMR (CDCl$_3$, 300 MHz): δ: 9.38 (s, 1H), 8.01 (s, 1H), 7.53 (d, J=7.8 Hz, 1H), 7.19-7.09 (m, 3H), 6.62 (s, 1H), 6.58 (d, J=7.2 Hz, 1H), 6.19 (s, 1H), 5.88 (dd, J=10.2, 3.9 Hz, 1H), 5.71 (s, 1H), 5.48 (d, J=6.0 Hz, 1H), 5.42 (d, J=10.2 Hz, 1H), 5.32 (s, 1H), 5.03 (s, 1H), 3.83 (s, 3H), 3.79-3.76 (m, 1H), 3.62 (s, 3H), 3.53 (d, J=16.5 Hz, 1H), 3.35 (s, 1H), 2.89 (s, 3H), 2.64 (s, 1H), 2.15 (s, 3H), 1.97 (s, 3H), 1.49 (m, 1H), 1.00 (t, J=7.5 Hz, 3H), 0.81 (t, J=7.2 Hz, 3H).

ESIMS (m/e) 832.5 [M+1]$^+$.

Example 33

Preparation of Compound BM33

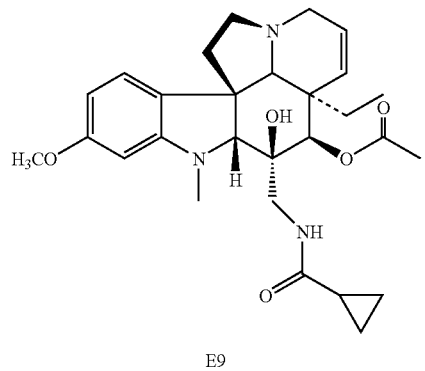

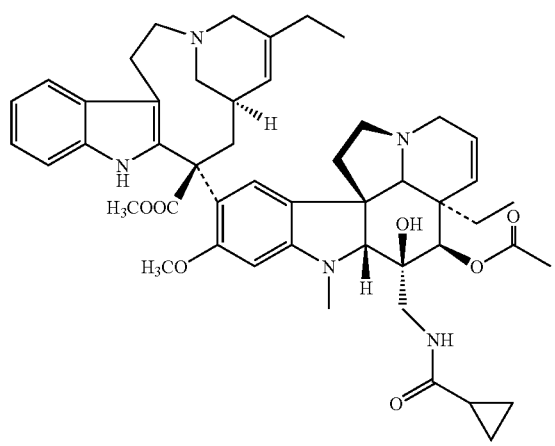

Compound BM33 was prepared following the procedure for preparing compound BM25.

$^1$H NMR (CDCl$_3$, 300 MHz): δ: 9.38 (s, 1H), 8.01 (s, 1H), 7.52 (d, J=7.5 Hz, 1H), 7.19-7.09 (m, 3H), 6.61 (s, 1H), 6.31 (d, J=7.2 Hz, 1H), 6.19 (s, 1H), 5.88 (dd, J=10.2, 3.6 Hz, 1H), 5.48 (d, J=6.0 Hz, 1H), 5.42 (d, J=10.2 Hz, 1H), 5.04 (s, 1H), 3.83 (s, 3H), 3.77-3.70 (m, 1H), 3.62 (s, 3H), 3.54 (d, J=16.5 Hz, 1H), 3.40 (s, 1H), 2.89 (s, 3H), 2.62 (s, 1H), 2.15 (s, 3H), 1.93 (q, J=7.5 Hz, 2H), 1.49 (m, 1H), 1.00 (t, J=7.5 Hz, 3H), 0.93 (m, 2H), 0.81 (t, J=7.2 Hz, 3H), 0.71 (m, 2H).

ESIMS (m/e) 832.5 [M+1]$^+$.

Example 34

Preparation of Compound BM34

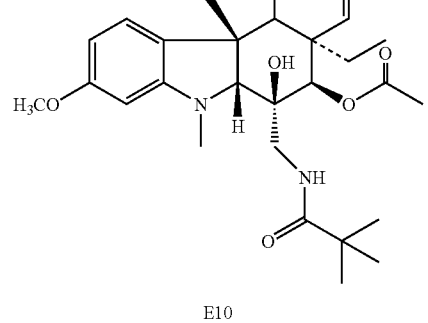

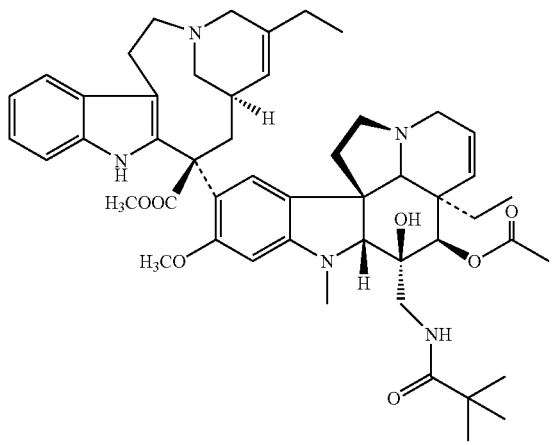

Compound BM34 was prepared following the procedure for preparing compound BM25.

$^1$H NMR (DMSO-d$_6$, 300 MHz): δ: 9.93 (s, 1H), 8.56 (s, 1H), 7.44 (d, J=8.1 Hz, 1H), 7.29 (d, J=8.1 Hz, 1H), 6.98 (m, 2H), 6.62 (s, 2H), 6.55 (s, 1H), 5.79 (m, 1H), 5.50 (d, J=5.7 Hz, 1H), 5.43 (d, J=10.2 Hz, 1H), 4.78 (s, 1H), 4.24 (s, 4H), 3.78 (s, 3H), 3.58 (s, 3H), 2.86 (s, 3H), 2.08 (s, 3H), 1.43 (m, 1H), 1.10 (s, 9H), 0.96 (t, J=7.2 Hz, 3H), 0.65 (t, J=6.9 Hz, 3H).

ESIMS (m/e) 848.5 [M+1]$^+$.

Example 35

Preparation of Compound BM35

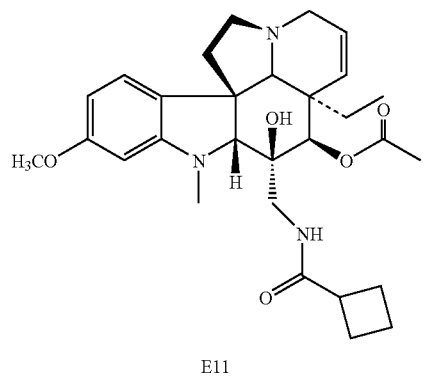

E11

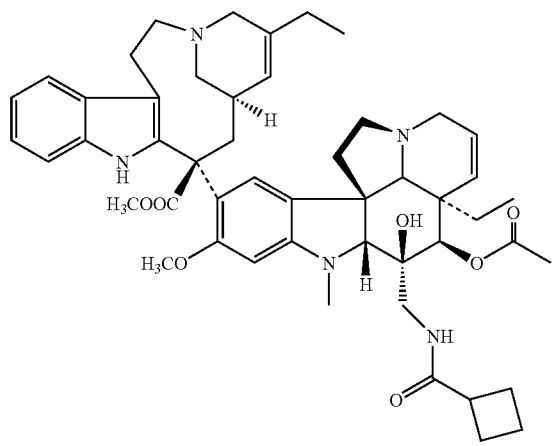

BM35

Compound BM35 was prepared following the procedure for preparing compound BM25.

$^1$H NMR (CDCl$_3$, 300 MHz): δ: 9.38 (s, 1H), 8.01 (s, 1H), 7.52 (d, J=7.8 Hz, 1H), 7.16-7.08 (m, 3H), 6.60 (s, 1H), 6.19 (s, 1H), 6.08 (d, J=7.8 Hz, 1H), 5.87 (dd, J=10.2, 3.6 Hz, 1H), 5.47 (d, J=6.0 Hz, 1H), 5.41 (d, J=10.2 Hz, 1H), 5.01 (s, 1H), 3.82 (s, 3H), 3.62 (s, 3H), 3.31 (s, 1H), 2.87 (s, 3H), 2.62 (s, 1H), 2.14 (s, 3H), 1.98-1.87 (m, 2H), 1.48 (m, 1H), 0.99 (t, J=7.5 Hz, 3H), 0.80 (t, J=7.5 Hz, 3H).

ESIMS (m/e) 846.5 [M+1]$^+$.

Example 36

Preparation of Compound BM36

E12

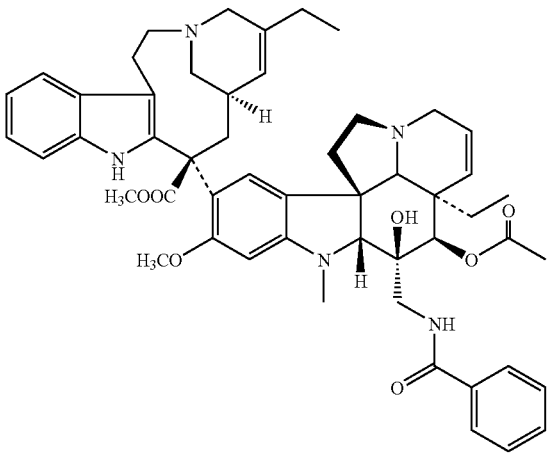

BM36

Compound BM36 was prepared following the procedure for preparing compound BM25.

$^1$H NMR (DMSO-d$_6$, 300 MHz): δ: 9.90 (s, 1H), 8.64 (s, 1H), 7.78 (d, J=7.8 Hz, 2H), 7.49 (m, 3H), 7.29 (d, J=7.8 Hz, 1H), 6.98 (m, 3H), 6.62 (s, 1H), 6.56 (s, 1H), 5.75 (dd, J=10.2, 4.5 Hz, 1H), 5.47 (m, 2H), 4.86 (s, 1H), 4.23 (s, 4H), 3.80 (s, 3H), 3.58 (s, 3H), 2.90 (s, 3H), 2.09 (s, 3H), 0.95 (t, J=7.2 Hz, 3H), 0.66 (t, J=6.9 Hz, 3H).

ESIMS (m/e) 868.5 [M+1]$^+$.

Example 37

Preparation of Compound BM37

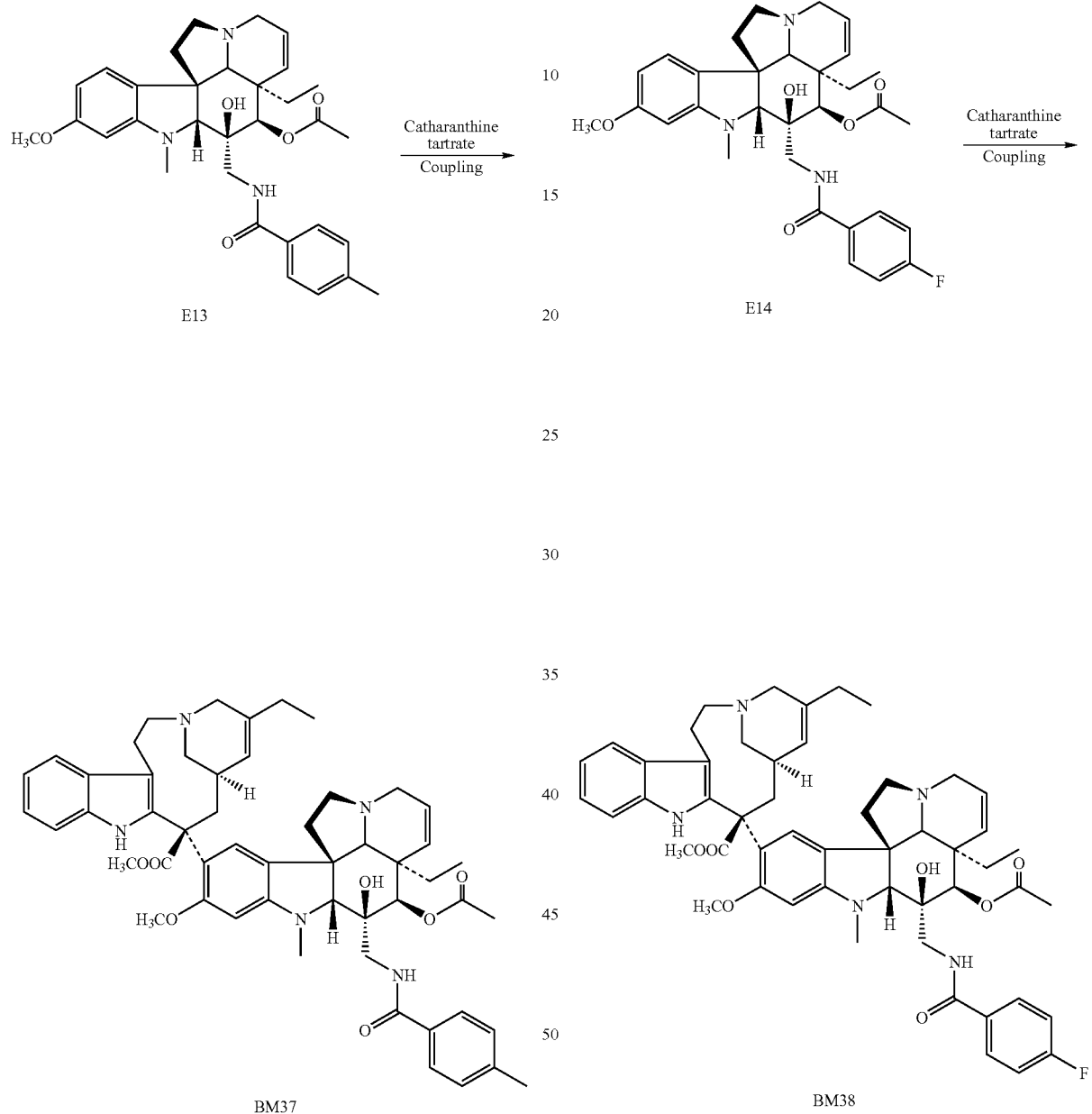

Compound BM37 was prepared following the procedure for preparing compound BM25.

$^1$H NMR (CDCl$_3$, 300 MHz): δ: 9.44 (s, 1H), 8.02 (s, 1H), 7.69 (d, J=8.4 Hz, 2H), 7.53 (d, J=8.1 Hz, 1H), 7.23 (d, J=8.4 Hz, 2H), 7.18-7.09 (m, 3H), 6.90 (d, J=7.5 Hz, 1H), 6.62 (s, 1H), 6.20 (s, 1H), 5.90 (dd, J=10.2, 3.9 Hz, 1H), 5.45 (m, 2H), 5.09 (s, 1H), 3.92 (dd, J=13.5, 8.1 Hz, 1H), 3.83 (s, 3H), 3.63 (s, 3H), 3.53 (d, J=16.5 Hz, 1H), 3.42 (s, 1H), 2.91 (s, 3H), 2.65 (s, 1H), 2.39 (s, 3H), 2.14 (s, 3H), 1.85 (m, 2H), 1.51 (m, 1H), 0.99 (t, J=7.5 Hz, 3H), 0.82 (t, J=7.2 Hz, 3H).

ESIMS (m/e) 882.5 [M+1]$^+$.

Example 38

Preparation of Compound BM38

Compound BM38 was prepared following the procedure for preparing compound BM25.

$^1$H NMR (CDCl$_3$, 300 MHz): δ: 9.51 (s, 1H), 8.03 (s, 1H), 7.80 (dd, J=8.4, 5.4 Hz, 2H), 7.53 (d, J=7.5 Hz, 1H), 7.19-7.08 (m, 5H), 6.90 (d, J=7.5 Hz, 1H), 6.63 (s, 1H), 6.21 (s, 1H), 5.90 (dd, J=10.2, 3.9 Hz, 1H), 5.46 (s, 1H), 5.44 (d, J=10.2 Hz, 1H), 5.09 (s, 1H), 3.95-3.88 (m, 1H), 3.83 (s, 3H), 3.63 (s, 3H), 3.53 (d, J=16.8 Hz, 1H), 3.41 (s, 1H), 2.91 (s, 3H), 2.85 (d, J=16.2 Hz, 1H), 2.66 (s, 1H), 2.14 (s, 3H), 1.93 (q, J=7.5 Hz, 2H), 1.54-1.49 (m, 1H), 0.99 (t, J=7.5 Hz, 3H), 0.82 (t, J=7.2 Hz, 3H).

ESIMS (m/e) 886.5 [M+1]$^+$.

Example 39

Preparation of Compound BM39

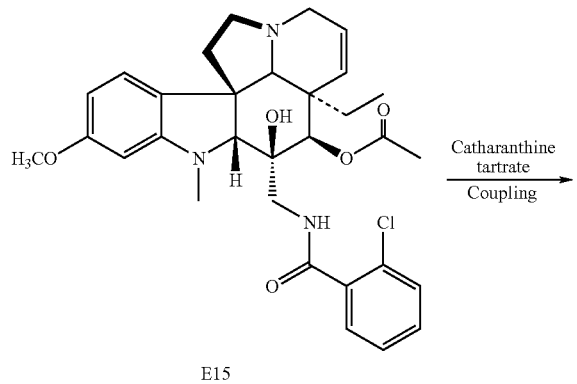

E15

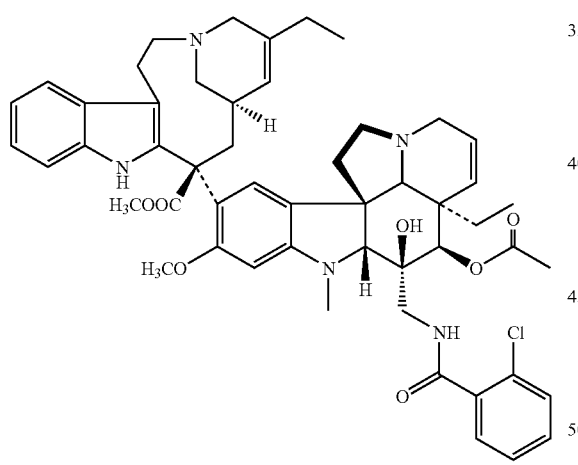

BM39

Compound BM39 was prepared following the procedure for preparing compound BM25.

$^1$H NMR (CDCl$_3$, 300 MHz): δ: 9.44 (s, 1H), 8.04 (s, 1H), 7.60 (dd, J=6.6, 2.2 Hz, 1H), 7.52 (d, J=7.8 Hz, 1H), 7.32 (m, 3H), 7.13 (m, 3H), 6.90 (d, J=7.5 Hz, 1H), 6.61 (s, 1H), 6.23 (s, 1H), 5.88 (dd, J=10.2, 4.2 Hz, 1H), 5.47 (s, 1H), 5.44 (d, J=10.2 Hz, 1H), 5.09 (s, 1H), 3.98 (m, 1H), 3.83 (s, 3H), 3.62 (s, 3H), 3.46 (s, 1H), 3.00 (s, 3H), 2.81 (d, J=15.6 Hz, 2H), 2.62 (s, 1H), 2.18 (s, 3H), 1.93 (q, J=7.5 Hz, 2H), 1.51 (m, 1H), 1.26 (m, 1H), 0.99 (t, J=7.5 Hz, 3H), 0.82 (t, J=6.9 Hz, 3H).

ESIMS (m/e) 902.5 [M+1]$^+$.

Example 40

Preparation of Compound BM40

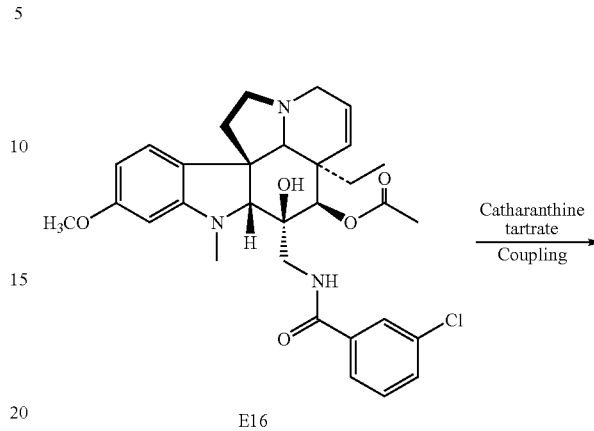

E16

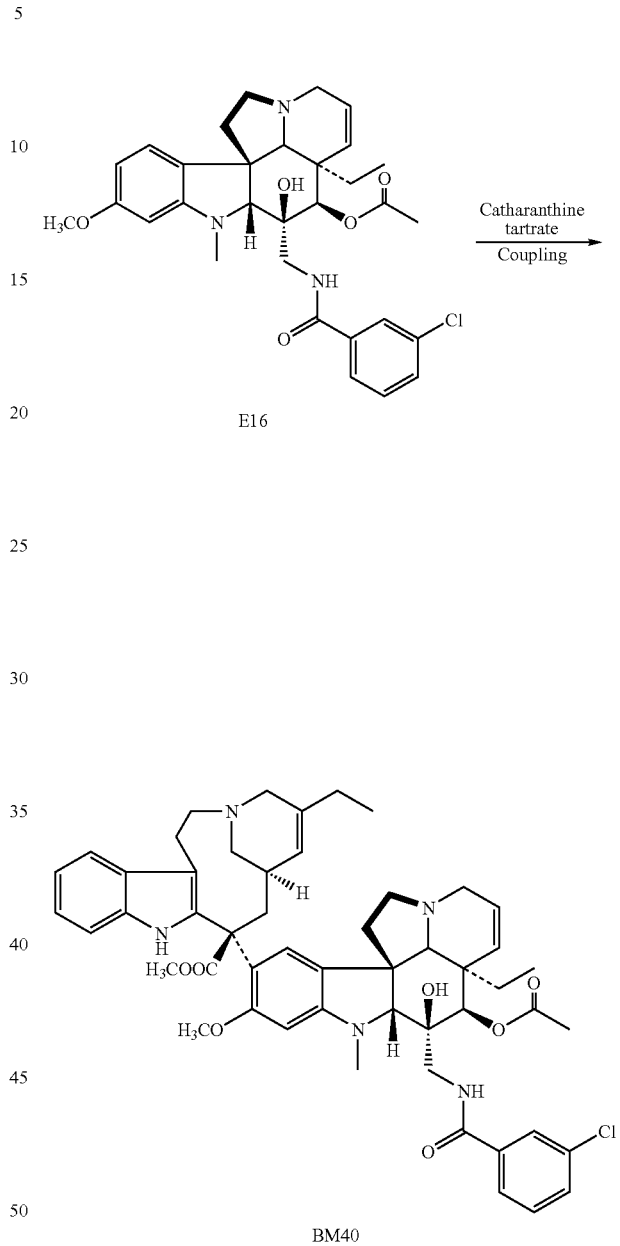

BM40

Compound BM40 was prepared following the procedure for preparing compound BM25.

$^1$H NMR (CDCl$_3$, 300 MHz): δ: 9.48 (s, 1H), 8.03 (s, 1H), 7.77 (s, 1H), 7.66 (d, J=7.8 Hz, 1H), 7.53 (d, J=7.8 Hz, 1H), 7.47 (d, J=7.8 Hz, 1H), 7.36 (t, J=7.8 Hz, 1H), 7.19-7.09 (m, 3H), 6.95 (d, J=7.8 Hz, 1H), 6.63 (s, 1H), 6.22 (s, 1H), 5.90 (dd, J=9.6, 4.5 Hz, 1H), 5.47-5.43 (m, 2H), 5.08 (s, 1H), 3.93 (dd, J=13.5, 7.5 Hz, 1H), 3.83 (s, 3H), 3.63 (s, 3H), 3.53 (d, J=16.5 Hz, 1H), 3.40 (s, 1H), 2.92 (s, 3H), 2.85 (d, J=15.9 Hz, 1H), 2.66 (s, 1H), 2.14 (s, 3H), 1.93 (q, J=7.2 Hz, 2H), 1.54-1.47 (m, 1H), 1.31-1.25 (m, 1H), 0.99 (t, J=7.5 Hz, 3H), 0.82 (t, J=7.2 Hz, 3H).

ESIMS (m/e) 902.5 [M+1]$^+$.

Example 41

Preparation of Compound BM41

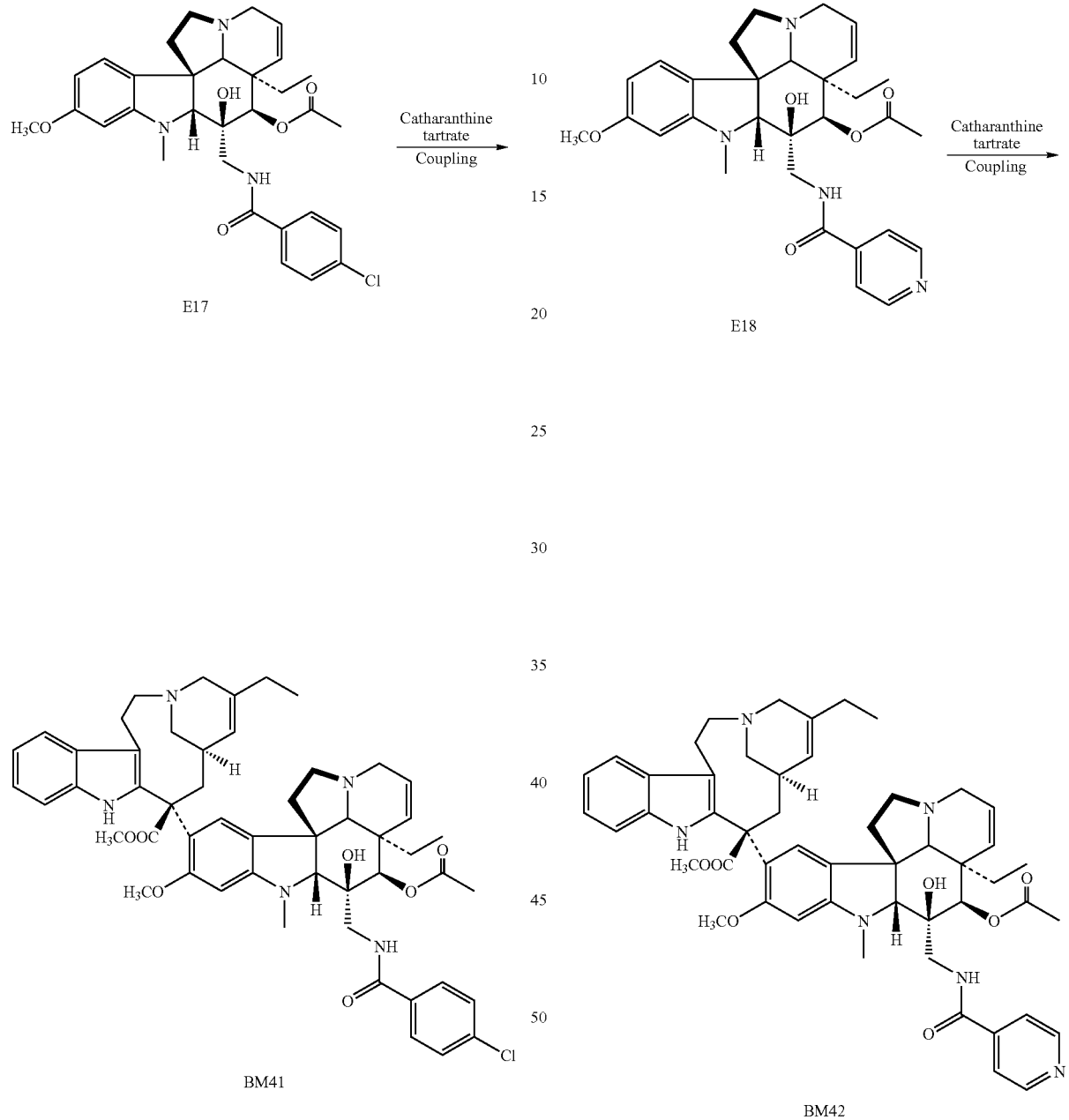

Compound BM41 was prepared following the procedure for preparing compound BM25.

$^1$H NMR (CDCl$_3$, 300 MHz): δ: 9.48 (s, 1H), 8.04 (s, 1H), 7.73 (d, J=8.7 Hz, 2H), 7.52 (d, J=7.5 Hz, 1H), 7.39 (d, J=8.7 Hz, 1H), 7.13 (m, 3H), 6.93 (d, J=6.9 Hz, 1H), 6.63 (s, 1H), 6.21 (s, 1H), 5.89 (dd, J=10.2, 4.2 Hz, 1H), 5.46 (s, 1H), 5.46 (d, J=10.2 Hz, 1H), 5.09 (s, 1H), 3.91 (m, 1H), 3.83 (s, 3H), 3.62 (s, 3H), 3.40 (s, 1H), 2.91 (s, 3H), 2.84 (d, J=16.5 Hz, 2H), 2.65 (s, 1H), 2.12 (s, 3H), 1.93 (q, J=7.2 Hz, 2H), 1.51 (m, 1H), 1.28 (m, 1H), 0.99 (t, J=7.5 Hz, 3H), 0.82 (t, J=7.2 Hz, 3H).

ESIMS (m/e) 902.5 [M+1]$^+$.

Example 42

Preparation of Compound BM42

Compound BM42 was prepared following the procedure for preparing compound BM25.

$^1$H NMR (CDCl$_3$, 300 MHz): δ: 9.57 (s, 1H), 8.73 (d, J=6.0 Hz, 2H), 8.03 (s, 1H), 7.62 (d, J=6.0 Hz, 2H), 7.52 (d, J=7.5 Hz, 1H), 7.20-7.09 (m, 3H), 6.63 (s, 1H), 6.22 (s, 1H), 5.90 (dd, J=10.2, 3.9 Hz, 1H), 5.46 (d, J=10.2 Hz, 1H), 5.43 (s, 1H), 5.09 (s, 1H), 3.97-3.90 (m, 1H), 3.83 (s, 3H), 3.63 (s, 3H), 3.52 (d, J=16.5 Hz, 1H), 3.38 (s, 1H), 2.91 (s, 3H), 2.67 (s, 1H), 2.13 (s, 3H), 1.92 (q, J=7.5 Hz, 2H), 1.53-1.48 (m, 1H), 0.99 (t, J=7.5 Hz, 3 μl), 0.82 (t, J=7.2 Hz, 3H).

ESIMS (m/e) 869.5 [M+1]$^+$.

Example 43

Preparation of Compound BM43

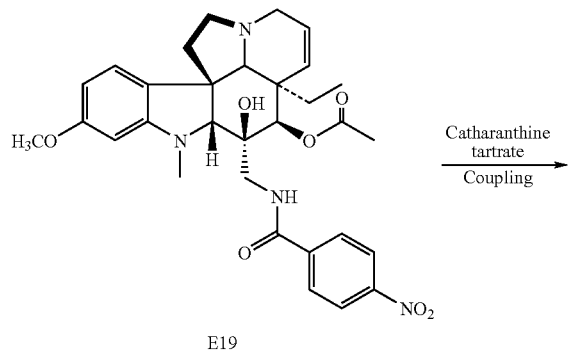

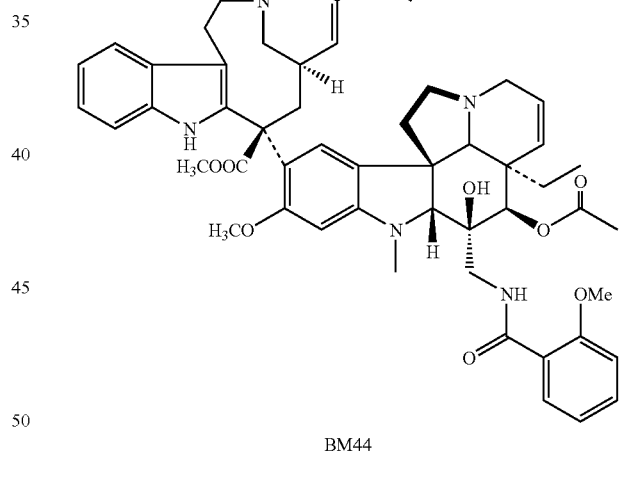

BM43

Compound BM43 was prepared following the procedure for preparing compound BM25.

$^1$H NMR (CDCl$_3$, 300 MHz): δ: 9.58 (s, 1H), 8.28 (d, J=8.7 Hz, 2H), 8.04 (s, 1H), 7.94 (d, J=8.7 Hz, 2H), 7.53 (d, J=7.5 Hz, 1H), 7.13 (m, 4H), 6.64 (s, 1H), 6.23 (s, 1H), 5.91 (dd, J=10.2, 4.2 Hz, 1H), 5.47 (s, 1H), 5.45 (d, J=10.2 Hz, 1H), 5.09 (s, 1H), 3.91 (m, 1H), 3.84 (s, 3H), 3.63 (s, 3H), 3.43 (s, 1H), 2.93 (s, 3H), 2.84 (d, J=16.5 Hz, 2H), 2.68 (s, 1H), 2.13 (s, 3H), 1.93 (q, J=7.2 Hz, 2H), 1.51 (m, 1H), 1.28 (m, 1H), 0.99 (t, J=7.5 Hz, 3H), 0.82 (t, J=7.2 Hz, 3H).

ESIMS (m/e) 913.5 [M+1]$^+$.

Example 44

Preparation of Compound BM44

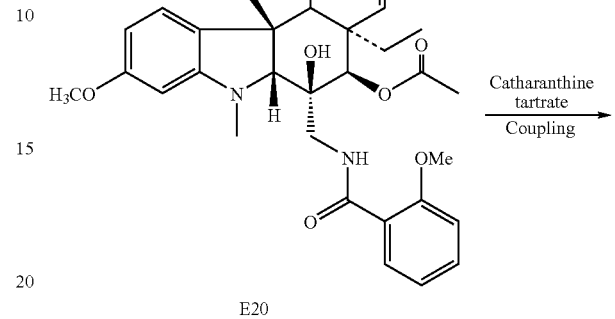

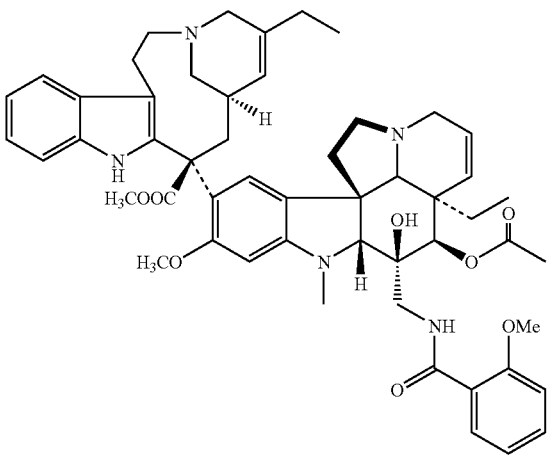

BM44

Compound BM44 was prepared following the procedure for preparing compound BM25.

$^1$H NMR (CDCl$_3$, 300 MHz): δ: 9.27 (s, 1H), 8.47 (d, J=7.2 Hz, 1H), 8.14 (d, J=7.5 Hz, 1H), 8.05 (s, 1H), 7.52 (d, J=7.5 Hz, 1H), 7.42 (t, J=7.5 Hz, 1H), 7.14 (m, 3H), 7.08 (t, J=7.5 Hz, 1H), 6.96 (d, J=7.5 Hz, 1H), 6.61 (s, 1H), 6.20 (s, 1H), 5.88 (dd, J=10.2, 4.2 Hz, 1H), 5.49 (s, 1H), 5.45 (d, J=10.2 Hz, 1H), 5.09 (s, 1H), 3.93 (m, 1H), 3.90 (s, 3H), 3.82 (s, 3H), 3.61 (s, 3H), 3.44 (s, 1H), 2.91 (s, 3H), 2.83 (d, J=15.6 Hz, 2H), 2.63 (s, 1H), 2.13 (s, 3H), 1.93 (q, J=7.5 Hz, 2H), 1.51 (m, 1H), 1.26 (m, 1H), 0.99 (t, J=7.5 Hz, 3H), 0.82 (t, J=6.9 Hz, 3H).

ESIMS (m/e) 898.4 [M+1]$^+$.

Example 45

Preparation of Compound BM45

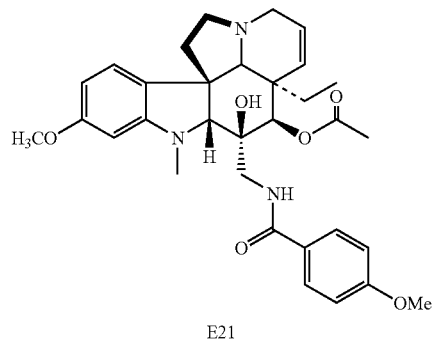

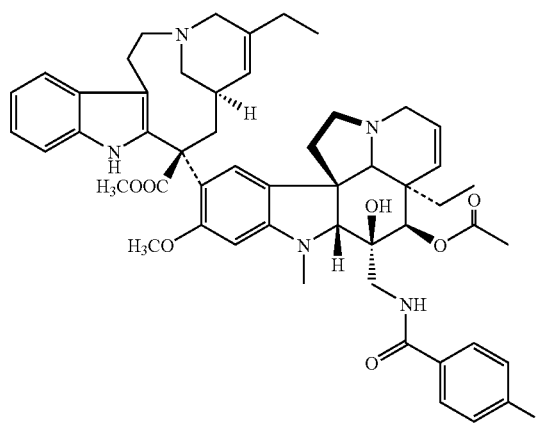

Compound BM45 was prepared following the procedure for preparing compound BM25.

$^1$H NMR (CDCl$_3$, 300 MHz): δ: 9.24 (s, 1H), 8.00 (s, 1H), 7.52 (d, J=7.8 Hz, 1H), 7.20 (d, J=8.7 Hz, 2H), 7.14-7.08 (m, 3H), 6.87 (d, J=8.7 Hz, 2H), 6.58 (s, 1H), 6.17 (d, J=8.4 Hz, 1H), 6.10 (s, 1H), 5.85 (dd, J=10.2, 4.2 Hz, 1H), 5.46 (s, 1H), 5.38 (d, J=10.2 Hz, 1H), 4.95 (s, 1H), 3.84 (s, 3H), 3.79 (s, 3H), 3.63 (s, 1H), 3.12 (s, 1H), 2.91 (d, J=13.5 Hz, 1H), 2.80 (d, J=15.9 Hz, 1H), 2.68 (s, 3H), 2.59 (s, 1H), 2.13 (s, 3H), 1.93 (q, J=7.2 Hz, 2H), 1.45 (m, 1H), 1.00 (t, J=7.5 Hz, 3H), 0.79 (t, J=7.2 Hz, 3H).

ESIMS (m/e) 898.5 [M+1]$^+$.

Example 46

Preparation of Compound BM46

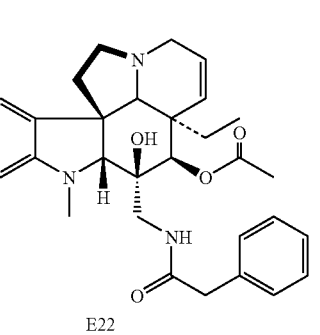

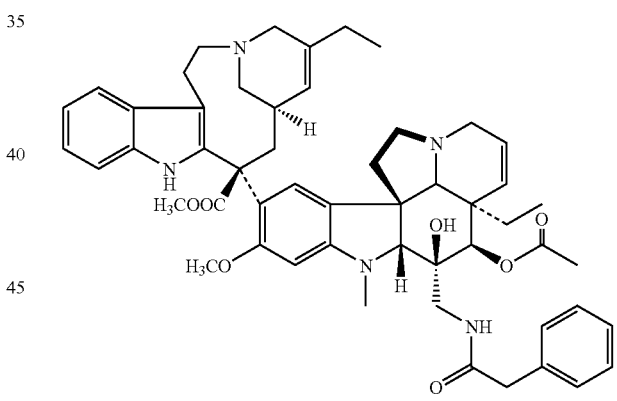

Compound BM46 was prepared following the procedure for preparing compound BM25.

$^1$H NMR (CDCl$_3$, 300 MHz): δ: 9.25 (s, 1H), 7.99 (s, 1H), 7.52 (d, J=7.5 Hz, 1H), 7.37-7.27 (m, 5H), 7.19-7.11 (m, 3H), 6.59 (s, 1H), 6.18 (d, J=8.7 Hz, 1H), 6.09 (s, 1H), 5.84 (dd, J=10.2, 4.2 Hz, 1H), 5.45 (s, 1H), 5.38 (d, J=10.2 Hz, 1H), 4.95 (s, 1H), 3.84 (s, 3H), 3.79-3.77 (m, 1H), 3.63 (s, 3H), 3.56 (s, 2H), 3.10 (s, 1H), 2.91 (d, J=13.8 Hz, 1H), 2.80 (d, J=15.9 Hz, 1H), 2.65 (s, 3H), 2.59 (s, 1H), 2.13 (s, 3H), 1.92 (q, J=7.5 Hz, 2H), 1.51-1.44 (m, 1H), 1.25-1.20 (m, 1H), 1.00 (t, J=7.5 Hz, 3H), 0.79 (t, J=7.2 Hz, 3H).

ESIMS (m/e) 882.5 [M+1]$^+$.

Example 47

Preparation of Compound BM47

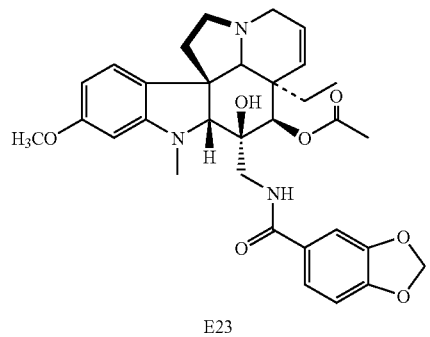

E23

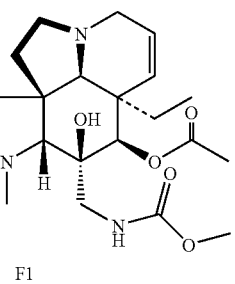

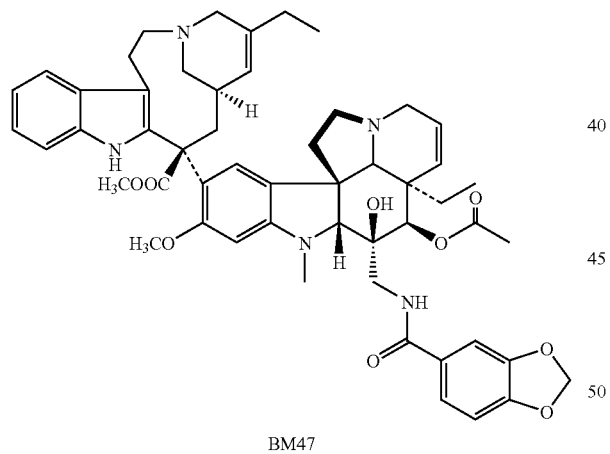

BM47

Compound BM47 was prepared following the procedure for preparing compound BM25.

$^1$H NMR (CDCl$_3$, 300 MHz): δ: 9.45 (s, 1H), 8.03 (s, 1H), 7.53 (d, J=8.1 Hz, 1H), 7.32 (d, J=8.1 Hz, 1H), 7.29 (s, 1H), 7.18-7.09 (m, 3H), 6.83 (m, 2H), 6.62 (s, 1H), 6.20 (s, 1H), 6.02 (s, 2H), 5.90 (dd, J=10.2, 3.9 Hz, 1H), 5.46 (m, 2H), 5.08 (s, 1H), 3.93-3.86 (m, 1H), 3.83 (s, 3H), 3.63 (s, 3H), 3.52 (d, J=16.5 Hz, 1H), 3.40 (s, 1H), 2.91 (s, 3H), 2.65 (s, 1H), 2.58 (d, J=12.9 Hz, 1H), 2.14 (s, 3H), 1.97-1.89 (m, 2H), 1.54-1.47 (m, 1H), 1.31-1.25 (m, 1H), 0.99 (t, J=7.5 Hz, 3H), 0.82 (t, J=7.2 Hz, 3H).

ESIMS (m/e) 912.4 [M+1]$^+$.

Example 48

Preparation of Compound BM48

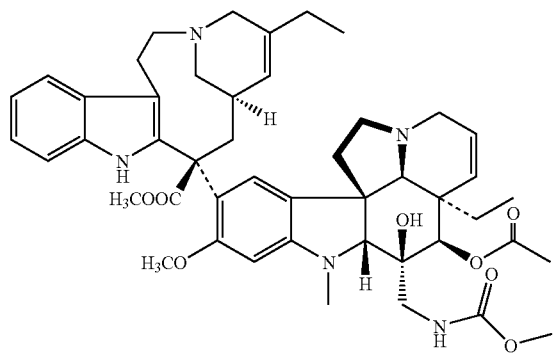

F1

BM48

Compound BM48 was prepared following the procedure for preparing compound BM25.

$^1$H NMR (CDCl$_3$, 300 MHz): δ: 9.26 (s, 1H), 8.04 (s, 1H), 7.51 (d, J=7.5 Hz, 1H), 7.12 (m, 3H), 6.59 (s, 1H), 6.20 (s, 1H), 5.87 (dd, J=10.2, 3.9 Hz, 1H), 5.48 (d, J=5.7 Hz, 1H), 5.42 (d, J=10.2 Hz, 1H), 5.36 (d, J=6.6 Hz, 1H), 5.02 (s, 1H), 3.82 (s, 3H), 3.65 (s, 3H), 3.61 (s, 3H), 3.38 (s, 1H), 2.92 (s, 3H), 2.80 (d, J=16.2 Hz, 1H), 2.60 (s, 1H), 2.14 (s, 3H), 1.93 (q, J=7.5 Hz, 2H), 1.46 (m, 1H), 1.23 (m, 1H), 0.99 (t, J=7.5 Hz, 3H), 0.80 (t, J=6.9 Hz, 3H).

ESIMS (m/e) 822.3 [M+1]$^+$.

Example 49

Preparation of Compound BM49

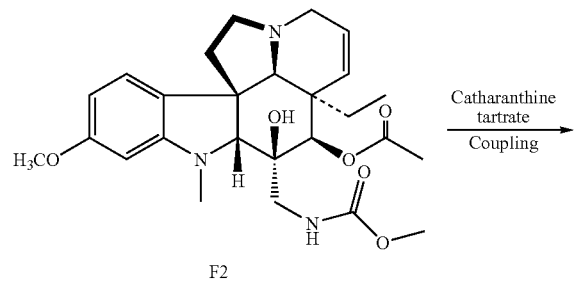

F2

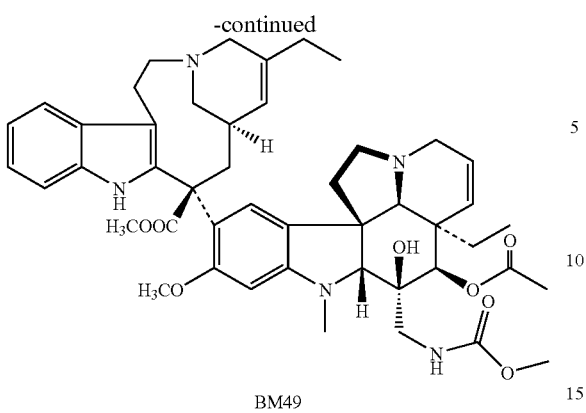

BM49

Compound BM49 was prepared following the procedure for preparing compound BM25.

$^1$H NMR (CDCl$_3$, 300 MHz): δ: 9.25 (s, 1H), 8.00 (s, 1H), 7.53 (d, J=7.5 Hz, 1H), 7.13 (m, 3H), 6.61 (s, 1H), 6.20 (s, 1H), 5.87 (dd, J=10.2, 3.9 Hz, 1H), 5.48 (d, J=6.3 Hz, 1H), 5.42 (d, J=10.2 Hz, 1H), 5.30 (d, J=3.9 Hz, 1H), 5.03 (s, 1H), 4.09 (q, J=7.2 Hz, 2H), 3.83 (s, 3H), 3.62 (s, 3H), 3.40 (s, 1H), 2.94 (s, 3H), 2.82 (d, J=15.9 Hz, 1H), 2.61 (s, 1H), 2.16 (s, 3H), 1.43 (m, 1H), 1.23 (t, J=7.2 Hz, 3H), 1.21 (m, 1H), 1.00 (t, J=7.5 Hz, 3H), 0.81 (t, J=6.9 Hz, 3H).

ESIMS (m/e) 836.4 [M+1]$^+$.

Example 50

Preparation of Compound BM50

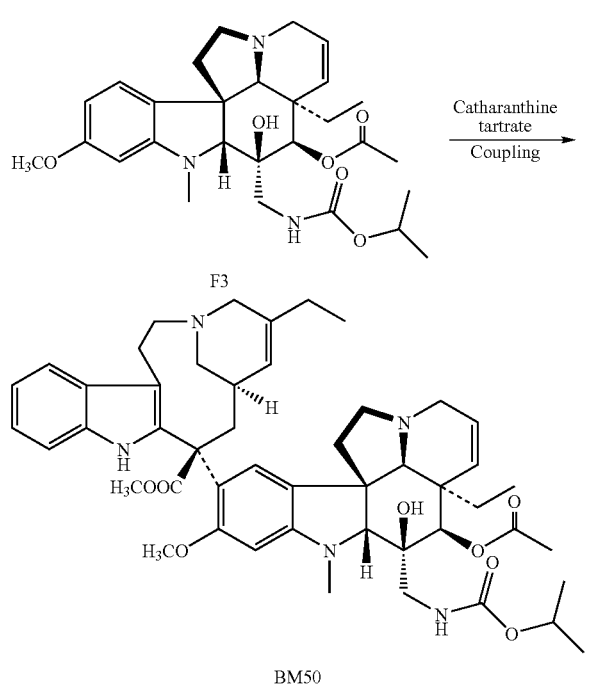

Compound BM50 was prepared following the procedure for preparing compound BM25.

$^1$H NMR (CDCl$_3$, 300 MHz): δ: 9.24 (s, 1H), 8.00 (s, 1H), 7.53 (d, J=7.5 Hz, 1H), 7.18 (m, 3H), 6.60 (s, 1H), 6.20 (s, 1H), 5.87 (dd, J=10.2, 3.9 Hz, 1H), 5.47 (d, J=6.0 Hz, 1H), 5.42 (d, J=10.2 Hz, 1H), 5.25 (d, J=3.9 Hz, 1H), 5.03 (s, 1H), 4.89 (m, 1H), 3.83 (s, 3H), 3.64 (s, 3H), 3.38 (s, 1H), 2.93 (s, 3H), 2.82 (d, J=15.9 Hz, 1H), 2.61 (s, 1H), 2.16 (s, 3H), 1.93 (q, J=7.5 Hz, 2H), 1.43 (m, 1H), 1.25 (m, 1H), 1.23 (d, J=7.2 Hz, 6H), 1.00 (t, J=7.5 Hz, 3H), 0.81 (t, J=6.9 Hz, 3H).

ESIMS (m/e) 850.3 [M+1]$^+$.

Example 51

Preparation of Compound BM51

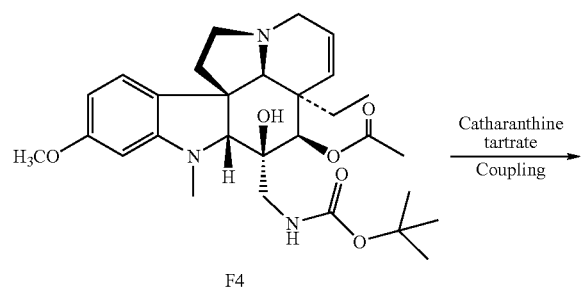

BM51

Compound BM51 was prepared following the procedure for preparing compound BM25.

$^1$H NMR (CDCl$_3$, 300 MHz): δ: 9.25 (s, 1H), 8.00 (s, 1H), 7.53 (d, J=7.5 Hz, 1H), 7.13 (m, 3H), 6.59 (s, 1H), 6.20 (s, 1H), 5.87 (dd, J=10.2, 3.9 Hz, 1H), 5.48 (d, J=6.0 Hz, 1H), 5.42 (d, J=10.2 Hz, 1H), 5.25 (d, J=3.9 Hz, 1H), 5.03 (s, 1H), 3.83 (s, 3H), 3.64 (s, 3H), 3.38 (s, 1H), 2.93 (s, 3H), 2.82 (d, J=15.9 Hz, 1H), 2.61 (s, 1H), 2.16 (s, 3H), 1.43 (m, 1H), 1.36 (s, 9H), 1.21 (m, 1H), 0.99 (t, J=7.5 Hz, 3H), 0.81 (t, J=6.9 Hz, 3H).

ESIMS (m/e) 864.4 [M+1]$^+$.

Example 52

Preparation of Compound BM52

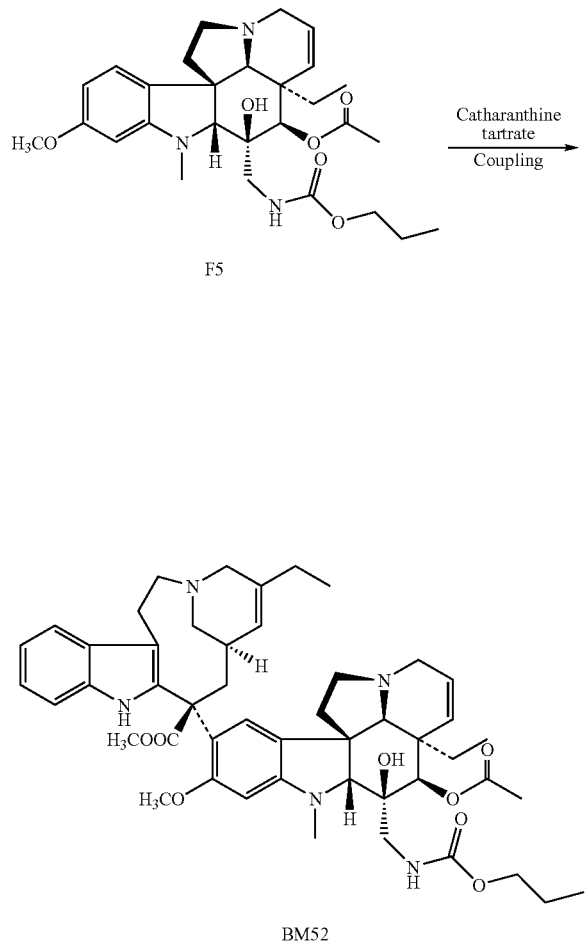

Compound BM52 was prepared following the procedure for preparing compound BM25.

$^1$H NMR (CDCl$_3$, 300 MHz): δ: 9.26 (s, 1H), 8.01 (s, 1H), 7.52 (d, J=8.1 Hz, 1H), 7.12 (m, 3H), 6.60 (s, 1H), 6.20 (s, 1H), 5.87 (dd, J=10.2, 3.9 Hz, 1H), 5.48 (d, J=5.7 Hz, 1H), 5.42 (d, J=10.2 Hz, 1H), 5.25 (d, J=6.6 Hz, 1H), 5.03 (s, 1H), 4.01 (t, J=6.3 Hz, 2H), 3.82 (s, 3H), 3.61 (s, 3H), 3.37 (s, 1H), 2.93 (s, 3H), 2.81 (d, J=16.2 Hz, 1H), 2.61 (s, 1H), 2.15 (s, 3H), 1.93 (q, J=7.5 Hz, 2H), 1.46 (m, 1H), 1.23 (m, 1H), 0.99 (t, J=7.2 Hz, 3H), 0.92 (t, J=7.2 Hz, 3H), 0.81 (t, J=6.9 Hz, 3H);

$^{13}$C NMR (CDCl$_3$, 75 MHz): δ: 174.9 (C), 171.0 (C), 158.1 (C), 157.2 (C), 153.7 (C), 140.1 (C), 135.1 (C), 131.0 (C), 130.1 (CH), 129.6 (C), 124.7 (CH), 124.0 (CH), 123.7 (CH), 123.7 (C), 122.4 (CH), 121.8 (C), 119.0 (CH), 118.5 (CH), 117.5 (C), 110.6 (CH), 95.2 (CH), 82.1 (CH), 77.2 (CH), 76.1 (C), 66.5 (CH$_2$), 66.1 (CH), 56.0 (OCH$_3$), 55.6 (C), 54.7 (CH$_2$), 52.7 (C), 52.5 (OCH$_3$), 52.3 (CH$_2$), 50.2 (2CH$_2$), 46.0 (CH$_2$), 45.3 (CH$_2$), 44.9 (CH$_2$), 42.9 (C), 40.7 (CH$_3$), 34.5 (CH$_2$), 33.0 (CH), 31.7 (CH$_2$), 28.0 (CH$_2$), 25.9 (CH$_2$), 22.5 (CH$_2$), 21.1 (CH$_3$), 12.4 (CH$_3$), 10.5 (CH$_3$), 8.4 (CH$_3$).

ESIMS (m/e) 850.3 [M+1]$^+$.

Example 53

Preparation of Compound BM53

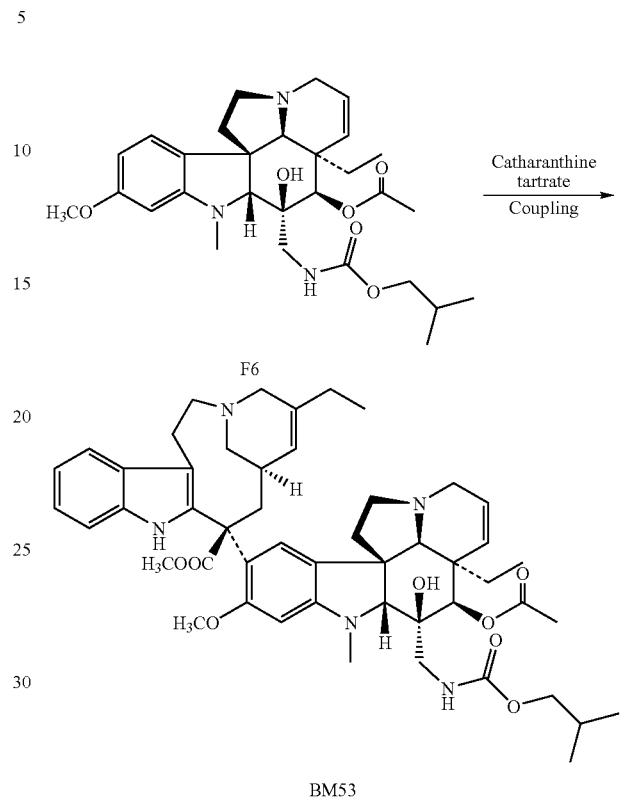

Compound BM53 was prepared following the procedure for preparing compound BM25.

$^1$H NMR (CDCl$_3$, 300 MHz): δ: 9.30 (s, 1H), 8.00 (s, 1H), 7.53 (d, J=7.5 Hz, 1H), 7.12 (m, 3H), 6.60 (s, 1H), 6.20 (s, 1H), 5.88 (dd, J=10.2, 3.9 Hz, 1H), 5.47 (d, J=5.4 Hz, 1H), 5.42 (d, J=10.2 Hz, 1H), 5.30 (d, J=3.9 Hz, 1H), 5.04 (s, 1H), 3.84 (d, J=6.0 Hz, 2H), 3.83 (s, 3H), 3.62 (s, 3H), 3.40 (s, 1H), 2.93 (s, 3H), 2.82 (d, J=15.9 Hz, 1H), 2.61 (s, 1H), 2.15 (s, 3H), 1.46 (m, 1H), 1.23 (m, 1H), 1.00 (t, J=7.2 Hz, 3H), 0.91 (d, J=6.0 Hz, 6H), 0.81 (t, J=7.2 Hz, 3H).

ESIMS (m/e) 864.5 [M+1]$^+$.

Example 54

Preparation of Compound BM54

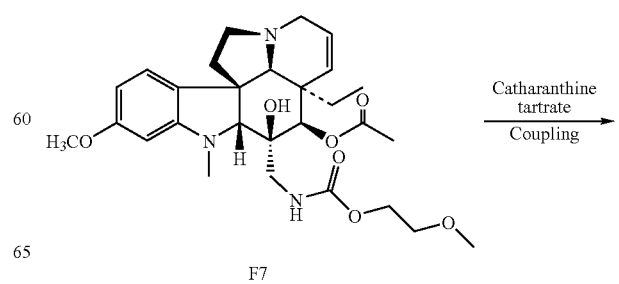

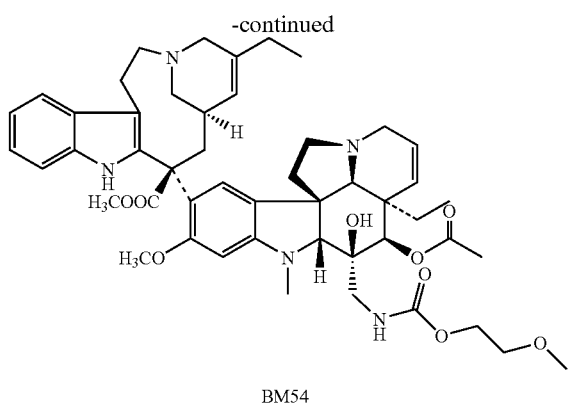

BM54

Compound BM54 was prepared following the procedure for preparing compound BM25.

$^1$H NMR (CDCl$_3$, 300 MHz): δ: 9.26 (s, 1H), 8.04 (s, 1H), 7.48 (d, J=7.2 Hz, 1H), 7.11 (m, 3H), 6.49 (s, 1H), 6.19 (s, 1H), 5.87 (dd, J=10.2, 4.5 Hz, 1H), 5.61 (d, J=5.4 Hz, 1H), 5.50 (d, J=6.6 Hz, 1H), 5.41 (d, J=10.2 Hz, 1H), 4.99 (s, 1H), 4.21 (s, 2H), 3.82 (s, 3H), 3.62 (s, 3H), 3.41 (s, 1H), 3.37 (s, 3H), 2.93 (s, 3H), 2.81 (d, J=16.2 Hz, 1H), 2.59 (s, 1H), 2.14 (s, 3H), 1.99 (q, J=7.5 Hz, 2H), 1.46 (m, 1H), 1.23 (m, 1H), 1.01 (t, J=7.2 Hz, 3H), 0.77 (t, J=6.9 Hz, 3H).

ESIMS (m/e) 866.4 [M+1]$^+$.

Example 55

Preparation of Compound BM55

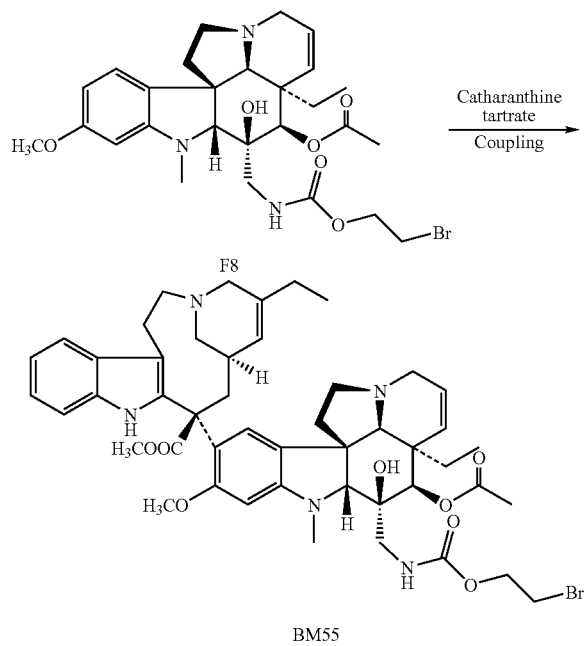

BM55

Compound BM55 was prepared following the procedure for preparing compound BM25.

$^1$H NMR (CDCl$_3$, 300 MHz): δ: 9.32 (s, 1H), 8.02 (s, 1H), 7.51 (d, J=7.8 Hz, 1H), 7.12 (m, 3H), 6.60 (s, 1H), 6.20 (s, 1H), 5.87 (dd, J=10.2, 4.5 Hz, 1H), 5.47 (m, 2H), 5.42 (d, J=10.2 Hz, 1H), 5.02 (s, 1H), 4.34 (m, 2H), 3.82 (s, 3H), 3.60 (s, 3H), 3.38 (s, 1H), 2.92 (s, 3H), 2.81 (d, J=16.2 Hz, 1H), 2.61 (s, 1H), 2.15 (s, 3H), 1.92 (q, J=7.5 Hz, 2H), 1.46 (m, 1H), 1.23 (m, 1H), 0.98 (t, J=7.5 Hz, 3H), 0.80 (t, J=6.6 Hz, 3H).

ESIMS (m/e) 916.2 [M+1]$^+$.

Example 56

Preparation of Compound BM56

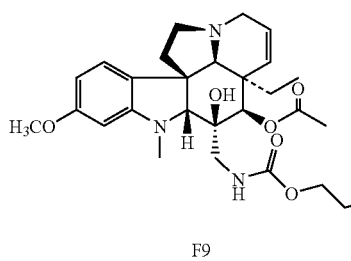

F9

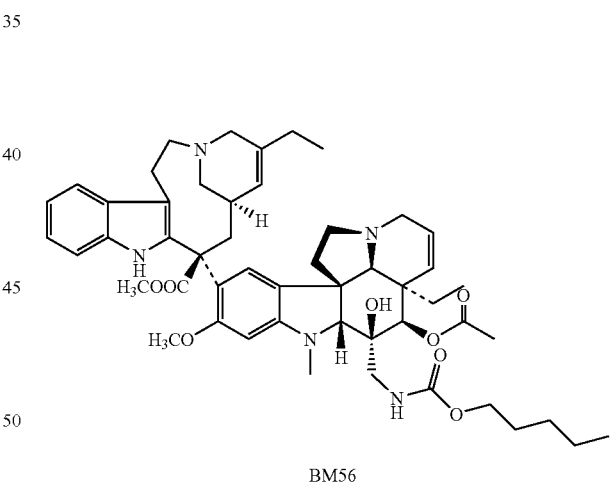

BM56

Compound BM56 was prepared following the procedure for preparing compound BM25.

$^1$H NMR (CDCl$_3$, 300 MHz): δ: 9.27 (s, 1H), 8.00 (s, 1H), 7.54 (d, J=7.5 Hz, 1H), 7.13 (m, 3H), 6.60 (s, 1H), 6.20 (s, 1H), 5.87 (dd, J=10.2, 3.9 Hz, 1H), 5.48 (d, J=6.0 Hz, 1H), 5.42 (d, J=10.2 Hz, 1H), 5.30 (d, J=3.9 Hz, 1H), 5.03 (s, 1H), 4.04 (t, J=6.0 Hz, 2H), 3.83 (s, 3H), 3.64 (s, 3H), 3.38 (s, 1H), 2.93 (s, 3H), 2.82 (d, J=15.9 Hz, 1H), 2.61 (s, 1H), 2.16 (s, 3H), 1.60 (m, 2H), 1.46 (m, 1H), 1.26 (m, 4H), 1.23 (m, 1H), 1.00 (t, J=7.2 Hz, 3H), 0.89 (d, J=6.6 Hz, 3H), 0.81 (t, J=7.2 Hz, 3H).

ESIMS (m/e) 878.4 [M+1]$^+$.

Example 57

Preparation of Compound BM57

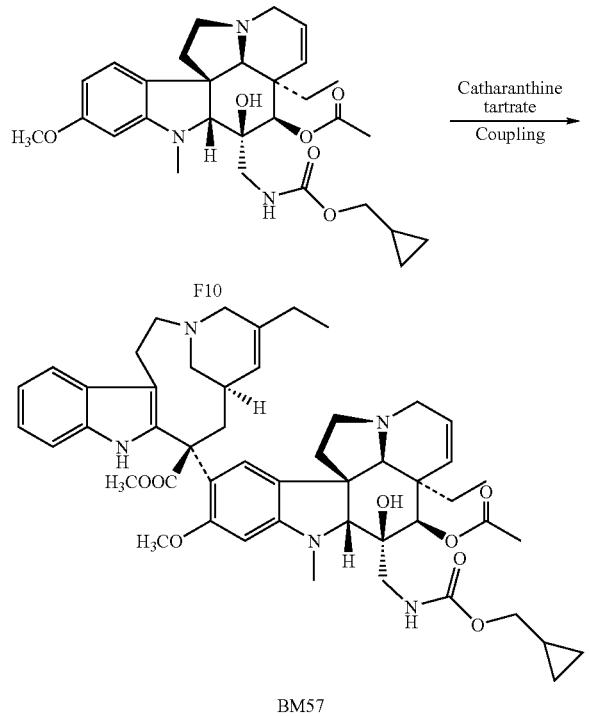

BM57

Compound BM57 was prepared following the procedure for preparing compound BM25.

$^1$H NMR (CDCl$_3$, 300 MHz): δ: 9.27 (s, 1H), 8.00 (s, 1H), 7.53 (d, J=7.5 Hz, 1H), 7.13 (m, 3H), 6.60 (s, 1H), 6.20 (s, 1H), 5.87 (dd, J=10.2, 4.2 Hz, 1H), 5.47 (d, J=6.0 Hz, 1H), 5.42 (d, J=10.2 Hz, 1H), 5.36 (d, J=4.5 Hz, 1H), 5.03 (s, 1H), 3.89 (d, J=7.2 Hz, 2H), 3.83 (s, 3H), 3.62 (s, 3H), 3.41 (s, 1H), 2.94 (s, 3H), 2.82 (d, J=15.9 Hz, 1H), 2.61 (s, 1H), 2.15 (s, 3H), 1.46 (m, 1H), 1.25 (m, 1H), 1.00 (t, J=7.2 Hz, 3H), 0.81 (t, J=7.2 Hz, 3H), 0.51 (d, J=4.8 Hz, 2H), 0.25 (d, J=4.8 Hz, 2H).

ESIMS (m/e) 862.3 [M+1]$^+$.

Example 58

Preparation of Compound BM58

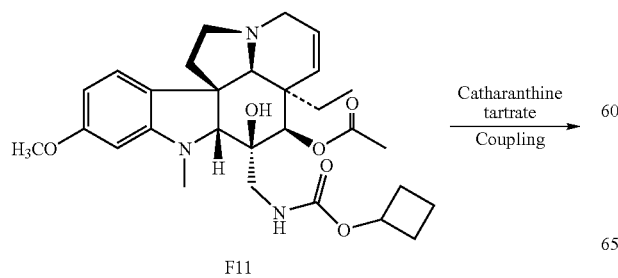

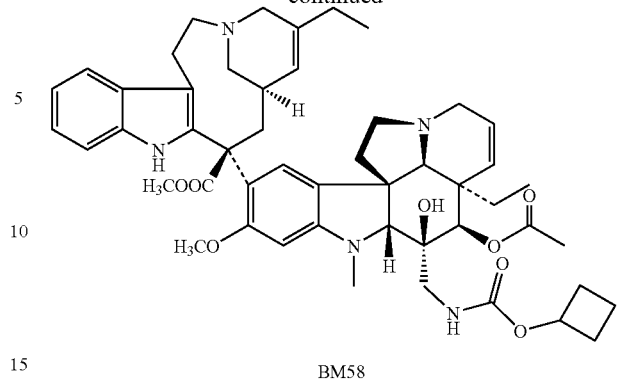

BM58

Compound BM58 was prepared following the procedure for preparing compound BM25.

$^1$H NMR (CDCl$_3$, 300 MHz): δ: 9.25 (s, 1H), 8.00 (s, 1H), 7.53 (d, J=7.5 Hz, 1H), 7.13 (m, 3H), 6.60 (s, 1H), 6.20 (s, 1H), 5.87 (dd, J=10.2, 3.9 Hz, 1H), 5.47 (d, J=5.4 Hz, 1H), 5.42 (d, J=10.2 Hz, 1H), 5.30 (d, J=3.9 Hz, 1H), 5.02 (s, 1H), 4.92 (m, 1H), 3.83 (s, 3H), 3.64 (s, 3H), 3.39 (s, 1H), 2.93 (s, 3H), 2.82 (d, J=15.9 Hz, 1H), 2.62 (s, 1H), 2.30 (m, 2H), 2.15 (s, 3H), 2.02 (m, 2H), 1.92 (q, J=7.5 Hz, 2H), 1.73 (m, 1H), 1.57 (m, 1H), 1.25 (m, 1H), 1.00 (t, J=7.5 Hz, 3H), 0.81 (t, J=6.9 Hz, 3H).

ESIMS (m/e) 862.3 [M+1]$^+$.

Example 59

Preparation of Compound BM59

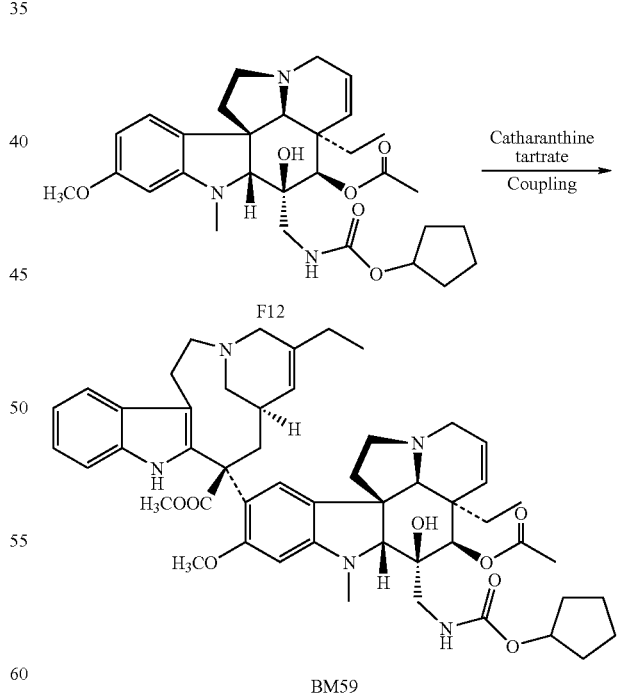

BM59

Compound BM59 was prepared following the procedure for preparing compound BM25.

$^1$H NMR (CDCl$_3$, 300 MHz): δ: 9.25 (s, 1H), 8.00 (s, 1H), 7.53 (d, J=7.5 Hz, 1H), 7.13 (m, 3H), 6.60 (s, 1H), 6.20 (s, 1H), 5.87 (dd, J=10.2, 3.9 Hz, 1H), 5.47 (d, J=5.1 Hz, 1H), 5.42 (d, J=10.2 Hz, 1H), 5.21 (d, J=3.9 Hz, 1H), 5.08 (m, 1H), 5.03 (s, 1H), 3.83 (s, 3H), 3.64 (s, 3H), 3.40 (s, 1H), 2.93 (s, 3H), 2.82 (d, J=15.9 Hz, 1H), 2.60 (s, 1H), 2.40 (m, 2H), 2.16 (s, 3H), 1.92 (q, J=7.5 Hz, 2H), 1.72 (m, 2H), 1.58 (m, 4H), 1.44 (m, 2H), 1.25 (m, 1H), 1.00 (t, J=7.5 Hz, 3H), 0.81 (t, J=6.9 Hz, 3H).

ESIMS (m/e) 876.3 [M+1]$^+$.

Example 60

Preparation of Compound BM60

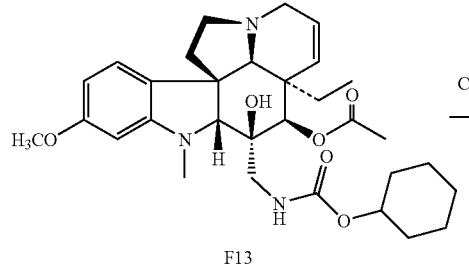

F13

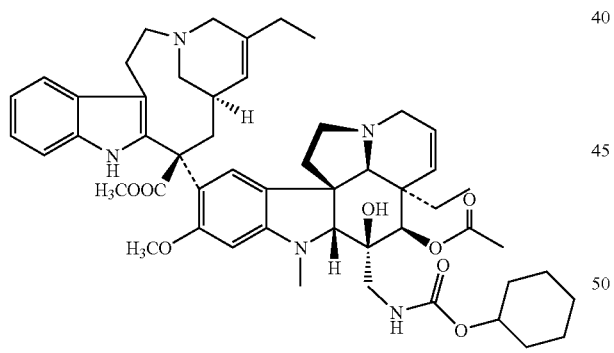

BM60

Compound BM60 was prepared following the procedure for preparing compound BM25.

$^1$H NMR (CDCl$_3$, 300 MHz): δ: 9.25 (s, 1H), 8.00 (s, 1H), 7.52 (d, J=7.5 Hz, 1H), 7.13 (m, 3H), 6.60 (s, 1H), 6.20 (s, 1H), 5.87 (dd, J=10.2, 3.9 Hz, 1H), 5.47 (d, J=5.1 Hz, 1H), 5.42 (d, J=10.2 Hz, 1H), 5.26 (d, J=6.0 Hz, 1H), 5.03 (s, 1H), 4.62 (m, 1H), 3.83 (s, 3H), 3.63 (s, 3H), 3.40 (s, 1H), 2.93 (s, 3H), 2.82 (d, J=15.9 Hz, 1H), 2.61 (s, 1H), 2.40 (m, 2H), 2.16 (s, 3H), 1.72 (m, 2H), 1.62 (m, 2H), 1.42 (m, 1H), 1.26 (m, 6H), 1.00 (t, J=7.5 Hz, 3H), 0.81 (t, J=6.9 Hz, 3H).

ESIMS (m/e) 890.3 [M+1]$^+$.

Example 61

Preparation of Compound BM61

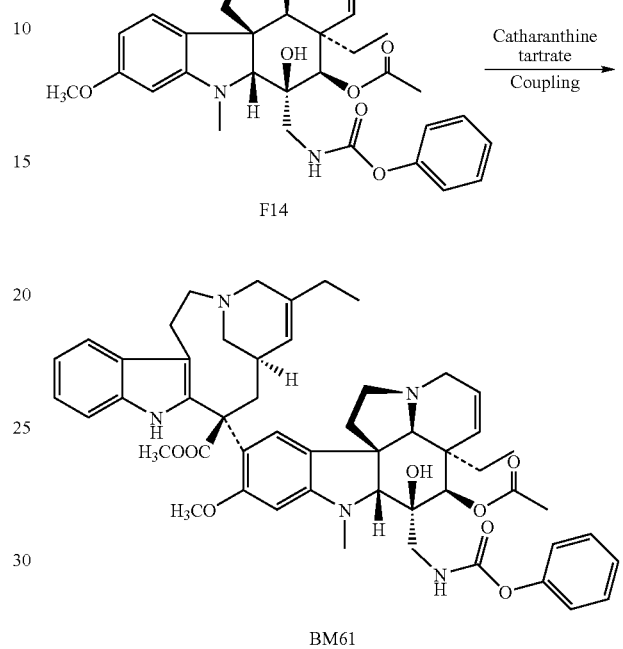

F14

BM61

Compound BM61 was prepared following the procedure for preparing compound BM25.

$^1$H NMR (CDCl$_3$, 300 MHz): δ: 9.38 (s, 1H), 8.01 (s, 1H), 7.53 (d, J=7.8 Hz, 1H), 7.35 (t, J=7.8 Hz, 2H), 7.14 (m, 6H), 6.63 (s, 1H), 6.23 (s, 1H), 5.89 (dd, J=10.2, 3.9 Hz, 1H), 5.76 (d, J=7.8 Hz, 1H), 5.46 (m, 2H), 5.07 (s, 1H), 3.83 (s, 3H), 3.63 (s, 3H), 3.45 (s, 1H), 2.99 (s, 3H), 2.85 (d, J=15.9 Hz, 1H), 2.65 (s, 1H), 2.18 (s, 3H), 1.43 (m, 1H), 1.21 (m, 1H), 1.00 (t, J=7.5 Hz, 3H), 0.82 (t, J=6.9 Hz, 3H).

ESIMS (m/e) 884.4 [M+1]$^+$.

Example 62

Preparation of Compound BM62

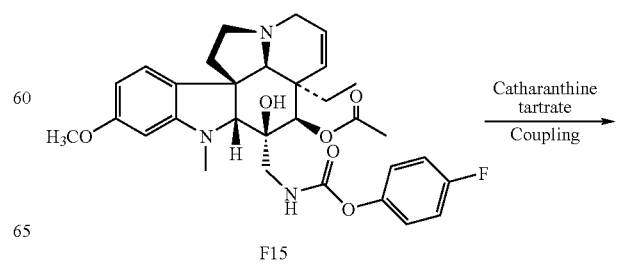

F15

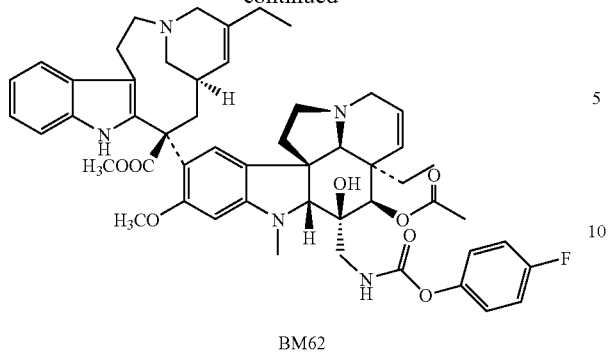

BM62

Compound BM62 was prepared following the procedure for preparing compound BM25.

$^1$H NMR (CDCl$_3$, 300 MHz): δ: 9.38 (s, 1H), 8.01 (s, 1H), 7.53 (d, J=7.8 Hz, 1H), 7.11 (m, 7H), 6.63 (s, 1H), 6.23 (s, 1H), 5.90 (dd, J=10.2, 3.9 Hz, 1H), 5.77 (d, J=7.8 Hz, 1H), 5.46 (m, 2H), 5.07 (s, 1H), 3.84 (s, 3H), 3.64 (s, 3H), 3.44 (s, 1H), 2.98 (s, 3H), 2.85 (d, J=15.9 Hz, 1H), 2.66 (s, 1H), 2.18 (s, 3H), 1.43 (m, 1H), 1.21 (m, 1H), 1.00 (t, J=7.5 Hz, 3H), 0.82 (t, J=6.9 Hz, 3H).

ESIMS (m/e) 902.3 [M+1]$^+$.

Example 63

Preparation of Compound BM63

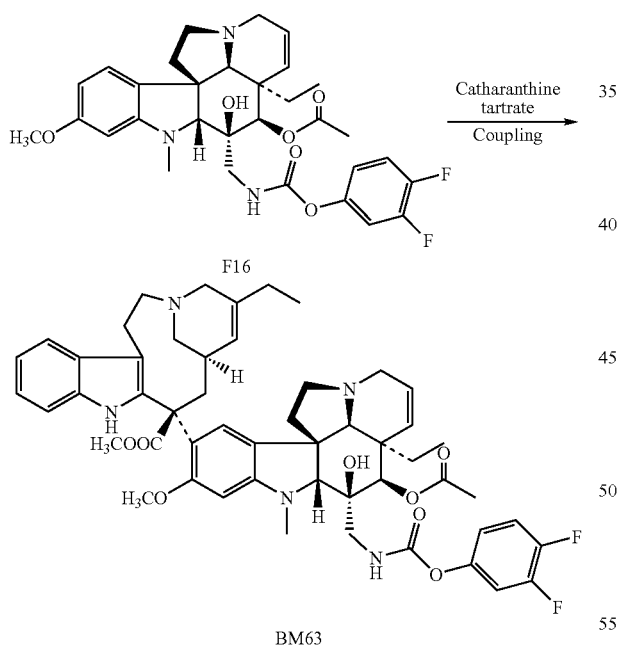

BM63

Compound BM63 was prepared following the procedure for preparing compound BM25.

$^1$H NMR (CDCl$_3$, 300 MHz): δ: 9.40 (s, 1H), 8.02 (s, 1H), 7.53 (d, J=7.5 Hz, 1H), 7.14 (m, 5H), 7.02 (m, 1H), 6.63 (s, 1H), 6.24 (s, 1H), 5.89 (dd, J=10.2, 3.9 Hz, 1H), 5.80 (d, J=7.8 Hz, 1H), 5.46 (m, 2H), 5.07 (s, 1H), 3.84 (s, 3H), 3.63 (s, 3H), 3.45 (s, 1H), 2.99 (s, 3H), 2.85 (d, J=15.9 Hz, 1H), 2.65 (s, 1H), 2.18 (s, 3H), 1.43 (m, 1H), 1.21 (m, 1H), 1.00 (t, J=7.5 Hz, 3H), 0.82 (t, J=6.9 Hz, 3H).

ESIMS (m/e) 920.4 [M+1]$^+$.

Example 64

Preparation of Compound BM64

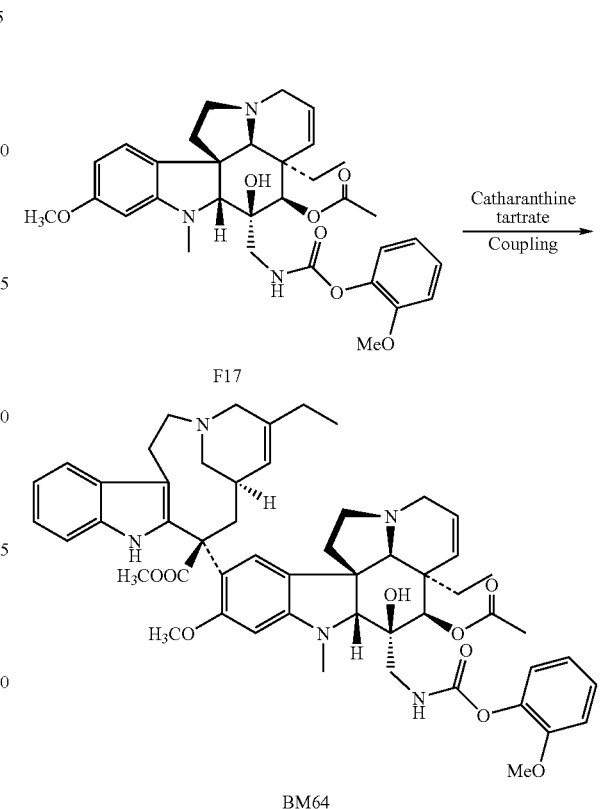

BM64

Compound BM64 was prepared following the procedure for preparing compound BM25.

$^1$H NMR (CDCl$_3$, 300 MHz): δ: 9.35 (s, 1H), 8.02 (s, 1H), 7.53 (d, J=7.8 Hz, 1H), 7.14 (m, 5H), 6.94 (d, J=8.4 Hz, 2H), 6.63 (s, 1H), 6.23 (s, 1H), 5.89 (dd, J=10.2, 3.9 Hz, 1H), 5.81 (d, J=8.1 Hz, 1H), 5.47 (m, 2H), 5.06 (s, 1H), 3.83 (s, 3H), 3.81 (s, 3H), 3.64 (s, 3H), 3.49 (s, 1H), 3.00 (s, 3H), 2.85 (d, J=15.9 Hz, 1H), 2.65 (s, 1H), 2.18 (s, 3H), 1.92 (q, J=7.5 Hz, 2H), 1.43 (m, 1H), 1.21 (m, 1H), 1.00 (t, J=7.5 Hz, 3H), 0.83 (t, J=6.9 Hz, 3H).

ESIMS (m/e) 914.4 [M+1]$^+$.

Example 65

Preparation of Compound BM65

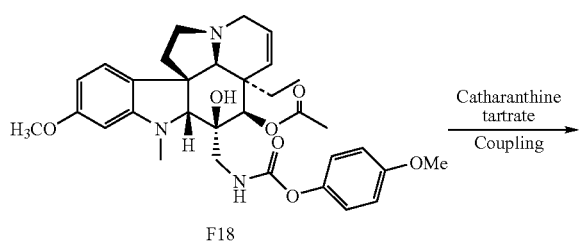

F18

-continued

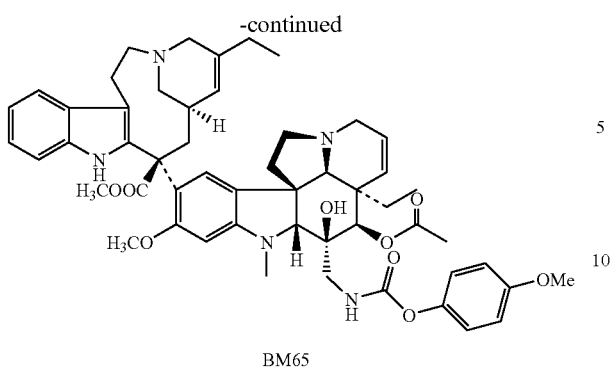

BM65

Compound BM65 was prepared following the procedure for preparing compound BM25.

$^1$H NMR (CDCl$_3$, 300 MHz): δ: 9.36 (s, 1H), 8.02 (s, 1H), 7.53 (d, J=7.5 Hz, 1H), 7.14 (m, 5H), 7.02 (d, J=8.4 Hz, 2H), 6.94 (d, J=8.4 Hz, 2H), 6.63 (s, 1H), 6.23 (s, 1H), 5.89 (dd, J=10.2, 3.9 Hz, 1H), 5.81 (d, J=8.1 Hz, 1H), 5.47 (m, 2H), 5.07 (s, 1H), 3.83 (s, 3H), 3.79 (s, 3H), 3.64 (s, 3H), 3.46 (s, 1H), 2.98 (s, 3H), 2.85 (d, J=15.9 Hz, 1H), 2.65 (s, 1H), 2.17 (s, 3H), 1.92 (q, J=7.5 Hz, 2H), 1.43 (m, 1H), 1.21 (m, 1H), 1.00 (t, J=7.5 Hz, 3H), 0.82 (t, J=6.9 Hz, 3H).

ESIMS (m/e) 914.4 [M+1]$^+$.

Example 66

Preparation of Compound BM66

3H), 3.63 (s, 3H), 3.40 (s, 1H), 2.93 (s, 3H), 2.82 (d, J=15.9 Hz, 1H), 2.63 (s, 1H), 2.14 (s, 3H), 1.95 (q, J=7.5 Hz, 2H), 1.46 (m, 1H), 1.28 (m, 1H), 1.01 (t, J=7.5 Hz, 3H), 0.83 (t, J=6.9 Hz, 3H).

ESIMS (m/e) 898.4 [M+1]$^+$.

Example 67

Preparation of Compound BM67

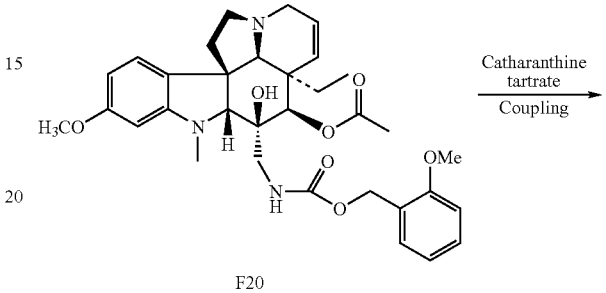

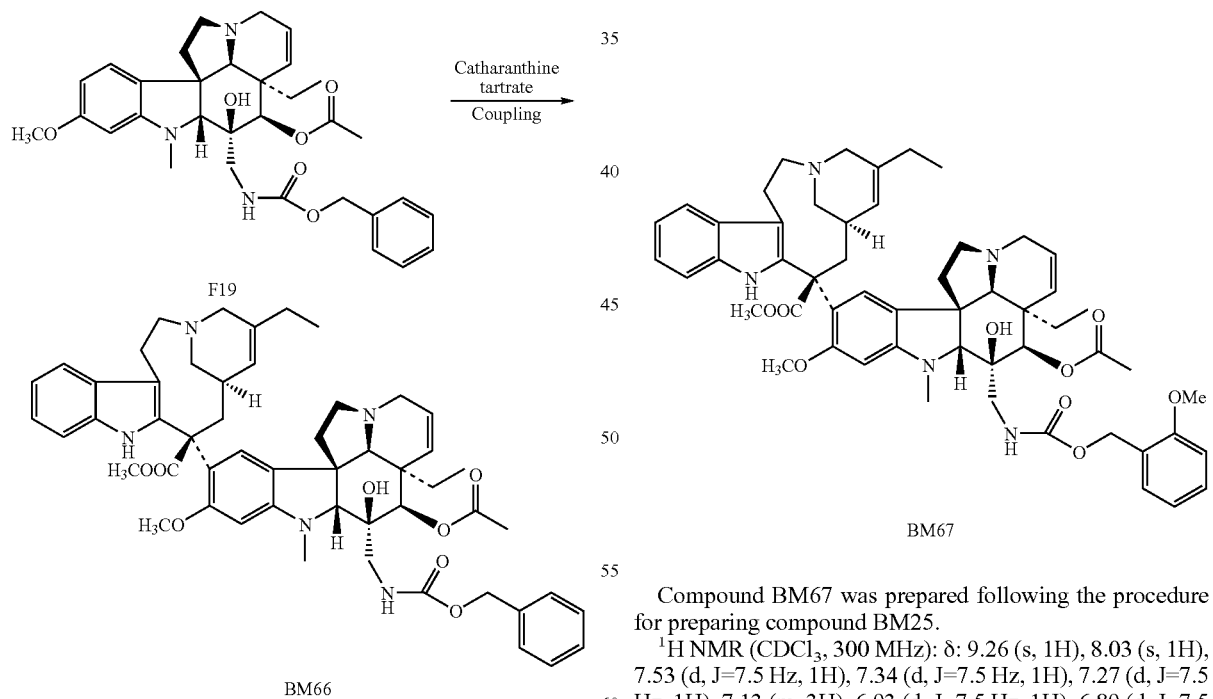

Compound BM66 was prepared following the procedure for preparing compound BM25.

$^1$H NMR (CDCl$_3$, 300 MHz): δ: 9.30 (s, 1H), 8.04 (s, 1H), 7.54 (d, J=7.5 Hz, 1H), 7.35 (m, 5H), 7.15 (m, 3H), 6.63 (s, 1H), 6.22 (s, 1H), 5.88 (dd, J=10.2, 4.5 Hz, 1H), 5.48 (m, 2H), 5.42 (d, J=10.2 Hz, 1H), 5.12 (s, 2H), 5.05 (s, 1H), 3.84 (s,

Compound BM67 was prepared following the procedure for preparing compound BM25.

$^1$H NMR (CDCl$_3$, 300 MHz): δ: 9.26 (s, 1H), 8.03 (s, 1H), 7.53 (d, J=7.5 Hz, 1H), 7.34 (d, J=7.5 Hz, 1H), 7.27 (d, J=7.5 Hz, 1H), 7.13 (m, 3H), 6.93 (d, J=7.5 Hz, 1H), 6.89 (d, J=7.5 Hz, 1H), 6.60 (s, 1H), 6.21 (s, 1H), 5.87 (dd, J=10.2, 3.9 Hz, 1H), 5.44 (m, 3H), 5.17 (s, 2H), 5.04 (s, 1H), 3.83 (s, 6H), 3.62 (s, 3H), 3.38 (s, 1H), 2.93 (s, 3H), 2.81 (d, J=15.3 Hz, 1H), 2.61 (s, 1H), 2.14 (s, 3H), 1.94 (q, J=7.5 Hz, 2H), 1.47 (m, 1H), 1.26 (m, 1H), 1.00 (t, J=7.5 Hz, 3H), 0.82 (t, J=6.9 Hz, 3H).

ESIMS (m/e) 928.4 [M+1]$^+$.

Example 68
Preparation of Compound BM68
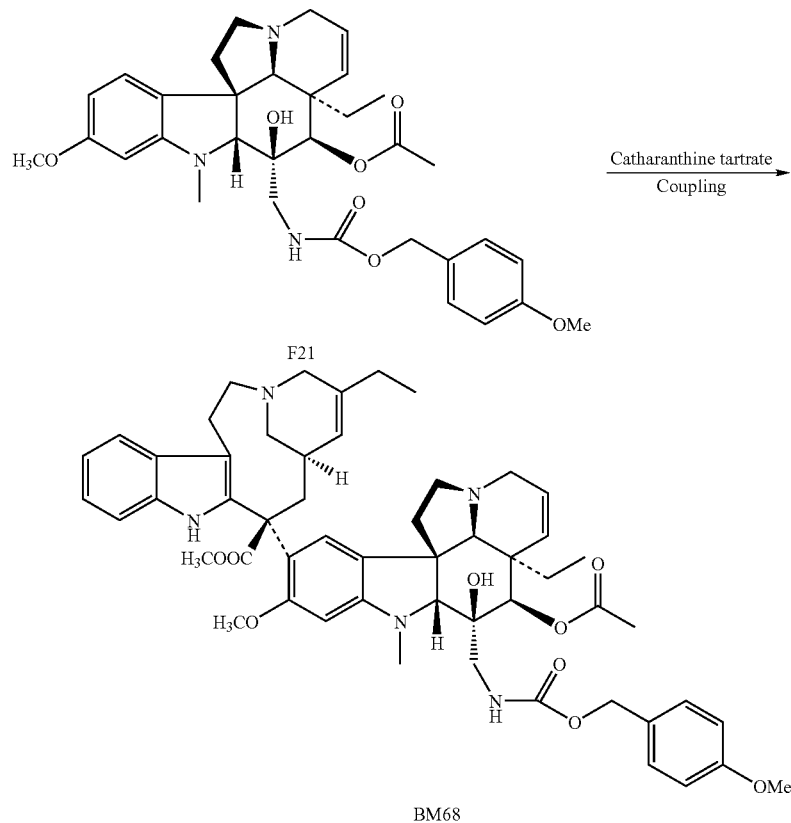
Compound BM68 was prepared following the procedure for preparing compound BM25.
$^1$H NMR (CDCl$_3$, 300 MHz): δ: 9.24 (s, 1H), 8.03 (s, 1H), 7.53 (d, J=7.5 Hz, 1H), 7.26 (d, J=7.5 Hz, 2H), 7.13 (m, 3H), 6.87 (d, J=7.5 Hz, 2H), 6.61 (s, 1H), 6.20 (s, 1H), 5.87 (dd, J=10.5, 4.5 Hz, 1H), 5.49 (d, J=5.4 Hz, 1H), 5.42 (m, 2H), 5.03 (s, 3H), 3.83 (s, 3H), 3.79 (s, 3H), 3.62 (s, 3H), 3.38 (s, 1H), 2.91 (s, 3H), 2.80 (d, J=16.2 Hz, 1H), 2.61 (s, 1H), 2.13 (s, 3H), 1.94 (q, J=7.5 Hz, 2H), 1.43 (m, 1H), 1.21 (m, 1H), 1.00 (t, J=7.5 Hz, 3H), 0.81 (t, J=6.9 Hz, 3H).
ESIMS (m/e) 928.4 [M+1]$^+$.
Example 69
Preparation of Compound BM69
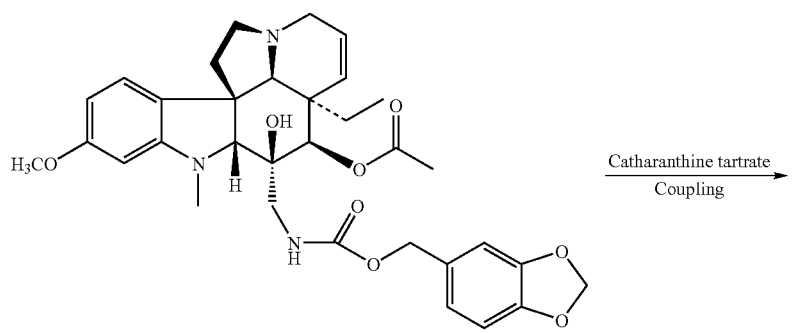

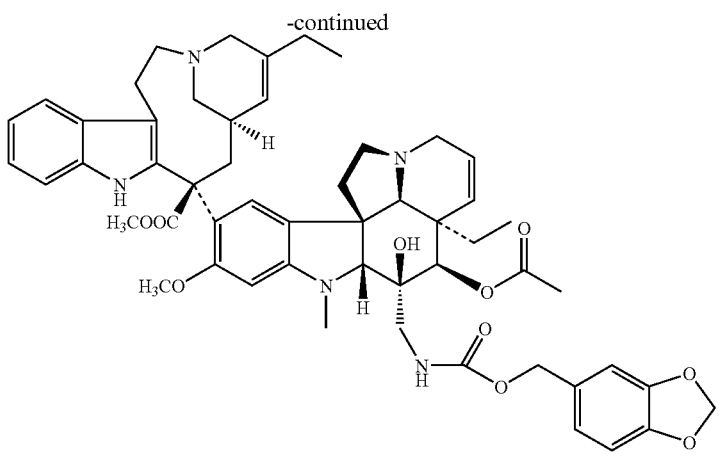

BM69

Compound BM69 was prepared following the procedure for preparing compound BM25.

$^1$H NMR (CDCl$_3$, 300 MHz): δ: 9.26 (s, 1H), 8.03 (s, 1H), 7.52 (d, J=7.5 Hz, 1H), 7.13 (m, 3H), 6.80 (m, 3H), 6.60 (s, 1H), 6.21 (s, 1H), 5.94 (s, 2H), 5.87 (dd, J=10.5, 4.5 Hz, 1H), 5.49 (d, J=6.0 Hz, 1H), 5.42 (d, J=10.5 Hz), 5.03 (s, 3H), 5.00 (s, 2H), 3.83 (s, 3H), 3.62 (s, 3H), 3.35 (s, 1H), 2.91 (s, 3H), 2.81 (d, J=15.9 Hz, 1H), 2.61 (s, 1H), 2.13 (s, 3H), 1.94 (q, J=7.5 Hz, 2H), 1.43 (m, 1H), 1.21 (m, 1H), 1.00 (t, J=7.5 Hz, 3H), 0.81 (t, J=6.9 Hz, 3H).

ESIMS (m/e) 942.4 [M+1]$^+$.

Example 70

Preparation of Compound BM70

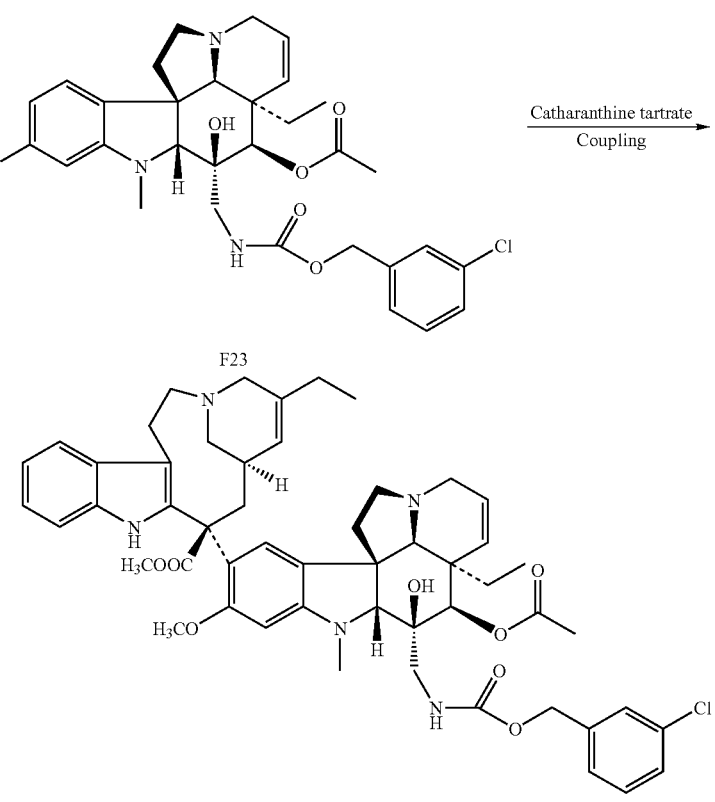

Compound BM70 was prepared following the procedure for preparing compound BM25.

$^1$H NMR (CDCl$_3$, 300 MHz): δ: 9.21 (s, 1H), 7.94 (s, 1H), 7.45 (d, J=7.5 Hz, 1H), 7.16 (m, 4H), 7.04 (m, 3H), 6.53 (s, 1H), 6.13 (s, 1H), 5.80 (dd, J=10.2, 3.9 Hz, 1H), 5.38 (m, 3H), 5.05 (s, 2H), 4.96 (s, 1H), 3.76 (s, 3H), 3.57 (s, 3H), 3.31 (s, 1H), 2.84 (s, 3H), 2.75 (d, J=15.9 Hz, 1H), 2.54 (s, 1H), 2.06 (s, 3H), 1.87 (q, J=7.5 Hz, 2H), 1.39 (m, 1H), 1.18 (m, 1H), 0.93 (t, J=7.5 Hz, 3H), 0.74 (t, J=6.9 Hz, 3H).
ESIMS (m/e) 932.4 [M+1]$^+$.
Example 71
Preparation of Compound BM71
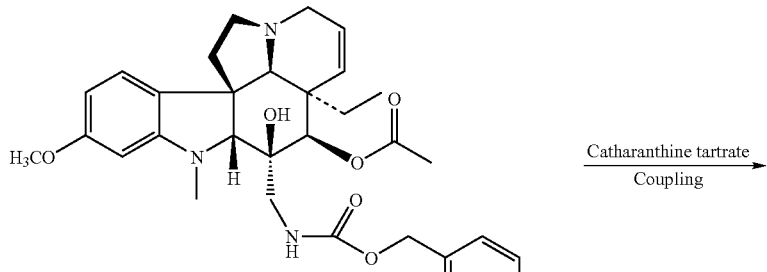
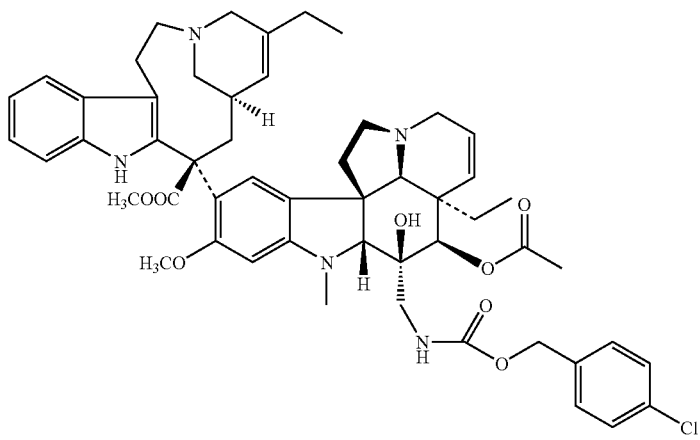
Compound BM71 was prepared following the procedure for preparing compound BM25.
$^1$H NMR (CDCl$_3$, 300 MHz): δ: 9.29 (s, 1H), 8.02 (s, 1H), 7.53 (d, J=7.8 Hz, 1H), 7.30 (m, 4H), 7.13 (m, 3H), 6.61 (s, 1H), 6.20 (s, 1H), 5.87 (dd, J=10.2, 3.9 Hz, 1H), 5.45 (m, 3H), 5.06 (s, 2H), 5.03 (s, 1H), 3.83 (s, 3H), 3.62 (s, 3H), 3.37 (s, 1H), 2.90 (s, 3H), 2.81 (d, J=15.9 Hz, 1H), 2.61 (s, 1H), 2.12 (s, 3H), 1.93 (q, J=7.5 Hz, 2H), 1.47 (m, 1H), 1.24 (m, 1H), 1.00 (t, J=7.5 Hz, 3H), 0.81 (t, J=6.9 Hz, 3H).
ESIMS (m/e) 932.4 [M+1]$^+$.

Example 72
Preparation of Compound BM72
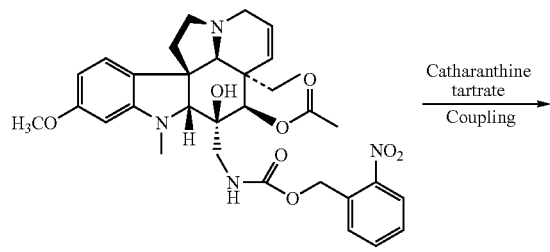
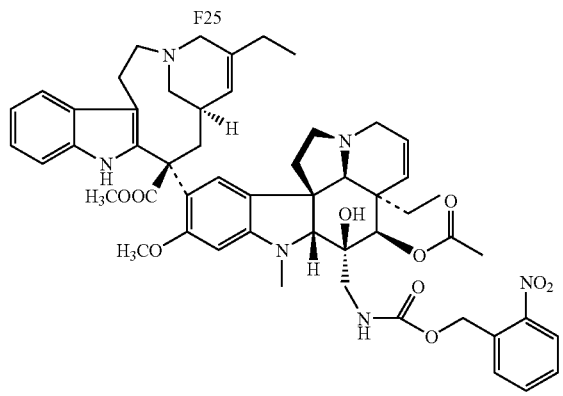
BM72
Compound BM72 was prepared following the procedure for preparing compound BM25.
$^1$H NMR (CDCl$_3$, 300 MHz): δ: 9.35 (s, 1H), 8.03 (s, 1H), 8.07 (d, J=8.1 Hz, 1H), 7.60 (m, 2H), 7.52 (d, J=7.5 Hz, 1H), 7.46 (m, 1H), 7.13 (m, 3H), 6.62 (s, 1H), 6.22 (s, 1H), 5.88 (dd, J=10.2, 3.9 Hz, 1H), 5.51 (m, 3H), 5.51 (s, 2H), 5.05 (s, 1H), 3.83 (s, 3H), 3.64 (s, 3H), 3.41 (s, 1H), 2.93 (s, 3H), 2.83 (d, J=16.2 Hz, 1H), 2.63 (s, 1H), 2.14 (s, 3H), 1.93 (q, J=7.5 Hz, 2H), 1.47 (m, 1H), 1.24 (m, 1H), 1.00 (t, J=7.5 Hz, 3H), 0.82 (t, J=6.9 Hz, 3H).
ESIMS (m/e) 943.3 [M+1]$^+$.
Example 73
Preparation of Compound BM73
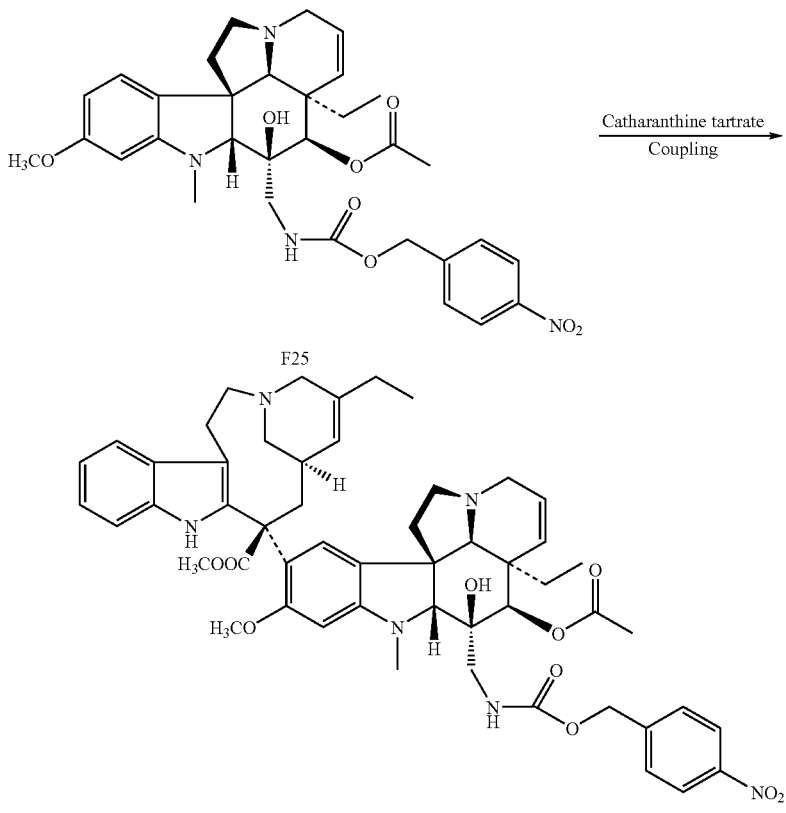
BM72

Compound BM73 was prepared following the procedure for preparing compound BM25.

$^1$H NMR (CDCl$_3$, 300 MHz): δ: 9.36 (s, 1H), 8.19 (d, J=8.7 Hz, 2H), 8.03 (s, 1H), 7.52 (d, J=7.5 Hz, 1H), 7.52 (d, J=8.7 Hz, 2H), 7.13 (m, 3H), 6.61 (s, 1H), 6.21 (s, 1H), 5.88 (dd, J=10.2, 3.9 Hz, 1H), 5.49 (m, 3H), 5.19 (s, 2H), 5.03 (s, 1H), 3.83 (s, 3H), 3.62 (s, 3H), 3.38 (s, 1H), 2.90 (s, 3H), 2.83 (d, J=16.2 Hz, 1H), 2.63 (s, 1H), 2.13 (s, 3H), 1.93 (q, J=7.5 Hz, 2H), 1.47 (m, 1H), 1.24 (m, 1H), 1.00 (t, J=7.5 Hz, 3H), 0.81 (t, J=6.9 Hz, 3H).

ESIMS (m/e) 943.3 [M+1]$^+$.

Example 74

Preparation of Compound BM74

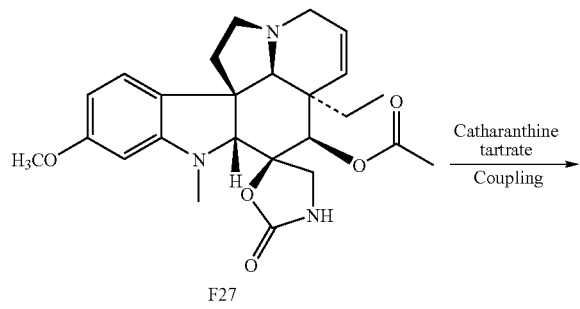

F27

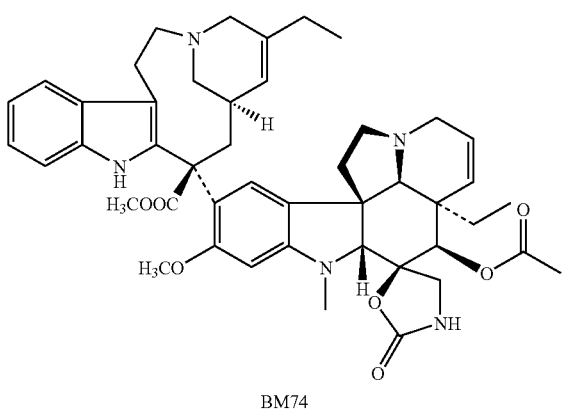

BM74

Compound BM74 was prepared following the procedure for preparing compound BM25.

$^1$H NMR (CDCl$_3$, 300 MHz): δ: 8.43 (s, 1H), 7.51 (d, J=7.2 Hz, 1H), 7.12 (m, 3H), 6.63 (s, 1H), 6.03 (s, 1H), 5.80 (s, 1H), 5.75 (dd, J=10.2, 3.9 Hz, 1H), 5.46 (d, J=5.7 Hz, 1H), 5.27 (d, J=10.2 Hz, 1H), 5.23 (s, 1H), 3.82 (s, 3H), 3.79 (s, 1H), 3.63 (s, 3H), 3.12 (s, 3H), 2.39 (s, 1H), 2.03 (s, 3H), 0.99 (t, J=7.5 Hz, 3H), 0.90 (t, J=6.9 Hz, 3H).

ESIMS (m/e) 790.3 [M+1]$^+$.

Example 75

Preparation of Compound BM75

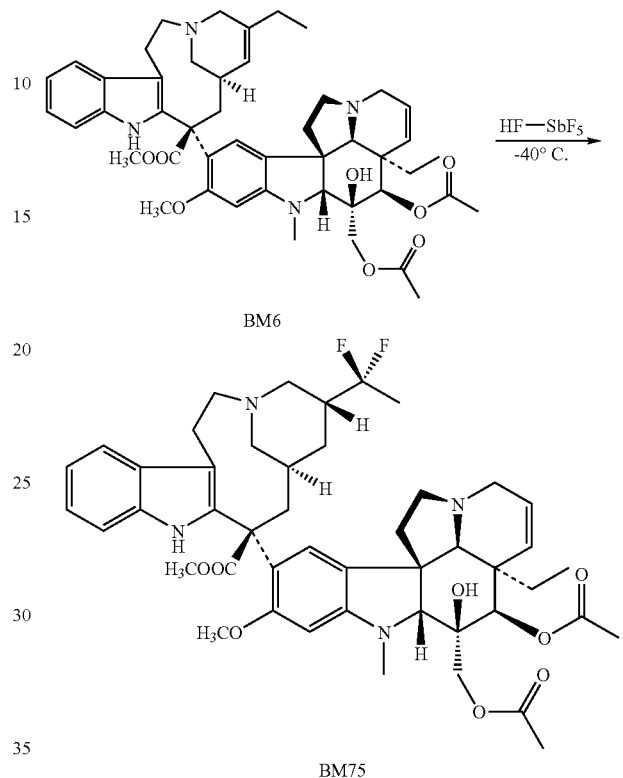

To a 100 ml round bottom Teflon flask, 12 mL (0.6 mmol) of Anhydrous hydrofluoric acid was injected L) and cooled to −35° C. with acetone/dry ice bath. Then 12 g (55 mmol) of anhydrous antimonium pentafluoride was added and cooled to −35° C. A solution of 1 g (1.2 mmol) of compound BM6 in 2 mL of chloroform was slowly added dropwise into the reactor under strong stirring at a temperature less than −30° C. After reacted for 1 h, the reaction mixture was slowly poured into a mixture containing 200 mL of ice water, 63.6 g (0.6 mol) of sodium carbonate and 30 mL of methylene chloride, and extracted with methylene chloride (50 mL×2). The organic phase was washed with saturated salt solution, dried over anhydrous magnesium sulfate and filtered to obtain a crude product, which was purified by silica gel chromatography (CHCl$_3$: CH$_3$OH=400:1) to give 312 mg of compound BM75 as a white powder in 31% yield.

$^1$H NMR (CDCl$_3$, 300 MHz): δ: 9.18 (s, 1H), 8.03 (s, 1H), 7.50 (d, J=7.5 Hz, 1H), 7.14 (m, 3H), 6.63 (s, 1H), 6.18 (s, 1H), 5.89 (dd, J=9.9, 4.2 Hz, 1H), 5.44 (d, J=9.9 Hz, 1H), 5.07 (s, 1H), 4.21 (d, J=11.7 Hz, 1H), 4.03 (d, J=11.7 Hz, 1H), 3.83 (s, 3H), 3.63 (s, 3H), 2.93 (s, 3H), 2.62 (s, 1H), 2.19 (s, 3H), 2.13 (s, 3H), 1.87-1.67 (m, 4H), 1.53 (t, J=19.2 Hz, 3H), 1.42-1.21 (m, 1H), 0.86 (m, 1H), 0.83 (t, J=7.2 Hz, 3H).

$^{13}$C NMR (CDCl$_3$, 75 MHz): δ: 174.7 (C), 170.9 (C), 170.5 (C), 157.8 (C), 153.3 (C), 134.9 (C), 130.4 (C), 129.5 (CH), 129.1 (C), 125.1 (C), 124.5 (CH), 123.5 (C), 123.3 (CH), 122.3 (CH), 121.1 (C), 118.8 (CH), 118.2 (CH), 116.8 (C), 110.3 (CH), 94.5 (CH), 81.5 (CH), 76.7 (CH), 76.0 (C), 66.4

(CH$_2$), 66.1 (CH), 56.5 (CH$_2$), 55.7 (OCH$_3$), 55.3 (C), 53.1 (CH$_2$), 52.4 (C), 52.3 (OCH$_3$), 50.2 (CH$_2$), 50.0 (CH$_2$), 47.3 (CH$_2$), 44.9 (CH$_2$), 42.3 (C), 39.8 (CH$_3$), 38.7 (CH), 33.2 (CH$_2$), 31.8 (CH$_2$), 31.4 (CH$_2$), 29.1 (CH), 29.0 (CH$_2$), 20.9 (2CH$_3$), 20.9 (CH$_3$), 8.2 (CH$_3$).
ESIMS (m/e) 845.4 [M+1]$^+$.

Example 76

Preparation of Compound BM76

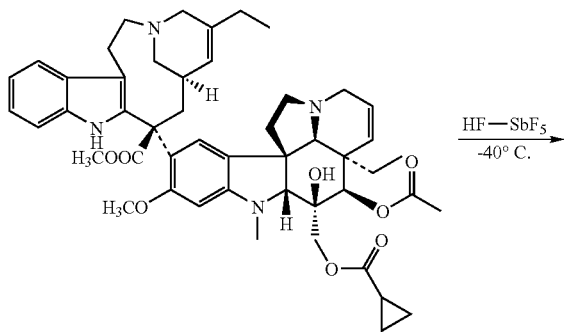

BM14

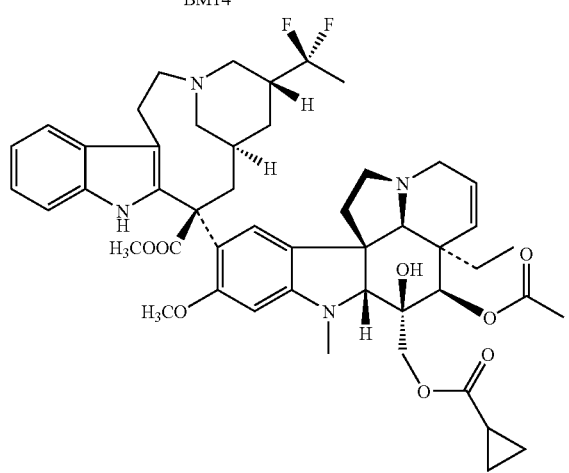

BM76

Compound BM76 was prepared following the procedure for preparing compound BM75.

$^1$H NMR (CDCl$_3$, 300 MHz): δ: 9.14 (s, 1H), 8.01 (s, 1H), 7.50 (d, J=7.8 Hz, 1H), 7.13 (m, 3H), 6.62 (s, 1H), 6.17 (s, 1H), 5.88 (dd, J=9.9, 3.9 Hz, 1H), 5.43 (d, J=9.9 Hz, 1H), 5.06 (s, 1H), 4.23 (d, J=11.4 Hz, 1H), 4.02 (d, J=11.4 Hz, 1H), 3.82 (s, 3H), 3.66 (s, 1H), 3.63 (s, 3H), 2.94 (s, 3H), 2.62 (s, 1H), 2.20 (s, 3H), 1.87-1.66 (m, 4H), 1.53 (t, J=19.2 Hz, 3H), 1.42-1.21 (m, 1H), 1.01 (m, 2H), 0.86 (m, 3H), 0.83 (t, J=7.2 Hz, 3H).

$^{13}$C NMR (CDCl$_3$, 75 MHz): δ: 175.0 (C), 174.9 (C), 171.2 (C), 158.1 (C), 153.7 (C), 135.3 (C), 130.8 (C), 129.8 (CH), 129.4 (C), 125.2 (C), 124.9 (CH), 123.9 (C), 123.6 (CH), 122.6 (CH), 121.3 (C), 119.1 (CH), 118.5 (CH), 117.2 (C), 110.7 (CH), 94.7 (CH), 81.9 (CH), 77.0 (CH), 76.3 (C), 66.7 (CH$_2$), 66.5 (CH), 56.9 (CH$_2$), 56.0 (OCH$_3$), 55.6 (C), 53.4 (CH$_2$), 52.7 (C), 52.6 (OCH$_3$), 50.5 (CH$_2$), 50.3 (CH$_2$), 47.6 (CH$_2$), 45.3 (CH$_2$), 42.7 (C), 40.1 (CH$_3$), 39.3 (CH), 33.5 (CH$_2$), 32.1 (CH$_2$), 31.7 (CH$_2$), 29.5 (CH), 29.3 (CH$_2$), 21.3 (CH$_3$), 21.2 (CH$_3$), 13.0 (CH), 8.9 (CH$_2$), 8.8 (CH$_2$), 8.5 (CH$_3$). ESIMS (m/e) 871.4 [M+1]$^+$.

Example 77

Preparation of Compound BM77

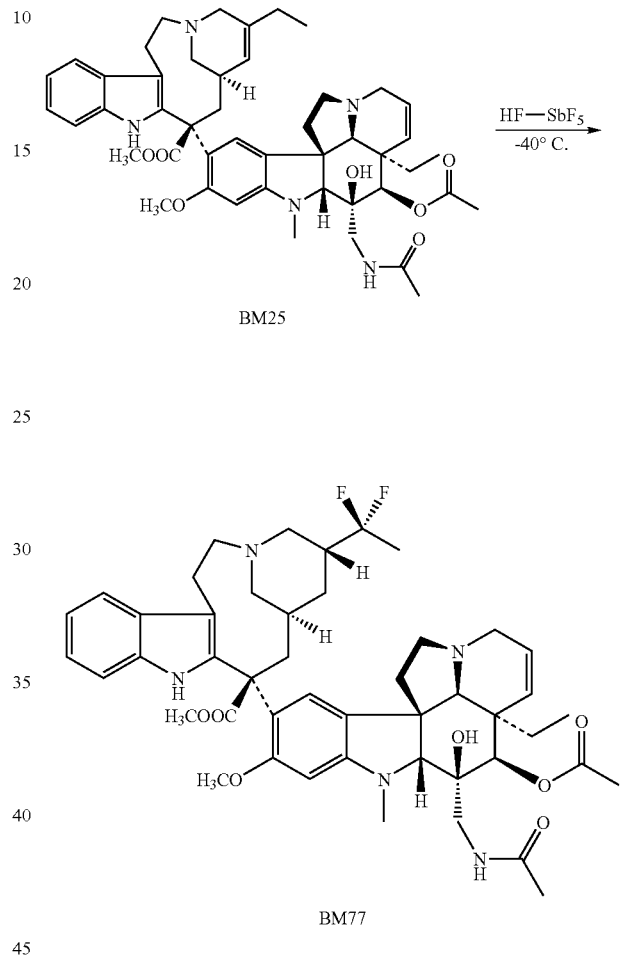

BM25

BM77

Compound BM77 was prepared following the procedure for preparing compound BM75.

$^1$H NMR (CDCl$_3$, 300 MHz): δ: 9.42 (s, 1H), 8.00 (s, 1H), 7.49 (d, J=7.5 Hz, 1H), 7.13 (m, 3H), 6.59 (s, 1H), 6.18 (s, 1H), 6.15 (s, 1H), 5.88 (dd, J=10.5, 4.2 Hz, 1H), 5.41 (d, J=10.5 Hz, 1H), 5.02 (s, 1H), 3.81 (s, 3H), 3.63 (s, 3H), 3.37 (s, 1H), 2.90 (s, 3H), 2.82 (d, J=14.1 Hz, 2H), 2.62 (s, 1H), 2.14 (s, 3H), 2.00 (s, 3H), 1.85-1.66 (m, 4H), 1.53 (t, J=18.9 Hz, 3H), 1.42-1.21 (m, 1H), 0.86 (m, 1H), 0.81 (t, J=7.2 Hz, 3H).

$^{13}$C NMR (CDCl$_3$, 75 MHz): δ: 174.9 (C); 170.9 (C), 170.5 (C), 157.1 (C), 153.7 (C), 135.2 (C), 130.6 (C), 130.1 (CH), 129.3 (C), 125.2 (C), 124.8 (CH), 123.6 (C), 123.5 (CH), 122.7 (CH), 121.5 (C), 119.2 (CH), 118.5 (CH), 117.0 (C), 110.7 (CH), 95.2 (CH), 82.3 (CH), 77.2 (CH), 76.0 (C), 66.0 (CH), 56.9 (CH$_2$), 56.0 (OCH$_3$), 55.5 (C), 53.3 (CH$_2$), 52.8 (C), 52.7 (OCH$_3$), 50.3 (2CH$_2$), 47.3 (CH$_2$), 45.4 (CH$_2$), 43.4 (CH$_2$), 42.9 (C), 40.8 (CH$_3$), 38.7 (CH), 33.5 (CH$_2$), 31.9 (CH$_2$), 31.5 (CH$_2$), 29.2 (CH), 28.8 (CH$_2$), 23.5 (CH$_3$), 21.2 (CH$_3$), 21.3 (CH$_3$), 8.5 (CH$_3$).
ESIMS (m/e) 844.4 [M+1]$^+$.

Example 78

Preparation of Compound BM78

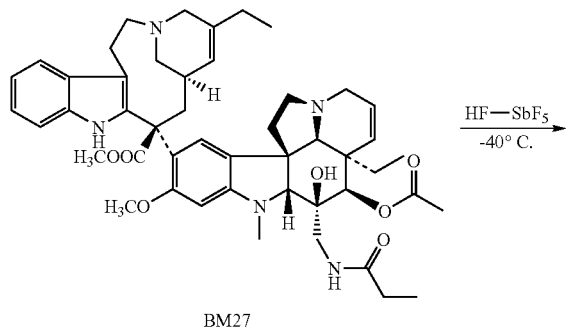

BM27

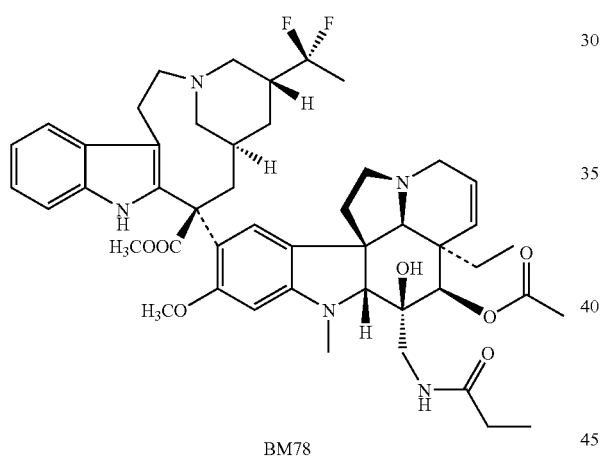

BM78

Compound BM78 was prepared following the procedure for preparing compound BM75.

$^1$H NMR (CDCl$_3$, 300 MHz): δ: 9.41 (s, 1H), 8.00 (s, 1H), 7.49 (d, J=7.5 Hz, 1H), 7.13 (m, 3H), 6.60 (s, 1H), 6.18 (s, 1H), 6.15 (s, 1H), 5.88 (dd, J=10.5, 4.2 Hz, 1H), 5.41 (d, J=10.5 Hz, 1H), 5.02 (s, 1H), 3.81 (s, 3H), 3.63 (s, 3H), 3.33 (s, 1H), 2.85 (s, 3H), 2.82 (d, J=14.1 Hz, 2H), 2.62 (s, 1H), 2.23 (q, J=7.2 Hz, 2H), 2.14 (s, 3H), 1.84-1.66 (m, 4H), 1.53 (t, J=18.9 Hz, 3H), 1.42-1.20 (m, 1H), 1.15 (t, J=7.2 Hz, 3H), 0.84 (m, 1H), 0.81 (t, J=7.2 Hz, 3H).

$^{13}$C NMR (CDCl$_3$, 75 MHz): δ: 174.9 (C), 174.2 (C), 170.9 (C), 158.1 (C), 153.7 (C), 135.2 (C), 130.6 (C), 130.1 (CH), 129.4 (C), 125.2 (C), 124.7 (CH), 123.7 (C), 123.5 (CH), 122.6 (CH), 121.5 (C), 119.1 (CH), 118.5 (CH), 117.1 (C), 110.7 (CH), 95.2 (CH), 82.3 (CH), 77.1 (CH), 76.0 (C), 66.0 (CH), 56.9 (CH$_2$), 56.0 (OCH$_3$), 55.5 (C), 53.3 (CH$_2$), 52.8 (C), 52.7 (OCH$_3$), 50.3 (2CH$_2$), 47.4 (CH$_2$), 45.4 (CH$_2$), 43.2 (CH$_2$), 42.9 (C), 40.8 (CH$_3$), 38.7 (CH), 33.4 (CH$_2$), 32.0 (CH$_2$), 31.5 (CH$_2$), 30.5 (CH$_2$), 29.3 (CH$_2$), 29.2 (CH$_2$), 21.3 (CH$_3$), 21.2 (CH$_3$), 10.2 (CH$_3$), 8.5 (CH$_3$).

ESIMS (m/e) 858.4 [M+1]$^+$.

Example 79

Preparation of Compound BM79

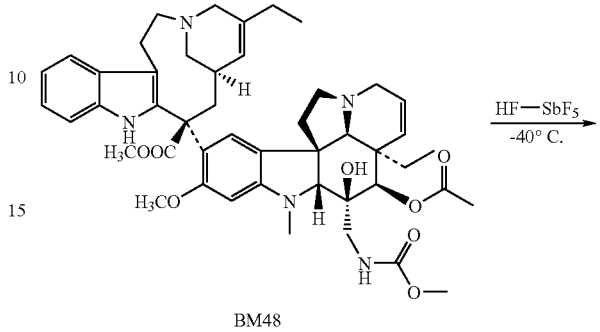

BM48

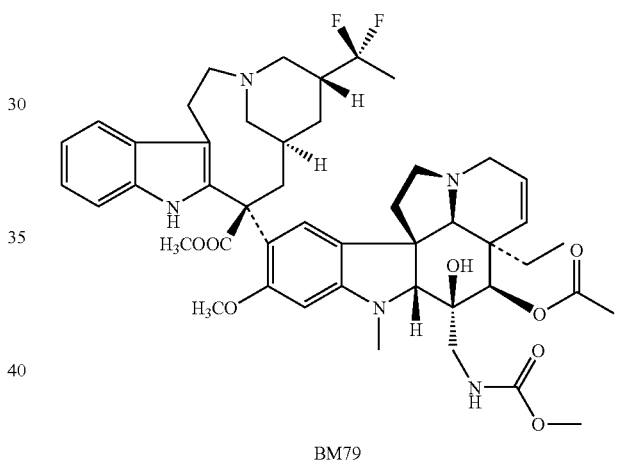

BM79

Compound BM79 was prepared following the procedure for preparing compound BM75.

$^1$H NMR (CDCl$_3$, 300 MHz): δ: 9.23 (s, 1H), 8.02 (s, 1H), 7.50 (d, J=7.5 Hz, 1H), 7.13 (m, 3H), 6.62 (s, 1H), 6.19 (s, 1H), 5.88 (dd, J=10.2, 4.2 Hz, 1H), 5.43 (d, J=10.2 Hz, 1H), 5.34 (bs, 1H), 5.03 (s, 1H), 3.81 (s, 3H), 3.66 (s, 3H), 3.63 (s, 3H), 3.41 (s; 1H), 2.95 (s, 3H), 2.82 (d, J=13.8 Hz, 2H), 2.62 (s, 1H), 2.16 (s, 3H), 2.12-2.02 (m, 2H), 1.84-1.66 (m, 2H), 1.53 (t, J=18.9 Hz, 3H), 1.42-1.20 (m, 1H), 0.84 (m, 1H), 0.81 (t, J=7.2 Hz, 3H).

$^{13}$C NMR (CDCl$_3$, 75 MHz): δ: 174.9 (C), 170.9 (C), 158.1 (C), 157.4 (C), 153.7 (C), 135.2 (C), 130.7 (C), 130.1 (CH), 129.4 (C), 125.2 (C), 124.7 (CH), 123.7 (C), 123.5 (CH), 122.5 (CH), 121.6 (C), 119.1 (CH), 118.5 (CH), 117.1 (C), 110.7 (CH), 95.2 (CH), 82.2 (CH), 77.1 (CH), 76.0 (C), 66.1 (CH), 56.8 (CH$_2$), 55.9 (OCH$_3$), 55.6 (C), 53.3 (CH$_2$), 52.8 (C), 52.6 (OCH$_3$), 52.2 (OCH$_3$), 50.2 (2CH$_2$), 47.5 (CH$_2$), 45.3 (CH$_2$), 44.9 (CH$_2$), 42.8 (C), 40.8 (CH$_3$), 38.9 (CH), 33.4 (CH$_2$), 32.1 (CH$_2$), 31.6 (CH$_2$), 29.4 (CH), 29.2 (CH$_2$), 21.2 (CH$_3$), 21.1 (CH$_3$), 8.4 (CH$_3$).

ESIMS (m/e) 860.4 [M+1]$^+$.

Example 80

Preparation of Compound BM80

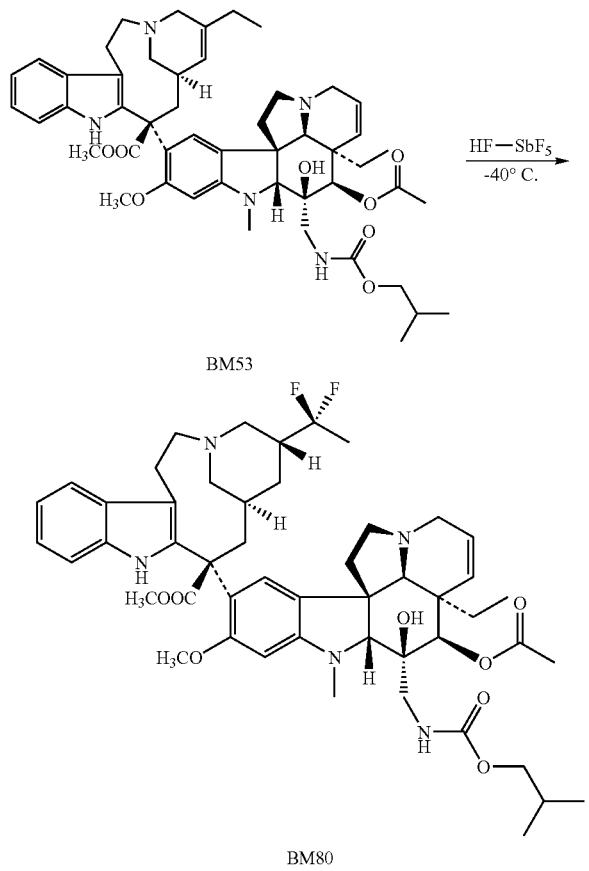

Compound BM80 was prepared following the procedure for preparing compound BM75.

$^1$H NMR (CDCl$_3$, 300 MHz): δ: 9.26 (s, 1H), 8.00 (s, 1H), 7.49 (d, J=7.5 Hz, 1H), 7.13 (m, 3H), 6.60 (s, 1H), 6.18 (s, 1H), 5.88 (dd, J=10.2, 4.2 Hz, 1H), 5.42 (d, J=10.2 Hz, 1H), 5.29 (bs, 1H), 5.04 (s, 1H), 3.87 (d, J=9.0 Hz, 1H), 3.82 (s, 3H), 3.63 (s, 3H), 3.42 (s, 1H), 2.94 (s, 3H), 2.82 (d, J=13.8 Hz, 2H), 2.61 (s, 1H), 2.15 (s, 3H), 2.10-2.03 (m, 1H), 1.94-1.70 (m, 3H), 1.53 (t, J=19.2 Hz, 3H), 1.45-1.20 (m, 1H), 0.91 (d, J=6.6 Hz, 6H), 0.81 (t, J=7.2 Hz, 3H).

$^{13}$C NMR (CDCl$_3$, 75 MHz): δ: 174.9 (C), 170.9 (C), 158.1 (C), 157.1 (C), 153.7 (C), 135.2 (C), 130.7 (C), 130.0 (CH), 129.3 (C), 125.2 (C), 124.7 (CH), 123.7 (C), 123.5 (CH), 122.5 (CH), 121.4 (C), 119.0 (CH), 118.4 (CH), 117.1 (C), 110.6 (CH), 95.0 (CH), 82.1 (CH), 77.3 (CH), 76.1 (C), 71.1 (CH$_2$), 66.2 (CH), 56.8 (CH$_2$), 55.9 (OCH$_3$), 55.5 (C), 53.3 (CH$_2$), 52.7 (C), 52.5 (OCH$_3$), 50.2 (2CH$_2$), 47.5 (CH$_2$), 45.2 (CH$_2$), 44.9 (CH$_2$), 42.8 (C), 40.6 (CH$_3$), 38.9 (CH), 33.4 (CH$_2$), 32.1 (CH$_2$), 31.6 (CH$_2$), 29.3 (CH), 29.2 (CH$_2$), 28.1 (CH), 21.2 (CH$_3$), 21.1 (CH$_3$), 19.1 (2CH$_3$), 8.4 (CH$_3$). ESIMS (m/e) 902.4 [M+1]$^+$.

The other vinblastine derivatives and physiologically acceptable salts thereof can also be prepared with reference to the above preparation examples for preparting vinblastine derivatives in combination with the prior art in the field.

EXPERIMENTAL EXAMPLES

Experimental Example 1

In Vitro Cytotoxicity Assay

1. Materials

Human non-small cell lung cancer cell line A-549 was obtained from American Type Culture Collection, and human cervical carcinoma cell line Hela was from the Cell Bank of Shanghai Institute of Materia Medica, Chinese Academy of Sciences.

Positive controls were vinblastine sulfate (VLB) isolated from Vinca, anhydrovinblastine tartrate (AVLB) and vinorelbine tartrate (NVB) prepared by conventional methods. The material purity was determined by HPLC-UV over 98%, and their structures were determined by NMR spectra.

The tested compounds and positive controls were diluted with normal saline to a series of solutions with concentration gradients of $10^{-4}$M, $10^{-5}$M, $10^{-6}$M, $10^{-7}$M and $10^{-8}$M.

2. Experimental

Sulforhodamine B (SRB) Assay: human nonsmall-cell lung cancer cell line A-549 and human cervical carcinoma cell line Hela.

According to cell growth rate, tumor cells in the log phase of growth were seeded into 96-well microculture plates at 100 μL per well, and allowed to attach for 24 hours, followed by addition of a test compound or positive control at 10 μL per well. For each concentration, the test was carried out in triplicate wells, and included control wells containing the aqueous medium of normal saline as negative controls and a blank well containing all medium without cells for zeroing. After the tumor cells were incubated for 72 hours at 37° C. under 5% CO$_2$, the culture medium (RPMI-1640) was removed, and the cells were fixed with 10% cool TCA and incubated for 1 h at 4° C. The cells were then washed with distilled water for 5 times, dried in the air, followed by addition of a solution of SRB (Sigma) (4 mg/mL) in 1% glacial acetic acid at 100 μL per well. The cells were stained for 15 minutes at room temperature, and the supernatant was discarded. The plates were washed for 5 times with 1% acetic acid, and dried in air. Finally, Tris solution was added at 150 μl, per well, and the absorbance (A) was measured at a wavelength of 515 nm on a microplate reader. The rate of inhibition of tumor cell proliferation was calculated according to the following formula:

Growth Inhibition(%)=[(Absorbance of negative control−Absorbance of blank)−(Absorbance of sample−Absorbance of blank)]/(Absorbance of negative control−Absorbance of blank)×100%

Drug concentration: 10 μM, 1 μM, 0.1 μM, 10 nM, 1 nM, 0.1 nM

IC$_{50}$ was fitted with GraphPad Prism 4.

TABLE 1

The Cytotoxic activity against human lung cancer cell line A-549 and human cervical carcinoma cell line Hela of the tested samples (Ditartrate of all compounds were used in bioassays)

| Compound | A549 (IC$_{50}$, nM) | Hela (IC$_{50}$, nM) |
|---|---|---|
| Vinblastine sulfate | 3.4 | 2.5 |
| Vinorelbine tartrate | 23.1 | 9.1 |
| Vincristine sufate | 25.1 | 11.3 |
| Anhydrovinblastine tartrate | 60.2 | 40.2 |
| BM1 | 348.3 | 154.0 |
| BM2 | 440.7 | 113.4 |
| BM3 | >1000 | >1000 |

TABLE 1-continued

The Cytotoxic activity against human lung cancer cell line A-549 and human cervical carcinoma cell line Hela of the tested samples (Ditartrate of all compounds were used in bioassays)

| Compound | A549 (IC$_{50}$, nM) | Hela (IC$_{50}$, nM) |
|---|---|---|
| BM4 | >1000 | 295.4 |
| BM5 | >1000 | 286.3 |
| BM6 | 124.0 | 47.6 |
| BM10 | 709.8 | 637 |
| BM11 | >1000 | >1000 |
| BM12 | 575.7 | 95.9 |
| BM13 | >1000 | >1000 |
| BM14 | >1000 | >1000 |
| BM15 | >1000 | 227.5 |
| BM22 | >1000 | >1000 |
| BM23 | >1000 | >1000 |
| BM24 | >1000 | >1000 |
| BM25 | >1000 | 476.7 |
| BM26 | 56.3 | 61.6 |
| BM27 | 42.9 | 13.4 |
| BM28 | 101.3 | 75.8 |
| BM29 | 348.2 | 126 |
| BM30 | >1000 | >1000 |
| BM31 | 395.3 | 245 |
| BM32 | 17.9 | 12.5 |
| BM33 | 26.4 | 17.0 |
| BM34 | 337.6 | 73.5 |
| BM35 | 116.9 | 45.2 |
| BM36 | 87.4 | 16.4 |
| BM37 | 20.7 | 16.0 |
| BM38 | 46.5 | 20.4 |
| BM40 | 102.8 | 42.0 |
| BM42 | 78.3 | 22.4 |
| BM45 | 578.3 | 135.2 |
| BM46 | 173.7 | 22.9 |
| BM47 | 14.4 | 19.0 |
| BM48 | 75.3 | 34.8 |
| BM49 | 23.7 | 34.8 |
| BM50 | 162.4 | 26.2 |
| BM51 | 504.6 | 171.5 |
| BM53 | 13.7 | 7.1 |
| BM54 | 632.1 | 425 |
| BM56 | 332.3 | 78.4 |
| BM57 | 60.6 | 13.2 |
| BM58 | 97.3 | 62.9 |
| BM59 | 169.5 | 79.8 |
| BM60 | 226.2 | 75.9 |
| BM61 | 977.6 | 683.3 |
| BM62 | >1000 | 377.0 |
| BM63 | >1000 | 263.9 |
| BM64 | 950.6 | 226.8 |
| BM65 | 344.4 | 158.9 |
| BM66 | 261.2 | 87.5 |
| BM67 | 480 | 176 |
| BM68 | 150 | 87.6 |
| BM69 | 230 | 127 |
| BM70 | >1000 | >1000 |
| BM71 | 510 | 347 |
| BM72 | 830 | 561 |
| BM73 | 780 | 432 |
| BM74 | 710 | 342 |
| BM75 | >1000 | >1000 |
| BM76 | >1000 | >1000 |
| BM77 | >1000 | >1000 |
| BM78 | >1000 | >1000 |
| BM79 | >1000 | >1000 |
| BM80 | >1000 | >1000 |

As shown in Table 1, it is obviously from the cell-based screening results that the vinblastine derivatives of the present invention have the activities to inhibit the tumor cell proliferation, and a few of them have better inhibiting efficacy than that of vinorelbine tartrate (NVB) and anhydrovinblastine tartrate (AVLB) which are the positive controls. The vinblastine derivatives BM27, BM33, BM47, BM48, BM53 and BM57 which show excellent cell-based efficacy were further selected as examples to perform the following pharmacodynamics assays in vivo. Although only the vinblastine derivatives BM27, BM33, BM47, BM48, BM53 and BM57 were used as examples in the following animal experiments, it should be noted that the above cell-based screening results indicate obviously that the other vinblastine derivatives should also have a similar efficacy.

Experimental Example 2

In Vivo Antitumor Assay

1. Assay on Sarcoma 180 (S180)
Experimental Protocol:

Seven-weeks-old specific pathogen free (SPF) KM mice (weight, 18-22 g) were available from Shanghai Laboratory Animal Center, Chinese Academy of Sciences (Certicate code: SCXK (Shanghai) 2003-0003). Female KM mice were used to study inhibition of tumor growth in vivo. 7-11 days S180 cells which were well-grown were dispersed into a suspension of about 2.5×10$^6$/ml, and subcutaneously implanted into the axilla of mice. The animals were grouped randomly (d0). The compounds were administrated intravenously (iv) at d1 or d1 and d4. Vinorelbine tartrate, anhydrovinblastine tartrate and vinflunine tartrate were delivered intravenously at d1 and d4 as positive controls. The tumor volume and mice weight were measured 2-3 times each week, and the data were recorded.

TABLE 2

Effects of some compounds of the present invention on the growth of sarcoma 180 in mice

| Group | Dosage mg/kg | Protocol | Mice (n) initial/end | Average weight (g) Before administration | At sacrifice | Tumor Weight (g) X ± SD | Inhibition rate % |
|---|---|---|---|---|---|---|---|
| Control |  |  | 16/16 | 21.6 | 31.9 | 1.60 ± 0.27 |  |
| BM27 | 10 | iv, d 1, 4 | 8/8 | 20.6 | 21.4 | 0.25 ± 0.06 | 84.4* |
|  | 20 | iv d 1 | 8/5 | 20.5 | 20.7 | 0.16 ± 0.03 | 90.0* |
| BM33 | 10 | iv, d 1, 4 | 8/7 | 20.4 | 22.2 | 0.30 ± 0.05 | 81.3* |
|  | 20 | iv d 1 | 8/5 | 20.5 | 23.9 | 0.18 ± 0.02 | 88.8* |
| BM47 | 10 | iv, d 1, 4 | 8/8 | 20.5 | 25.3 | 0.67 ± 0.07 | 58.1* |
|  | 20 | iv d 1 | 8/6 | 20.8 | 23.3 | 0.54 ± 0.17 | 66.3* |
| BM48 | 10 | iv, d 1, 4 | 8/8 | 20.6 | 27.1 | 0.85 ± 0.11 | 46.9* |
|  | 20 | iv d 1 | 8/5 | 20.4 | 24.2 | 0.35 ± 0.03 | 78.1* |

TABLE 2-continued

Effects of some compounds of the present invention on the growth of sarcoma 180 in mice

| Group | Dosage mg/kg | Protocol | Mice (n) initial/end | Average weight (g) Before administration | At sacrifice | Tumor Weight (g) X ± SD | Inhibition rate % |
|---|---|---|---|---|---|---|---|
| BM53 | 10 | iv, d 1, 4 | 8/8 | 24.4 | 25.4 | 0.24 ± 0.09 | 85.0* |
| BM57 | 10 | | 8/8 | 24.3 | 25.2 | 0.26 ± 0.07 | 83.8* |
| BM75 | 20 | | 8/8 | 21.8 | 30.9 | 1.53 ± 0.56 | 4.4 |
| | 40 | | 8/8 | 21.8 | 33.3 | 1.85 ± 0.32 | 0.0 |
| BM76 | 20 | | 8/8 | 21.5 | 31.4 | 1.20 ± 0.09 | 25.0 |
| | 40 | | 8/8 | 21.3 | 31.8 | 1.25 ± 0.45 | 21.9 |
| BM78 | 20 | iv, d 1, 4 | 8/8 | 21.3 | 30.1 | 0.76 ± 0.29 | 52.5* |
| | 40 | iv d 1 | 8/8 | 21.4 | 28.8 | 0.48 ± 0.15 | 70.0* |
| | 40 | iv, d 1, 4 | 8/8 | 24.4 | 29.0 | 0.36 ± 0.11 | 77.5* |
| BM79 | 20 | iv, d 1, 4 | 8/8 | 21.8 | 33.0 | 1.47 ± 0.15 | 8.1 |
| | 40 | | 8/8 | 21.8 | 29.5 | 0.84 ± 0.49 | 47.5* |
| BM80 | 20 | | 8/8 | 21.5 | 34.5 | 1.55 ± 0.34 | 3.1 |
| | 40 | | 8/8 | 21.3 | 32.5 | 1.58 ± 0.12 | 1.2 |
| AVLB | 10 | | 8/8 | 24.3 | 27.9 | 0.49 ± 0.10 | 69.4* |
| Vinflunine | 40 | | 8/8 | 24.3 | 28.4 | 0.44 ± 0.13 | 72.5* |
| Vinorelbine | 10 | | 8/8 | 24.1 | 27.5 | 0.60 ± 0.23 | 62.5* |

*P < 0.01, compared with control groups. Vinorelbine, vinflunine and anhydrovinblastine as positive controls.

Vinflunine (VFL), a vinblastine derivative with broad spectrum, low-toxicity and higher therapeutic index, was developed in the Pierre Fabre Laboratoires by application of super-acid chemistry into modification of the structure of vinblastine. Under a strong acidic condition, C20', the inactive site of vinorelbine, is introduced two fluorine atoms, and the double bond between C3' and C4' is reduced into a single bond. VFL has an in vitro activity depending on its concentration and action time, and an $IC_{50}$ in the range of about 60-300 nM, which is lower than that of NVB by one order of magnitude or more. However, further animal tests showed that it had a lower toxicity and a higher therapeutic index. The results obtained from the clinical studies showed that VFL is superior than vinorelbine in respect to their efficacy, tolerance and activity-range. The phase III of clinical study is in progress. Based on the same principle, vinblastine derivatives BM75, BM76, BM78, BM79 and BM80 were prepared respectively by fluoridation of vinblastine derivatives BM6, BM14, BM27, BM48 and BM53 having strong activities in vivo and in vitro, and assayed in respect to their in vivo antitumor activity. The result showed that vinblastine derivative BM78 has strong antitumor activity in vivo.

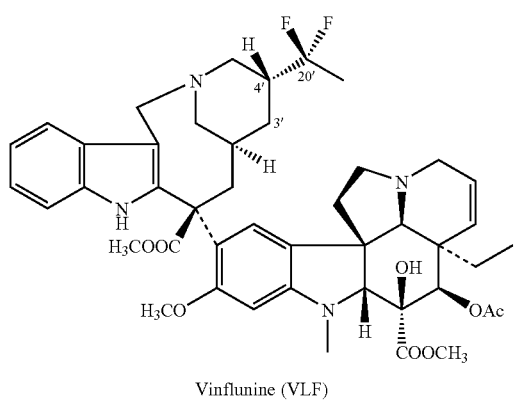

Vinflunine (VLF)

2. Assay on Nude Mice Models Bearing Human Non-Small Cell Lung Cancer (A549) Xenografts Experimental Protocol Specific pathogen free (SPF) BALB/cA-nude mice were available from Shanghai SLAC Laboratory Animal CO. LTD (Certicate code: SCXK (Shanghai) 2004-0005). Human non-small cell lung cacer (A549) cells were subcutaneously implanted into the axilla of the nude mice. After the tumor grows to 100-300 mm³, the animals were grouped randomly (d0). The doses were 1.5 mg/kg, 3.0 mg/kg and 6.0 mg/kg for BM48 tartrate, and 10 mg/kg for vinorelbine tartrate. Both BM48 tartrate and vinorelbine tartrate were delivered intravenously. The BM48 tartrate was administrated at d0 once, and vinorelbine tartrate was delivered twice at d0 and d4 respectively. The tumor volume and mice weights were measured 2-3 times each week, and the data were recorded. The tumor volume (V) was calculated by the formula below:

$V = \frac{1}{2} \times a \times b^2$, wherein a and b represent length and width respectively.

The proliferation of human lung cancer cells (A549) were significantly inhibited by one intravenous injection of BM48, and the inhibiting activity has an apparent dose-effect relationship. The mice appeared to show toxicity after the administration of BM48, but could recover well later. Vinorelbine tartrate, which was intravenously injected twice, had a little better efficacy than BM48 tartrate, but had a higher toxicity. Therefore, in general, the efficacy of BM48 tartrate is comparable to or even a little better than vinorelbine tartrate.

TABLE 3

The efficacy of intravenously delivered BM48 on nude mice models bearing human non-small cell lung cancer (A549) xenografts

| Group | Dosage (mg/kg) | Number of the animal | | Body weight (g) | | TV (mm³) x ± SD | | RTV x ± SD | T/C (%) |
|---|---|---|---|---|---|---|---|---|---|
| | | d0 | dn | d0 | dn | d0 | dn | | |
| Control | | 12 | 12 | 18.8 | 21.4 | 214 ± 48 | 2194 ± 868 | 11.06 ± 5.49 | |
| BM48 | 1.5 | 6 | 6 | 19.2 | 21.3 | 256 ± 41 | 2080 ± 542 | 8.18 ± 2.20 | 74.0 |
| BM48 | 3 | 6 | 6 | 19.3 | 20.4 | 228 ± 68 | 1545 ± 410 | 6.96 ± 1.79 | 62.9* |
| BM48 | 6 | 6 | 6 | 19.1 | 18.8 | 241 ± 30 | 808 ± 336 | 3.48 ± 1.83 | 31.5* |
| Vinorelbine | 10 | 6 | 6 | 19.0 | 16.4 | 218 ± 54 | 550 ± 206 | 2.66 ± 1.18 | 24.1* | d0: the administration time after the mice were grouped;
dn: 12 days after the first administration;
TV: tumor volume;
RTV: The relative tumor volume;
*P < 0.01 vs control

The invention claimed is:

1. A compound having structure represented by the following formula 1 or physiologically acceptable salt thereof,

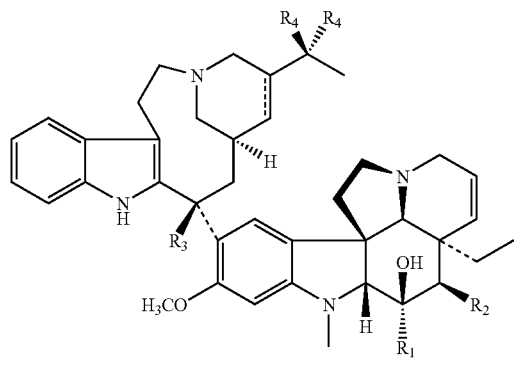

1 wherein,

"━ ━ ━ ━" represents a double bond or a single bond;

$R_1$ is

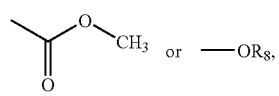

$R_2$ is —$OR_7'$ $R_3$ is

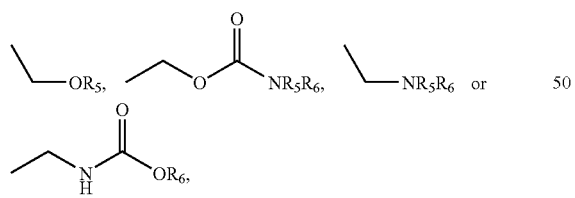

wherein, $R_5$, $R_6$, $R_7$ and $R_8$ are independently hydrogen, $C_1$-$C_5$ alkylcarboxyl, $C_3$-$C_8$ cycloalkylcarbonyl, $C_2$-$C_4$ unsatuated hydrocarbylcarbonyl, $C_6$-$C_{12}$ arylcarbonyl, $C_1$-$C_5$ alkyl, $C_3$-$C_8$ cycloalkyl, $C_2$-$C_4$ unsatuated hydrocarbyl or $C_6$-$C_{12}$ aryl, $R_4$ is hydrogen or fluorine.

2. The compound according to claim 1 or a physiologically acceptable salt thereof, selected from the group consisting of

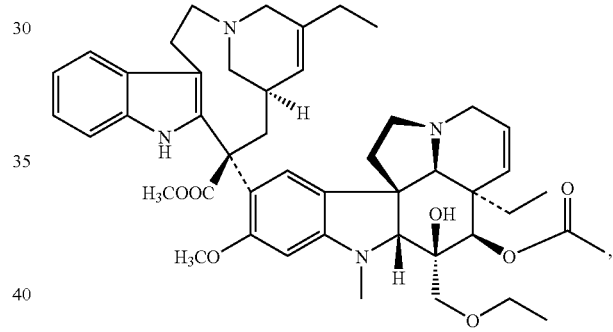

BM1

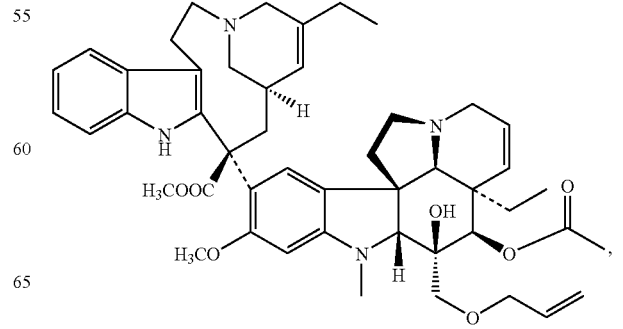

BM2

-continued
BM3
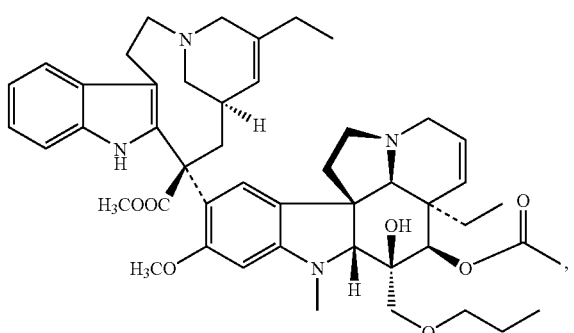
BM7
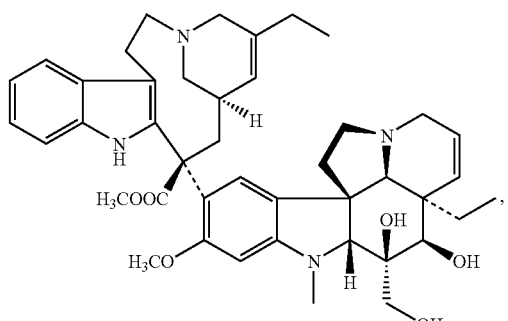
BM4
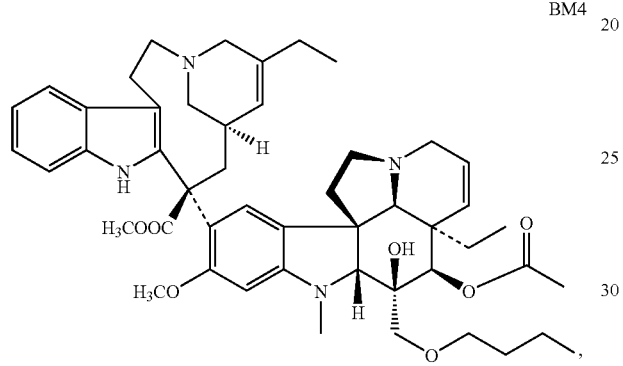
BM8
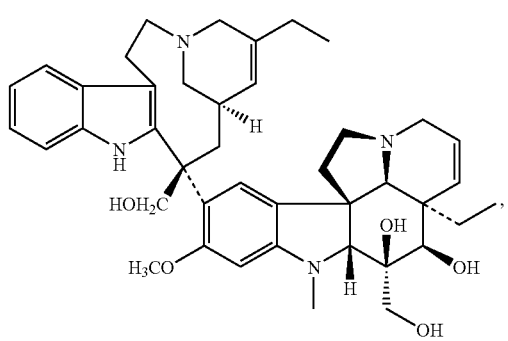
BM5
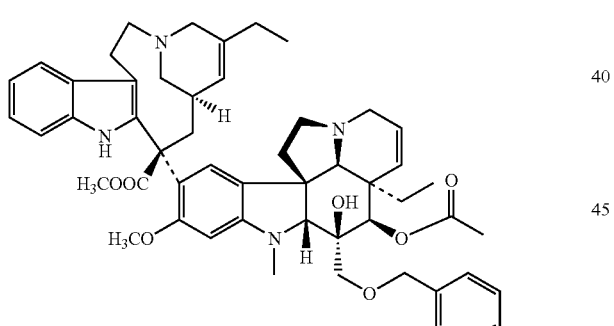
BM9
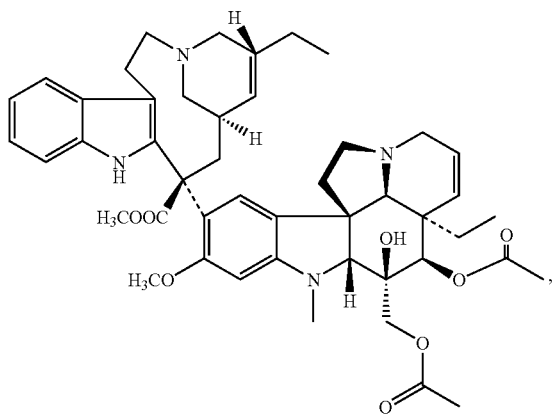
BM6
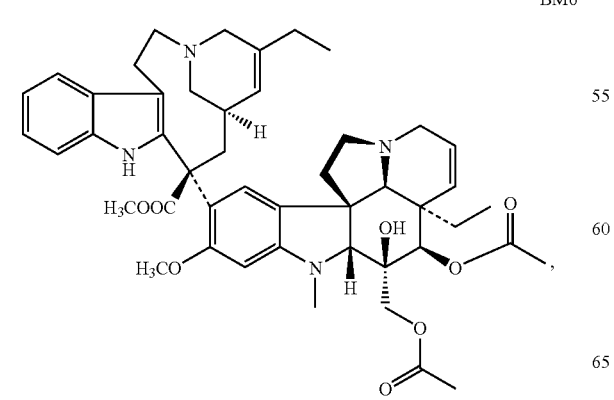
BM10
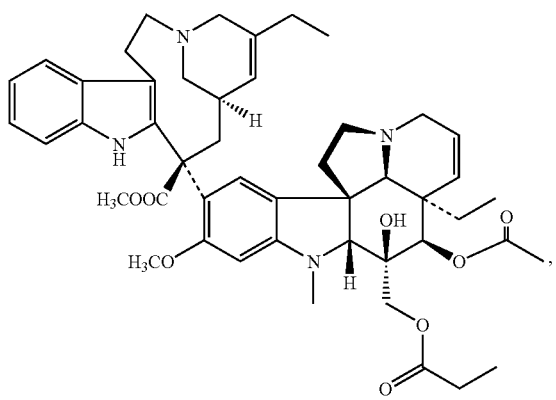

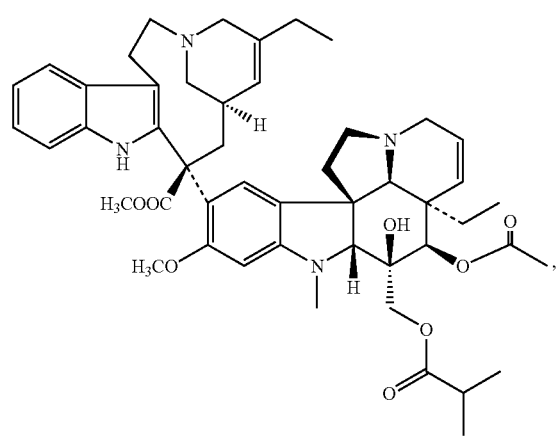
BM11
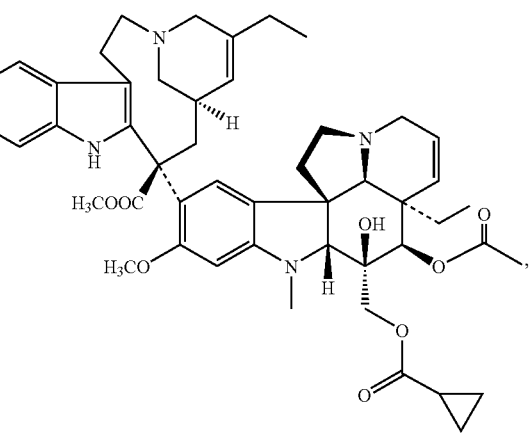
BM14
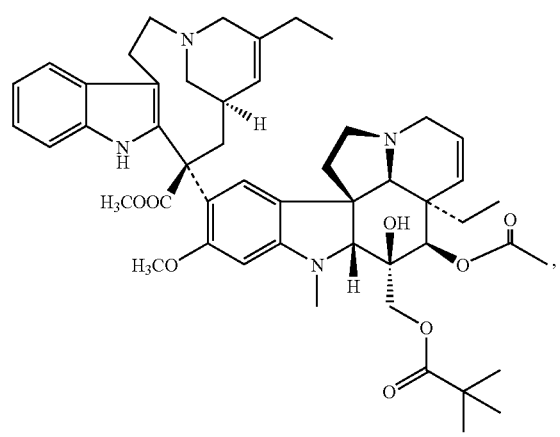
BM12
BM15
BM13
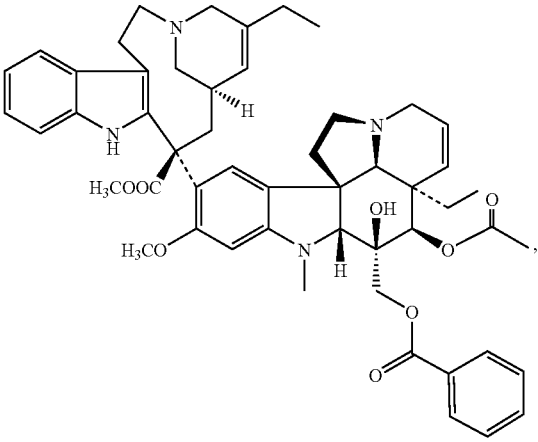
BM16

BM17
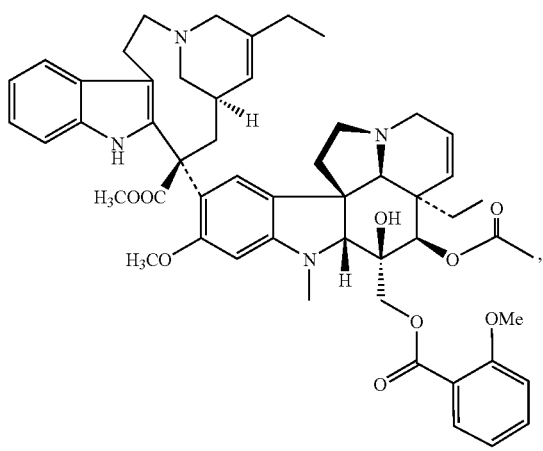
BM20
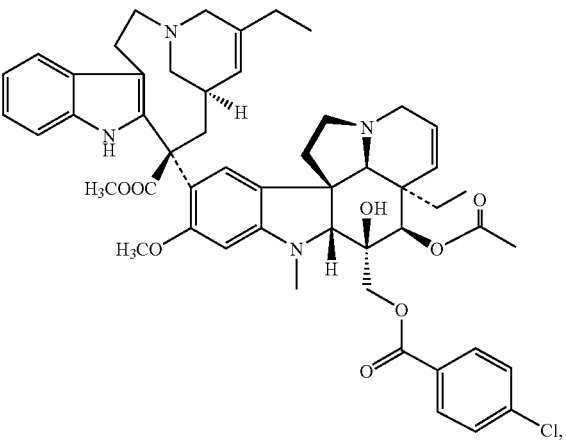
BM18
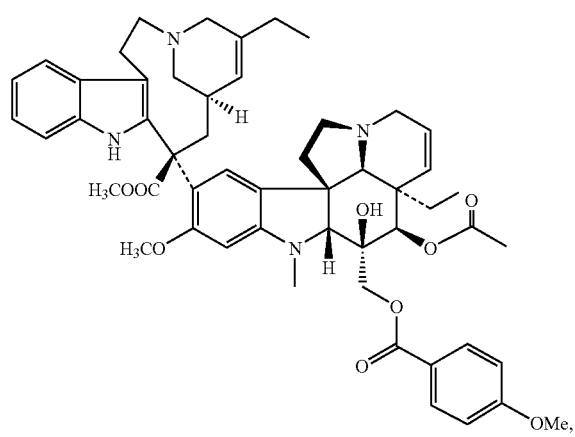
BM21
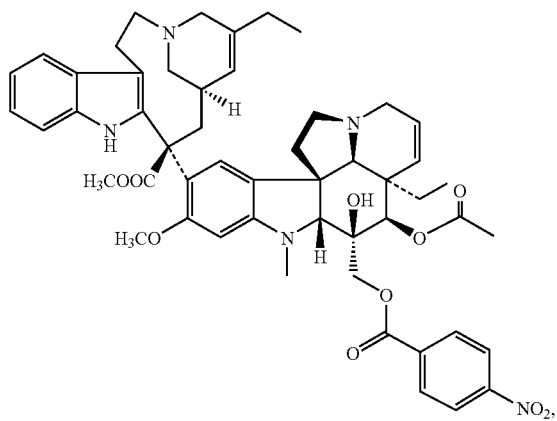
BM19
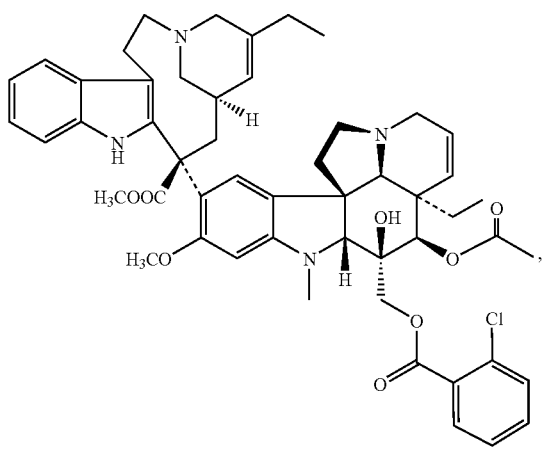
BM22
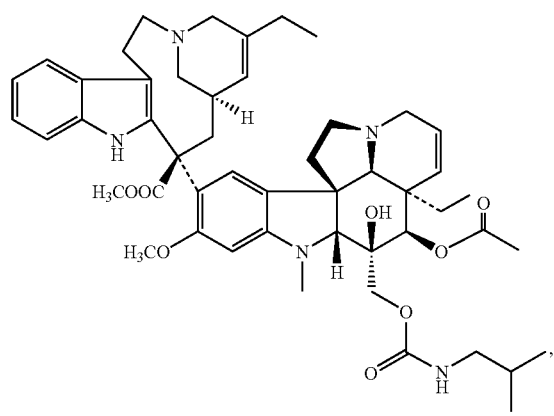

BM23
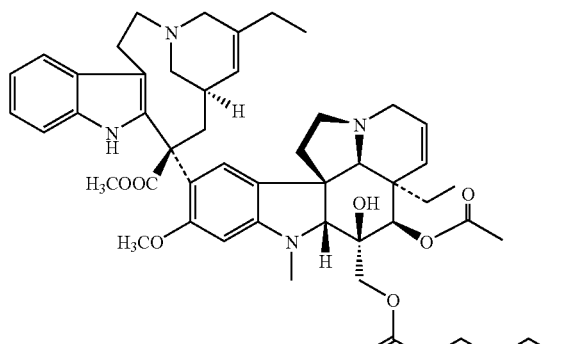
BM24
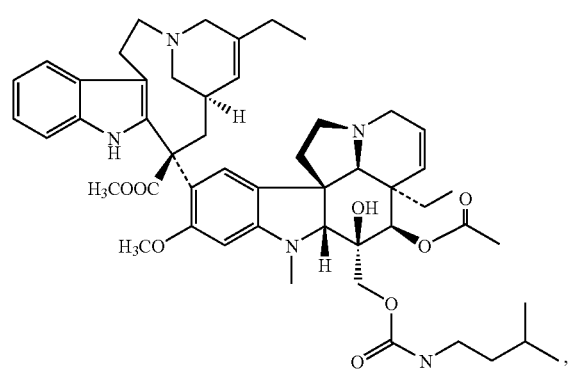
BM25
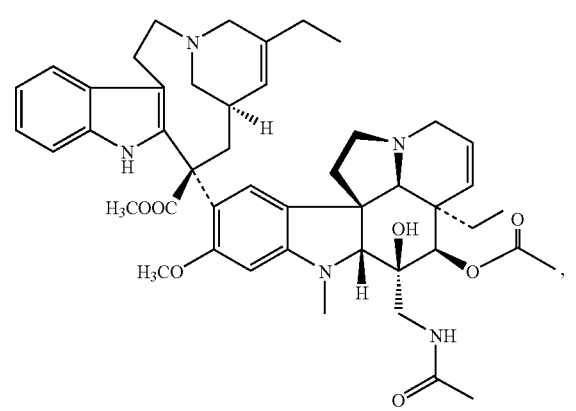
BM26
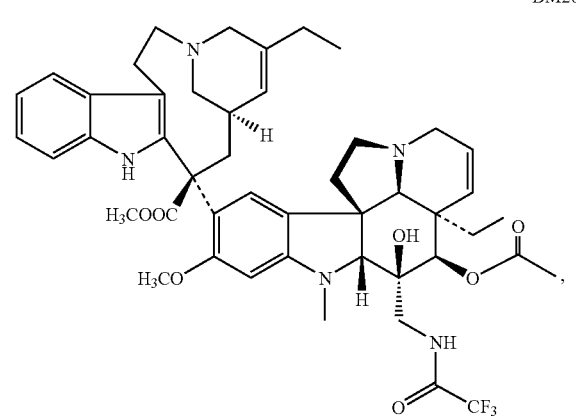
BM27
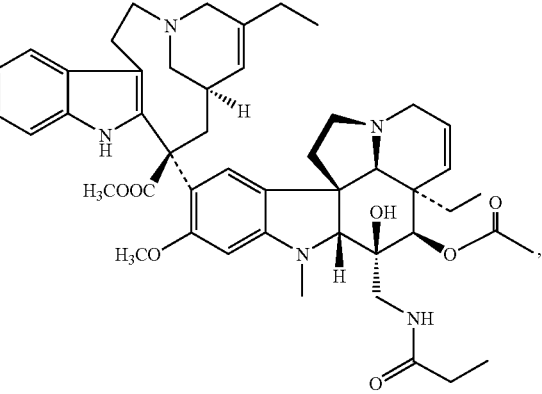
BM28
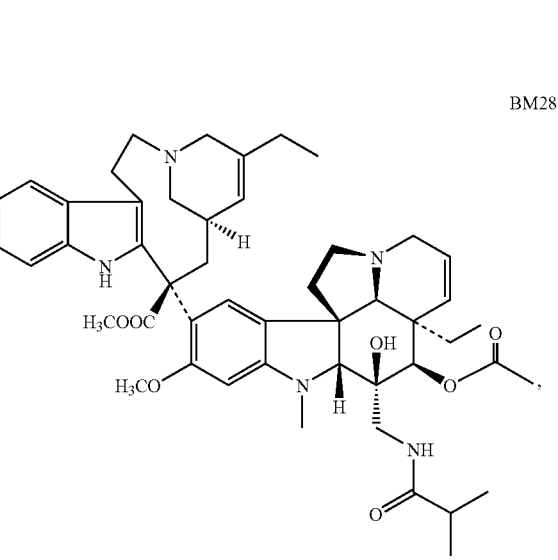
BM29

-continued
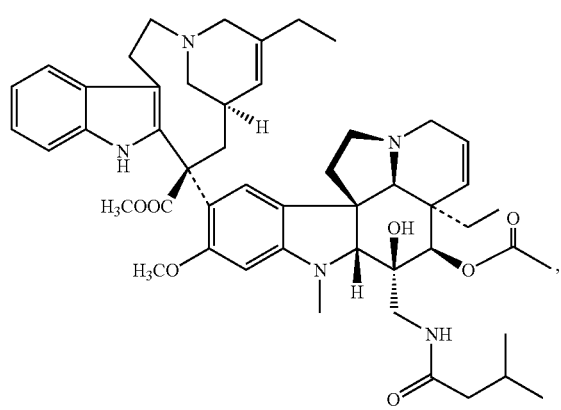
BM30
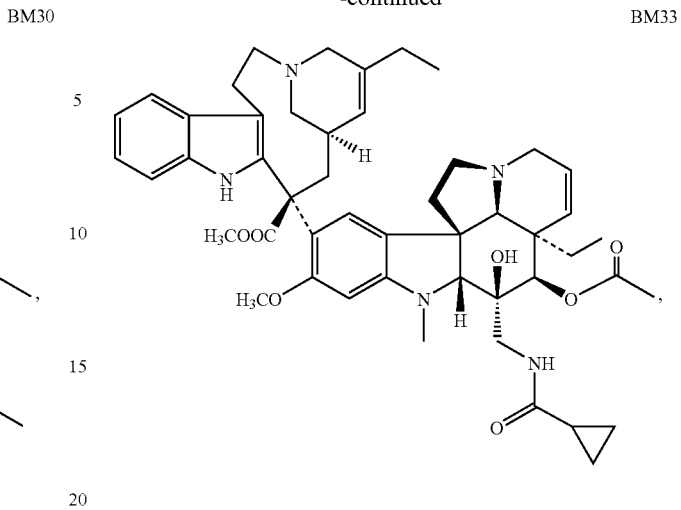
BM33
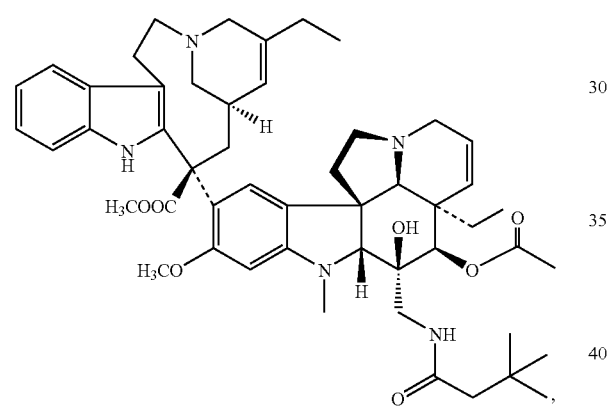
BM31
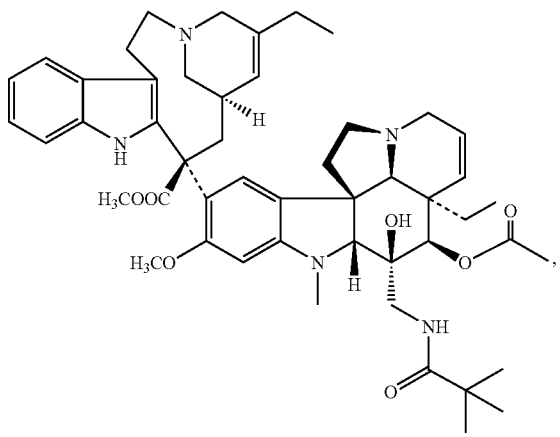
BM34
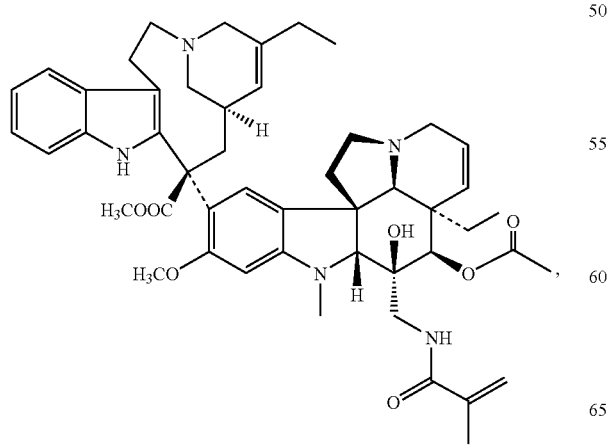
BM32
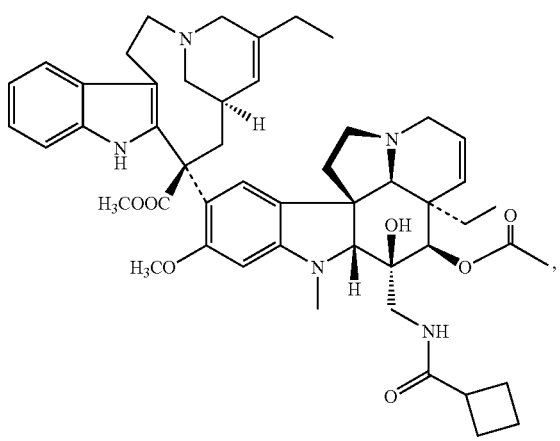
BM35

BM36
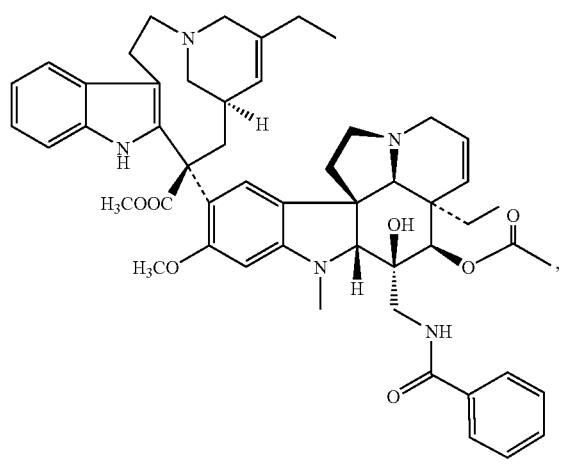
BM39
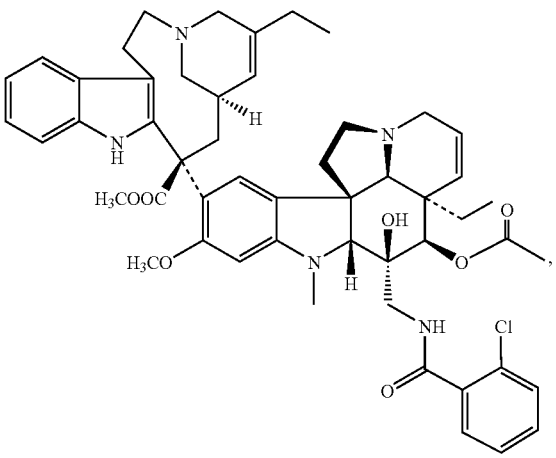
BM37
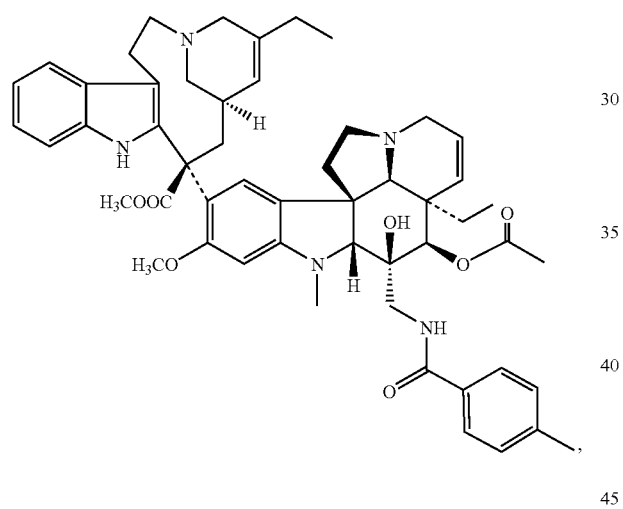
BM40
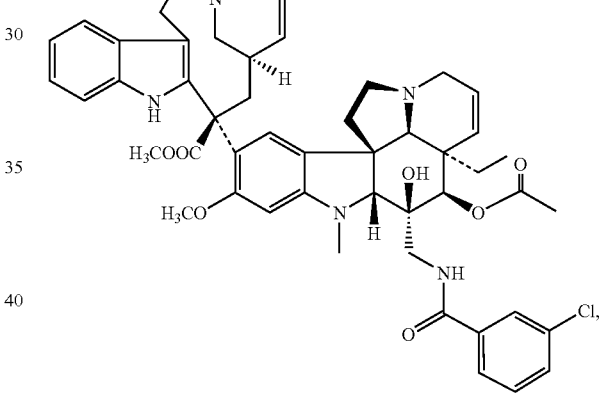
BM38
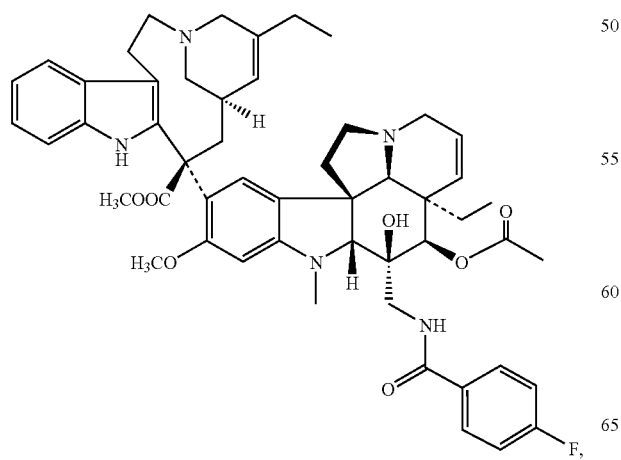
BM41
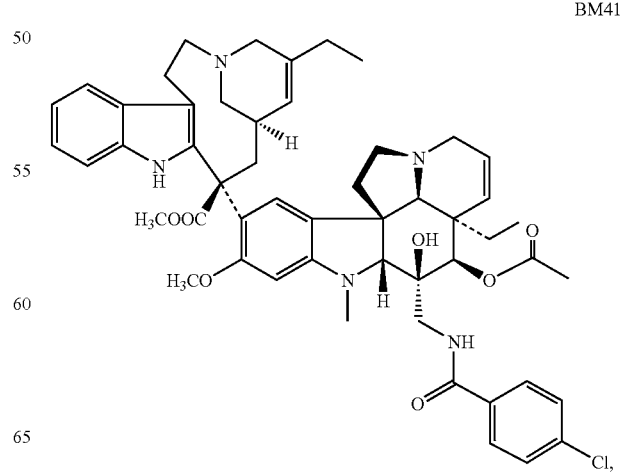

-continued
BM42
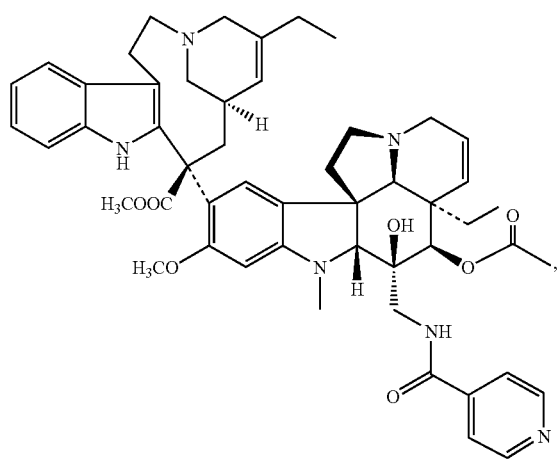
BM45
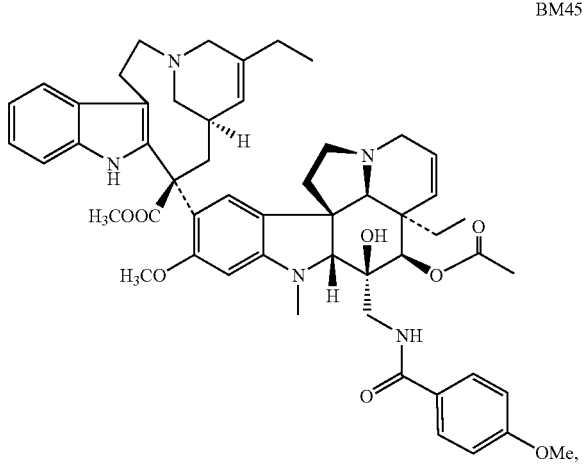
BM43
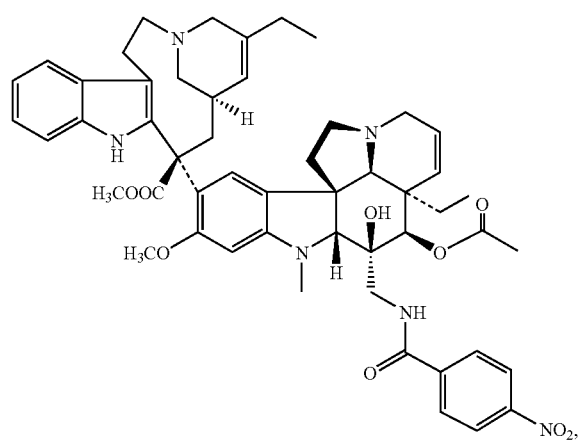
BM46
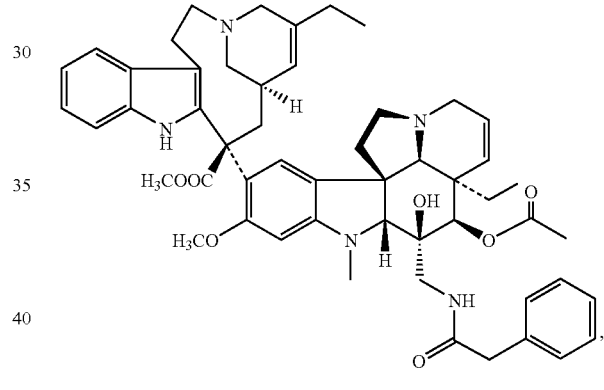
BM44
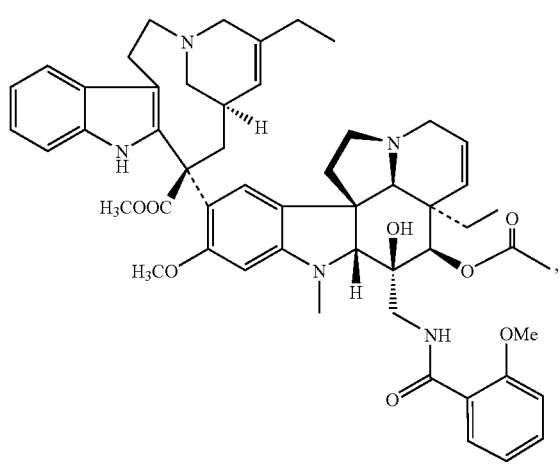
BM47
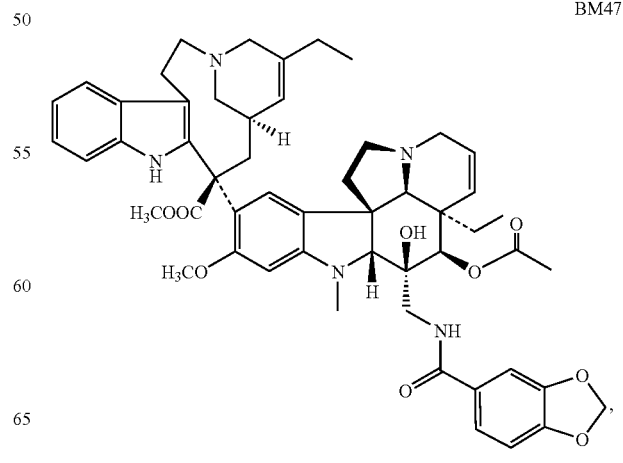

BM48
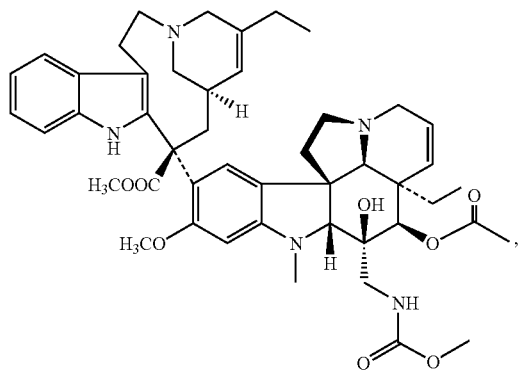
BM49
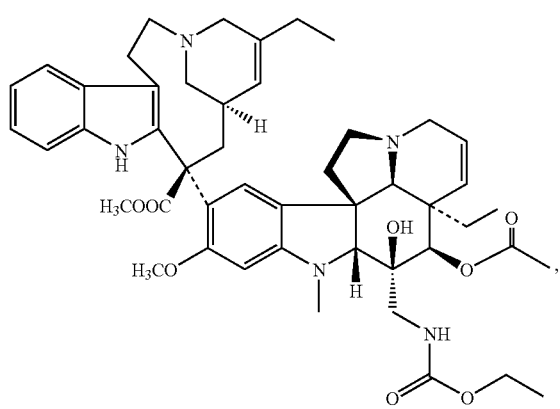
BM50
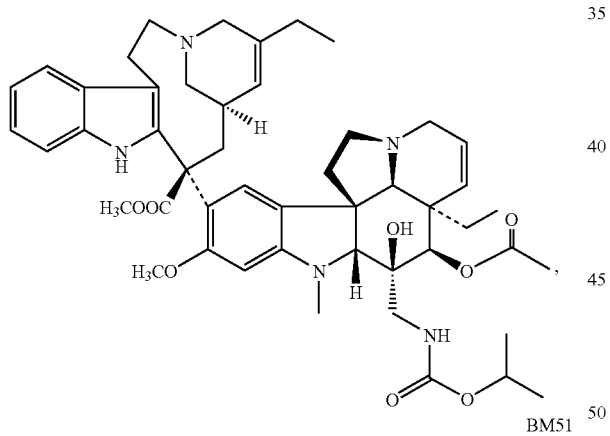
BM51
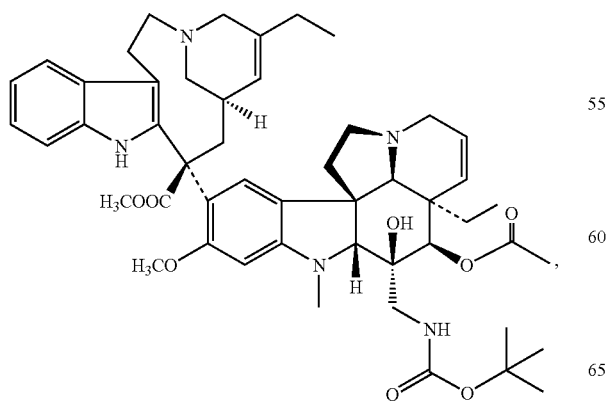
BM52
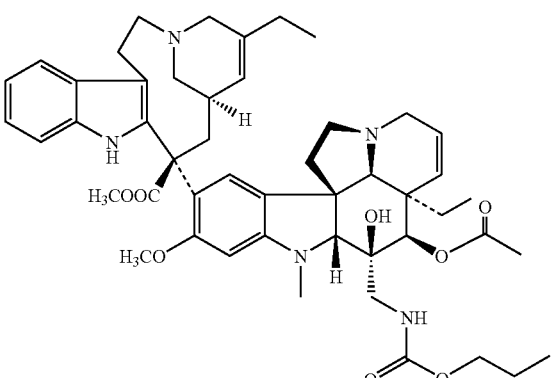
BM53
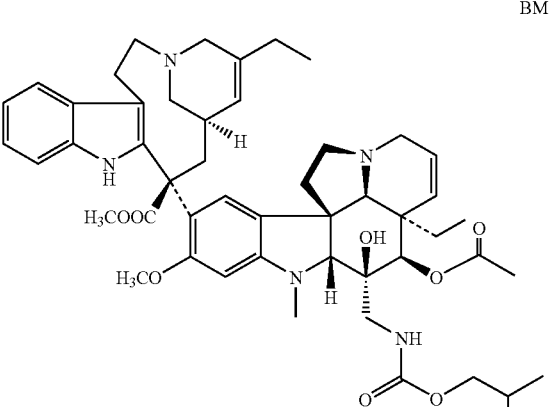
BM54
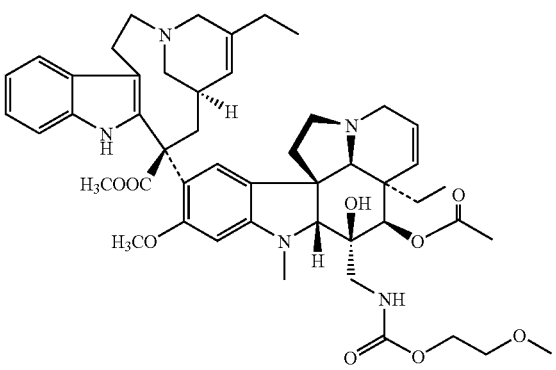
BM55

BM56
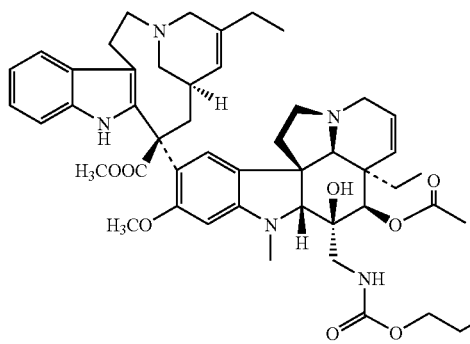
BM60
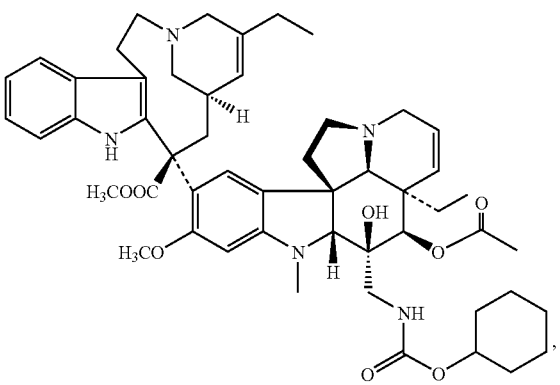
BM57
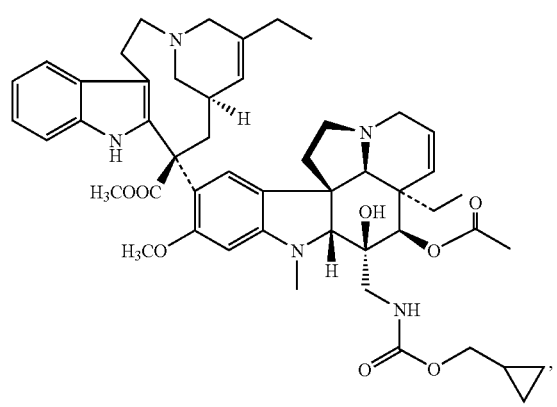
BM61
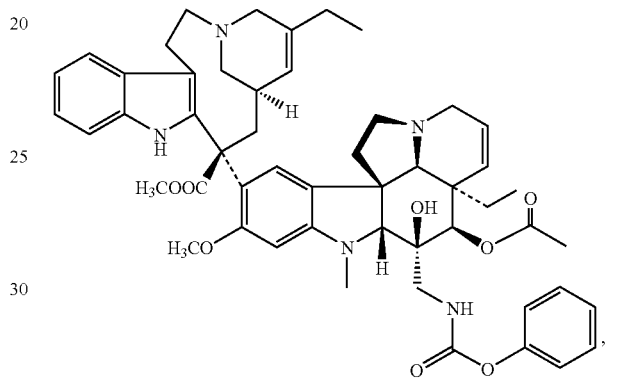
BM58
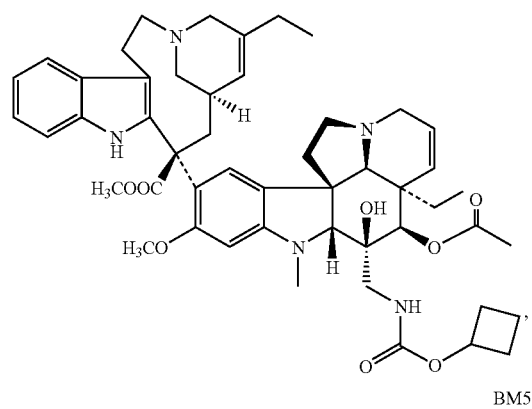
BM62
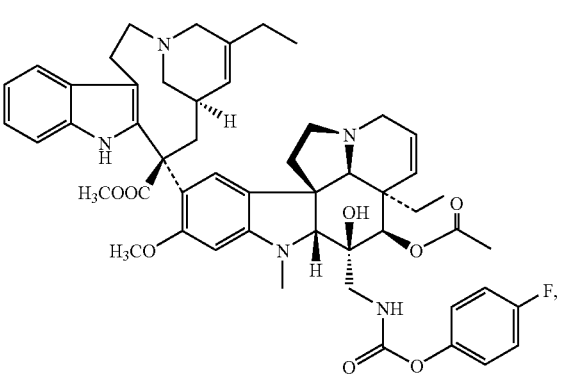
BM59
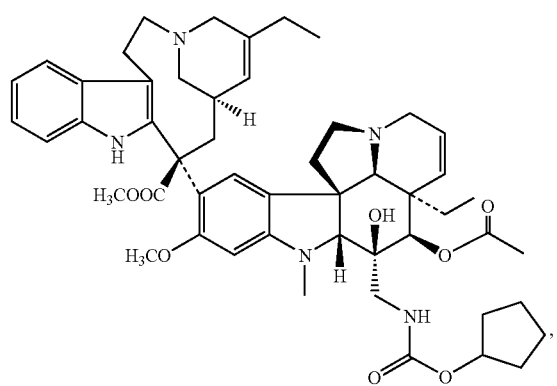
BM63
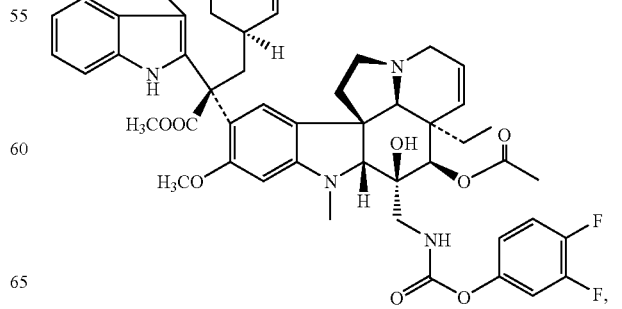

-continued
BM64
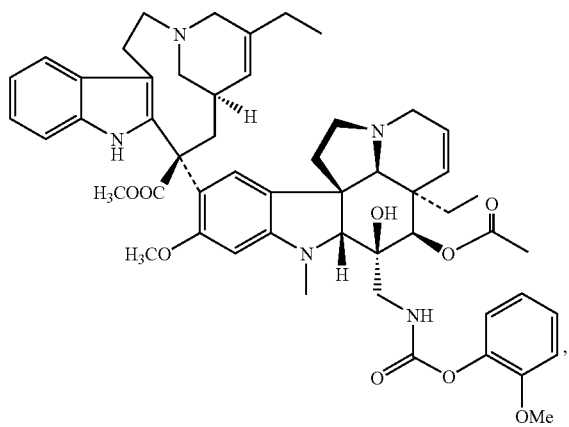
BM65
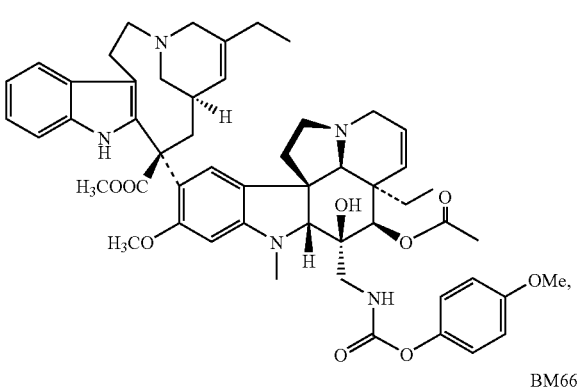
BM66
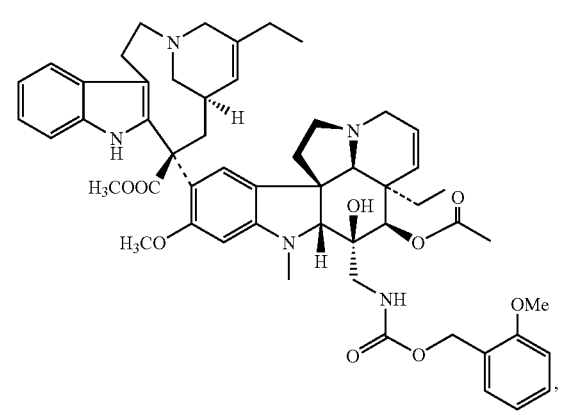
-continued
BM68
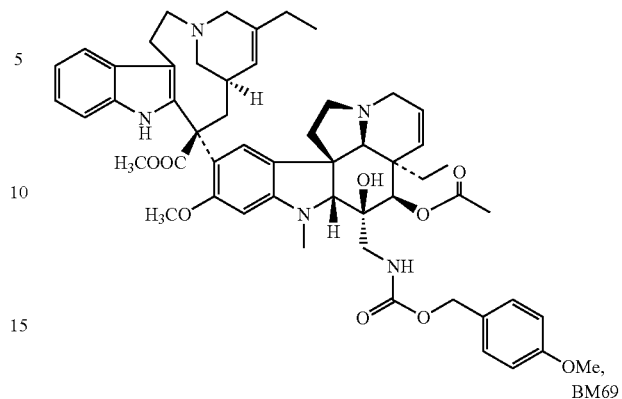
BM69
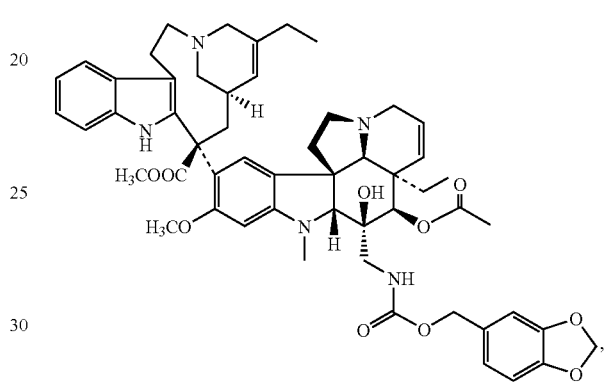
BM70
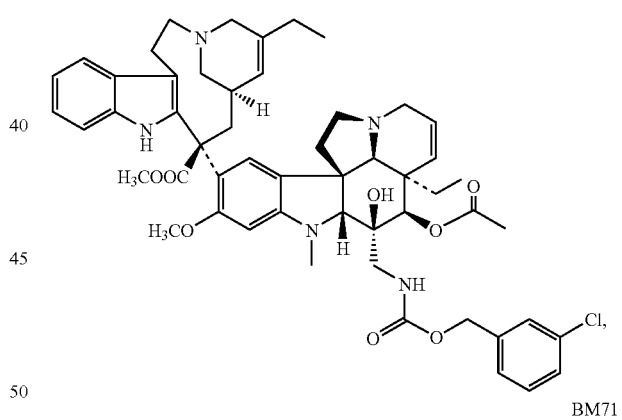
BM67
BM71
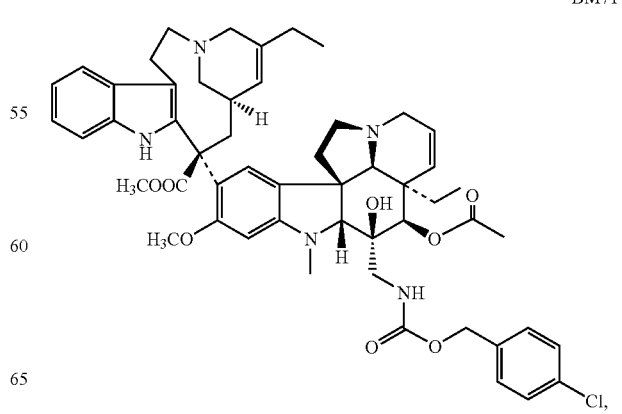

BM72
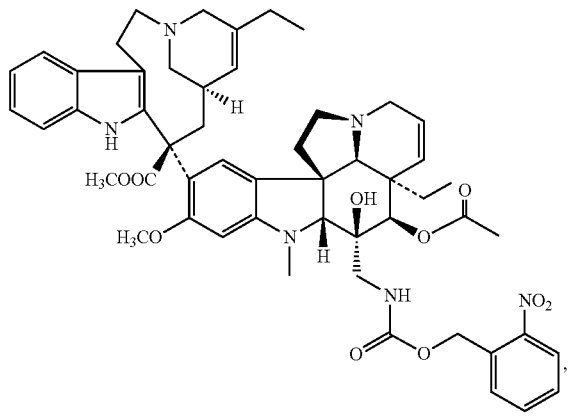
BM75
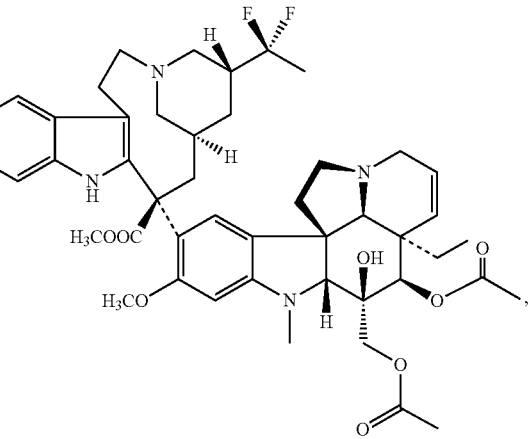
BM73
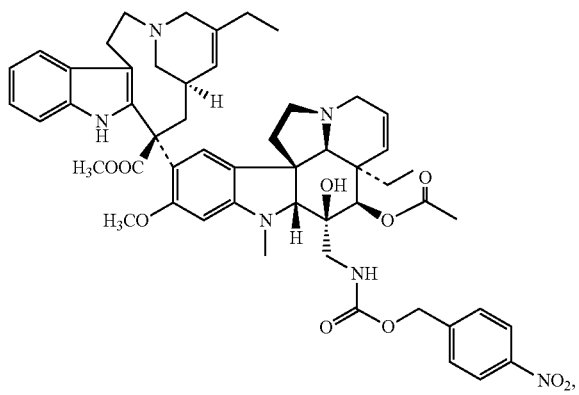
BM76
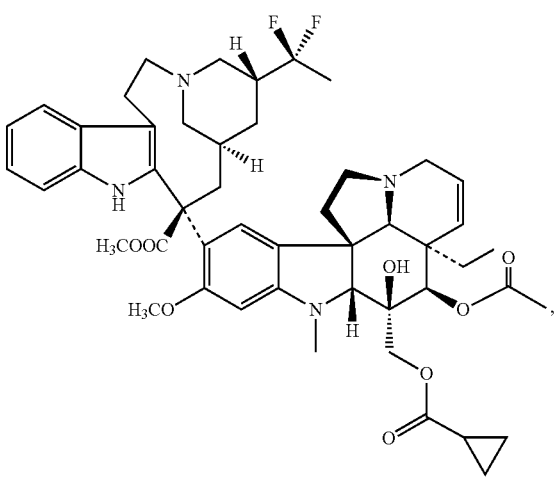
BM74
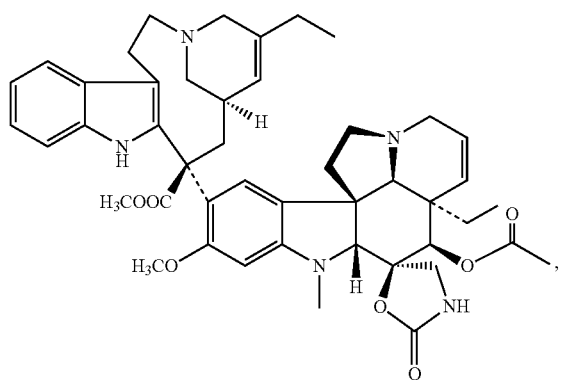
BM77
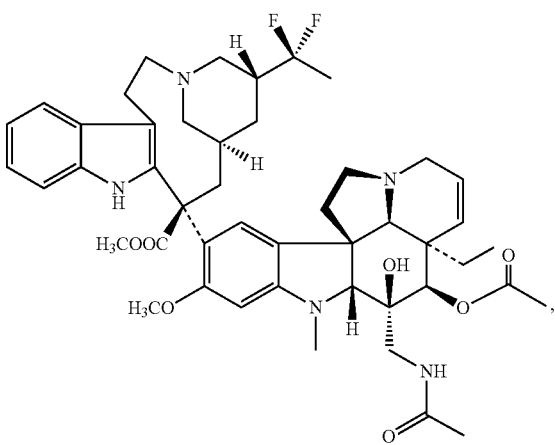

-continued

BM78

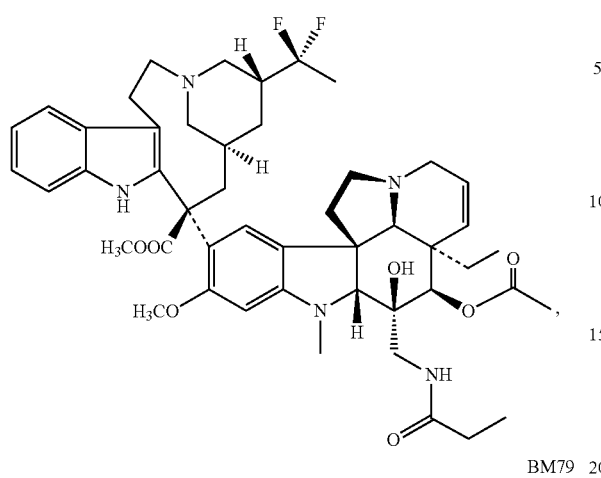

BM79

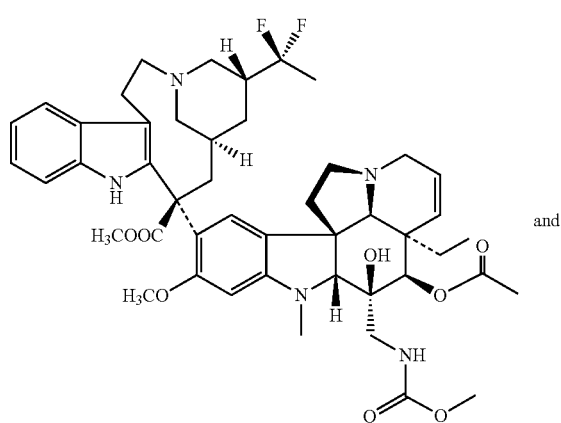

and

-continued

BM80

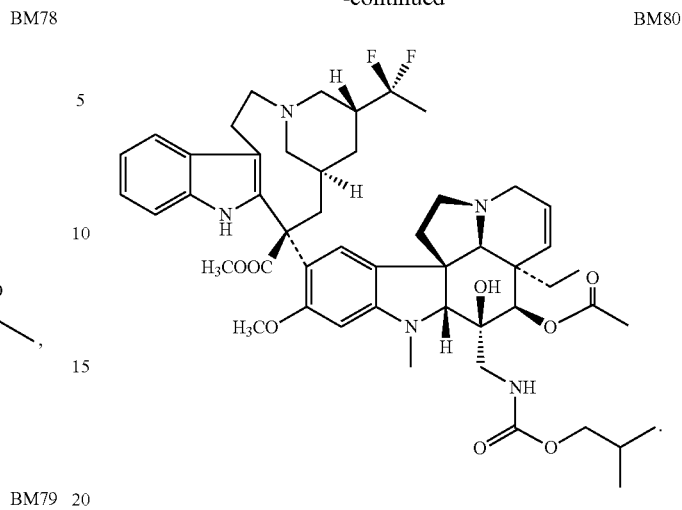

3. A method for treating lung cancer and/or cervical carcinoma, comprising administering to a patient in need of such treatment an effective amount of the compound or physiologically acceptable salt thereof according to claim 1.

4. A pharmaceutical composition, comprising a therapeutically effective amount of the compound or physiologically acceptable salt thereof according to claim 1.

* * * * *